United States Patent
Crawford et al.

(10) Patent No.: US 8,754,077 B2
(45) Date of Patent: Jun. 17, 2014

(54) 8-FLUOROPHTHALAZIN-1(2H)-ONE COMPOUNDS

(71) Applicant: Genentech, Inc., South San Francisco, CA (US)

(72) Inventors: James J. Crawford, San Francisco, CA (US); Daniel F. Ortwine, San Ramon, CA (US); BinQing Wei, Belmont, CA (US); Wendy B. Young, San Mateo, CA (US)

(73) Assignee: F. Hoffmann-La Roche AG, Basel (CH)

( * ) Notice: Subject to any disclaimer, the term of this patent is extended or adjusted under 35 U.S.C. 154(b) by 0 days.

(21) Appl. No.: 14/154,008

(22) Filed: Jan. 13, 2014

(65) Prior Publication Data
US 2014/0128401 A1    May 8, 2014

Related U.S. Application Data

(63) Continuation of application No. 13/667,126, filed on Nov. 2, 2012.

(60) Provisional application No. 61/555,398, filed on Nov. 3, 2011.

(51) Int. Cl.
    *A61K 31/5377* (2006.01)
    *A61K 31/502* (2006.01)
    *A61K 31/5383* (2006.01)

(52) U.S. Cl.
    USPC ............ 514/230.5; 514/248; 514/234.5; 514/249

(58) Field of Classification Search
    USPC ......... 514/234.5, 249, 230.5, 248; 544/119, 544/105, 237
    See application file for complete search history.

(56) References Cited

U.S. PATENT DOCUMENTS

| | | | |
|---|---|---|---|
| 7,683,064 B2 | 3/2010 | Dewdney et al. | |
| 7,884,108 B2 | 2/2011 | Blomgren et al. | |
| 7,902,194 B2 | 3/2011 | Dewdney et al. | |
| 7,906,509 B2 | 3/2011 | Kennedy-Smith et al. | |
| 8,058,446 B2 | 11/2011 | Blomgren et al. | |
| 8,124,604 B2 | 2/2012 | Dewdney et al. | |
| 2009/0186898 A1 | 7/2009 | Dewdney et al. | |
| 2010/0004231 A1 | 1/2010 | Dewdney et al. | |
| 2010/0016301 A1 | 1/2010 | Dewdney et al. | |
| 2012/0040949 A1 | 2/2012 | Berthel et al. | |
| 2012/0295885 A1 | 11/2012 | Billedeau et al. | |
| 2013/0045965 A1* | 2/2013 | Brotherton-Pleiss et al. | 514/210.21 |

* cited by examiner

*Primary Examiner* — Kristin Vajda
(74) *Attorney, Agent, or Firm* — Alex Andrus; Genentech, Inc.

(57) ABSTRACT

8-Fluorophthalazin-1(2h)-one compounds of Formula I where one or two of $X^1$, $X^2$, and $X^3$ are N, are provided, including stereoisomers, tautomers, and pharmaceutically acceptable salts thereof, useful for inhibiting Btk kinase, and for treating immune disorders such as inflammation mediated by Btk kinase. Methods of using compounds of Formula I for in vitro, in situ, and in vivo diagnosis, and treatment of such disorders in mammalian cells, or associated pathological conditions, are disclosed.

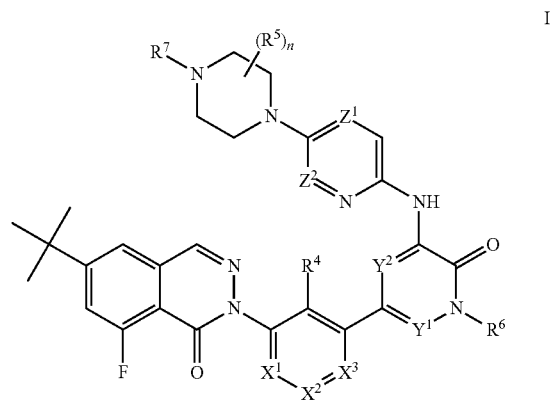

21 Claims, 5 Drawing Sheets

8-FLUOROPHTHALAZIN-1(2H)-ONE COMPOUNDS

CROSS REFERENCE TO RELATED APPLICATIONS

This application is a continuation of U.S. Ser. No. 13/667,126, filed 2 Nov. 2012, and also claims the benefit of priority under 35 USC §119(e) of U.S. Provisional Application Ser. No. 61/555,398 filed on 3 Nov. 2011, which are incorporated by reference in entirety.

FIELD OF THE INVENTION

The invention relates generally to compounds for treating disorders mediated by Bruton's Tyrosine Kinase (Btk) including inflammation, immunological, and cancer, and more specifically to compounds which inhibit Btk activity. The invention also relates to methods of using the compounds for in vitro, in situ, and in vivo diagnosis or treatment of mammalian cells, or associated pathological conditions.

BACKGROUND OF THE INVENTION

Protein kinases, the largest family of human enzymes, encompass well over 500 proteins. Bruton's Tyrosine Kinase (Btk) is a member of the Tec family of tyrosine kinases, and is a regulator of early B-cell development as well as mature B-cell activation, signaling, and survival.

B-cell signaling through the B-cell receptor (BCR) can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation. Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice can also be resistant to developing collagen-induced arthritis and can be less susceptible to Staphylococcus-induced arthritis. A large body of evidence supports the role of B-cells and the humoral immune system in the pathogenesis of autoimmune and/or inflammatory diseases. Protein-based therapeutics (such as Rituxan) developed to deplete B-cells, represent an approach to the treatment of a number of autoimmune and/or inflammatory diseases. Because of Btk's role in B-cell activation, inhibitors of Btk can be useful as inhibitors of B-cell mediated pathogenic activity (such as autoantibody production). Btk is also expressed in osteoclasts, mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases such as: SLE, rheumatoid arthritis, multiple vasculitides, idiopathic thrombocytopenic purpura (ITP), myasthenia gravis, allergic rhinitis, and asthma (Di Paolo et al (2011) Nature Chem. Biol. 7(1):41-50; Liu et al (2011) Jour. of Pharm. and Exper. Ther. 338(1):154-163). In addition, Btk has been reported to play a role in apoptosis; thus, inhibition of Btk activity can be useful for cancer, as well as the treatment of B-cell lymphoma, leukemia, and other hematological malignancies. Moreover, given the role of Btk in osteoclast function, the inhibition of Btk activity can be useful for the treatment of bone disorders such as osteoporosis. Specific Btk inhibitors have been reported (Liu (2011) Drug Metab. and Disposition 39(10):1840-1849; U.S. Pat. No. 7,884,108, WO 2010/056875; U.S. Pat. No. 7,405,295; U.S. Pat. No. 7,393,848; WO 2006/053121; U.S. Pat. No. 7,947,835; US 2008/0139557; U.S. Pat. No. 7,838,523; US 2008/0125417; US 2011/0118233; PCT/US2011/050034 "PYRIDINONES/PYRAZINONES, METHOD OF MAKING, AND METHOD OF USE THEREOF", filed 31 Aug. 2011; PCT/US2011/050013 "PYRIDAZINONES, METHOD OF MAKING, AND METHOD OF USE THEREOF", filed 31 Aug. 2011; U.S. Ser. No. 13/102,720 "PYRIDONE AND AZA-PYRIDONE COMPOUNDS AND METHODS OF USE", filed 6 May 2011).

SUMMARY OF THE INVENTION

The invention relates generally to Formula I and II compounds, 8-fluorophthalazin-1(2h)-one compounds with Bruton's Tyrosine Kinase (Btk) modulating activity, having the structures:

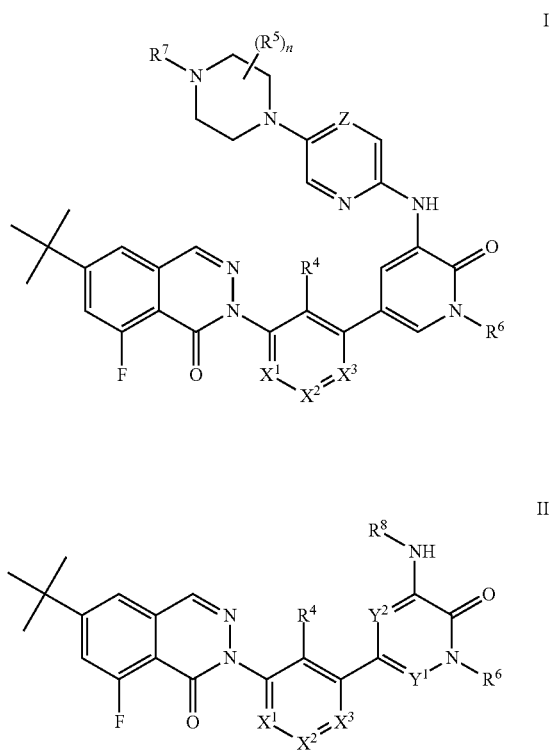

including stereoisomers, tautomers, or pharmaceutically acceptable salts thereof. The various substituents are defined herein below.

One aspect of the invention is a pharmaceutical composition comprised of a Formula I or II compound, and a pharmaceutically acceptable carrier, glidant, diluent, or excipient. The pharmaceutical composition may further comprise a second therapeutic agent.

Another aspect of the invention is a process for making a pharmaceutical composition which comprises combining a Formula I or II compound with a pharmaceutically acceptable carrier.

The invention includes a method of treating a disease or disorder which method comprises administering a therapeutically effective amount of a Formula I or II compound to a patient with a disease or disorder selected from immune disorders, cancer, cardiovascular disease, viral infection, inflammation, metabolism/endocrine function disorders and neurological disorders, and mediated by Bruton's tyrosine kinase.

The invention includes a kit for treating a condition mediated by Bruton's tyrosine kinase, comprising: a) a first pharmaceutical composition comprising a Formula I or II compound; and b) instructions for use.

The invention includes a Formula I or II compound for use as a medicament, and for use in treating a disease or disorder selected from immune disorders, cancer, cardiovascular disease, viral infection, inflammation, metabolism/endocrine function disorders and neurological disorders, and mediated by Bruton's tyrosine kinase.

The invention includes use of a Formula I or II compound in the manufacture of a medicament for the treatment of immune disorders, cancer, cardiovascular disease, viral infection, inflammation, metabolism/endocrine function disorders and neurological disorders, and where the medicament mediates Bruton's tyrosine kinase.

The invention includes methods of making a Formula I or II compound.

BRIEF DESCRIPTION OF THE DRAWINGS

FIG. 1 shows the preparation of 6-tert-Butyl-8-fluoro-2-(2-(hydroxymethyl)-3-(1-methyl-5-(5-(4-methylpiperazin-1-yl)pyridin-2-ylamino)-6-oxo-1,6-dihydropyridin-3-yl)phenyl)phthalazin-1(2H)-one 101 starting with 4-tert-Butylbenzoyl Chloride 101a FIG. 2 shows the preparation of 6-tert-Butyl-8-fluoro-2-(3-(hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)phthalazin-1(2H)-one 102 starting with 2,6-Dibromo-4-fluorobenzaldehyde 102a FIG. 3 shows the preparation of 6-tert-butyl-8-fluoro-2-(3-(hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)-phthalazin-1(2H)-one 103 starting with 2-Bromo-4-chloronicotinaldehyde 103a FIG. 4 shows the preparation of (S)-6-tert-butyl-8-fluoro-2-(3-(hydroxymethyl)-4-(1-methyl-5-(3-methyl-5-(4-(oxetan-3-yl)piperazine-1-yl)pyridin-2-ylamino)-6-oxo-1,6-dihydropyridin-3-yl)pyridin-2-yl)phthalazin-1(2H)-one 105 starting with (3S)-tert-Butyl 3-Methyl-4-(6-nitropyridin-3-yl)piperazine-1-carboxylate 105a FIG. 5 shows the preparation of R-6-tert-Butyl-8-fluoro-2-(3-(hydroxymethyl)-4-(1-methyl-5-(5-(2-methyl-4-(oxetan-3-yl)piperazine-1-yl)pyridin-2-ylamino)-6-oxo-1,6-dihydropyridin-3-yl)pyridin-2-yl)phthalazin-1(2H)-one 106 starting with 1-Methyl-3-(5-(2-methyl-4-(oxetan-3-yl)piperazine-1-yl)pyridin-2-ylamino)-5-(4,4,5,5-tetramethyl-1,3,2-dioxaborolan-2-yl)pyridin-2(1H)-one 106a FIG. 6 shows the preparation of (S)-6-tert-Butyl-8-fluoro-2-(4-(hydroxymethyl)-5-(1-methyl-5-(5-(2-methyl-4-(oxetan-3-yl)piperazin-1-yl)pyridin-2-ylamino)-6-oxo-1,6-dihydropyridin-3-yl)pyridin-3-yl)phthalazin-1(2H)-one 109 starting with 3-Bromo-5-(6-tert-butyl-8-fluoro-1-oxo-1,2-dihydrophthalazin-2-yl)pyridine-4-carbaldehyde 109a FIG. 7 shows the preparation of 6-tert-Butyl-2-(4-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-8-fluorophthalazin-1(2H)-one 110 starting with 2-(6-tert-Butyl-8-fluoro-1-oxophthalazin-2(1H)-yl)-4-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)nicotinaldehyde 110a FIG. 8 shows the preparation of (S)-6-tert-Butyl-2-(4-(5-(5-(2-ethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-8-fluorophthalazin-1(2H)-one 112 starting with (S)-2-(6-tert-Butyl-8-fluoro-1-oxophthalazin-2(1H)-yl)-4-(5-(5-(2-ethyl-4-(oxetan-3-yl)piperazin-1-yl)pyridin-2-ylamino)-1-methyl-6-oxo-1,6-dihydropyridin-3-yl)nicotinaldehyde 112a

DETAILED DESCRIPTION OF EXEMPLARY EMBODIMENTS

Figure 1:
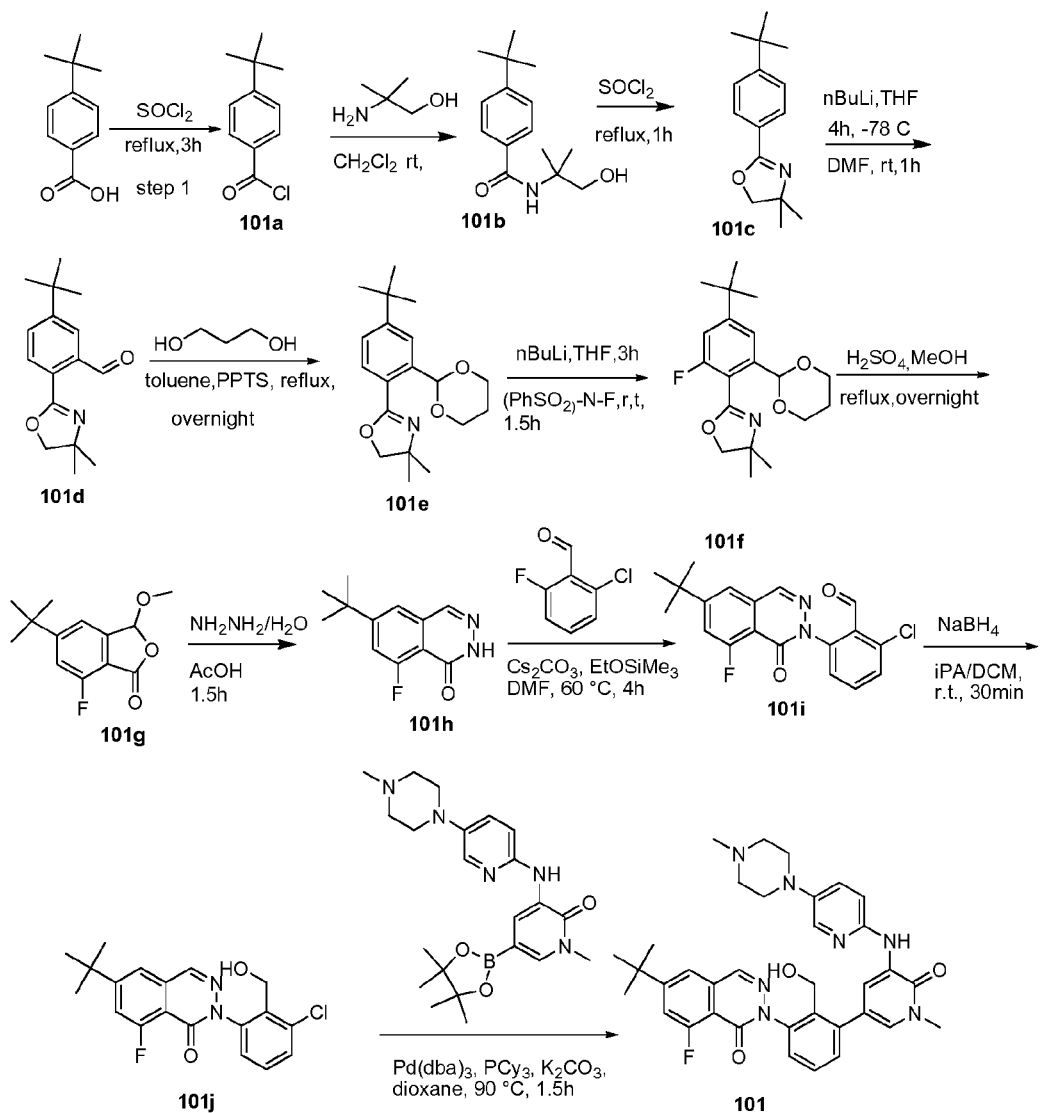

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

Definitions

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), i-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-i-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo [4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I and II compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms ("cancer"), and they are generally treated by specialists in hematology and/or oncology. In some centers "Hematology/oncology" is a single subspecialty of internal medicine while in others they are considered separate divisions (there are also surgical and radiation oncologists). Not all hematological disorders are malignant ("cancerous"); these other blood conditions may also be managed by a hematologist. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL), Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (all subtypes).

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE0); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/

044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the Btk inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I or II compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Table 1 structures for illustrative purposes, while stereochemical determination awaits, such as x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as $IC_{70}$, $IC_{90}$, etc., may be calculated.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I and II compounds, is also intended to represent hydrates, solvates, and polymorphs of such compounds, and mixtures thereof.

Any formula or structure given herein, including Formula I and II compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

8-Fluorophthalazin-1(2H)-One Compounds

The present invention provides 8-fluorophthalazin-1(2h)-one compounds of Formula I, including Formulas Ia-If, and pharmaceutical formulations thereof, which are potentially useful in the treatment of diseases, conditions and/or disorders modulated by Btk kinase:

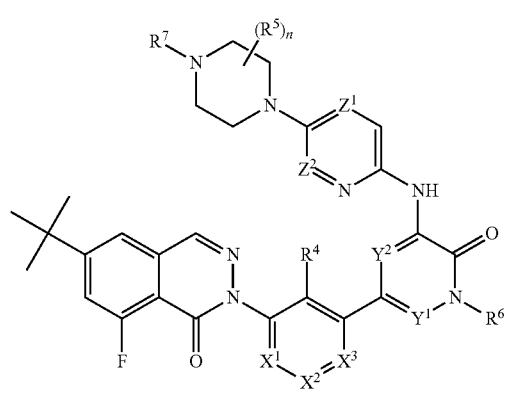

or stereoisomers, tautomers, or pharmaceutically acceptable salts thereof, wherein:

$X^1$ is $CR^1$ or N;
$X^2$ is $CR^2$ or N;
$X^3$ is $CR^3$ or N;

where one or two of $X^1$, $X^2$, and $X^3$ are N;

$R^1$, $R^2$ and $R^3$ are independently selected from H, F, Cl, CN, —CH$_3$, —CH$_2$CH$_3$, —CH$_2$OH, —CH$_2$F, —CHF$_2$, —CF$_3$, —CH$_2$CH$_2$OH, —NH$_2$, —NHCH$_3$, —N(CH$_3$)$_2$, —OH, —OCH$_3$, —OCH$_2$CH$_3$, and —OCH$_2$CH$_2$OH;

$R^4$ is selected from H, F, Cl, CN, —CH$_2$OH, —CH(CH$_3$)OH, —C(CH$_3$)$_2$OH, —CH(CF$_3$)OH, —CH$_2$F, —CHF$_2$, —CH$_2$CHF$_2$, —CF$_3$, —C(O)NH$_2$, —C(O)NHCH$_3$, —C(O)N(CH$_3$)$_2$, —NH$_2$, —NHCH$_3$, —N(CH$_3$)$_2$, —NHC(O)CH$_3$, —OH, —OCH$_3$, —OCH$_2$CH$_3$, —OCH$_2$CH$_2$OH, cyclopropyl, cyclopropylmethyl, 1-hydroxycyclopropyl, imidazolyl, pyrazolyl, 3-hydroxy-oxetan-3-yl, oxetan-3-yl, and azetidin-1-yl;

$R^5$ is selected from —CH$_3$, —CH$_2$CH$_3$, —CH$_2$OH, —CH$_2$F, —CHF$_2$, —CF$_3$, —CN, and —CH$_2$CH$_2$OH;

or two $R^5$ groups form a 3-, 4-, 5-, or 6-membered carbocyclic or heterocyclic ring;

or an $R^5$ group and an $R^7$ group form a 3-, 4-, 5-, or 6-membered carbocyclic or heterocyclic ring;

n is 0, 1, 2, 3, or 4;

$R^6$ is selected from H, —CH$_3$, —CH$_2$CH$_3$, —CH$_2$CH$_2$OH, —CH$_2$F, —CHF$_2$, —CF$_3$, —NH$_2$, —NHCH$_3$, —N(CH$_3$)$_2$, —OH, —OCH$_3$, —OCH$_2$CH$_3$, and —OCH$_2$CH$_2$OH;

$R^7$ is selected from H, —CH$_3$, —S(O)$_2$CH$_3$, cyclopropyl, azetidin-3-yl, oxetan-3-yl, and morpholin-4-yl;

$Z^1$ is $CR^8$ or N, where $R^8$ is selected from H, F, Cl, —CH$_3$, —CH$_2$CH$_3$, —CH$_2$CH$_2$OH, —NH$_2$, —NHCH$_3$, —N(CH$_3$)$_2$, —OH, —OCH$_3$, —OCH$_2$CH$_3$, and —OCH$_2$CH$_2$OH;

$Z^2$ is $CR^9$ or N, where $R^9$ is selected from H, —CH$_3$, —CH$_2$CH$_3$, and —CH$_2$CH$_2$OH; and $Y^1$ and $Y^2$ are independently selected from CH and N, where $Y^1$ and $Y^2$ are not each N.

Exemplary embodiments of Formula I compounds include compounds of Formulas Ia-If:

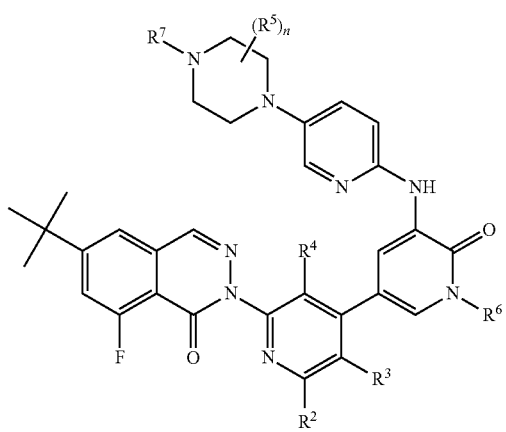

Ia

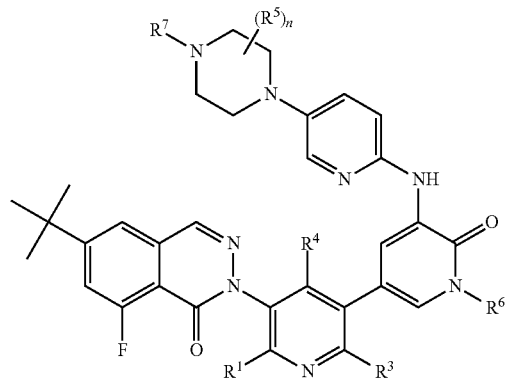

Ib

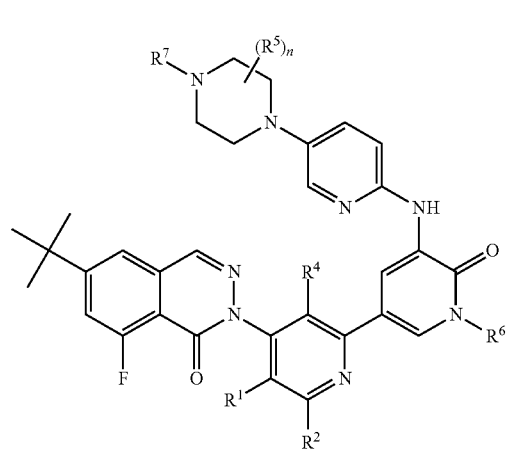

Ic

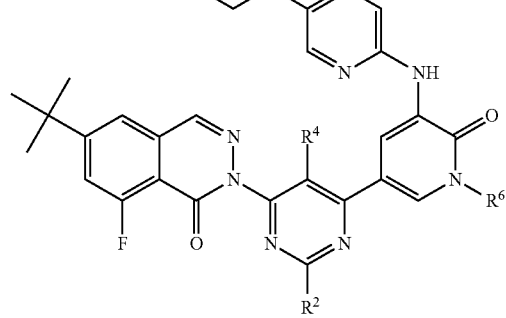

Id

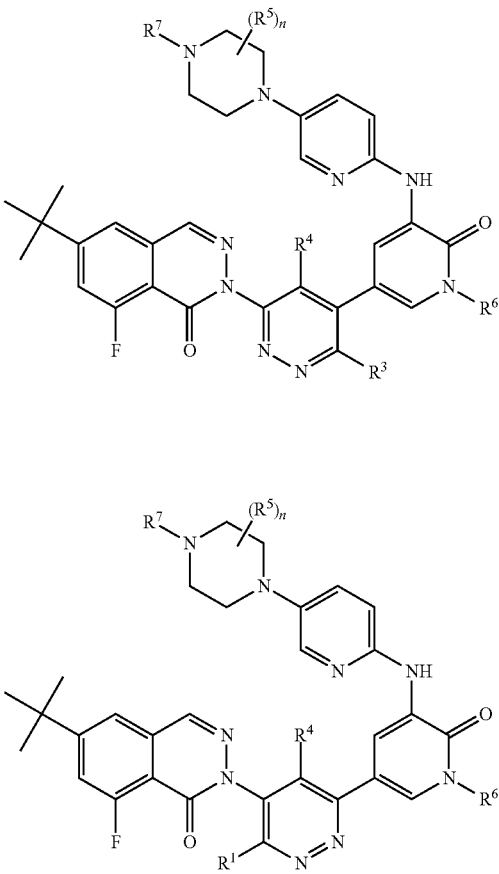

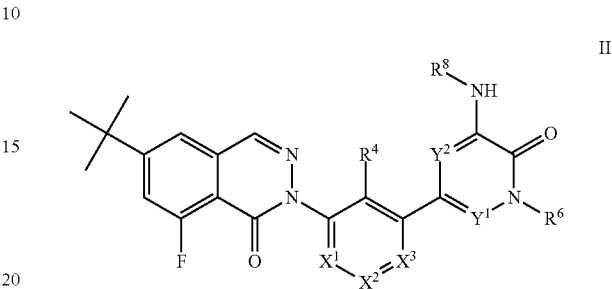

Exemplary embodiments of Formula I compounds include wherein $X^1$ is N, $X^2$ is $CR^2$, and $X^3$ is $CR^3$.

Exemplary embodiments of Formula I compounds include wherein $X^1$ is $CR^1$, $X^2$ is N, and $X^3$ is $CR^3$.

Exemplary embodiments of Formula I compounds include wherein $X^1$ is $CR^1$, $X^2$ is $CR^2$, and $X^3$ is N.

Exemplary embodiments of Formula I compounds include wherein: $X^1$ and $X^3$ are N, $X^1$ and $X^2$ are N, or $X^2$ and $X^3$ are N.

Exemplary embodiments of Formula I compounds include wherein $X^2$ is $CR^2$, and $R^2$ is F.

Exemplary embodiments of Formula I compounds include wherein $X^1$ and $X^3$ are CH.

Exemplary embodiments of Formula I compounds include wherein $R^4$ is —$CH_2OH$.

Exemplary embodiments of Formula I compounds include wherein $R^5$ is —$CH_3$, and n is 1 or 2.

Exemplary embodiments of Formula I compounds include wherein $R^7$ is oxetan-3-yl.

Exemplary embodiments of Formula I compounds include wherein $Y^1$ is CH.

Exemplary embodiments of Formula I compounds include wherein $Y^2$ is CH.

Exemplary embodiments of Formula I compounds include wherein $Y^1$ is N.

Exemplary embodiments of Formula I compounds include wherein $Y^2$ is N.

Exemplary embodiments of Formula I compounds include wherein $Z^1$ is CH.

Exemplary embodiments of Formula I compounds include wherein $Z^2$ is CH.

Exemplary embodiments of Formula I compounds include wherein $Z^1$ is N.

Exemplary embodiments of Formula I compounds include wherein $Z^2$ is N.

The present invention also provides 8-fluorophthalazin-1(2h)-one compounds of Formula II, which are potentially useful in the treatment of diseases, conditions and/or disorders modulated by Btk kinase:

or stereoisomers, tautomers, or pharmaceutically acceptable salts thereof, wherein:

$X^1$ is $CR^1$ or N;

$X^2$ is $CR^2$ or N;

$X^3$ is $CR^3$ or N;

where one or two of $X^1$, $X^2$, and $X^3$ are N;

$Y^1$ and $Y^2$ are independently selected from CH and N, where $Y^1$ and $Y^2$ are not each N;

$R^1$, $R^2$ and $R^3$ are independently selected from H, F, Cl, CN, —$CH_3$, —$CH_2CH_3$, —$CH_2OH$, —$CH_2F$, —$CHF_2$, —$CF_3$, —$CH_2CH_2OH$, —$NH_2$, —$NHCH_3$, —$N(CH_3)_2$, —OH, —$OCH_3$, —$OCH_2CH_3$, and —$OCH_2CH_2OH$;

$R^4$ is selected from H, F, Cl, CN, —$CH_2OH$, —$CH(CH_3)OH$, —$C(CH_3)_2OH$, —$CH(CF_3)OH$, —$CH_2F$, —$CHF_2$, —$CH_2CHF_2$, —$CF_3$, —$C(O)NH_2$, —$C(O)NHCH_3$, —$C(O)N(CH_3)_2$, —$NH_2$, —$NHCH_3$, —$N(CH_3)_2$, —$NHC(O)CH_3$, —OH, —$OCH_3$, —$OCH_2CH_3$, —$OCH_2CH_2OH$, —$OP(O)(OH)_2$, cyclopropyl, cyclopropylmethyl, 1-hydroxycyclopropyl, imidazolyl, pyrazolyl, 3-hydroxy-oxetan-3-yl, oxetan-3-yl, and azetidin-1-yl;

$R^6$ is selected from H, —$CH_3$, —$CH_2CH_3$, —$CH_2CH_2OH$, —$CH_2F$, —$CHF_2$, —$CF_3$, —$NH_2$, —$NHCH_3$, —$N(CH_3)_2$, —OH, —$OCH_3$, —$OCH_2CH_3$, and —$OCH_2CH_2OH$;

$R^8$ is selected from $C_6$-$C_{20}$ aryl, $C_3$-$C_{12}$ carbocyclyl, $C_2$-$C_{20}$ heterocyclyl, $C_1$-$C_{20}$ heteroaryl, —($C_6$-$C_{20}$ aryl)-($C_2$-$C_{20}$ heterocyclyl), —($C_1$-$C_{20}$ heteroaryl)-($C_2$-$C_{20}$ heterocyclyl), —($C_1$-$C_{20}$ heteroaryl)-($C_2$-$C_{20}$ heterocyclyl)-($C_2$-$C_{20}$ heterocyclyl), —($C_1$-$C_{20}$ heteroaryl)-($C_2$-$C_{20}$ heterocyclyl)-($C_1$-$C_6$ alkyl), —($C_1$-$C_{20}$ heteroaryl)-($C_1$-$C_6$ alkyl), and —($C_1$-$C_{20}$ heteroaryl)-C(=O)—($C_2$-$C_{20}$ heterocyclyl);

where aryl, carbocyclyl, heterocyclyl, and heteroaryl are optionally substituted with one or more groups selected from F, Cl, Br, I, CN, —$CH_3$, —$CH_2CH_3$, $CH(CH_3)_2$, —$CH_2CH(CH_3)_2$, —$CH_2OH$, —$CH_2OCH_3$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$C(CH_3)_2CONH_2$, —$CH_2OCH_3$, —$CH_2CH_2OH$, —$CH_2CH_2OCH_3$, —$CH_2F$, —$CHF_2$, —$CF_3$, —$CH_2CF_3$, —$CH_2CHF_2$, —$CH(CH_3)CN$, —$C(CH_3)_2CN$, —$CH_2CN$, $CO_2H$, —$CO_2CH_3$, —$CO_2C(CH_3)_3$, —$COCH(OH)CH_3$, —$C(O)CH_3$, —$C(O)CH_2CH_3$, —$C(O)CH(CH_3)_2$, —$C(O)NH_2$, —$C(O)NHCH_3$, —$C(O)N(CH_3)_2$, —$NH_2$, —$NHCH_3$, —$N(CH_3)_2$, —$NHC(O)CH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —$NO_2$, =O, —$OCH_2CH_2N(CH_3)_2$, —$OP(O)(OH)_2$, —OH, —$OCH_3$, —OCH$_2$CH$_3$, —OCH$_2$CH$_2$OCH$_3$, —OCH$_2$CH$_2$OH, —S(O)$_2$N(CH$_3$)$_2$, —SCH$_3$, —S(O)$_2$CH$_3$, —S(O)$_3$H, cyclopropyl, oxetanyl, azetidinyl, 1-methylazetidin-3-yl)oxy, N-methyl-N-oxetan-3-ylamino, azetidin-1-ylmethyl, and morpholino.

Exemplary embodiments of Formula II compounds include wherein R$^8$ is —(C$_1$-C$_{20}$ heteroaryl)-(C$_2$-C$_{20}$ heterocyclyl).

Exemplary embodiments of Formula II compounds include wherein R$^8$ is pyridinyl.

Exemplary embodiments of Formula II compounds include wherein R$^8$ is -(pyridinyl)-(piperazinyl).

Exemplary embodiments of Formula II compounds include wherein R$^8$ is C$_1$-C$_{20}$ heteroaryl.

Exemplary embodiments of Formula II compounds include wherein R$^8$ is selected from:
pyrimidinyl,
6,7-dihydro-4H-thiazolo[5,4-c]pyridin-2-yl,
5-(morpholine-4-carbonyl)-2-pyridyl,
pyrazolyl,
thiazolyl,
6,7-dihydro-4H-pyrazolo[1,5-a]pyrazin-2-yl,
oxazolyl,
isoxazolyl,
imidazolyl,
5-(6,7-dihydro-4H-pyrazolo[5,1-c][1,4]oxazin-2-yl,
1,2,3-triazolyl,
4,5,6,7-tetrahydropyrazolo[1,5-a]pyrazine,
pyrazinyl, and
5,6-dihydro-4H-pyrrolo[1,2-b]pyrazol-2-yl.

Exemplary embodiments of Formula II compounds include wherein R$^8$ is

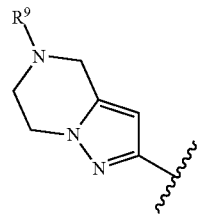

where R$^9$ is selected from H, —CH$_3$, —CH$_2$OCH$_3$, —CH$_2$CH$_3$, —CH(CH$_3$)$_2$, —CH$_2$CH$_2$OH, —CH$_2$CH$_2$OCH$_3$, —CH$_2$F, —CHF$_2$, —CF$_3$, —CH$_2$CF$_3$, —CH$_2$CHF$_2$, —CH(CH$_3$)CN, —C(CH$_3$)$_2$CN, —CH$_2$CN, —CH$_2$CH$_2$CN, —C(O)CH$_3$, —C(O)CH$_2$CH$_3$, —C(O)CH(CH$_3$)$_2$, —NH$_2$, —NHCH$_3$, —N(CH$_3$)$_2$, —OH, —OCH$_3$, —OCH$_2$CH$_3$, —OCH$_2$CH$_2$OH, cyclopropyl, cyclopropylmethyl, oxetanyl and oxetanylmethyl.

Exemplary embodiments of Formula II compounds include wherein X$^1$ is N, X$^2$ is CR$^2$, and X$^3$ is CR$^3$.

Exemplary embodiments of Formula II compounds include wherein X$^1$ is CR$^1$, X$^2$ is N, and X$^3$ is CR$^3$.

Exemplary embodiments of Formula II compounds include wherein X$^1$ is CR$^1$, X$^2$ is CR$^2$, and X$^3$ is N.

Exemplary embodiments of Formula II compounds include wherein X$^1$ and X$^3$ are N, X$^1$ and X$^2$ are N, or X$^2$ and X$^3$ are N.

Exemplary embodiments of Formula II compounds include wherein X$^2$ is CR$^2$, and R$^2$ is F.

Exemplary embodiments of Formula II compounds include wherein X$^1$ and X$^3$ are CH.

Exemplary embodiments of Formula II compounds include wherein R$^4$ is —CH$_2$OH.

The Formula I and II compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all diastereomers, including cis-trans (geometric) and conformational isomers. For example, if a Formula I compound incorporates a double bond or a fused ring, the cis- and trans-forms, as well as mixtures thereof, are embraced within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "IC$_{50}$". Determination of IC$_{50}$ values can be accomplished using conventional techniques known in the art. In general, an IC$_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the IC$_{50}$ value. Analogously, other inhibitory concentrations can be defined through appropriate determinations of activity. For example, in some settings it can be desirable to establish a 90% inhibitory concentration, i.e., IC$_{90}$, etc.

Formula I compounds were tested by a standard biochemical Btk Kinase Assay (Example 901).

A general procedure for a standard cellular Btk Kinase Assay that can be used to test Formula I compounds is a Ramos Cell Btk Assay (Example 902).

A standard cellular B-cell proliferation assay can be used to test Formula I compounds with B-cells purified from spleen of Balb/c mice (Example 903).

A standard T cell proliferation assay can be used to test Formula I compounds with T-cells purified from spleen of Balb/c mice (Example 904).

A CD86 Inhibition assay can be conducted on Formula I compounds for the inhibition of B cell activity using total mouse splenocytes purified from spleens of 8-16 week old Balb/c mice (Example 905).

A B-ALL Cell Survival Assay can be conducted on Formula I compounds to measure the number of viable B-ALL cells in culture (Example 906).

A CD69 Whole Blood Assay can be conducted on Formula I compounds to determine the ability of compounds to inhibit the production of CD69 by B lymphocytes in human whole blood activated by crosslinking surface IgM with goat F(ab')2 anti-human IgM (Example 907). CD69 is a type II C-type lectin involved in lymphocyte migration and cytokine secretion. CD69 expression represents one of the earliest available indicators of leukocyte activation and its rapid induction occurs through transcriptional activation (Vazquez et al (2009) Jour. of Immunology Published Oct. 19, 2009, doi: 10.4049/jimmunol.0900839). Concentration-dependent inhibition of antigen receptor stimulation by selective Btk inhibitors induces cell surface expression of the lymphocyte activation marker CD69 (Honigberg et al (2010) Proc. Natl. Acad. Sci. 107(29):13075-13080). Thus, CD69 inhibition by selective Btk inhibitors may be correlated with therapeutic efficacy of certain B-cell disorders. The CD69 Hu Blood FACS IC70 values are displayed for exemplary Formula I compounds in Tables 1 and 2.

The cytotoxic or cytostatic activity of Formula I exemplary compounds can be measured by: establishing a proliferating mammalian tumor cell line in a cell culture medium, adding a Formula I compound, culturing the cells for a period from about 6 hours to about 5 days; and measuring cell viability (Example 908). Cell-based in vitro assays are used to measure viability, i.e. proliferation ($IC_{50}$), cytotoxicity ($EC_{50}$), and induction of apoptosis (caspase activation) and may be useful in predicting clinical efficacy against hematological malignancies and solid tumors.

The in vitro potency of the combinations of Formula I compounds with chemotherapeutic agents can be measured by the cell proliferation assay of Example 908; the CellTiter-Glo® Luminescent Cell Viability Assay, commercially available from Promega Corp., Madison, Wis. This homogeneous assay method is based on the recombinant expression of Coleoptera luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602, 677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

The anti-proliferative efficacy of Formula I exemplary compounds and combinations with chemotherapeutic agents are measured by the CellTiter-Glo® Assay (Example 908) against certain hematological tumor cell lines. $EC_{50}$ values are established for the tested compounds and combinations.

Exemplary Formula I compounds in Tables 1 and 2 were made, characterized, and tested for inhibition of Btk according to the methods of this invention, and have the following structures and corresponding names (ChemDraw Ultra, Version 9.0.1, and ChemBioDraw, Version 11.0, CambridgeSoft Corp., Cambridge Mass.). Where more than one name is associated with a Formula I compound or intermediate, the chemical structure shall define the compound.

TABLE 1

| No. | Structure | IUPAC_Name | Mol Weight | CD69 Hu Blood FACS IC70 |
|---|---|---|---|---|
| 101 | 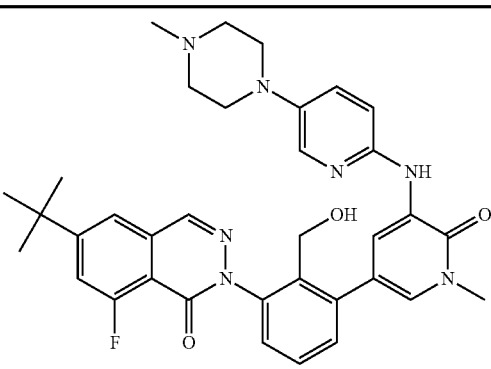 | 6-tert-butyl-8-fluoro-2-(2-(hydroxymethyl)-3-(1-methyl-5-(5-(4-methyl piperazin-1-yl)pyridin-2-yl-amino)-6-oxo-1,6-dihydropyridin-3-yl)phenyl)phthalazin-1(2H)-one | 623.30 | 0.024 |

TABLE 1-continued

| No. | Structure | IUPAC_Name | Mol Weight | CD69 Hu Blood FACS IC70 |
|---|---|---|---|---|
| 102 | 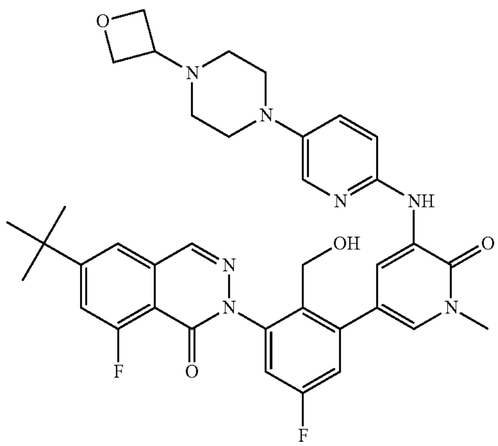 [SMILES: Cn1cc(-c2cc(F)cc(-n3ncc4cc(C(C)(C)C)cc(F)c4c3=O)c2CO)cc(Nc2ccc(N3CCN(C4COC4)CC3)cn2)c1=O] | 6-tert-butyl-8-fluoro-2-(5-fluoro-2-(hydroxymethyl)-3-(1-methyl-5-(5-(4-(oxetan-3-yl)piperazin-1-yl)pyridin-2-ylamino)-6-oxo-1,6-dihydropyridin-3-yl)phenyl)phthalazin-1(2H)-one | 684 | 0.012 |
| 103 | 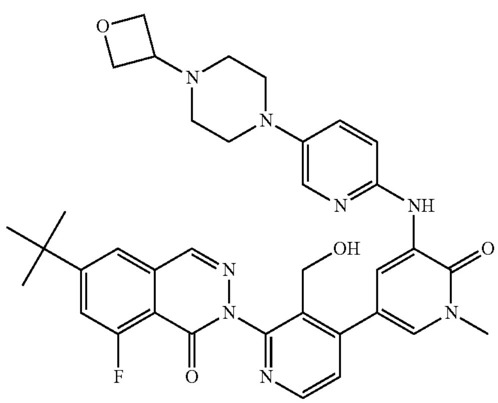 [SMILES: Cn1cc(-c2ccnc(-n3ncc4cc(C(C)(C)C)cc(F)c4c3=O)c2CO)cc(Nc2ccc(N3CCN(C4COC4)CC3)cn2)c1=O] | 6-tert-butyl-8-fluoro-2-(3-(hydroxymethyl)-4-(1-methyl-5-(5-(4-(oxetan-3-yl)piperazin-1-yl)pyridin-2-ylamino)-6-oxo-1,6dihydropyridin-3-yl)pyridin-2-yl)phthalazin-1(2H)-one | 667 | 0.013 |
| 104 | 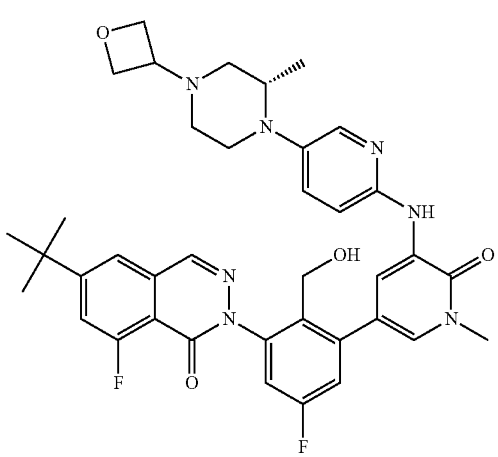 [SMILES: C[C@H]1CN(C2COC2)CCN1c1ccc(Nc2cc(-c3cc(F)cc(-n4ncc5cc(C(C)(C)C)cc(F)c5c4=O)c3CO)cn(C)c2=O)nc1] | (S)-6-tert-butyl-8-fluoro-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)phthalazin-1(2H)-one | 697.32 | 0.0329 |

TABLE 1-continued

| No. | Structure | IUPAC_Name | Mol Weight | CD69 Hu Blood FACS IC70 |
|---|---|---|---|---|
| 105 | 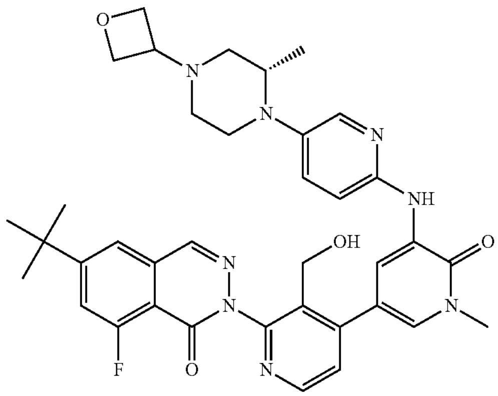 [SMILES: C[C@H]1CN(C2COC2)CCN1c1ccc(Nc2cc(-c3ccnc(-n4ncc5cc(C(C)(C)C)cc(F)c5c4=O)c3CO)cn(C)c2=O)nc1] | (S)-6-tert-butyl-8-fluoro-2-(3-(hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)phthalazin-1(2H)one | 680.32 | 0.0060 |
| 106 | 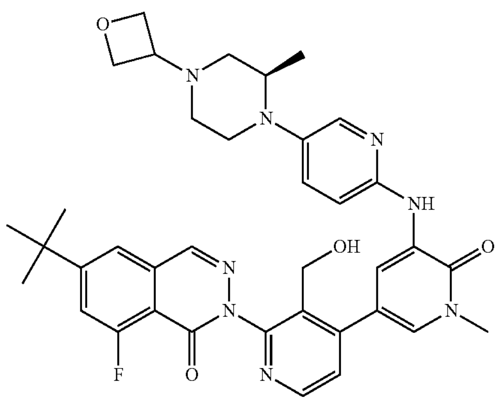 [SMILES: C[C@@H]1CN(C2COC2)CCN1c1ccc(Nc2cc(-c3ccnc(-n4ncc5cc(C(C)(C)C)cc(F)c5c4=O)c3CO)cn(C)c2=O)nc1] | (R)-6-tert-butyl-8-fluoro-2-(3-(hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)phthalazin-1(2H)-one | 680.32 | |
| 107 | 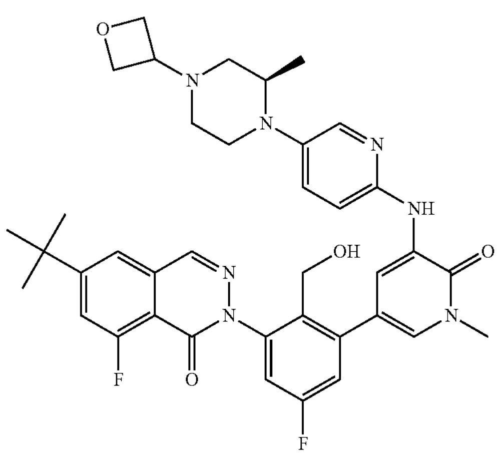 [SMILES: C[C@@H]1CN(C2COC2)CCN1c1ccc(Nc2cc(-c3cc(F)cc(-n4ncc5cc(C(C)(C)C)cc(F)c5c4=O)c3CO)cn(C)c2=O)nc1] | (R)-6-tert-butyl-8-fluoro-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)phthalazin-1(2H)-one | 697.32 | 0.0263 |

TABLE 1-continued

| No. | Structure | IUPAC_Name | Mol Weight | CD69 Hu Blood FACS IC70 |
|---|---|---|---|---|
| 108 | 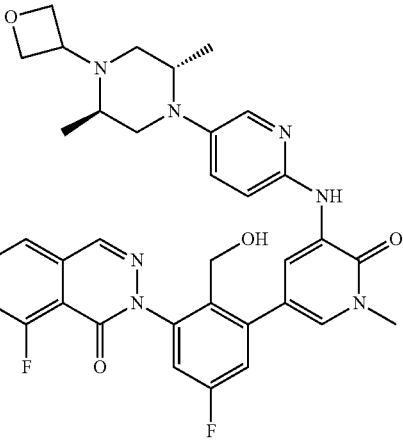 | 6-tert-butyl-2-(3-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-8-fluorophthalazin-1(2H)-one | 711.33 | |
| 109 | 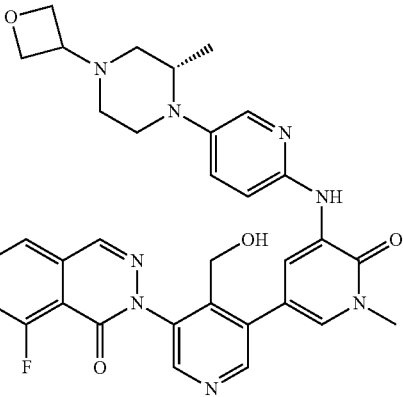 | (S)-6-tert-butyl-8-fluoro-2-(4-(hydroxymethyl)-5-(1-methyl-5-(5-(2-methyl-4-(oxetan-3-yl)piperazin-1-yl)pyridin-2-ylamino)-6-oxo-1,6-dihydropyridin-3-yl)pyridin-3-yl)phthalazin-1(2H)-one | 680.32 | 0.012 |
| 110 | 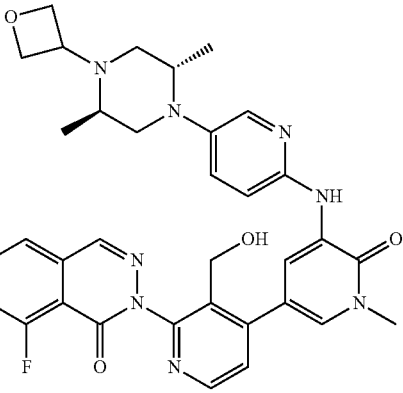 | 6-tert-butyl-2-(4-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-8-fluorophthalazin-1(2H)-one | 694.34 | 0.0059 |

TABLE 1-continued

| No. | Structure | IUPAC_Name | Mol Weight | CD69 Hu Blood FACS IC70 |
|---|---|---|---|---|
| 111 | 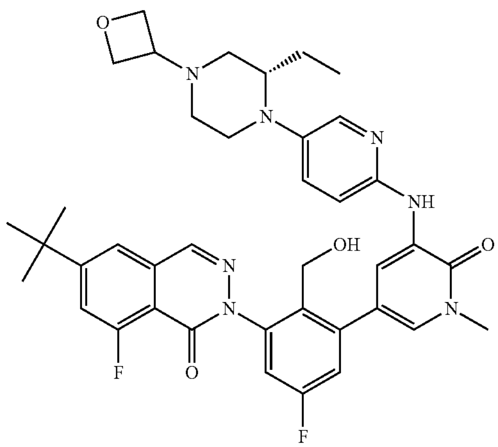 [SMILES: CC[C@H]1CN(C2COC2)CCN1c1ccc(Nc2cc(-c3cc(F)cc(-n4ncc5cc(C(C)(C)C)cc(F)c5c4=O)c3CO)cn(C)c2=O)nc1] | (S)-6-tert-butyl-2-(3-(5-(5-(2-ethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-8-fluorophthalazin-1(2H)-one | 711.33 | 0.0374 |
| 112 | 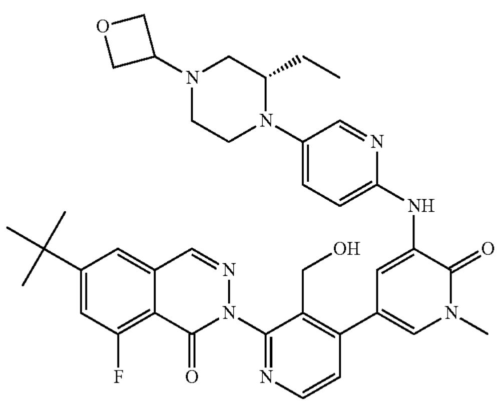 [SMILES: CC[C@H]1CN(C2COC2)CCN1c1ccc(Nc2cc(-c3ccnc(-n4ncc5cc(C(C)(C)C)cc(F)c5c4=O)c3CO)cn(C)c2=O)nc1] | (S)-6-tert-butyl-2-(4-(5-(5-(2-ethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-8-fluorophthalazin-1(2H)-one | 694.34 | 0.0329 |

TABLE 2

| No. | Structure | IUPAC_Name | CD69 Hu Blood FACS (IC70) |
|---|---|---|---|
| 113 | 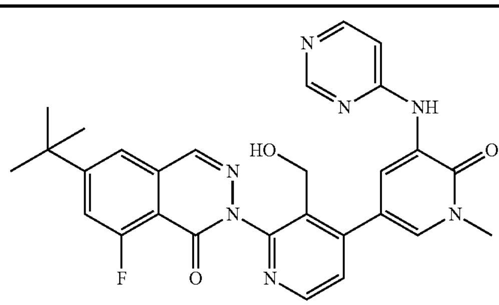 | 6-tert-butyl-8-fluoro-2-[3-(hydroxymethyl)-4-[1-methyl-6-oxo-5-(pyrimidin-4-ylamino)-3-pyridyl]-2-pyridyl]phthalazin-1-one | 0.0823 |

TABLE 2-continued

| No. | Structure | IUPAC_Name | CD69 Hu Blood FACS (IC70) |
|---|---|---|---|
| 114 | 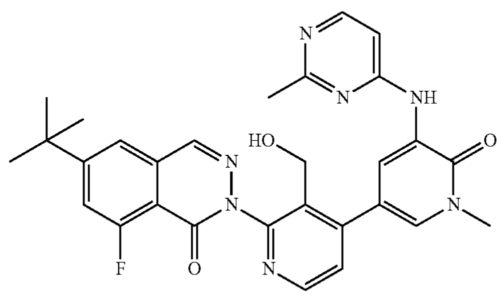 [SMILES: Cc1nccc(Nc2cc(-c3ccnc(-n4ncc5cc(C(C)(C)C)cc(F)c5c4=O)c3CO)cn(C)c2=O)n1] | 6-tert-butyl-8-fluoro-2-[3-(hydroxymethyl)-4-[1-methyl-5-[(2-methylpyrimidin-4-yl)amino]-6-oxo-3-pyridyl]-2-pyridyl]phthalazin-1-one | 0.114 |
| 115 | 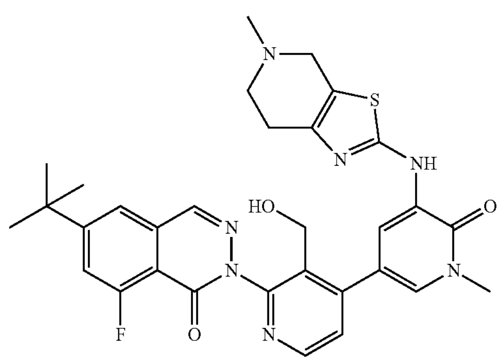 [SMILES: CN1CCc2nc(Nc3cc(-c4ccnc(-n5ncc6cc(C(C)(C)C)cc(F)c6c5=O)c4CO)cn(C)c3=O)sc2C1] | 6-tert-butyl-8-fluoro-2-[3-(hydroxymethyl)-4-[1-methyl-5-[(5-methyl-6,7-dihydro-4H-thiazolo[5,4-c]pyridin-2-yl)amino]-6-oxo-3-pyridyl]-2-pyridyl]phthalazin-1-one | 0.0732 |
| 116 | 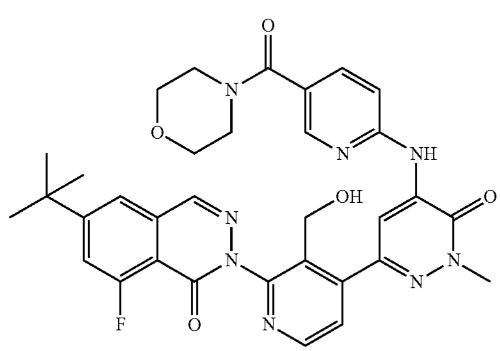 [SMILES: Cn1nc(-c2ccnc(-n3ncc4cc(C(C)(C)C)cc(F)c4c3=O)c2CO)cc(Nc2ccc(C(=O)N3CCOCC3)cn2)c1=O] | 6-tert-butyl-8-fluoro-2-[3-(hydroxymethyl)-4-[1-methyl-5-[[5-(morpholine-4-carbonyl)-2-pyridyl]amino]-6-oxo-pyridazin-3-yl]-2-pyridyl]phthalazin-1-one | 0.0935 |
| 117 | 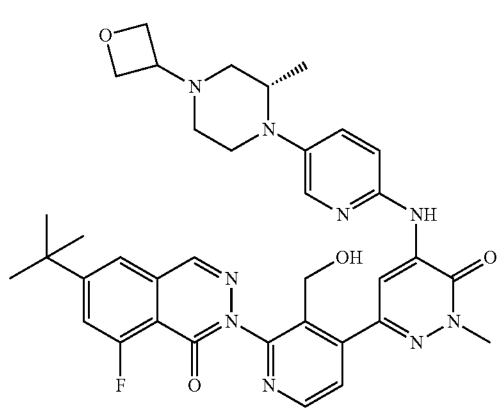 | 6-tert-butyl-8-fluoro-2-[3-(hydroxymethyl)-4-[1-methyl-5-[[5-[(2S)-2-methyl-4-(oxetan-3-yl)piperazin-1-yl]-2-pyridyl]amino]-6-oxo-pyridazin-3-yl]-2-pyridyl]phthalazin-1-one | 0.0165 |

TABLE 2-continued

| No. | Structure | IUPAC_Name | CD69 Hu Blood FACS (IC70) |
|---|---|---|---|
| 118 | 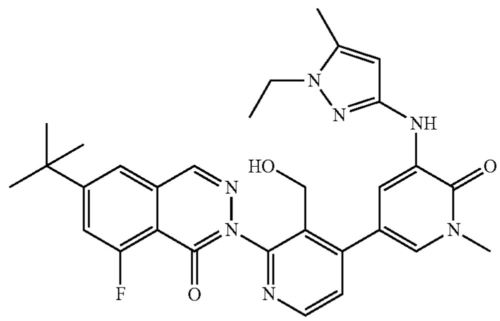 | 6-tert-butyl-2-[4-[5-[(1-ethyl-5-methyl-pyrazol-3-yl)amino]-1-methyl-6-oxo-3-pyridyl]-3-(hydroxymethyl)-2-pyridyl]-8-fluoro-phthalazin-1-one | 0.112 |
| 119 | 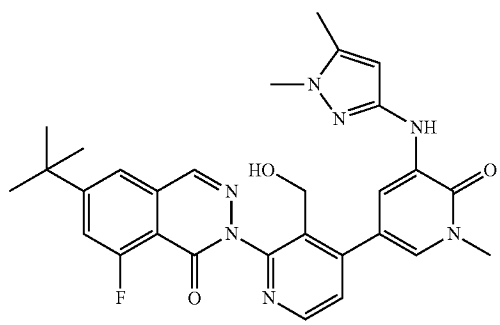 [SMILES: Cc1cc(Nc2cc(-c3ccnc(-n4ncc5cc(C(C)(C)C)cc(F)c5c4=O)c3CO)cn(C)c2=O)nn1C] | 6-tert-butyl-2-[4-[5-[(1,5-dimethylpyrazol-3-yl)amino]-1-methyl-6-oxo-3-pyridyl]-3-(hydroxymethyl)-2-pyridyl]-8-fluoro-phthalazin-1-one | 0.0247 |
| 120 | 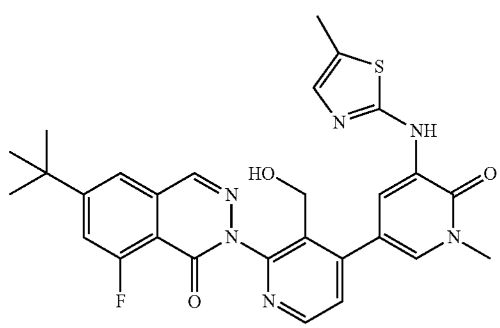 [SMILES: Cc1cnc(Nc2cc(-c3ccnc(-n4ncc5cc(C(C)(C)C)cc(F)c5c4=O)c3CO)cn(C)c2=O)s1] | 6-tert-butyl-8-fluoro-2-[3-(hydroxymethyl)-4-[1-methyl-5-[(5-methylthiazol-2-yl)amino]-6-oxo-3-pyridyl]-2-pyridyl]phthalazin-1-one | 0.139 |
| 121 | 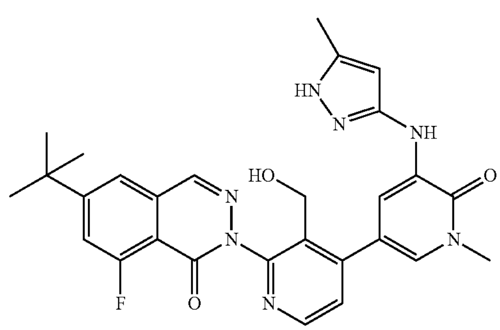 | 6-tert-butyl-8-fluoro-2-[3-(hydroxymethyl)-4-[1-methyl-5-[(5-methyl-1H-pyrazol-3-yl)amino]-6-oxo-3-pyridyl]-2-pyridyl]phthalazin-1-one | 0.0793 |

TABLE 2-continued

| No. | Structure | IUPAC_Name | CD69 Hu Blood FACS (IC70) |
|---|---|---|---|
| 122 | 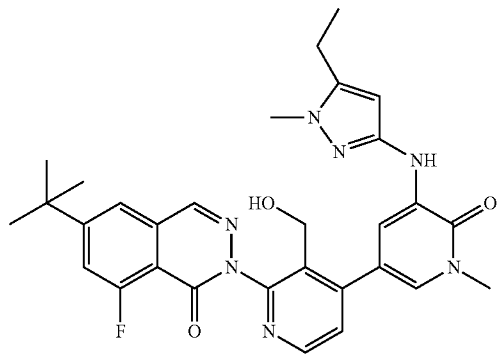 [SMILES: CCc1cc(Nc2cc(-c3ccnc(-n4ncc5cc(C(C)(C)C)cc(F)c5c4=O)c3CO)cn(C)c2=O)nn1C] | 6-tert-butyl-2-[4-[5-[(5-ethyl-1-methyl-pyrazol-3-yl)amino]-1-methyl-6-oxo-3-pyridyl]-3-(hydroxymethyl)-2-pyridyl]-8-fluoro-phthalazin-1-one | 0.0375 |
| 123 | 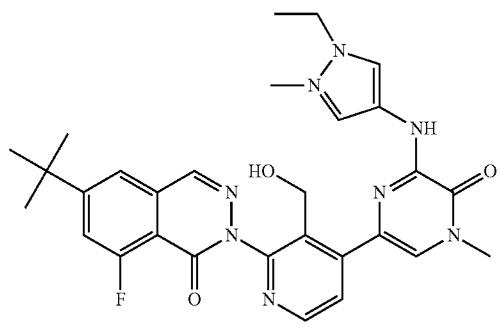 | 6-tert-butyl-2-[4-[6-[(1-ethylpyrazol-4-yl)amino]-4-methyl-5-oxo-pyrazin-2-yl]-3-(hydroxymethyl)-2-pyridyl]-8-fluoro-phthalazin-1-one | 0.156 |
| 124 | 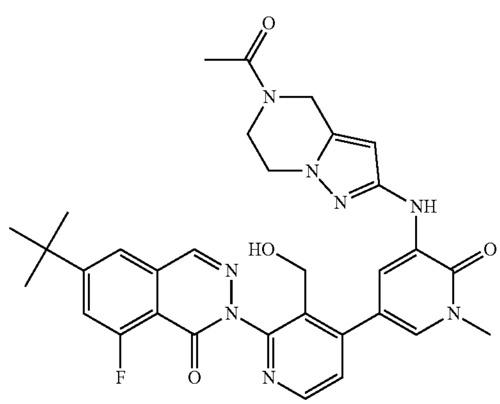 [SMILES: CC(=O)N1CCn2nc(Nc3cc(-c4ccnc(-n5ncc6cc(C(C)(C)C)cc(F)c6c5=O)c4CO)cn(C)c3=O)cc2C1] | 2-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-6-tert-butyl-8-fluoro-phthalazin-1-one | 0.0415 |
| 125 | 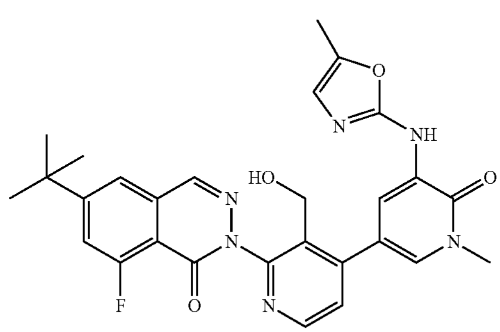 [SMILES: Cc1cnc(Nc2cc(-c3ccnc(-n4ncc5cc(C(C)(C)C)cc(F)c5c4=O)c3CO)cn(C)c2=O)o1] | 6-tert-butyl-8-fluoro-2-[3-(hydroxymethyl)-4-[1-methyl-5-[(5-methyloxazol-2-yl)amino]-6-oxo-3-pyridyl]-2-pyridyl]phthalazin-1-one | 0.521 |

TABLE 2-continued

| No. | Structure | IUPAC_Name | CD69 Hu Blood FACS (IC70) |
|---|---|---|---|
| 126 | 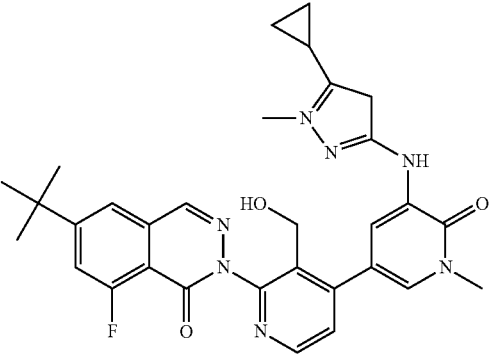 | 6-tert-butyl-2-[4-[5-[(5-cyclopropyl-1-methyl-pyrazol-3-yl)amino]-1-methyl-6-oxo-3-pyridyl]-3-(hydroxymethyl)-2-pyridyl]-8-fluoro-phthalazin-1-one | 0.0445 |
| 127 | 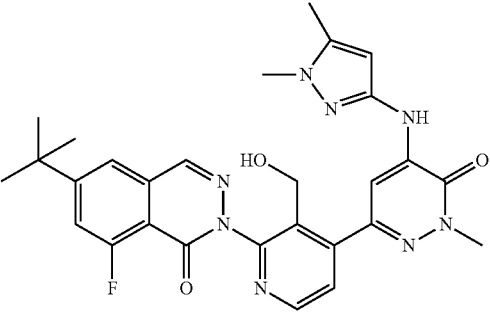 | 6-tert-butyl-2-[4-[5-[(1,5-dimethylpyrazol-3-yl)amino]-1-methyl-6-oxo-pyridazin-3-yl]-3-(hydroxymethyl)-2-pyridyl]-8-fluoro-phthalazin-1-one | 0.115 |
| 128 | 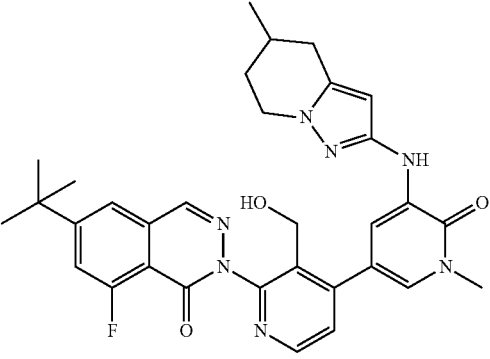 [SMILES: CC1CCn2nc(Nc3cc(-c4ccnc(-n5ncc6cc(C(C)(C)C)cc(F)c6c5=O)c4CO)cn(C)c3=O)cc2C1] | 6-tert-butyl-8-fluoro-2-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]phthalazin-1-one | 0.0272 |
| 129 | 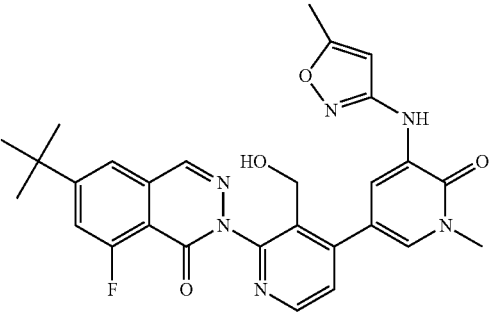 [SMILES: Cc1cc(Nc2cc(-c3ccnc(-n4ncc5cc(C(C)(C)C)cc(F)c5c4=O)c3CO)cn(C)c2=O)no1] | 6-tert-butyl-8-fluoro-2-[3-(hydroxymethyl)-4-[1-methyl-5-[(5-methylisoxazol-3-yl)amino]-6-oxo-3-pyridyl]-2-pyridyl]phthalazin-1-one | 0.0488 |

TABLE 2-continued

| No. | Structure | IUPAC_Name | CD69 Hu Blood FACS (IC70) |
|---|---|---|---|
| 130 | 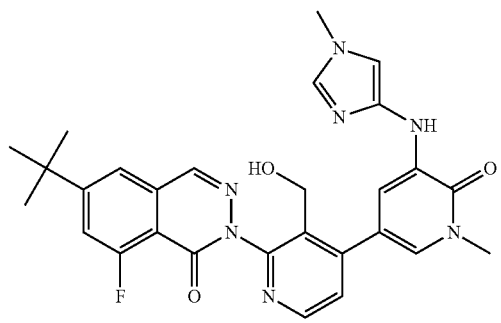 [SMILES: Cn1cnc(Nc2cc(-c3ccnc(-n4ncc5cc(C(C)(C)C)cc(F)c5c4=O)c3CO)cn(C)c2=O)c1] | 6-tert-butyl-8-fluoro-2-[3-(hydroxymethyl)-4-[1-methyl-5-[(1-methylimidazol-4-yl)amino]-6-oxo-3-pyridyl]-2-pyridyl]phthalazin-1-one | 0.152 |
| 131 | 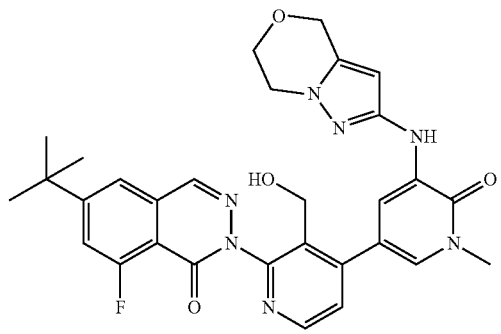 [SMILES: Cn1cc(-c2ccnc(-n3ncc4cc(C(C)(C)C)cc(F)c4c3=O)c2CO)cc(Nc2cc3n(n2)CCOC3)c1=O] | 6-tert-butyl-2-[4-[5-(6,7-dihydro-4H-pyrazolo[5,1-c][1,4]oxazin-2-ylamino)-1-methyl-6-oxo-3-pyridyl]-3-(hydroxymethyl)-2-pyridyl]-8-fluoro-phthalazin-1-one | 0.0171 |
| 132 | 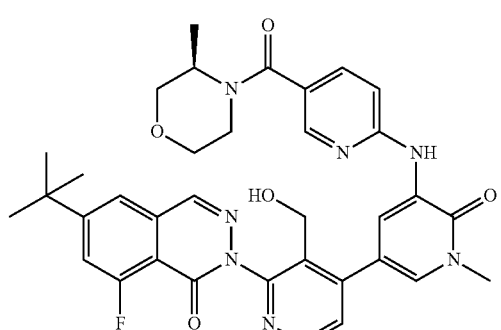 | 6-tert-butyl-8-fluoro-2-[3-(hydroxymethyl)-4-[1-methyl-5-[[5-[(3R)-3-methylmorpholine-4-carbonyl]-2-pyridyl]amino]-6-oxo-3-pyridyl]-2-pyridyl]phthalazin-1-one | 0.014 |
| 133 | 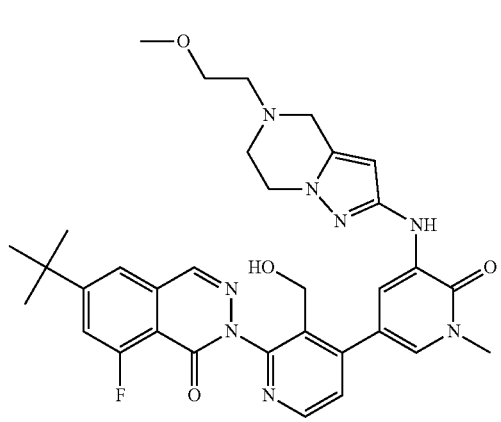 [SMILES: COCCN1CCn2nc(Nc3cc(-c4ccnc(-n5ncc6cc(C(C)(C)C)cc(F)c6c5=O)c4CO)cn(C)c3=O)cc2C1] | 6-tert-butyl-8-fluoro-2-[3-(hydroxymethyl)-4-[5-[[5-(2-methoxyethyl)-6,7-dihydro-4H-pyrazolo[1,5-a]pyrazin-2-yl]amino]-1-methyl-6-oxo-3-pyridyl]-2-pyridyl]phthalazin-1-one | 0.0145 |

TABLE 2-continued

| No. | Structure | IUPAC_Name | CD69 Hu Blood FACS (IC70) |
|---|---|---|---|
| 134 | 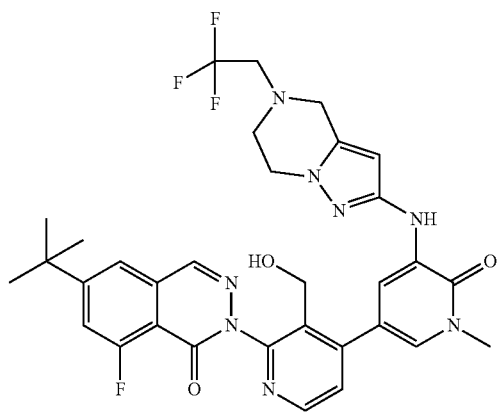 [SMILES: Cn1cc(-c2ccnc(-n3ncc4cc(C(C)(C)C)cc(F)c4c3=O)c2CO)cc(Nc2cc3n(n2)CCN(CC(F)(F)F)C3)c1=O] | 6-tert-butyl-8-fluoro-2-[3-(hydroxymethyl)-4-[1-methyl-6-oxo-5-[[5-(2,2,2-trifluoroethyl)-6,7-dihydro-4H-pyrazolo[1,5-a]pyrazin-2-yl]amino]-3-pyridyl]-2-pyridyl]phthalazin-1-one | 0.0216 |
| 135 | 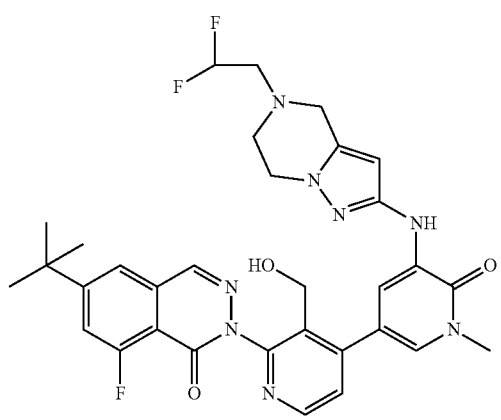 [SMILES: Cn1cc(-c2ccnc(-n3ncc4cc(C(C)(C)C)cc(F)c4c3=O)c2CO)cc(Nc2cc3n(n2)CCN(CC(F)F)C3)c1=O] | 6-tert-butyl-2-[4-[5-[[5-(2,2-difluoroethyl)-6,7-dihydro-4H-pyrazolo[1,5-a]pyrazin-2-yl]amino]-1-methyl-6-oxo-3-pyridyl]-3-(hydroxymethyl)-2-pyridyl]-8-fluoro-phthalazin-1-one | 0.02 |
| 136 | 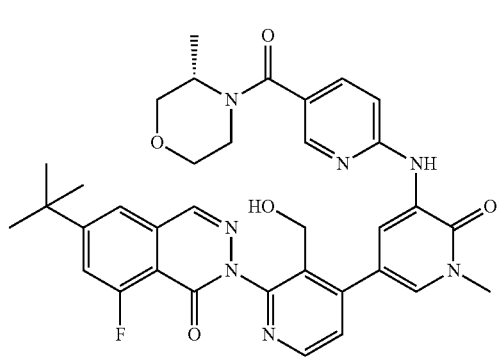 [SMILES: C[C@H]1COCCN1C(=O)c1ccc(Nc2cc(-c3ccnc(-n4ncc5cc(C(C)(C)C)cc(F)c5c4=O)c3CO)cn(C)c2=O)nc1] | 6-tert-butyl-8-fluoro-2-[3-(hydroxymethyl)-4-[1-methyl-5-[[5-[(3S)-3-methylmorpholine-4-carbonyl]-2-pyridyl]amino]-6-oxo-3-pyridyl]-2-pyridyl]phthalazin-1-one | 0.0145 |

TABLE 2-continued

| No. | Structure | IUPAC_Name | CD69 Hu Blood FACS (IC70) |
|---|---|---|---|
| 137 | | | |
| 138 | 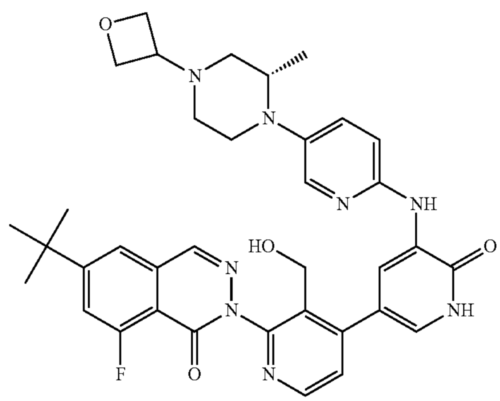 [SMILES: C[C@H]1CN(C2COC2)CCN1c1ccc(Nc2cc(-c3ccnc(-n4ncc5cc(C(C)(C)C)cc(F)c5c4=O)c3CO)c[nH]c2=O)nc1] | 6-tert-butyl-8-fluoro-2-[3-(hydroxymethyl)-4-[5-[[5-[(2S)-2-methyl-4-(oxetan-3-yl)piperazin-1-yl]-2-pyridyl]amino]-6-oxo-1H-pyridin-3-yl]-2-pyridyl]phthalazin-1-one | 0.0124 |
| 139 | 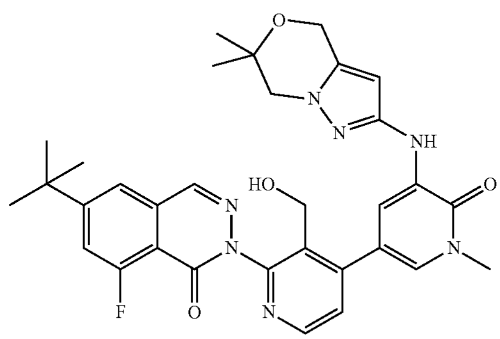 [SMILES: Cn1cc(-c2ccnc(-n3ncc4cc(C(C)(C)C)cc(F)c4c3=O)c2CO)cc(Nc2cc3n(n2)CC(C)(C)OC3)c1=O] | 6-tert-butyl-2-[4-[5-[(6,6-dimethyl-4,7-dihydropyrazolo[5,1-c][1,4]oxazin-2-yl)amino]-1-methyl-6-oxo-3-pyridyl]-3-(hydroxymethyl)-2-pyridyl]-8-fluoro-phthalazin-1-one | 0.0616 |
| 140 | 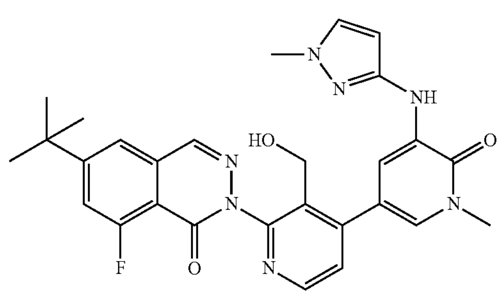 [SMILES: Cn1ccc(Nc2cc(-c3ccnc(-n4ncc5cc(C(C)(C)C)cc(F)c5c4=O)c3CO)cn(C)c2=O)n1] | 6-tert-butyl-8-fluoro-2-[3-(hydroxymethyl)-4-[1-methyl-5-[(1-methylpyrazol-3-yl)amino]-6-oxo-3-pyridyl]-2-pyridyl]phthalazin-1-one | 0.068 |
| 141 | 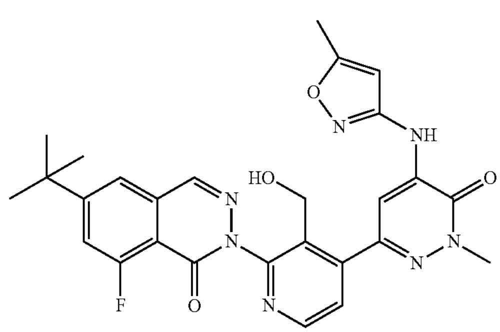 [SMILES: Cc1cc(Nc2cc(-c3ccnc(-n4ncc5cc(C(C)(C)C)cc(F)c5c4=O)c3CO)nn(C)c2=O)no1] | 6-tert-butyl-8-fluoro-2-[3-(hydroxymethyl)-4-[1-methyl-5-[(5-methylisoxazol-3-yl)amino]-6-oxo-pyridazin-3-yl]-2-pyridyl]phthalazin-1-one | 0.295 |

TABLE 2-continued

| No. | Structure | IUPAC_Name | CD69 Hu Blood FACS (IC70) |
|---|---|---|---|
| 142 | 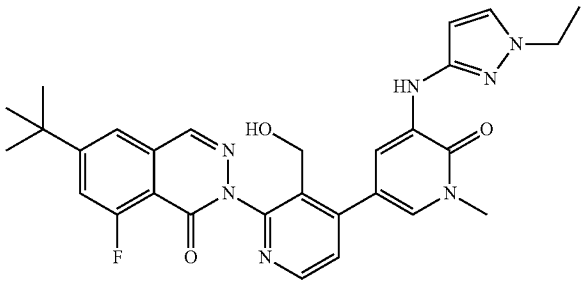 [SMILES: CCn1ccc(Nc2cc(-c3ccnc(-n4ncc5cc(C(C)(C)C)cc(F)c5c4=O)c3CO)cn(C)c2=O)n1] | 6-tert-butyl-2-[4-[5-[(1-ethylpyrazol-3-yl)amino]-1-methyl-6-oxo-3-pyridyl]-3-(hydroxymethyl)-2-pyridyl]-8-fluoro-phthalazin-1-one | 0.168 |
| 143 | 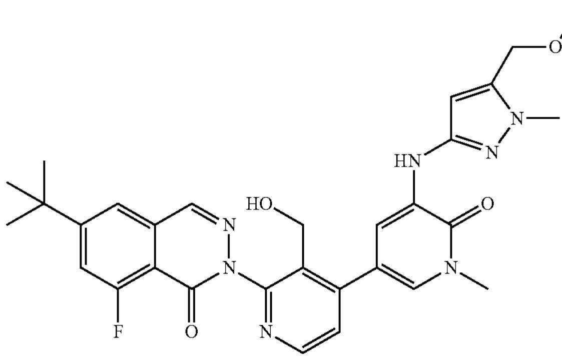 | 6-tert-butyl-8-fluoro-2-[3-(hydroxymethyl)-4-[5-[[5-(methoxymethyl)-1-methyl-pyrazol-3-yl]amino]-1-methyl-6-oxo-3-pyridyl]-2-pyridyl]phthalazin-1-one | 0.0131 |
| 144 | 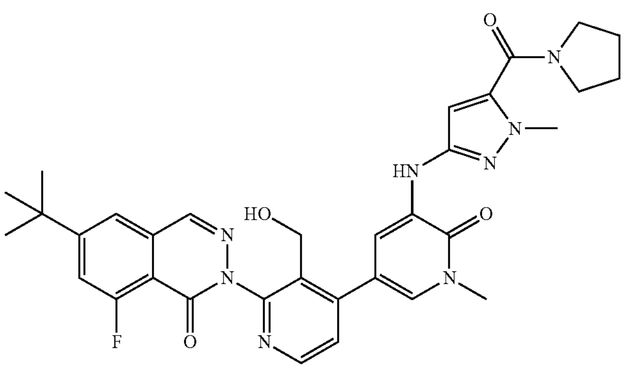 [SMILES: Cn1nc(Nc2cc(-c3ccnc(-n4ncc5cc(C(C)(C)C)cc(F)c5c4=O)c3CO)cn(C)c2=O)cc1C(=O)N1CCCC1] | 6-tert-butyl-8-fluoro-2-[3-(hydroxymethyl)-4-[1-methyl-5-[[1-methyl-5-(pyrrolidine-1-carbonyl)pyrazol-3-yl]amino]-6-oxo-3-pyridyl]-2-pyridyl]phthalazin-1-one | 0.0203 |
| 145 | 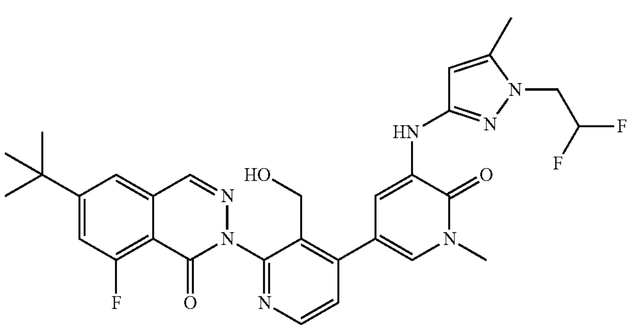 [SMILES: Cc1cc(Nc2cc(-c3ccnc(-n4ncc5cc(C(C)(C)C)cc(F)c5c4=O)c3CO)cn(C)c2=O)nn1CC(F)F] | 6-tert-butyl-2-[4-[5-[[1-(2,2-difluoroethyl)-5-methyl-pyrazol-3-yl]amino]-1-methyl-6-oxo-3-pyridyl]-3-(hydroxymethyl)-2-pyridyl]-8-fluoro-phthalazin-1-one | 0.163 |

TABLE 2-continued

| No. | Structure | IUPAC_Name | CD69 Hu Blood FACS (IC70) |
|---|---|---|---|
| 146 | 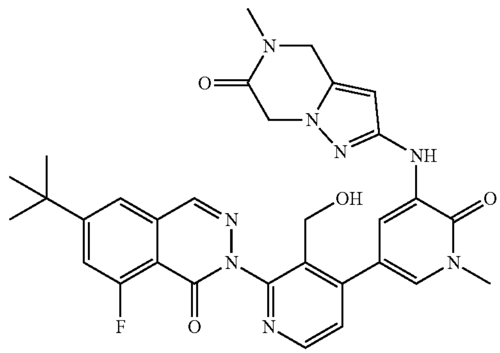 [SMILES: CN1Cc2cc(Nc3cc(-c4ccnc(-n5ncc6cc(C(C)(C)C)cc(F)c6c5=O)c4CO)cn(C)c3=O)nn2CC1=O] | 6-tert-butyl-8-fluoro-2-[3-(hydroxymethyl)-4-[1-methyl-5-[(5-methyl-6-oxo-4,7-dihydropyrazolo[1,5-a]pyrazin-2-yl)amino]-6-oxo-3-pyridyl]-2-pyridyl]phthalazin-1-one | 0.0209 |
| 147 | 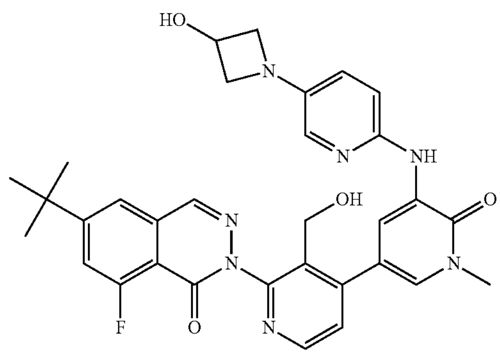 [SMILES: Cn1cc(-c2ccnc(-n3ncc4cc(C(C)(C)C)cc(F)c4c3=O)c2CO)cc(Nc2ccc(N3CC(O)C3)cn2)c1=O] | 6-tert-butyl-8-fluoro-2-[4-[5-[[5-(3-hydroxyazetidin-1-yl)-2-pyridyl]amino]-1-methyl-6-oxo-3-pyridyl]-3-(hydroxymethyl)-2-pyridyl]phthalazin-1-one | 0.0333 |
| 148 | 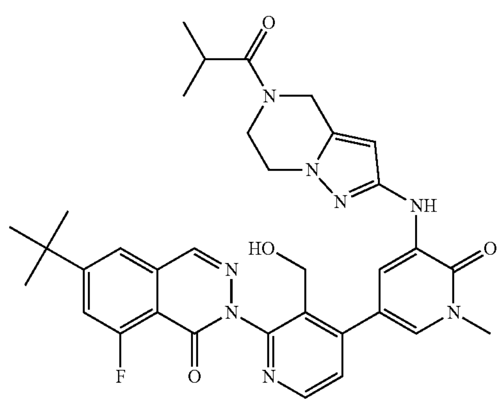 [SMILES: CC(C)C(=O)N1CCn2nc(Nc3cc(-c4ccnc(-n5ncc6cc(C(C)(C)C)cc(F)c6c5=O)c4CO)cn(C)c3=O)cc2C1] | 6-tert-butyl-8-fluoro-2-[3-(hydroxymethyl)-4-[1-methyl-5-[[5-(2-methylpropanoyl)-6,7-dihydro-4H-pyrazolo[1,5-a]pyrazin-2-yl]amino]-6-oxo-3-pyridyl]-2-pyridyl]phthalazin-1-one | 0.0139 |
| 149 | 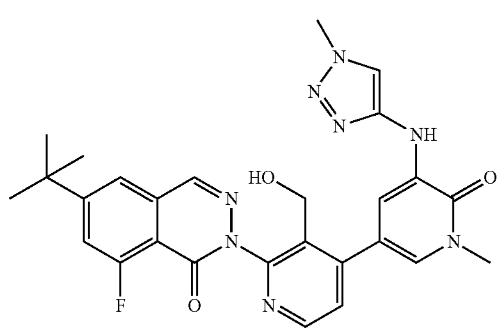 [SMILES: Cn1cc(Nc2cc(-c3ccnc(-n4ncc5cc(C(C)(C)C)cc(F)c5c4=O)c3CO)cn(C)c2=O)nn1] | 6-tert-butyl-8-fluoro-2-[3-(hydroxymethyl)-4-[1-methyl-5-[(1-methyltriazol-4-yl)amino]-6-oxo-3-pyridyl]-2-pyridyl]phthalazin-1-one | 0.093 |

TABLE 2-continued

| No. | Structure | IUPAC_Name | CD69 Hu Blood FACS (IC70) |
|---|---|---|---|
| 150 | 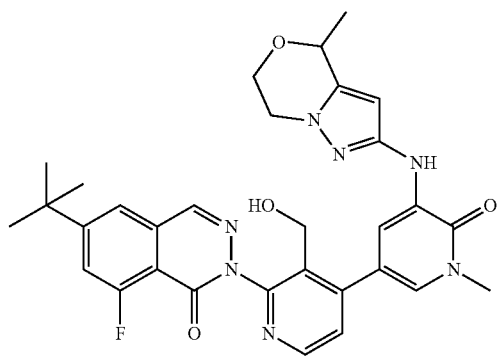 [SMILES: CC1OCCn2nc(Nc3cc(-c4ccnc(-n5ncc6cc(C(C)(C)C)cc(F)c6c5=O)c4CO)cn(C)c3=O)cc21] | 6-tert-butyl-8-fluoro-2-[3-(hydroxymethyl)-4-[1-methyl-5-[(4-methyl-6,7-dihydro-4H-pyrazolo[5,1-c][1,4]oxazin-2-yl)amino]-6-oxo-3-pyridyl]-2-pyridyl]phthalazin-1-one | 0.0428 |
| 151 | 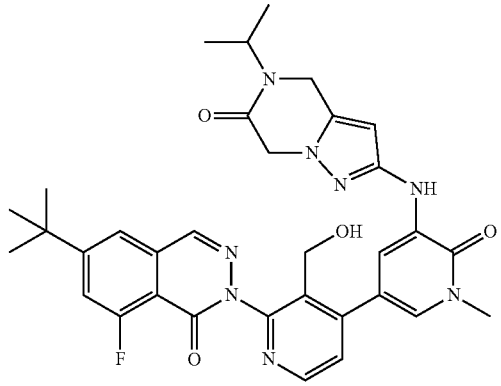 [SMILES: CC(C)N1Cc2cc(Nc3cc(-c4ccnc(-n5ncc6cc(C(C)(C)C)cc(F)c6c5=O)c4CO)cn(C)c3=O)nn2CC1=O] | 6-tert-butyl-8-fluoro-2-[3-(hydroxymethyl)-4-[5-[(5-isopropyl-6-oxo-4,7-dihydropyrazolo[1,5-a]pyrazin-2-yl)amino]-1-methyl-6-oxo-3-pyridyl]-2-pyridyl]phthalazin-1-one | 0.0141 |
| 152 | 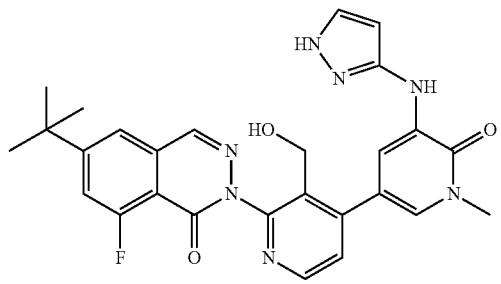 [SMILES: Cn1cc(-c2ccnc(-n3ncc4cc(C(C)(C)C)cc(F)c4c3=O)c2CO)cc(Nc2cc[nH]n2)c1=O] | 6-tert-butyl-8-fluoro-2-[3-(hydroxymethyl)-4-[1-methyl-6-oxo-5-(1H-pyrazol-3-ylamino)-3-pyridyl]-2-pyridyl]phthalazin-1-one | 0.0459 |
| 153 | 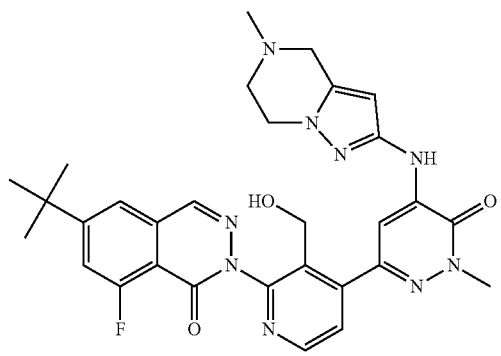 [SMILES: CN1CCn2nc(Nc3cc(-c4ccnc(-n5ncc6cc(C(C)(C)C)cc(F)c6c5=O)c4CO)nn(C)c3=O)cc2C1] | 6-tert-butyl-8-fluoro-2-[3-(hydroxymethyl)-4-[1-methyl-5-[(5-methyl-6,7-dihydro-4H-pyrazolo[1,5-a]pyrazin-2-yl)amino]-6-oxo-pyridazin-3-yl]-2-pyridyl]phthalazin-1-one | 0.0596 |

TABLE 2-continued

| No. | Structure | IUPAC_Name | CD69 Hu Blood FACS (IC70) |
|---|---|---|---|
| 154 | 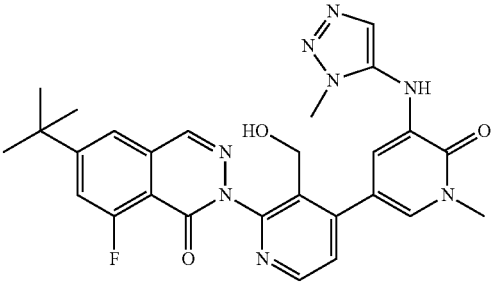 [SMILES: Cn1nncc1Nc1cc(-c2ccnc(-n3ncc4cc(C(C)(C)C)cc(F)c4c3=O)c2CO)cn(C)c1=O] | 6-tert-butyl-8-fluoro-2-[3-(hydroxymethyl)-4-[1-methyl-5-[(3-methyltriazol-4-yl)amino]-6-oxo-3-pyridyl]-2-pyridyl]phthalazin-1-one | |
| 155 | 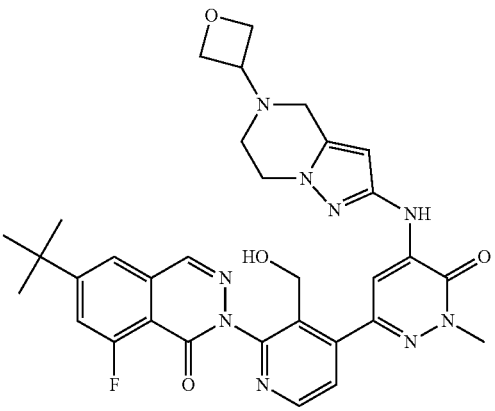 [SMILES: Cn1nc(-c2ccnc(-n3ncc4cc(C(C)(C)C)cc(F)c4c3=O)c2CO)cc(Nc2cc3n(n2)CCN(C2COC2)C3)c1=O] | 6-tert-butyl-8-fluoro-2-[3-(hydroxymethyl)-4-[1-methyl-5-[[5-(oxetan-3-yl)-6,7-dihydro-4H-pyrazolo[1,5-a]pyrazin-2-yl]amino]-6-oxo-pyridazin-3-yl]-2-pyridyl]phthalazin-1-one | 0.0266 |
| 156 | 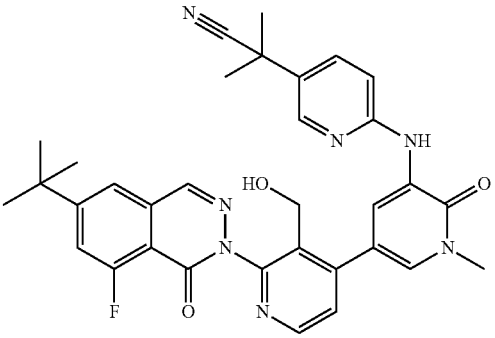 [SMILES: Cn1cc(-c2ccnc(-n3ncc4cc(C(C)(C)C)cc(F)c4c3=O)c2CO)cc(Nc2ccc(C(C)(C)C#N)cn2)c1=O] | 2-[6-[[5-[2-(6-tert-butyl-8-fluoro-1-oxo-phthalazin-2-yl)-3-(hydroxymethyl)-4-pyridyl]-1-methyl-2-oxo-3-pyridyl]amino]-3-pyridyl]-2-methyl-propanenitrile | 0.031 |
| 157 | 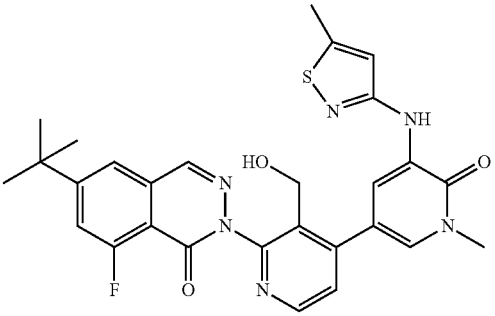 [SMILES: Cc1cc(Nc2cc(-c3ccnc(-n4ncc5cc(C(C)(C)C)cc(F)c5c4=O)c3CO)cn(C)c2=O)ns1] | 6-tert-butyl-8-fluoro-2-[3-(hydroxymethyl)-4-[1-methyl-5-[(5-methylisothiazol-3-yl)amino]-6-oxo-3-pyridyl]-2-pyridyl]phthalazin-1-one | 0.157 |

TABLE 2-continued

| No. | Structure | IUPAC_Name | CD69 Hu Blood FACS (IC70) |
|---|---|---|---|
| 158 | 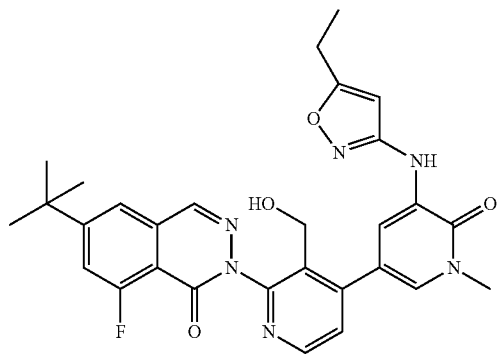 [SMILES: CCc1cc(Nc2cc(-c3ccnc(-n4ncc5cc(C(C)(C)C)cc(F)c5c4=O)c3CO)cn(C)c2=O)no1] | 6-tert-butyl-2-[4-[5-[(5-ethylisoxazol-3-yl)amino]-1-methyl-6-oxo-3-pyridyl]-3-(hydroxymethyl)-2-pyridyl]-8-fluoro-phthalazin-1-one | 0.0667 |
| 159 | 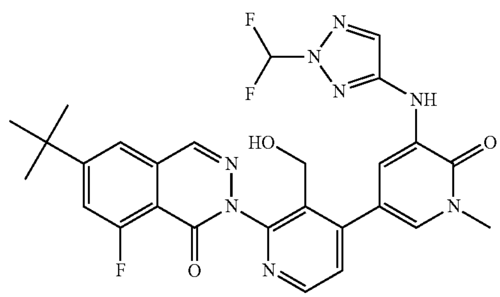 [SMILES: Cn1cc(-c2ccnc(-n3ncc4cc(C(C)(C)C)cc(F)c4c3=O)c2CO)cc(Nc2cnn(C(F)F)n2)c1=O] | 6-tert-butyl-2-[4-[5-[[2-(difluoromethyl)triazol-4-yl]amino]-1-methyl-6-oxo-3-pyridyl]-3-(hydroxymethyl)-2-pyridyl]-8-fluoro-phthalazin-1-one | 0.208 |
| 160 | 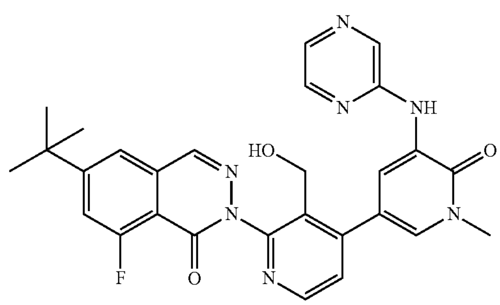 [SMILES: Cn1cc(-c2ccnc(-n3ncc4cc(C(C)(C)C)cc(F)c4c3=O)c2CO)cc(Nc2cnccn2)c1=O] | 6-tert-butyl-8-fluoro-2-[3-(hydroxymethyl)-4-[1-methyl-6-oxo-5-(pyrazin-2-ylamino)-3-pyridyl]-2-pyridyl]phthalazin-1-one | 0.116 |
| 161 | 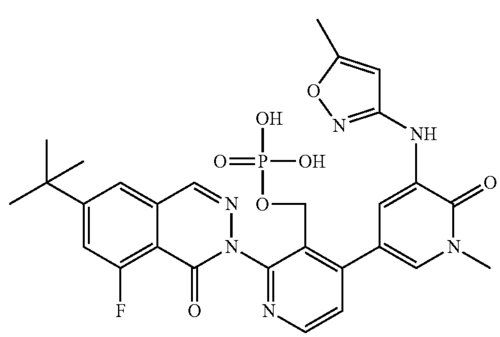 [SMILES: Cc1cc(Nc2cc(-c3ccnc(-n4ncc5cc(C(C)(C)C)cc(F)c5c4=O)c3COP(=O)(O)O)cn(C)c2=O)no1] | [2-(6-tert-butyl-8-fluoro-1-oxo-phthalazin-2-yl)-4-[1-methyl-5-[(5-methylisoxazol-3-yl)amino]-6-oxo-3-pyridyl]-3-pyridyl]methyl dihydrogen phosphate | |

TABLE 2-continued

| No. | Structure | IUPAC_Name | CD69 Hu Blood FACS (IC70) |
|---|---|---|---|
| 162 | 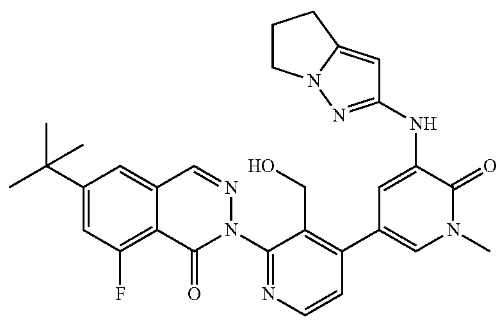 [SMILES: Cn1cc(-c2ccnc(-n3ncc4cc(C(C)(C)C)cc(F)c4c3=O)c2CO)cc(Nc2cc3n(n2)CCC3)c1=O] | 6-tert-butyl-2-[4-[5-(5,6-dihydro-4H-pyrrolo[1,2-b]pyrazol-2-ylamino)-1-methyl-6-oxo-3-pyridyl]-3-(hydroxymethyl)-2-pyridyl]-8-fluoro-phthalazin-1-one | |

Administration of Formula I Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of a Formula I or II compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I and II Compounds

Formula I and II compounds of the present invention are useful for treating a human or animal patient suffering from a disease or disorder arising from abnormal cell growth, function or behavior associated with Btk kinase such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Formula I and II compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Methods of the invention also include treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjögren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

The methods of the invention can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of Btk activity may result in reduced amounts of reperfusion injury in such situations.

Pharmaceutical Formulations

In order to use a compound of this invention for the therapeutic treatment of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I or II having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I or II may be prepared. Suitable examples of sustained-release preparations include semipermeable matrices of solid hydrophobic polymers containing a compound of Formula I or II, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I or II suitable for oral administration may be prepared as discrete units such as pills, capsules, cachets or tablets each containing a predetermined amount of a compound of Formula I or II. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I or II intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formulas I and II compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formulas I and II may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formulas I and II may be employed alone or in combination with other therapeutic agents for the treatment of a disease or disorder described herein, such as inflammation or a hyperproliferative disorder (e.g., cancer). In certain embodiments, a compound of Formula I or II is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic may be an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I or II such that they do not adversely affect each other. Such compounds are suitably present in combination in amounts that are effective for the purpose intended. In one embodiment, a composition of this invention comprises a compound of Formula I or II, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I or II, or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I or II, or a stereoisomer, tautomer, solvate, metabolite, or pharmaceutically acceptable salt or prodrug thereof, and the use of at least one other cancer treatment method. The amounts of the compound(s) of Formula I or II, and the other pharmaceutically active therapeutic agent(s) and the relative timings of administration will be selected in order to achieve the desired combined therapeutic effect.

Metabolites of Compounds of Formulas I and II

Also falling within the scope of this invention are the in vivo metabolic products of Formulas I and II compounds described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I and II, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I or II, or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or II, or a formulation thereof which is effective for treating the condition and may have a sterile access port (for example, the container may be an intravenous solution bag or a vial having a stopper pierceable by a hypodermic injection needle). At least one active agent in the composition is a compound of Formula I or II. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I or II can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I or II and, if present, the second pharmaceutical formulation. For example, if the kit comprises a first composition comprising a compound of Formula I or II, and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I or II, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I or II contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I or II and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formulas I and II Compounds

Compounds of Formula I and II may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I and II compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I and II may be prepared singly or as compound libraries comprising at least 2, for example 5 to 1,000 compounds, or 10 to 100 compounds. Libraries of compounds of Formula I and II may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The Figures and Examples provide exemplary methods for preparing Formula I and II compounds. Those skilled in the art will appreciate that other synthetic routes may be used to synthesize the Formula I and II compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Experimental procedures, intermediates and reagents useful for useful for the preparation of Formula I and II compounds may be found in US 2012/0010191, "PYRIDONE AND AZA-PYRIDONE COMPOUNDS AND METHODS OF USE", filed 6 May 2011, which is incorporated by reference in its entirety.

Figure 2:
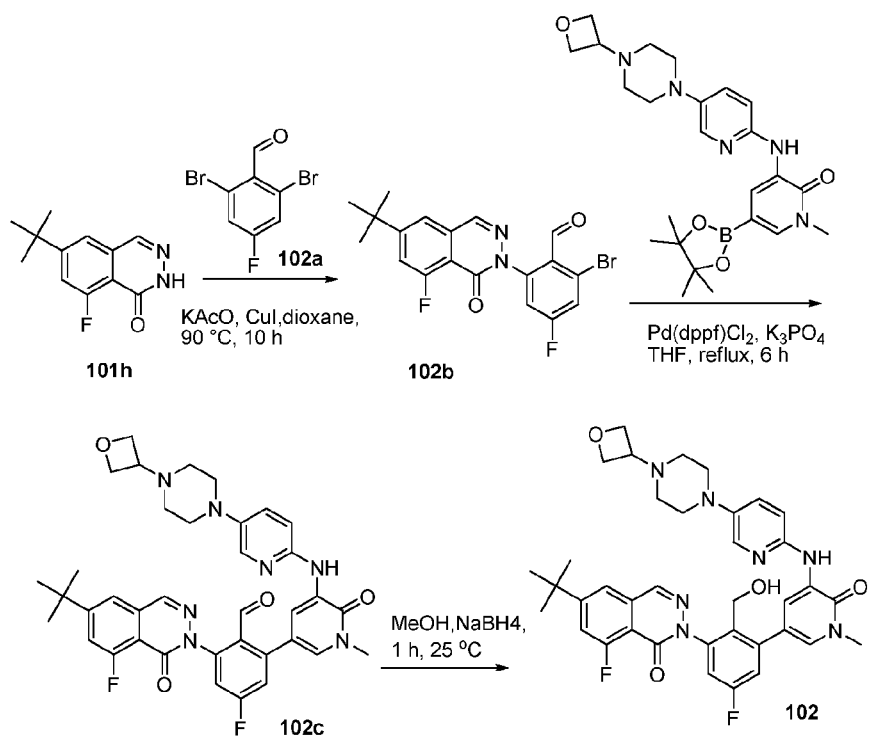
Figure 3:
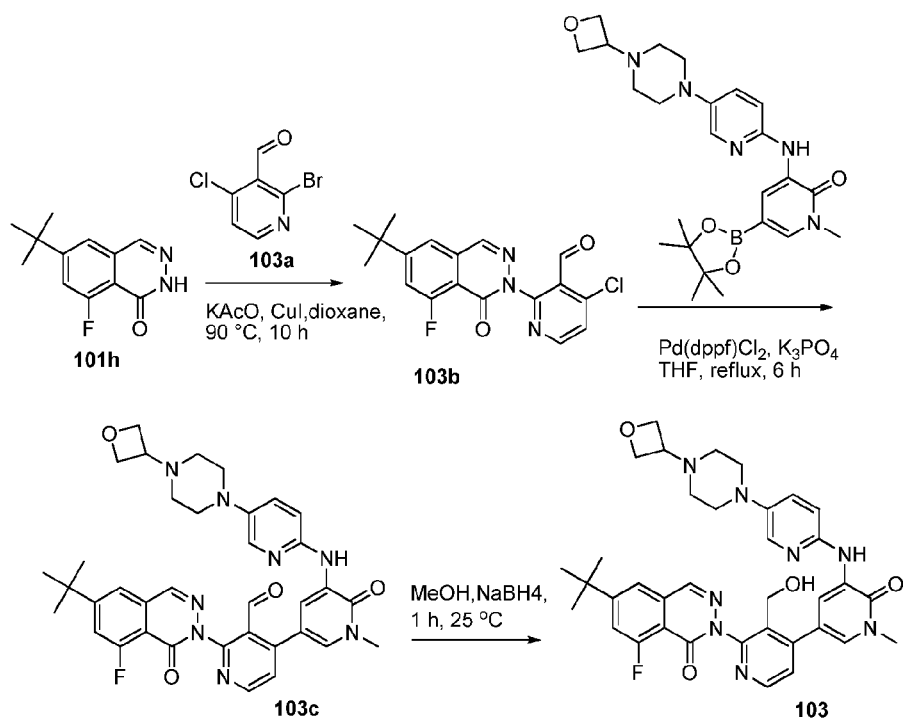
Figure 4:
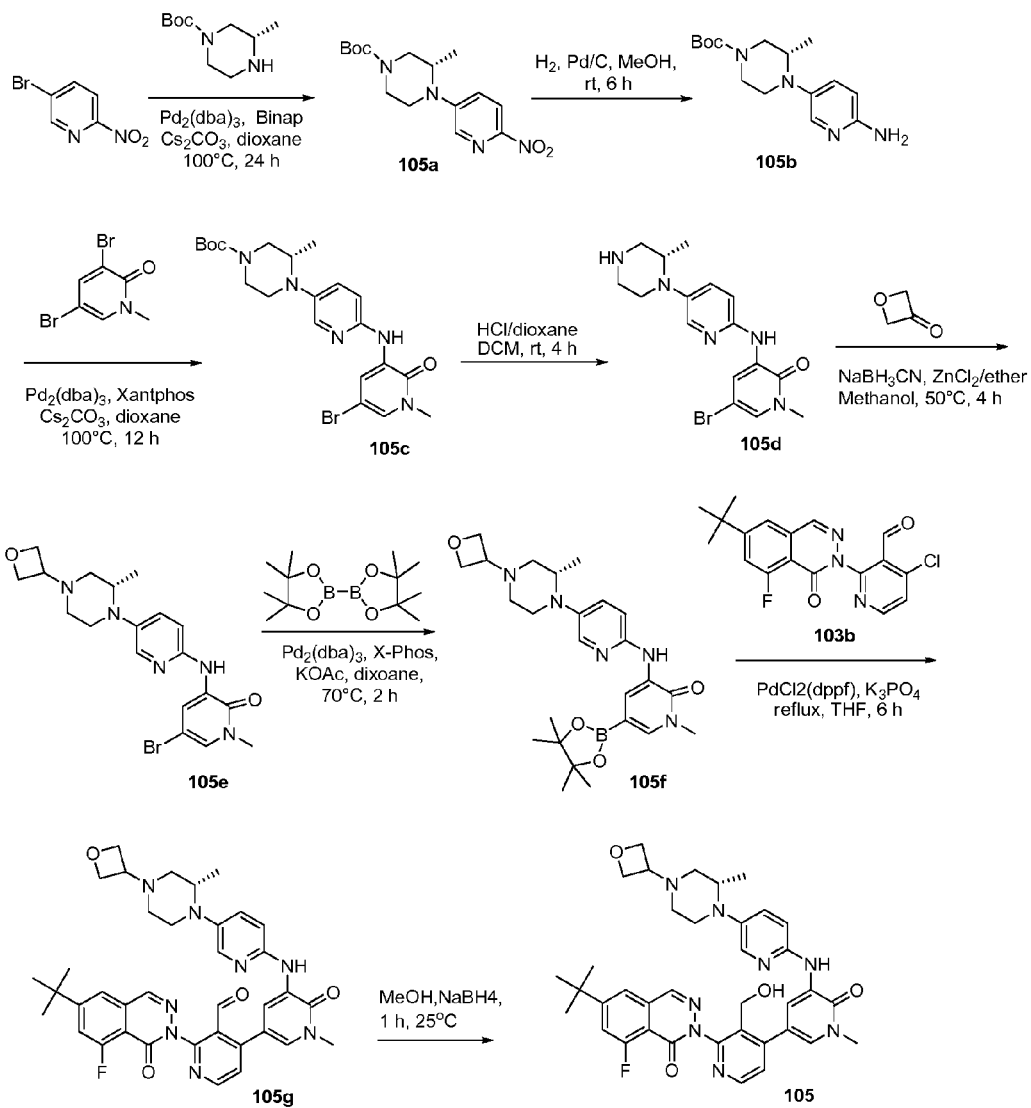
Figure 5:
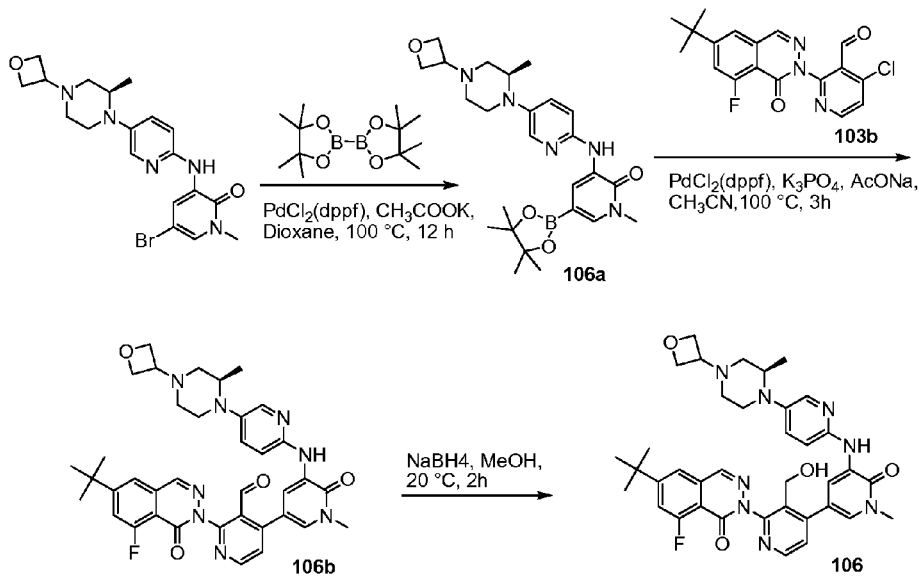
Figure 6:
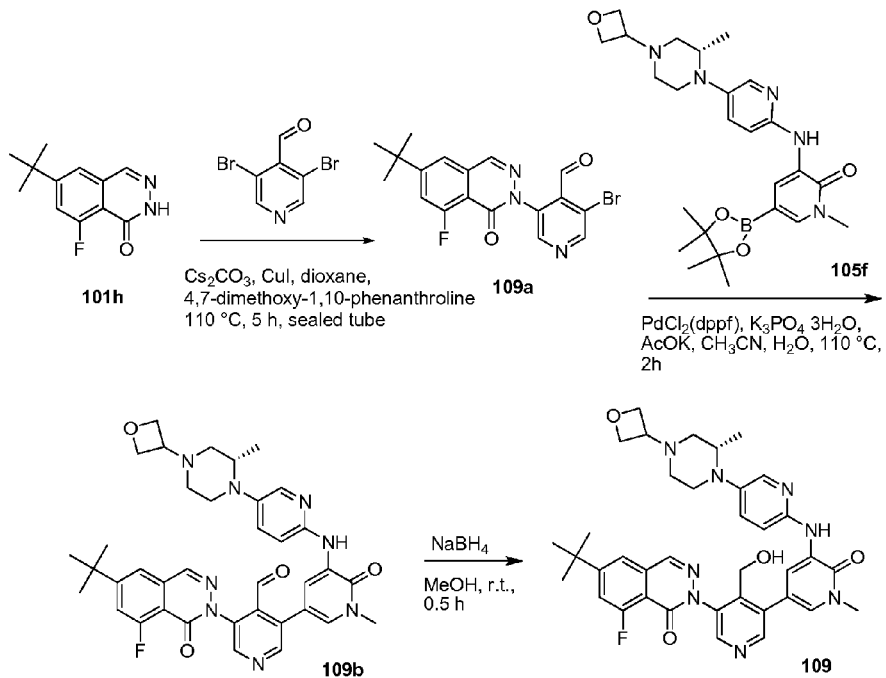
Figure 7:
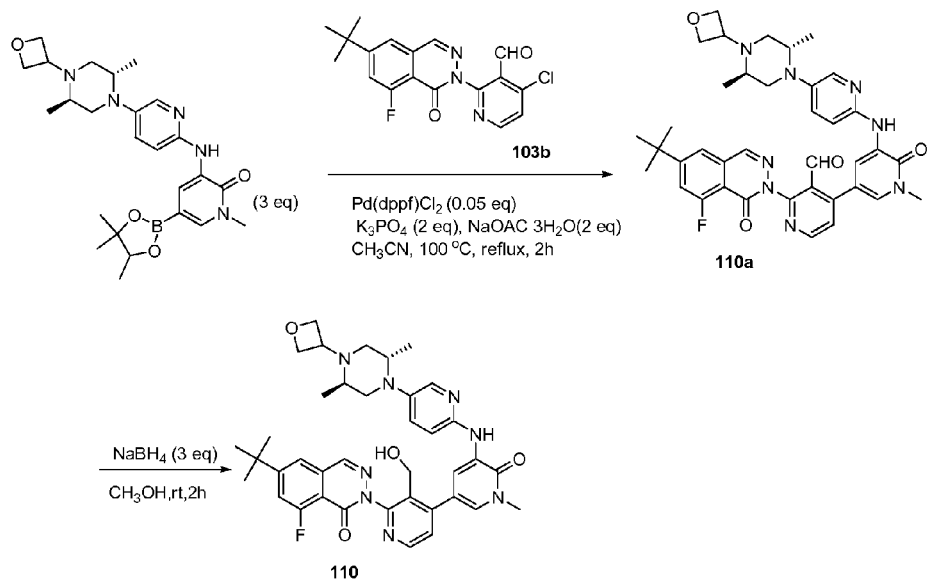
Figure 8:
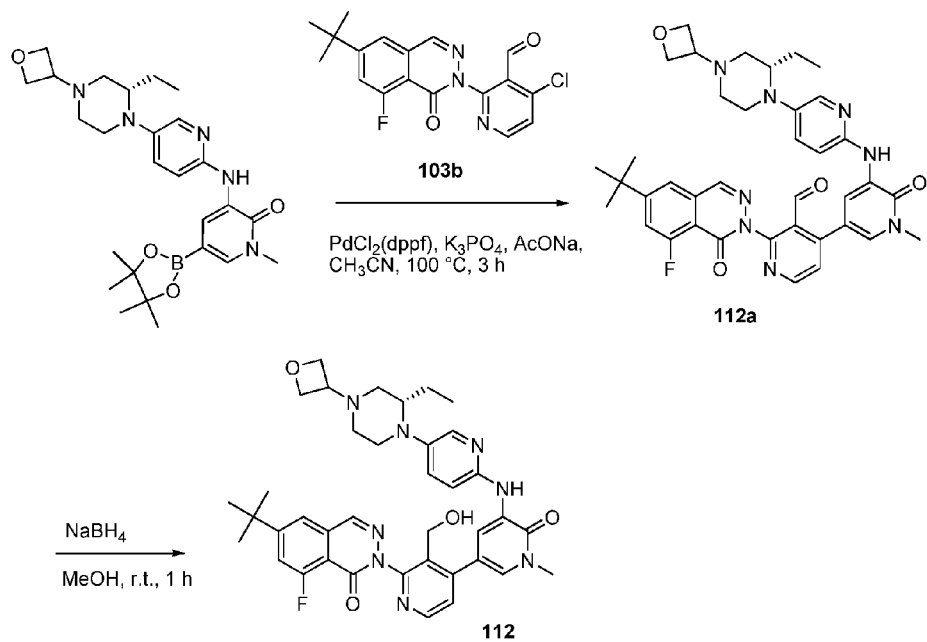

FIGS. 1-8 describe the synthesis of exemplary embodiments of Formula I or II, more fully described in Examples 101-112, and may be useful for the preparation of other Formula I and II compounds.

General Preparative Procedures

General Procedure: Suzuki Coupling

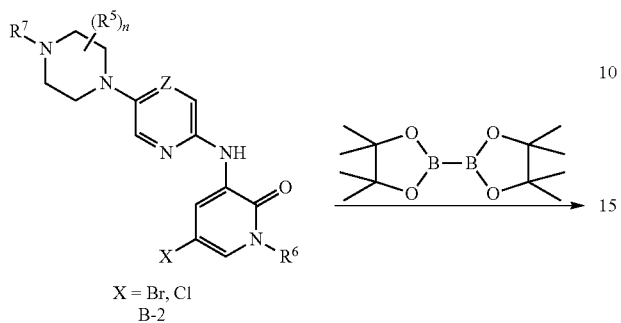

X = Br, Cl
B-2

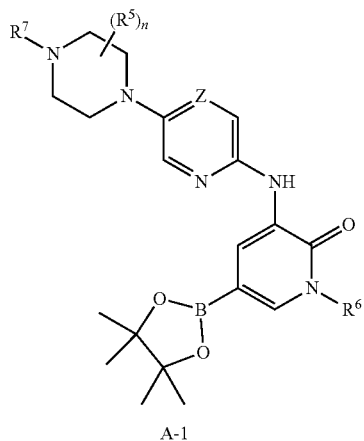

A-1

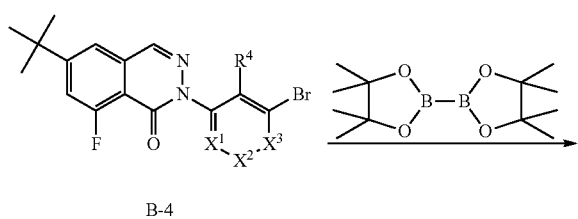

B-4

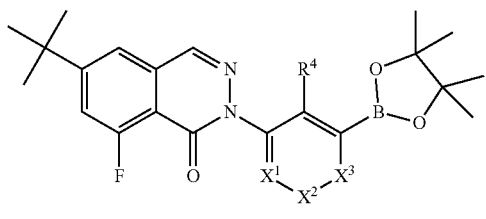

A-2

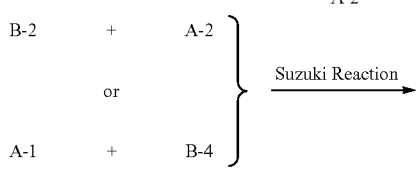

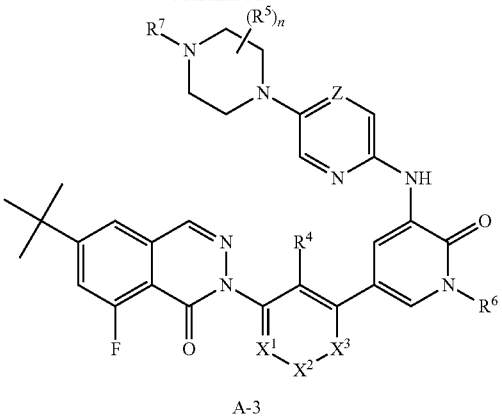

A-3

The Suzuki-type coupling reaction is useful to form carbon-carbon bonds to attach the rings of Formula I and II compounds and intermediates A-3 (Suzuki (1991) Pure Appl. Chem. 63:419-422; Miyaura and Suzuki (1979) Chem. Reviews 95(7):2457-2483; Suzuki (1999) J. Organometal. Chem. 576:147-168). Suzuki coupling is a palladium mediated cross coupling reaction of a heteroarylhalide, such as B-2 or B-4, with a boronic acid such as A-1 or A-2. For example, B-2 may be combined with about 1.5 equivalents of 4,4,4',4', 5,5,5',5'-octamethyl-2,2'-bi(1,3,2-dioxaborolane), and dissolved in about 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. In some cases potassium acetate is used in place of sodium carbonate to adjust the pH of the aqueous layer. The reaction is then heated to about 140-150° C. under pressure in a microwave reactor (Biotage AB, Uppsala, Sweden) for 10 to 30 minutes. The contents are extracted with ethyl acetate, or another organic solvent. After evaporation of the organic layer the boron ester A-1 may be purified on silica or by reverse phase HPLC. Substituents are as defined, or protected forms or precursors thereof. Likewise, bromide intermediate B-4 can be boronylated to give A-2.

Suzuki coupling of B-2 and A-2, or of A-1 and B-4, gives Formula I compound or intermediate A-3. Boronic ester (or acid) (1.5 eq) A-1 or A-2, and a palladium catalyst such as bis(triphenylphosphine)palladium(II) chloride (0.05 eq) is added to a mixture of halo intermediate (1 eq) B-2 or B-4 in acetonitrile and 1 M of sodium carbonate aqueous solution (equal volume as acetonitrile). The reaction mixture is heated to about 150° C. in a microwave for about 15 min. LC/MS indicates when the reaction is complete. Water is added to the mixture, and the precipitated product is filtered and purified by HPLC to yield the product A-3. Substituents are as defined, or protected forms or precursors thereof.

A variety of palladium catalysts can be used during the Suzuki coupling step. Various low valent, Pd(II) and Pd(0) catalysts may be used in the Suzuki coupling reaction, including PdCl2(PPh$_3$)$_2$, Pd(t-Bu)$_3$, PdCl$_2$ dppf CH$_2$Cl$_2$, Pd(PPh$_3$)$_4$, Pd(OAc)/PPh$_3$, Cl$_2$Pd[(Pet$_3$)]$_2$, Pd(DIPHOS)$_2$, Cl$_2$Pd(Bipy), [PdCl(Ph$_2$PCH$_2$PPh$_2$)]$_2$, Cl$_2$Pd[P(o-tol)$_3$]$_2$, Pd$_2$(dba)$_3$/P(o-tol)$_3$, Pd$_2$(dba)/P(furyl)$_3$, Cl$_2$Pd[P(furyl)$_3$]$_2$, Cl$_2$Pd(PMePh$_2$)$_2$, Cl$_2$Pd[P(4-F-Ph)$_3$]$_2$, Cl$_2$Pd[P(C$_6$F$_6$)$_3$]$_2$, Cl$_2$Pd[P(2-COOH-Ph)(Ph)$_2$]$_2$, Cl$_2$Pd[P(4-COOH-Ph)(Ph)$_2$]$_2$, and encapsulated catalysts Pd EnCat™ 30, Pd EnCat™ TPP30, and Pd(II)EnCat™ BINAP30 (US 2004/0254066).

General Procedure: Buchwald reaction

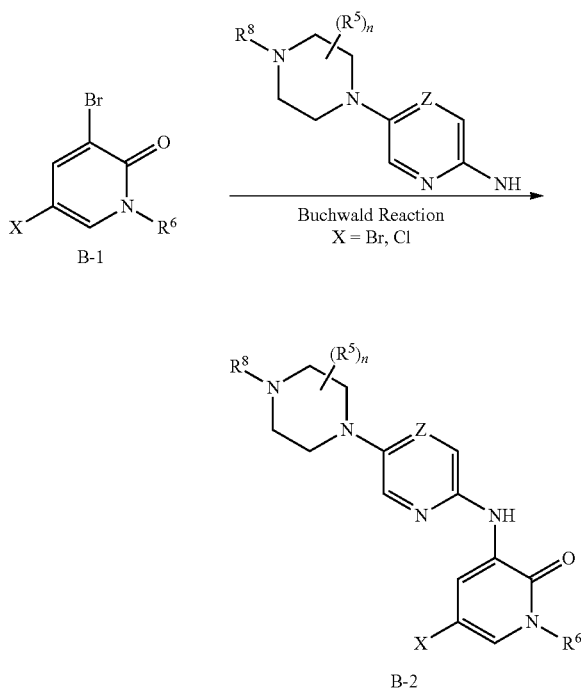

The Buchwald reaction is useful to aminate 6-bromo intermediates B-1 (Wolf and Buchwald (2004) Org. Synth Coll. Vol. 10:423; Paul et al (1994) Jour. Amer. Chem. Soc. 116: 5969-5970). To a solution of halo intermediate B-1 in DMF is added the appropriate piperazinyl-pyridinyl or piperazinyl-pyrimidinyl amine (200 mol %), $Cs_2CO_3$ (50 mol %), $Pd_2(dba)_3$ (5 mol %), and 4,5-bis(diphenylphosphino)-9,9-dimethylxanthene (Xantphos, CAS Reg. No. 161265-03-8, 10 mol %). The reaction is heated to about 110° C. under pressure in a microwave reactor (Biotage AB, Uppsala, Sweden) for about 30 min. The resulting solution is concentrated in vacuo to give B-2. Other palladium catalysts and phosphine ligands may be useful.

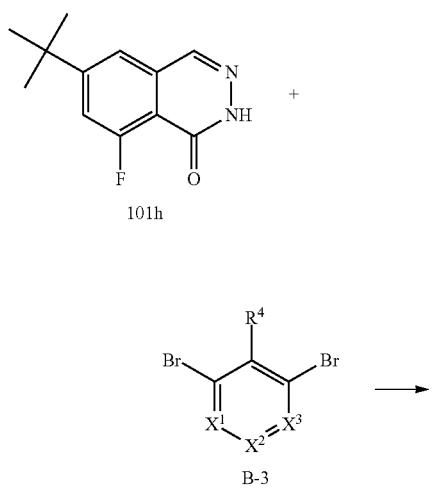

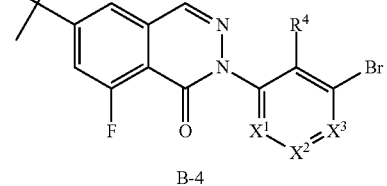

N-Heteroaryl amide intermediates B-4 can also be prepared under Buchwald conditions with cyclic amide intermediates ($R^7$) such as 6-tert-butyl-8-fluorophthalazin-1(2H)-one 101h and heteroaryl dibromides B-3.

Methods of Separation

In the methods of preparing Formula I and II compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

EXAMPLES

Example 101a 4-tert-Butylbenzoyl Chloride 101a

A mixture of 4-tert-butylbenzoic acid (1000 g, 5.6 mol) in sulfurous dichloride (1.5 L) was refluxed for 3 hours. Then the mixture was concentrated in vacuo, and the crude 101a was used in next step without further purification.

Example 101b 4-tert-Butyl-N-(2-hydroxy-1,1-dimethyl-ethyl)-benzamide 101b

A solution of 101a in DCM (200 mL) was added to a solution of 2-amino-2-methyl-1-propanol (1000 g, 10.5 mol) in $CH_2Cl_2$ (2000 mL) dropwise at 0-10° C. A white precipitate formed 5 minutes after the initial addition. The resulting slurry was stirred at room temperature overnight. The solid was removed by filtration and washed with $CH_2Cl_2$ (1000 mL). The filtrate was concentrated on by rotary evaporation to give 101b as a light yellow resin which was used in the next step without further purification.

Example 101c 2-(4-tert-Butyl-phenyl)-4,4-dimethyl-4,5-dihydrooxazole 101c

A mixture of 101b (1000 g, crude) in thionyl chloride (1.5 L) was refluxed for 1 hour. The reaction mixture was cooled to room temperature and poured into 500 mL of stirred $Et_2O$, during which time a white precipitate formed. The precipitate was collected by filtration and washed with $Et_2O$, dissolved in 500 mL of water and neutralized with 25 percent NaOH. The yellow aqueous solution was extracted with EtOAC (3×500 mL) and the combined organic phase was washed with 500 mL of brine, dried over $Na_2SO_4$, filtered and concentrated in vacuo to provide 101c (530 g, 40.8% over 3 steps) as a white solid. $^1$HNMR (300 MHz, $CDCl_3$) δ 7.87 (d, J=8.4 Hz, 2H), 7.41 (d, J=8.4 Hz, 2H), 4.08 (s, 2H), 1.37 (s, 6H), 1.33 (s, 9H).

Example 101d 5-tert-Butyl-2-(4,4-dimethyl-4,5-dihydro-oxazol-2-yl)-benzaldehyde 101d To a solution of 101c (50 g, 0.22 mol) in anhydrous THF (750 mL) was added 2.4 M solution of n-butyllithium in hexane (225 mL) at −78° C. under nitrogen atmosphere. The clear amber solution was warmed to −20° C. and stirred for 4 hr. The reaction mixture became red-amber and cloudy. The mixture was re-cooled to −78° C. and stirred rapidly before 72 mL of DMF was added drop wise at such a rate that the temperature was controlled below −60° C. After the addition, the reaction mixture was stirred at −78° C. for 15 min then stirred at −20° C. for 1 hr and room temperature for 1 hr. The reaction mixture was quenched with 200 mL of 0.5 M aqueous $KHSO_4$. More $KHSO_4$ solution was added in until the pH was adjusted to 4-5. The aqueous phase was extracted with EtOAc (3×500 mL) and the combined organic phases was washed with 400 mL of brine and dried over $Na_2SO_4$, filtered and concentrated in vacuo to give 101d (35 g, 62%) as a yellow solid which was used in the next step without further purification. LCMS, ESI, m/z 260 (M+1)$^+$.

Example 101e 2-(4-tert-Butyl-2-1,3-dioxinan-2-yl-phenyl)-4,4-dimethyl-4,5-dihydrooxazole 101e A mixture of 101d (60 g, 0.23 mol), pyridinium p-toluenesulfonate (4 g, 0.02 mol) and 1,3-propanediol (60 mL) in toluene (500 mL) was heated to reflux overnight and cooled to room temperature upon the completion of reaction determined by LCMS. The reaction mixture was washed with 200 mL of 50 percent aqueous $NaHCO_3$, 200 mL of water, and 200 mL of brine. The organic layer was dried over $Na_2SO_4$, filtered and concentrated in vacuo to give a residue which was purified by silica gel chromatography using EtOAc/petroleum ether=1:5 as eluent to provide 101e (16 g, 21.7%) as a clear yellow gum. LCMS (ESI) 318 (M+H)$^+$. $^1$HNMR (300 MHz, $CDCl_3$) δ 7.79 (s, 1H), 7.67 (d, J=8.0 Hz, 1H), 7.36 (dd, J=1.6, 8.4 Hz, 1H), 6.32 (s, 1H), 4.23 (dd, J=5.2, 11.2 Hz, 2H), 4.06 (s, 2H), 4.04-3.98 (m, 2H), 2.27-2.21 (m, 1H), 1.48-1.38 (m, 1H), 1.38 (s, 6H), 1.32 (s, 9H).

Example 101f 2-(4-tert-Butyl-2-1,3-dioxinan-2-yl-6-fluoro-phenyl)-4,4-dimethyl-4,5-dihydro-oxazole 101f To a solution of 101e (20 g, 63 mmol) in anhydrous THF (400 mL) was added 2.4 M solution of n-butyllithium in hexane (65 mL) at −78° C. under $N_2$ atmosphere. The clear yellow solution was stirred at −17° C. for 3 hr, when it showed a deep red-orange color. The reaction solution was re-cooled to −78° C., stirred rapidly and a solution of N-fluorobenzenesulfonimide (29 g, 92 mmol) in anhydrous THF (100 mL) was added in dropwise over 10 min. The reaction mixture was stirred at −78° C. for 5 min, −20° C. for 30 min, then room temperature for 1 h. The reaction mixture was poured into 150 mL of 50% aqueous $NH_4Cl$ and extracted with 300 mL of EtOAc. The separated organic phase was washed with 150 mL of water and 150 mL of brine, dried over $Na_2SO_4$, filtered, and concentrated in vacuo to give a residue which was purified by silica gel chromatography using $EtOAc/CH_2Cl_2=1:5$ as eluent to afford 101f (7 g, 33%) as yellow solid. LCMS (ESI) m/z 336 (M+H)$^+$. $^1$HNMR (300 MHz, CDCl$_3$) δ 7.53 (d, J=1.6 Hz, 1H), 7.08 (dd, J=2.0, 12.0 Hz, 1H), 5.90 (s, 1H), 4.24 (dd, J=5.2, 10.8 Hz, 2H), 4.06 (s, 2H), 3.98-3.91 (m, 2H), 2.26-2.19 (m, 1H), 1.45-1.42 (m, 1H), 1.42 (s, 6H), 1.30 (s, 9H).

Example 101g 5-tert-Butyl-7-fluoro-3-methoxyisobenzofuran-1(3H)-one 101g

A mixture of 101f (68.8 g, 205.4 mmol), methanol (1340 mL) and 50% aqueous sulfuric acid (881 mL) was stirred at reflux overnight. The reaction mixture was poured into 400 mL of water, extracted with DCM (3×1000 mL). The combined organic extracts were washed with 400 mL of brine, dried over $Na_2SO_4$, filtered and concentrated to dry to provide 101g (43 g) as a off-white solid which was used in the next step without further purification LCMS (ESI) m/z 225 (M+H)$^+$.

Example 101h 6-tert-Butyl-8-fluorophthalazin-1(2H)-one 101h

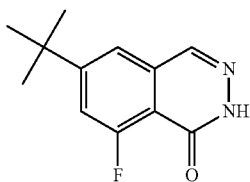

101h

To a solution of 101g (40 g, 168 mmol) in glacial acetic acid (360 mL) was added hydrazine monohydrate (240 mL) at 0-10° C. under $N_2$ protection. The resulting slurry was stirred under nitrogen at 50° C. for 1.5 hours. The reaction mixture was poured into 300 mL of water with continuous stirring. The aqueous phase was extracted with DCM (2×500 mL), and the combined organic phase was dried over $Na_2SO_4$, filtered and concentrated to give a residue, which was purified by re-crystallization in DMC and $Et_2O$ to provide 101h (17 g, 37.6% over 2 steps) as an off-white solid. $^1$HNMR (300 MHz, CDCl$_3$) δ 8.11 (d, J=2.7 Hz, 1H), 7.46 (m, 2H), 1.39 (s, 9H). LCMS (ESI) m/z 221 (M+H)$^+$.

Example 101i 2-(6-tert-Butyl-8-fluoro-1-oxophthalazin-2(1H)-yl)-6-chlorobenzaldehyde 101i

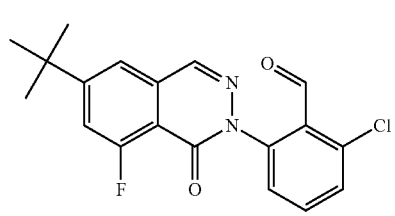

101i

To a 10 mL round bottom flask were added 6-tert-butyl-8-fluoro-2H-phthalazin-1-one 101h (640 mg, 2.9 mmol), 2-chloro-6-fluorobenzaldehyde (506 mg, 3.2 mmol), and cesium carbonate (488 mg, 1.5 mmol). The flask was evacuated and backfilled with nitrogen three times then ethoxytrimethylsilane (684 mg, 5.8 mmol) and DMF (5 mL) were added to the reaction flask. The resulting mixture was heated to 60° C. After 4 h of stirring, the solution was allowed to cool down to ambient temperature and the reaction was quenched by addition of 2 mL of $H_2O$ drop-wise. The desired product started to precipitate from the DMF and water mixture. The solid was collected by filtration after cooling down to 5° C., and washed with DMF/water (2/1, 2 mL, pre-cooled to 6° C.) and $H_2O$ (2 mL). The filter cake was dried under vacuum oven at 65° C. for overnight to afford 519 mg (52%) of 101i as a yellow solid. MS: [M+H]+: 359

Example 101j 6-tert-Butyl-2-(3-chloro-2-(hydroxymethyl)phenyl)-8-fluorophthalazin-1(2H)-one 101j

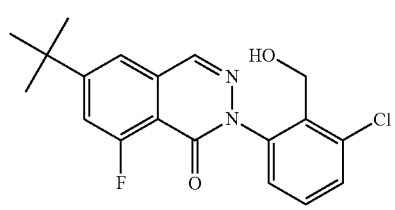

101j 2-(6-tert-Butyl-8-fluoro-1-oxo-1H-phthalazin-2-yl)-6-chloro-benzaldehyde 101i (519 mg, 1.4 mmol) was dissolved in DCM (2 mL) with stirring at room temperature, and then 1 mL of iPA was added to the solution. The resulting solution was cooled to 4° C., and NaBH$_4$ (27 mg, 0.7 mmol) was added in one portion. After 30 min stirring, the reaction was quenched by adding $H_2O$ (2 mL). The aqueous layer was extracted with $CH_2Cl_2$ (2×5 mL), washed with brine and dried over MgSO$_4$. The filtrate was concentrated to give a residue which was purified by silica gel chromatography eluting with 0-20% EtOAc/CH₂Cl₂ to furnish 101j as a white solid (385 mg, 72%). MS: [M+H]+: 361

Example 101

6-tert-Butyl-8-fluoro-2-(2-(hydroxymethyl)-3-(1-methyl-5-(5-(4-methylpiperazin-1-yl)pyridin-2-ylamino)-6-oxo-1,6-dihydropyridin-3-yl)phenyl)phthalazin-1(2H)-one 101

To a 10 mL flask were added 6-tert-butyl-2-(3-chloro-2-hydroxymethyl-phenyl)-8-fluoro-2H-phthalazin-1-one 101j (100 mg, 0.27 mmol), 1-methyl-3-[5-(4-methyl-piperazin-1-yl)-pyridin-2-ylamino]-5-(4,4,5,5-tetramethyl-[1,3,2]dioxaborolan-2-yl)-1H-pyridin-2-one (141 mg, 0.33 mmol), PCy3 (6 mg), Pd(dba)₂ (6 mg) and K₂CO₃ (112 mg, 0.8 mmol) in order. The flask was evacuated and backfilled with nitrogen. This sequence was repeated three times. Then, 20 percent aqueous 1,4-dioxane was added to the reaction mixture. The resulting mixture was heated to 90° C. for gentle reflux and stirred for 1.5 hr under Nitrogen atmosphere. The reaction mixture was cooled to room temperature and filtered through a diatomaceous earth filtration agent pad (CELITE®) and concentrated to afford a residue which was purified by prep-TLC (10% MeOH in CH₂Cl₂) to afford 101 (80 mg, 46%) as a yellow solid. MS: [M+H]⁺624. ¹H NMR (400 MHz, DMSO-d₆) δ 8.53 (d, J=2.0 Hz, 1H), 8.50 (d, J=1.6 Hz, 1H), 8.36 (s, 1H), 7.87 (d, J=3.2 Hz, 2H), 7.73 (d, J=12.8 Hz, 1H), 7.51 (t, J=7.6 Hz, 1H), 7.41 (d, J=3.2 Hz, 1H), 7.39 (d, J=3.6 Hz, 1H), 7.35 (dd, J=2.8, 9.2 Hz, 1H), 7.28 (d, J=2. Hz, 1H), 7.20 (d, J=9.2 Hz, 1H), 4.58 (t, J=4.8 Hz, 1H), 4.36 (s, 2H), 3.58 (s, 3H), 3.04 (m, 4H), 2.44 (m, 4H), 2.21 (s, 3H), 1.38 (s, 9H).

Example 102a 2,6-Dibromo-4-fluorobenzaldehyde 102a

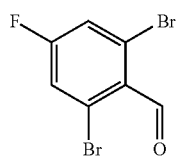

102a

A solution of 1,3-dibromo-5-fluoro-2-iodobenzene (50 g, 132 mmol) in anhydrous toluene (300 mL) cooled to −35° C. was added the solution of isopropylmagnesium chloride (84 mL, 171 mmol, 2.0 M in diethyl ether) over a period of 30 minutes while maintaining the internal temperature below −25° C. A clear brown solution was obtained. Stirring was continued for 1.5 h. Then anhydrous DMF (34 mL, 436 mmol) was added over a period of 30 minutes. The temperature of the reaction mixture increased to −19° C. The reaction mixture was warmed to 10° C. (room temperature) over 1 h and stirred at this temperature for 1.5 h. The reaction was quenched with saturated aqueous NH₄Cl (100 mL), filtered and evaporated under reduced pressure. The residue was purified by silica-gel column chromatography (eluting with petroleum ether/ethyl acetate: from 50:1 to 20:1) to give 102a (20 g, yield 54%) as a yellow solid.

Example 102b

2-Bromo-6-(6-tert-butyl-8-fluoro-1-oxophthalazin-2(1H)-yl)-4-fluorobenzaldehyde 102b To a solution of 102a (767 mg, 2.72 mmol), 6-tert-butyl-8-fluorophthalazin-1(2H)-one 101h (300 mg, 1.36 mmol) in dioxane (50 mL) was added KOAc (267 mg, 2.72 mmol), CuI (259 mg, 1.36 mmol), and 4,7-dimethoxy-1,10-phenanthroline (327 mg, 1.36 mmol). After bubbling nitrogen through the resulting solution for 30 min, the mixture was stirred at 90 degree for 10 h. It was allowed to cool down to room temperature and H₂O (100 mL) was added. The aqueous layer was separated and extracted with ethyl acetate (2×200 mL). The combined organic layers was washed with brine (100 mL) and dried over sodium sulfate. The drying agent was removed by filtration and the filtrate was concentrated under reduced pressure. The residue was purified on flash column eluting with PE/EA (15:1) to afford 102b (172 mg, 30%). LCMS: [M+H]⁺ 421. ¹H NMR (500 MHz, CDCl₃) δ 10.20 (s, 1H), 8.20 (s, 1H), 7.49-7.51 (m, 3H), 7.25 (m, 1H), 1.36 (s, 9H).

Example 102c 2-(6-tert-Butyl-8-fluoro-1-oxophthalazin-2(1H)-yl)-4-fluoro-6-(1-methyl-5-(5-(4-(oxetan-3-yl)piperazin-1-yl)pyridin-2-ylamino)-6-oxo-1,6-dihydropyridin-3-yl)benzaldehyde 102c A round-bottomed flask was charged with 2-bromo-6-(6-tert-butyl-8-fluoro-1-oxophthalazin-2(1H)-yl)-4-fluorobenzaldehyde 102b (100 mg, 0.24 mmol), 1-methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one (131 mg, 0.28 mmol), PdCl₂(dppf) (25 mg, 0.03 mmol), K₃PO₄·3H₂O(149 mg, 0.56 mmol), THF (10 mL), and H₂O (5 mL). After three cycles of vacuum/argon flash, the mixture was heated at 70° C. for 6 h. It was then filtered and the filtrate was evaporated in vacuo. The residue was purified on flash column chromatography eluting with 1:3 petroleum/ethyl acetate to afford 102c as a yellow solid (98 mg, 60%). LCMS: [M+H]⁺ 682

Example 102

6-tert-Butyl-8-fluoro-2-(3-(hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)phthalazin-1(2H)-one 102

A mixture of 2-(6-tert-butyl-8-fluoro-1-oxophthalazin-2 (1H)-yl)-4-fluoro-6-(1-methyl-5-(5-(4-(oxetan-3-yl)piperazin-1-yl)pyridin-2-ylamino)-6-oxo-1,6-dihydro-pyridin-3-yl)benzaldehyde 102c (98 mg, 0.14 mmol), NaBH₄ (17 mg, 0.43), and CH₃OH (10 mL) was stirred at 25° C. for 1 h. It was then concentrated at reduce pressure and water (10 mL) was added. The resulting mixture was extracted with CH₂Cl₂ (10 mL×2). The combined CH₂Cl₂ extract was concentrated under reduced pressure and the residue was purified with reverse-phase prep-HPLC to afford 102 (45 mg, 46%). LCMS: [M+H]⁺ 684. ¹H NMR (500 MHz, DMSO-d₆) δ 8.52-8.56 (m, 2H), 8.40 (s, 1H), 7.88 (d, J=6.0 Hz, 2H), 7.74-7.77 (m, 1H), 7.34-7.40 (m, 3H), 7.29 (d, J=3.0 Hz, 1H), 7.22 (d, J=9.5 Hz, 1H), 4.54-4.56 (m, 2H), 4.44-4.47 (m, 2H), 4.32 (s, 2H), 3.58 (s, 3H), 3.43 (s, 1H), 3.06-3.08 (m, 4H), 2.36-2.39 (m, 5H), 1.38 (s, 9H).

Example 103a

2-Bromo-4-chloronicotinaldehyde 103a

To a solution of 2-bromo-4-chloropyridine (1.6 g, 8.0 mmol) in anhydrous tetrahydrofuran (40 mL) cooled at −70° C. was added the solution of lithium diisopropyl-amide (5.0 mL, 10.0 mmol, 2.0 M) over a period of 5 minutes and stirred at −70° C. for another 1 h. Anhydrous DMF (1.3 g) was introduced over a period of 3 minutes and the mixture was stirred for another 30 minutes. It was then quenched with saturated $NH_4Cl$ (30 mL) and extracted with ethyl acetate (20 mL×3). The combined organic layer was dried over anhydrous $Mg_2SO_4$, filtered, and evaporated under reduced pressure. The residue was purified by silica-gel column chromatography eluting with petroleum ether/ethyl acetate (20:1) to afford 103a as a yellow solid (900 mg, 48%). $^1$H NMR (500 MHz, DMSO-$d_6$) δ 10.21 (s, 1H), 8.52 (d, J=5.5 Hz, 1H), 7.79 (d, J=5.0 Hz, 1H).

Example 103b 2-(6-tert-Butyl-8-fluoro-1-oxophthalazin-2(1H)-yl)-4-chloronicotinaldehyde 103b

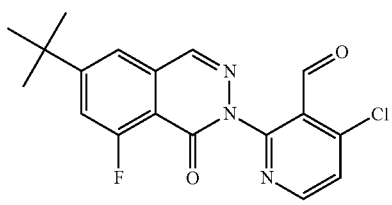

103b

Into a solution of 2-bromo-4-chloronicotinaldehyde 103a (446 mg, 2.05 mmol), 6-tert-butyl-8-fluorophthalazin-1(2H)-one 101h (300 mg, 1.36 mmol) in dioxane (50 mL) was added KAcO (267 mg, 2.72 mmol), CuI(259 mg, 1.36 mmol), and 4,7-dimethoxy-1,10-phenanthroline (327 mg, 1.36 mmol). After bubbling nitrogen through the resulting solution for 30 min, the mixture was stirred at 90° C. for 10 h. It was allowed to cool down to room temperature and $H_2O$ (100 mL) was added. The aqueous layer was separated and extracted with ethyl acetate (2×200 mL). The combined organic layer was washed with brine (100 mL) and dried over sodium sulfate. The drying agent was removed by filtration and the filtrate was concentrated under reduced pressure. The residue was purified on flash column eluting with 10:1 PE/EA to afford 103b (120 mg, 25%). LCMS: [M+H]$^+$ 360. $^1$H NMR (500 MHz, CDCl$_3$) δ 10.36 (s, 1H), 8.69 (d, J=5.5, 1H), 8.28 (d, J=2.0, 1H), 7.28-7.56 (m, 3H), 1.49 (s, 9H)

Example 103c 2-(6-tert-Butyl-8-fluoro-1-oxophthalazin-2(1H)-yl)-4-(1-methyl-5-(5-(4-(oxetan-3-yl)piperazin-1-yl)pyridin-2-ylamino)-6-oxo-1,6-dihydropyridin-3-yl)nicotinaldehyde 103c A mixture of 103b (100 mg, 0.28 mmol), 1-methyl-3-(5-(4-(oxetan-3-yl)piperazin-1-yl)pyridine-2-ylamino)-5-(4,4,5,5-tetramethyl-1,3,2-dioxaborolan-2-yl)pyridin-2(1H)-one (131 mg, 0.28 mmol), PdCl$_2$(dppf) (25 mg, 0.03 mmol), and $K_3PO_4.3H_2O$ (149 mg, 0.56 mmol) was suspended in THF (10 mL)/H$_2$O (5 mL). After three cycles of vacuum/argon flash, the mixture was heated at 70° C. for 6 h. It was then filtered and the filtrate was evaporated in vacuo. The residue was purified on flash column chromatography eluting with 1:3 petroleum/ethyl acetate to afford 103c as a yellow solid (150 mg, 60%). LCMS: [M+H]$^+$ 665

Example 103

6-tert-butyl-8-fluoro-2-(3-(hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)-phthalazin-1(2H)-one 103

A mixture of 103c (120 mg, 0.18 mmol), NaBH$_4$ (21 mg, 0.54), and CH$_3$OH (10 mL) was stirred at 25° C. for 1 h. It was then concentrated under reduced pressure and water (10 mL) was added. The resulting mixture was extracted with CH$_2$Cl$_2$ (10 mL×2). The combined CH$_2$Cl$_2$ extract was concentrated under reduced pressure and the residue was purified with reverse-phase prep-HPLC to afford 103 (45 mg, 38%). LCMS: [M+H]$^+$ 667. $^1$H NMR (500 MHz, CDCl$_3$) δ 8.66-8.68 (m, 2H), 8.35 (s, 1H), 7.96 (d, J=3.0, 1H), 7.81 (s, 1H), 7.65 (d, J=2.5, 1H), 7.55-7.59 (m, 3H), 6.83 (d, J=8.5, 1H), 4.71-4.74 (m, 4H), 4.51-4.52 (m, 2H), 4.07-4.08 (m, 1H), 3.73 (s, 3H), 3.56 (s, 1H), 3.20-3.22 (m, 4H), 2.56-2.58 (m, 4H), 1.59 (s, 9H)

Example 104a (S)-2-(6-tert-Butyl-8-fluoro-1-oxophthalazin-2(1H)-yl)-4-fluoro-6-(1-methyl-5-(5-(2-methyl-4-(oxetan-3-yl)piperazin-1-yl)pyridin-2-ylamino)-6-oxo-1,6-dihydropyridin-3-yl)benzaldehyde 104a A 50-mL single-neck round-bottomed flask equipped with a magnetic stirrer and a reflux condenser was charged with 2-bromo-6-(6-tert-butyl-8-fluoro-1-oxophthalazin-2(1H)-yl)-4-fluorobenzaldehyde 102b (100 mg, 0.24 mmol), (S)-1-methyl-3-(5-(2-methyl-4-(oxe-tan-3-yl)piperazin-1-yl)pyridin-2-ylamino)-5-(4,4,5,5-tetramethyl-1,3,2-dioxaborolan-2-yl)pyridin-2(1H)-one 105f (115 mg, 0.24 mmol), PdCl$_2$(dppf) (22 mg, 0.03 mmol), K$_3$PO$_4$ (102 mg, 0.48 mmol), sodium acetate (39 mg, 0.48 mmol), THF (15 mL), and water (5 mL). After three cycles of vacuum/argon flush, the mixture was heated at 100° C. for 2 h. It was then filtered and the filtrate was evaporated under reduced pressure. The residue was purified by silica-gel column chromatography eluting with 40:1 dichloromethane/methanol to afford 104a as a yellow solid (82 mg, 49%). MS: [M+H]$^+$ 696.3

Example 104

(S)-6-tert-Butyl-8-fluoro-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)phthalazin-1(2H)-one 104

A mixture of (S)-2-(6-tert-butyl-8-fluoro-1-oxophthalazin-2(1H)-yl)-4-fluoro-6-(1-methyl-5-(5-(2-methyl-4-(oxetan-3-yl)piperazin-1-yl)pyridin-2-ylamino)-6-oxo-1,6-dihydropyridin-3-yl)benzaldehyde 104a (80 mg, 0.12 mmol), NaBH$_4$ (14 mg, 0.36), and methanol (20 mL) was stirred at 25° C. for 1 h. Then the reaction mixture was quenched with water (10 mL) and concentrated under reduced pressure. The residue was extracted with dichloromethane (2×30 mL) and the combined dichloromethane extract was concentrated under reduced pressure. The residue was purified by reverse-phase prep-HPLC to afford 104 (46 mg, 55%) as a yellow solid. MS: [M+H]$^+$ 698.3. $^1$H NMR (500 MHz, DMSO-d$_6$) δ 8.54 (d, J=2.0 Hz, 1H), 8.52 (d, J=2.0 Hz, 1H), 8.42 (s, 1H), 7.88 (s, 1H), 7.86 (d, J=3.0 Hz, 1H), 7.77-7.74 (m, 1H), 7.40-7.34 (m, 3H), 7.30 (dd, J=2.5, 9.5 Hz, 1H), 7.23 (d, J=9.0 Hz, 1H), 4.57-4.54 (m, 2H), 4.49-4.45 (m, 1H), 4.43-4.40 (m, 1H), 4.34-4.29 (m, 2H), 3.70-3.65 (m, 1H), 3.58 (s, 3H), 3.40-3.38 (m, 2H), 3.12-3.06 (m, 1H), 2.97-2.91 (m, 1H), 2.36-2.29 (m, 3H), 2.19-2.15 (m, 1H), 1.38 (s, 9H), 0.93 (d, J=6.5 Hz, 3H), Example 105a (3S)-tert-Butyl 3-Methyl-4-(6-nitropyridin-3-yl)piperazine-1-carboxylate 105a

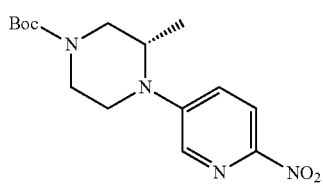

Into a solution of 5-bromo-2-nitropyridine (30 g, 148 mmol) in DMSO (350 mL) were added K$_2$CO$_3$ (14 g, 104 mmol) and (3S)-tert-butyl-3-methylpiperazine-1-carboxylate (10.0 g, 50 mmol). The mixture was stirred at 65° C. overnight and then after cooling to room temperature, poured into water (700 mL). The solid precipitate was collected and dried under vacuum. It was further purified on a flash column eluting with 20:1 petroleum ether/ethyl acetate and then with CH$_2$Cl$_2$ to give 105a as a yellow solid (8.05 g, 50%). LCMS: [M+H]$^+$ 323

Example 105b (3S)-tert-Butyl 4-(6-Aminopyridin-3-yl)-3-methylpiperazine-1-carboxylate 105b

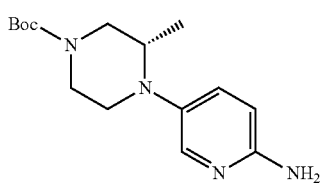

A 500-mL bottle was purged with nitrogen and charged with 105a (5.8 g, 18 mmol), 10% palladium on carbon (50% wet, 2.0 g) and ethanol (200 mL). It was evacuated, charged with hydrogen gas, and stirred for 16 h at room temperature. The hydrogen was then removed in vacuo and replaced with nitrogen. The catalyst was removed by filtration through a pad of CELITE® and the filtrate concentrated under reduced pressure to afford 105b as a brown solid (4.9 g, 96%). LCMS: [M+H]$^+$ 293

Example 105c (3S)-tert-Butyl-4-(6-(5-bromo-1-methyl-2-oxo-1,2-dihydropyridin-3-ylamino)pyridine-3-yl)-3-methylpiperazine-1-carboxylate 105c

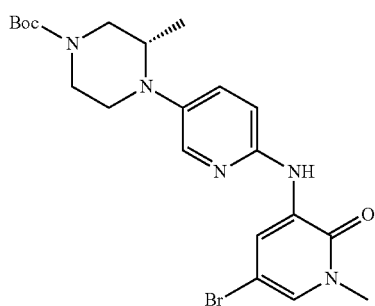

A 100-mL single-neck round-bottomed flask equipped with a magnetic stirrer and reflux condenser was charged with 1,4-dioxane (50 mL), 105b (4.0 g, 13.7 mmol), 3,5-dibromo-1-methylpyridin-2(1H)-one (5.5 g, 20.8 mmol), and cesium carbonate (11 g, 35 mmol). After bubbling nitrogen through the resulting mixture for 30 minutes, XantPhos (272 mg, 0.47 mmol) and tris(dibenzylideneacetone)dipalladium(0) (430 mg, 0.47 mmol) were added, and the reaction mixture was heated at reflux for 3 h. After this time the reaction was cooled to room temperature, partitioned between ethyl acetate (300 mL) and water (300 mL), and filtered. The aqueous layer was separated and extracted with ethyl acetate (150 mL×2). The organic layers were combined, washed with brine (150 mL), and dried over sodium sulfate. The drying agent was removed by filtration and the filtrate was concentrated under reduced pressure. The residue was purified on flash column eluting with 50:1 CH$_2$Cl$_2$/methanol to afford 105c as a yellow solid (5.4 g, 83%). LCMS: [M+H]$^+$ 478

Example 105d (3S)-5-Bromo-1-methyl-3-(5-(2-methylpiperazin-1-yl)pyridin-2-ylamino)pyridine-2(1H)-one 105d

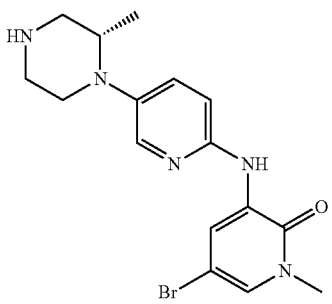

A mixture of 105c (3.1 g, 6.5 mmol) and 4.0 M HCl/dioxane (10 mL) was stirred for 5 h at room temperature. It was then concentrated in vacuo. The residue was basified with aqueous 1.0M NaOH and extracted twice with CH$_2$Cl$_2$. The combined organic layers were washed with water and concentrated under reduced pressure to give 105d as a yellow solid (2.3 g, 95%). LCMS: [M+H]$^+$ 380.

Example 105e (3S)-5-Bromo-1-methyl-3-(5-(2-methyl-4-(oxetan-3-yl)piperazine-1-yl)pyridine-2-ylamino)pyridin-2(1H)-one 105e

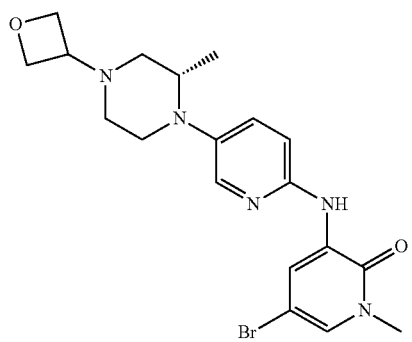

105e

A mixture of 105d (2.35 g, 6.2 mmol) and oxetan-3-one (0.49 g, 6.8 mmol) NaBH$_3$CN (4.75 g, 22.5 mmol), and zinc chloride (3 g, 22.7 mmol) in methanol (125 mL) was stirred for 5 hours at 50° C. The mixture was added to water and extracted with CH$_2$Cl$_2$ three times. The organic layers were concentrated under reduced pressure. The residue was purified by column chromatography eluting with 25:1 CH$_2$Cl$_2$/methanol to give 105e as a yellow solid (2.6 g, 98%). LCMS: [M+H]$^+$ 434.

Example 105f (3S)-1-methyl-3-(5-(2-methyl-4-(oxetan-3-yl)piperazine-1-yl)pyridin-2-ylamino)-5-(4,4,5,5-tetramethyl-1,3,2-dioxaborolan-2-yl)pyridin-2(1H)-one 105f

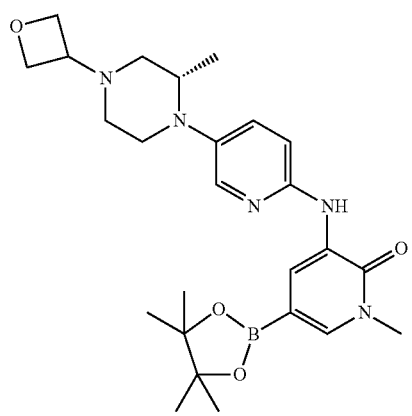

105f

A 100 mL single-neck round-bottomed flask equipped with a magnetic stirrer and a reflux condenser was charged with 105e (1.0 g, 1.0 eq., 2.3 mmol), Pin$_2$B$_2$ (1.46 g, 2.50 eq., 5.75 mmol), Pd$_2$(dba)$_3$ (105 mg, 0.05 eq., 0.125 mmol), X-Phos (93 mg, 0.1 eq., 0.23 mmol), KOAc (676 mg, 3.0 eq., 6.9 mmol), and dioxane (50 mL). After three cycles of vacuum/argon flush, the mixture was heated at 90° C. for 4 h. It was then cooled to room temperature and filtered. The filtrate was concentrated under reduced pressure and the resulting residue was washed with 3:1 petroleum ether/ethyl acetate (80 mL) to afford 105f as yellow solid (1.0 g, 90%). MS: [M+H]$^+$ 482.

Example 105g (S)-2-(6-tert-Butyl-8-fluoro-1-oxophthalazin-2(1H)-yl)-4-(1-methyl-5-(5-(2-methyl-4-(oxetan-3-yl)piperazin-1-yl)pyridin-2-ylamino)-6-oxo-1,6-dihydropyridin-3-yl)nicotinaldehyde 105g

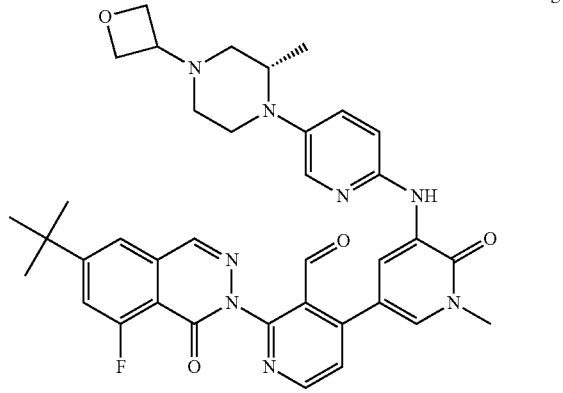

105g

A round-bottomed flask was charged with 2-(6-tert-butyl-8-fluoro-1-oxophthalazin-2(1H)-yl)-4-chloronicotinaldehyde 103b (100 mg, 0.28 mmol), 105f (135 mg, 0.28 mmol), PdCl$_2$(dppf) (25 mg, 0.03 mmol), K$_3$PO$_4$.3H$_2$O (149 mg, 0.56 mmol), THF (10 mL), and H$_2$O (5 mL). After three cycles of vacuum/argon flush, the mixture was heated at 70° C. for 6 h. It was then filtered and the filtrate was evaporated in vacuo. The residue was purified on flash column chromatography eluting with 1:3 petroleum/ethyl acetate to afford 105g as a yellow solid (113 mg, 60%). LCMS: [M+H]$^+$ 679

Example 105

(S)-6-tert-butyl-8-fluoro-2-(3-(hydroxymethyl)-4-(1-methyl-5-(3-methyl-5-(4-(oxetan-3-yl)piperazine-1-yl)pyridin-2-ylamino)-6-oxo-1,6-dihydropyridin-3-yl)pyridin-2-yl)phthalazin-1(2H)-one 105

A mixture of 105g (100 mg, 0.15 mmol), NaBH$_4$ (17 mg, 0.45), and CH$_3$OH (10 mL) was stirred at 25° C. for 1 h. The mixture was extracted with CH$_2$Cl$_2$ (10 mL×2). The combined CH$_2$Cl$_2$ extracts were concentrated under reduced pressure. The residue was purified by reverse-phase prep-HPLC to afford 105 (65 mg, 65%). LCMS: [M+H]$^+$ 681. $^1$H NMR (500 MHz, DMSO-d6) δ 8.62 (d, J=2.0, 1H), 8.53-8.57 (m, 1H), 8.42 (s, 2H), 7.90 (d, J=1.5, 1H), 7.85 (d, J=2.0, 1H), 7.76-7.79 (m, 1H), 7.52 (d, J=5.0, 1H), 7.46 (d, J=2.0, 1H), 7.36-7.38 (m, 1H), 7.24-7.26 (m, 1H), 4.54-4.57 (m, 2H), 4.46-4.48 (m, 1H), 4.40-4.41 (m, 3H), 3.68-3.70 (m, 1H), 3.57 (s, 3H), 3.37-3.40 (m, 1H), 3.09-3.11 (m, 1H), 2.93-2.95 (m, 1H), 2.52-2.54 (m, 2H), 2.32-2.36 (m, 2H), 2.18 (s, 1H), 1.39 (s, 9H), 0.93 (d, J=6.0, 3H)

Example 106a (R)-1-Methyl-3-(5-(2-methyl-4-(oxetan-3-yl)piperazine-1-yl)pyridin-2-ylamino)-5-(4,4,5,5-tetramethyl-1,3,2-dioxaborolan-2-yl)pyridin-2(1H)-one 106a

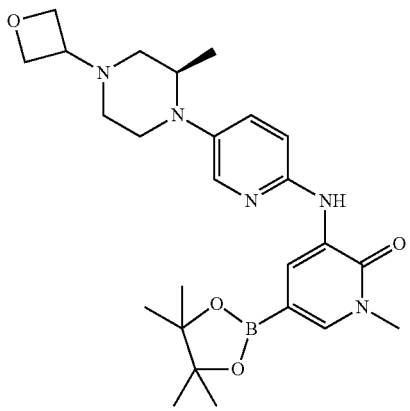

106a

To a solution of (R)-5-bromo-1-methyl-3-(5-(2-methyl-4-(oxetan-3-yl)piperazine-1-yl)pyridin-2-ylamino)pyridin-2(1H)-one (2.0 g, 4.60 mmol), 4,4,4',4',5,5,5',5'-octa-methyl-2,2'-bi(1,3,2-dioxaborolane) (3.50 g, 13.80 mmol) in dioxane (50 mL) was added $PdCl_2(dppf)$ (377.10 mg, 0.46 mmol) and KOAc (2.70 g, 27.80 mmol). See FIG. 6. The mixture was stirred at 100° C. for 12 h under argon. The mixture was filtered and the filtrate was evaporated in vacuo. The residue was purified by column chromatography eluting with $CH_2Cl_2$/methanol (15:1) to give 106a (1.10 g, 49%) as a brown solid. MS: $[M+H]^+$ 482.3

Example 106b (R)-2-(6-tert-Butyl-8-fluoro-1-oxophthalazin-2(1H)-yl)-4-(1-methyl-5-(5-(2-methyl-4-(oxetan-3-yl)piperazine-1-yl)pyridin-2-ylamino)-6-oxo-1,6-dihydro-pyridin-3-yl)nicotinaldehyde 106b

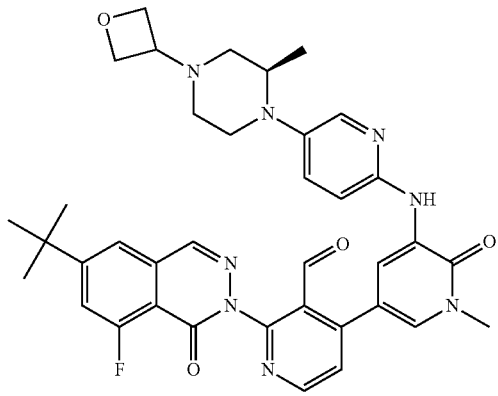

106b

A mixture of 106a (260.0 mg, 0.56 mmol), 2-(6-tert-butyl-8-fluoro-1-oxophthalazin-2(1H)-yl)-4-chloronicotinaldehyde 103b (200.0 mg, 0.56 mmol), $PdCl_2(dppf)$ (50.0 mg, 0.056 mmol), NaOAc (90.0 mg, 1.1 mmol), $K_3PO_4$ (300 mg, 1.1 mmol) in acetonitrile (30 mL) was heated at 100° C. for 3 h. The solvent was evaporated in vacuo. The residue was purified by flash column chromatography eluting with $CH_2Cl_2$/methanol (10:1) to afford 106b (120 mg, 34%) as a brown solid. LCMS: $[M+H]^+$ 679.3

Example 106

(R)-6-tert-Butyl-8-fluoro-2-(3-(hydroxymethyl)-4-(1-methyl-5-(5-(2-methyl-4-(oxetan-3-yl)piperazine-1-yl)pyridin-2-ylamino)-6-oxo-1,6-dihydropyridin-3-yl)pyridin-2-yl)phthalazin-1(2H)-one 106

A solution of 106b (90.0 mg, 0.13 mmol) in MeOH (10 mL) was added $NaBH_4$ (15.0 mg, 0.39 mmol). The mixture was stirred at 20° C. for 2 h. It was then evaporated and the residue was purified by reverse-phase prep-HPLC to afford 106 (7.3 mg, 8%) as a white solid. LCMS: $(M+H)^+$ 681.4. $^1H$ NMR (500 MHz, DMSO) δ 8.63 (d, J=2.5, 1H), 8.57 (d, J=5.0, 1H), 8.54 (d, J=2.0, 1H), 8.47 (s, 1H), 7.91 (s, 1H), 7.86 (d, J=3.0, 1H), 7.78 (d, J=12.5, 1H), 7.53 (d, J=5.0, 1H), 7.47 (d, J=2.0, 1H), 7.36-7.39 (m, 1H), 7.25 (d, J=9.5, 1H), 4.90 (s, 1H), 4.54-4.58 (m, 2H), 4.47 (t, J=6.0, 1H), 4.39-4.43 (m, 3H), 3.69 (s, 1H), 3.61 (s, 3H), 3.37-3.42 (m, 1H), 3.09-3.11 (m, 1H), 2.95 (t, J=9.0, 1H), 2.54-2.56 (m, 1H), 2.30-2.37 (m, 2H), 2.19 (t, J=8.0, 1H), 1.39 (s, 9H), 0.94-0.93 (d, J=6.5, 3H)

Example 107a (R)-2-(6-tert-butyl-8-fluoro-1-oxophthalazin-2(1H)-yl)-4-fluoro-6-(1-methyl-5-(5-(2-methyl-4-(oxetan-3-yl)piperazin-1-yl)pyridin-2-ylamino)-6-oxo-1,6-dihydro-pyridin-3-yl)benzaldehyde 107a A 50-mL single-neck round-bottomed flask equipped with a magnetic stirrer and a reflux condenser was charged with (R)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one (173 mg, 1.0 eq., 0.36 mmol), 2-bromo-6-(6-tert-butyl-8-fluoro-1-oxophthalazin-2(1H)-yl)-4-fluorobenzaldehyde 101i (152 mg, 1.0 eq., 0.36 mmol), $K_3PO_4$ (152 mg, 2.0 eq., 0.72 mmol), $PdCl_2(dppf)$ (26 mg, 0.1 eq., 0.036 mmol), NaOAc (59 mg, 2.0 eq., 0.72 mmol), $CH_3CN$ (20 mL), and $H_2O$ (0.8 mL). After three cycles of vacuum/argon flush, the mixture was heated at 80° C. for 2 h. It was then cooled to room temperature and filtered. The filtrate was concentrated under reduced pressure and the resulting residue was purified by silica-gel column chromatography eluting with 40:1 DCM/EtOH to afford 107a as yellow solid (77 mg, 31%). MS: $[M+H]^+$ 696.3.

Example 107

(R)-6-tert-Butyl-8-fluoro-2-(5-fluoro-2-(hydroxymethyl)-3-(1-methyl-5-(5-(2-methyl-4-(oxetan-3-yl)piperazin-1-yl)pyridin-2-ylamino)-6-oxo-1,6-dihydropyridin-3-yl)phenyl)phthalazin-1(2H)-one 107

A 50-mL single-neck round-bottomed flask equipped with a magnetic stirrer was charged with 107a (77 mg, 1.0 eq., 0.11 mmol), $NaBH_4$ (21 mg, 5.0 eq., 0.55 mmol), and MeOH (10 mL). The mixture was stirred at room temperature for 1 h. It was then filtered and the filtrate was concentrated. The residue was purified by reverse-phase prep-HPLC to afford 107 (38 mg, 49%). MS: $[M+H]^+$ 698.3. $^1H$ NMR (500 MHz, $CDCl_3$) δ 8.59 (d, J=2.0 Hz, 1H), 8.29 (d, J=2.5 Hz, 1H), 7.98 (d, J=2.5 Hz, 1H), 7.81 (s, 1H), 7.56-7.54 (m, 2H), 7.40 (s, 1H), 7.31-7.27 (m, 2H), 7.11-7.10 (m, 1H), 6.81 (d, J=9.0 Hz, 1H), 4.71-4.62 (m, 4H), 4.35 (s, 2H), 3.73-3.70 (m, 4H), 3.53-3.46 (m, 2H), 3.08 (t, J=5.0 Hz, 2H), 2.56-2.46 (m, 3H), 2.22-2.18 (m, 1H), 1.43 (s, 9H), 0.98 (d, J=6.5 Hz, 3H).

Example 108a 2-(6-tert-Butyl-8-fluoro-1-oxophthalazin-2(1H)-yl)-6-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-4-fluorobenzaldehyde 108a

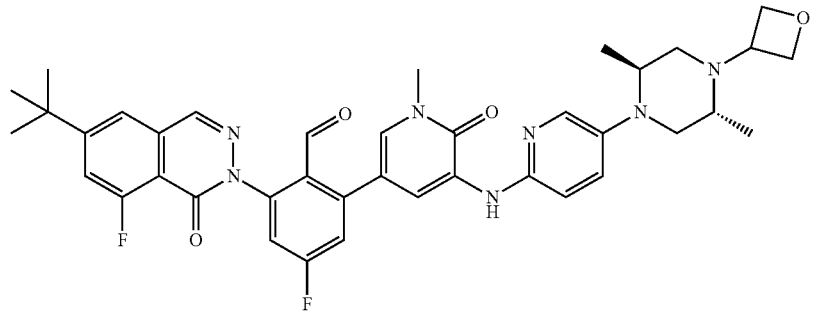 [SMILES: C[C@@H]1CN(c2ccc(Nc3cc(-c4cc(F)cc(-n5ncc6cc(C(C)(C)C)cc(F)c6c5=O)c4C=O)cn(C)c3=O)nc2)[C@@H](C)CN1C1COC1]

A 25-mL single-neck round-bottomed flask equipped with a magnetic stirrer and a reflux condenser was charged with 2-bromo-6-(6-tert-butyl-8-fluoro-1-oxophthalazin-2(1H)-yl)-4-fluorobenzaldehyde 102b (84 mg, 0.20 mmol), 3-(5-((2S,5R)-2,5-dimethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one (99 mg, 0.20 mmol), Pd(dppf)Cl$_2$ (15 mg, 0.02 mmol), K$_3$PO$_4$ (127 mg, 0.6 mmol), sodium acetate (49 mg, 0.6 mmol), acetonitrile (5 mL), and water (0.5 mL). After three cycles of vacuum/argon flush, the mixture was heated at reflux for 2 h. It was then cooled to room temperature and filtered. The filtrate was concentrated under reduced pressure and the resulting residue was purified by silica-gel column chromatography eluting with 30:1 dichloromethane/methanol to 108a as a white solid (54 mg, 38%). MS: [M+H]$^+$ 710.3

Example 108

6-tert-Butyl-2-(3-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-5-fluoro-2-(hydroxymethyl)phenyl)-8-fluorophthalazin-1(2H)-one 108

At 0° C., to a solution of 2-(6-tert-butyl-8-fluoro-1-oxophthalazin-2(1H)-yl)-6-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-4-fluorobenzaldehyde 108a (54 mg, 0.076 mmol) in methanol (5 mL) was added sodium borohydride (9.0 mg, 0.23 mmol). The mixture was stirred for 60 minutes. It was then quenched with water (1.0 mL) and concentrated under reduced pressure. The residue was purified by reverse-phase prep-HPLC to afford 108 (12 mg, 22%). MS: [M+H]$^+$ 712.3. $^1$H NMR (500 MHz, CDCl$_3$) δ 8.63 (d, J=2.5 Hz, 1H), 8.31 (d, J=2.0 Hz, 1H), 8.05 (d, J=2.5 Hz, 1H), 7.87 (s, 1H), 7.58-7.55 (m, 2H), 7.44 (d, J=2.0 Hz, 1H), 7.36 (s, 1H), 7.30 (d, J=2.0 Hz, 1H), 7.12 (dd, J=2.5, 8.5 Hz, 1H), 6.82 (d, J=8.5 Hz, 1H), 4.76-4.73 (m, 2H), 4.68-4.61 (m, 2H), 4.38-4.36 (m, 2H), 3.74-3.72 (m, 2H), 3.72 (s, 3H), 3.22-3.20 (m, 1H), 2.94-2.92 (m, 1H), 2.74-2.72 (m, 2H), 2.50-2.48 (m, 1H), 1.98-1.96 (m, 1H), 1.45 (s, 9H), 0.93-0.91 (m, 6H).

Example 109a

3-Bromo-5-(6-tert-butyl-8-fluoro-1-oxo-1,2-dihydrophthalazin-2-yl)pyridine-4-carbaldehyde 109a

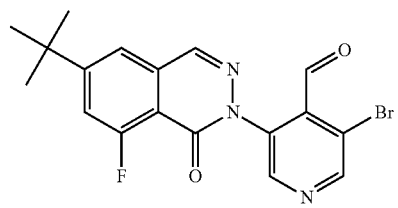

A sealed tube equipped with a magnetic stirrer was charged with 6-tert-butyl-8-fluoro-1,2-dihydrophthalazin-1-one 101h (220 mg, 1.0 mmol), 3,5-dibromopyridine-4-carbaldehyde (530 mg, 2.0 mmol), CuI (190 mg, 1.0 mmol), 4,7-dimethoxy-1,10-phenanthroline (244 mg, 1.0 mmol), Cs$_2$CO$_3$ (652 mg, 2.0 mmol) and dioxane (8 mL). After three cycles of vacuum/argon flush, the mixture was heated at 110° C. for 5 h. It was then filtered and the filtrate was evaporated in vacuo. The residue was purified by silica gel column chromatography eluting with ethyl acetate/petroleum ether (1:3, V/V) to afford 109a (118 mg, 29.3%) as a solid. LCMS: [M+H]$^+$ 406

Example 109b 3-(6-tert-Butyl-8-fluoro-1-oxo-1,2-dihydrophthalazin-2-yl)-5-[1-methyl-5-({5-[(2S)-2-methyl-4-(oxetan-3-yl)piperazin-1-yl]pyridin-2-yl}amino)-6-oxo-1,6-dihydro-pyridin-3-yl]pyridine-4-carbaldehyde 109b

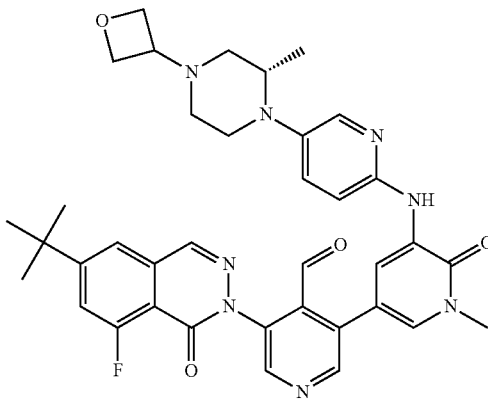

A 25 mL single-neck round-bottomed flask equipped with a magnetic stirrer and reflux condenser was charged with 109a (118 mg, 0.29 mmol), 1-methyl-3-({5-[(2S)-2-methyl-4-(oxetan-3-yl)piperazin-1-yl]pyridin-2-yl}amino)-5-(tetramethyl-1,3,2-dioxaborolan-2-yl)-1,2-dihydropyridin-2-one 105f (140 mg, 0.29 mmol), Pd(dppf)Cl$_2$ (24.8 mg, 0.03 mmol), KOAc (58.9 mg, 0.60 mmol), K$_3$PO$_4$.3H$_2$O (159.8 mg, 0.60 mmol), acetonitrile (6 mL) and water (3 d). After three cycles of vacuum/argon flush, the mixture was heated at 110° C. for 2 h. The reaction mixture was then cooled to room temperature, filtered and the filtrate was evaporated in vacuo. The residue was purified by prep-TLC developing with dichloromethane/methanol (20:1, UV) to afford 109b (95 mg, 36%) as a red solid. MS: [M+H]$^+$ 679

Example 109

(S)-6-tert-butyl-8-fluoro-2-(4-(hydroxymethyl)-5-(1-methyl-5-(5-(2-methyl-4-(oxetan-3-yl)piperazin-1-yl)pyridin-2-ylamino)-6-oxo-1,6-dihydropyridin-3-yl)pyridin-3-yl)phthalazin-1(2H)-one 109

To a suspension of 109b (95 mg, 0.106 mmol) at 0° C. in methanol (5 mL) was added sodium borohydride (24 mg, 0.636 mmol) and the mixture was stirred for 30 minutes. Then the reaction mixture was quenched with water (1.0 mL) and concentrated. The residue was purified by reverse-phase prep-HPLC to afford 109 (13.5 mg, 18.7%). LCMS: [M+H]$^+$ 681.

$^1$H NMR (500 MHz, CDCl$_3$) δ 8.76 (s, 1H), 8.65 (d, J=2.0, 1H), 8.61 (s, 1H), 8.32 (d, J=2.5, 1H), 7.96 (d, J=3.0, 1H), 7.82 (s, 1H), 7.56-7.58 (m, 2H), 7.40 (d, J=2.0, 1H), 7.28-7.31 (m, 1H), 6.81 (d, J=9.0, 1H), 4.61-4.70 (m, 4H), 4.43 (s, 2H), 3.95 (s, 1H), 3.72 (s, 3H), 3.45-3.53 (m, 2H), 3.07 (t, J=5.25, 2H), 2.43-2.56 (m, 3H), 2.18-2.22 (m, 1H), 1.43 (s, 9H), 0.99 (d, J=6.5, 3H)

Example 110a 2-(6-tert-Butyl-8-fluoro-1-oxophthalazin-2(1H)-yl)-4-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)nicotinaldehyde 110a

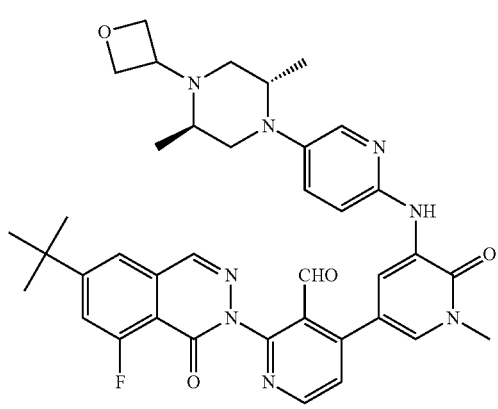

A 100-mL single-neck round-bottomed flask was charged with 2-(6-tert-butyl-8-fluoro-1-oxophthalazin-2(1H)-yl)-4- chloronicotinaldehyde 103b (216 mg, 0.6 mmol), 3-(5-((2S, 5R)-2,5-dimethyl-4-(oxetan-3-yl)piperazin-1-yl)pyridin-2-ylamino)-1-methyl-5-(4,4,5-trimethyl-1,3,2-dioxaborolan-2-yl)pyridin-2(1H)-one (360 mg, 0.72 mmol), Pd(dppf)Cl$_2$ (30 mg, 0.03 mmol), K$_3$PO$_4$ (270 mg, 1.2 mmol), and NaOAc.3H$_2$O (180 mg, 1.2 mmol) in CH$_3$CN (80 mL). The system was evacuated and refilled with N$_2$. The reaction mixture was heated at 100° C. for 2 h. It was then cooled to room temperature and filtered. The filtrate was concentrated under reduced pressure and the resulting residue was purified by flash column chromatography eluting with 25:1 of CH$_2$Cl$_2$/MeOH to afford 110a (160 mg, 42%) as a yellow brown solid. MS: [M+H]$^+$ 693.3.

Example 110

6-tert-Butyl-2-(4-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-8-fluorophthalazin-1(2H)-one 110

A mixture of 110a (100 mg, 0.15 mmol) and NaBH$_4$ (20 mg, 0.45 mmol) in MeOH (30 mL) was stirred at 30° C. for 2 h. The mixture was quenched with water and extracted with EtOAc (10 mL×3). The combined EtOAc extract was concentrated under reduced pressure and the residue was purified by reverse-phase prep-HPLC to afford 110 (80 mg, 80%). MS: [M+H]$^+$ 695.3. $^1$H NMR (500 MHz, CDCl$_3$) δ 8.72 (d, J=2, 1H), 8.67 (d, J=5, 1H), 8.35 (d, J=2.5, 1H), 8.05 (d, J=3, 1H), 7.88 (s, 1H), 7.68 (d, J=2.5, 1H), 7.58-7.55 (m, 3H), 7.38-7.36 (m, 1H), 6.82 (d, J=8.5, 1H), 4.78-4.71 (m, 2H), 4.67-4.61 (m, 2H), 4.50 (s, 2H), 4.07 (t, J=6, 1H), 3.78-3.74 (m, 4H), 3.22-3.20 (m, 1H), 2.92 (d, J=3, 1H), 2.77-2.71 (m, 2H), 2.51-2.48 (m, 1H), 1.20-1.95 (m, 1H), 1.45 (s, 9H), 0.93-0.90 (m, 6H)

Example 111a (S)-tert-Butyl 3-Ethyl-4-(6-nitropyridin-3-yl)piperazine-1-carboxylate 111a

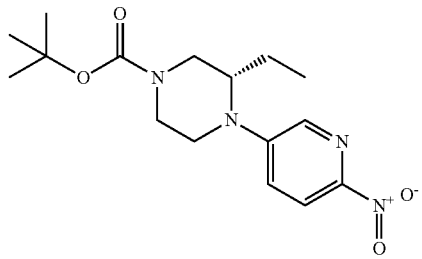

A 250-mL single-neck round-bottomed flask equipped with a magnetic stirrer and a reflux condenser was charged with 1,4-dioxane (50 mL), 5-bromo-2-nitropyridine (2.02 g, 10 mmol), (S)-tert-butyl 3-ethylpiperazine-1-carboxylate (2.14 g, 10.0 mmol), Pd$_2$(dba)$_3$ (458 mg, 0.50 mmol), Xant-Phos (576 mg, 1.0 mmol), and cesium carbonate (6.52 g, 20 mmol). After three cycles of vacuum/argon flush, the mixture was heated at 100° C. overnight. After this time the reaction was cooled to room temperature. It was then filtered and the filtrate was evaporated under reduced pressure. The residue was purified by silica-gel column chromatography eluting with 3:1 petroleum ether/ethyl acetate to afford 111a (700 mg, 22%) as a yellow solid. MS: [M+H]$^+$ 336

Example 111b (S)-tert-Butyl 4-(6-Aminopyridin-3-yl)-3-ethylpiperazine-1-carboxylate 111b A 100-mL single-neck round-bottomed flask was purged with nitrogen and charged with 111a (0.7 g, 2.08 mmol), 10% palladium on carbon (50% wet, 208 mg), and methanol (40 mL). The mixture was evacuated, charged with hydrogen gas, and stirred at room temperature for 6 h. The hydrogen was then evacuated and nitrogen was charged into the flask. The catalyst was removed by filtration through a pad of CELITE® and the filtrate was concentrated under reduced pressure to afford 111b (568 mg, 89%). MS: [M+H]$^+$ 306

Example 111c (S)-tert-Butyl 4-(6-(5-Bromo-1-methyl-2-oxo-1,2-dihydropyridin-3-ylamino)pyridin-3-yl)-3-ethylpiperazine-1-carboxylate 111c A 100-mL single-neck round-bottomed flask equipped with a magnetic stirrer and a reflux condenser was charged with 1,4-dioxane (50 mL), 111b (568 mg, 1.86 mmol), 3,5-dibromo-1-methylpyridin-2(1H)-one (498 mg, 1.86 mmol), Pd$_2$(dba)$_3$ (85 mg, 0.093 mmol), XantPhos (107 mg, 0.186 mmol), and cesium carbonate (1.198 g, 3.72 mmol). After three cycles of vacuum/argon flush, the mixture was heated at 100° C. for 6 h. It was then filtered and the filtrate was evaporated under reduced pressure. The residue was purified by silica-gel column chromatography eluting with 100:1 dichloromethane/methanol to afford 111c (502 mg, 55%) as a yellow solid. MS: [M+H]$^+$ 492.

Example 111d (S)-5-Bromo-3-(5-(2-ethylpiperazin-1-yl)pyridin-2-ylamino)-1-methylpyridin-2(1H)-one 111d A mixture of 111c (502 mg, 1.02 mmol), dichloromethane (2 mL), and 4.0 M HCl/dioxane (4 mL) was stirred at room temperature for 5 h. It was then concentrated under reduced pressure to afford crude 111d as a yellow solid (263 mg, 66%), which was used in the next step without further purification. MS: [M+H]$^+$ 392.

Example 111e (S)-5-Bromo-3-(5-(2-ethyl-4-(oxetan-3-yl)piperazin-1-yl)pyridin-2-ylamino)-1-methylpyridin-2(1H)-one 111e

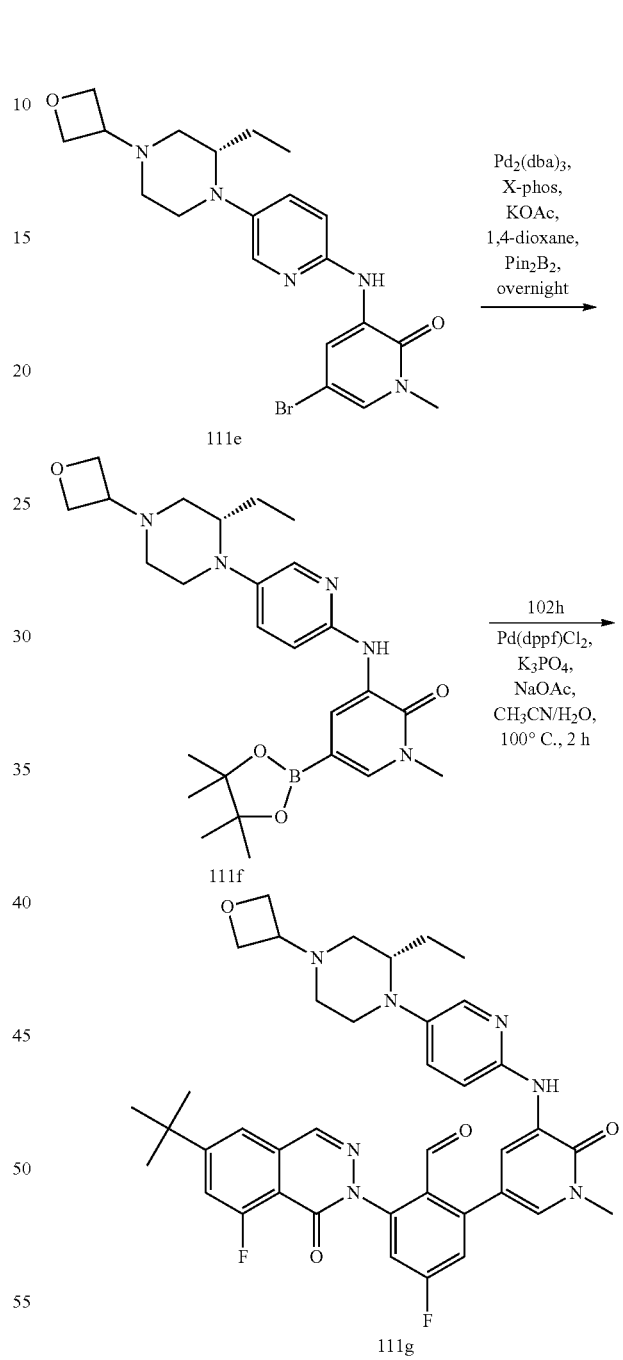

A mixture of 111d (263 mg, 0.67 mmol), oxetan-3-one (96 mg, 1.34 mmol), NaBH$_3$CN 104 mg, 1.68 mmol), and zinc chloride (227 mg, 1.68 mmol) in methanol (10 mL) was stirred at 50° C. for 5 hours. water (10 mL) was then added to the reaction. The resulting mixture was concentrated under reduced pressure. The residue was extracted with dichloromethane three times. The combined organic layer was concentrated under reduced pressure and the residue was purified by silica-gel column chromatography eluting with 50:1 dichloromethane/methanol to afford 111e (203 mg, 68%). MS: [M+H]+ 448.

Example 111f (S)-3-(5-(2-Ethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 111f A 100-mL single-neck round-bottomed flask equipped with a magnetic stirrer and a reflux condenser was charged with 111e (3219 mg, 7.20 mmol), Pin$_2$B$_2$ (9072 mg, 36.0 mmol), Pd$_2$(dba)$_3$ (329 mg, 0.36 mmol), X-phos (302 mg, 0.72 mmol), potassium acetate (2117 mg, 21.6 mmol), and dioxane (50 mL). After three cycles of vacuum/argon flush, the mixture was heated at 60° C. for 16 h. It was then cooled to room temperature and filtered. The filtrate was concentrated under reduced pressure and the resulting residue was washed with 8:1 petroleum ether/ethyl acetate (80 mL) to afford 111f as a yellow solid (3.0 g, 84%).

Example 111g (S)-2-(6-tert-Butyl-8-fluoro-1-oxophthalazin-2(1H)-yl)-6-(5-(5-(2-ethyl-4-(oxetan-3-yl)piperazin-1-yl)pyridin-2-ylamino)-1-methyl-6-oxo-1,6-dihydropyridin-3-yl)-4-fluorobenzaldehyde 111g A 25-mL single-neck round-bottomed flask equipped with a magnetic stirrer and a reflux condenser was charged with 2-bromo-6-(6-tert-butyl-8-fluoro-1-oxophthalazin-2(1H)-yl)-4-fluorobenzaldehyde 102h (168 mg, 0.40 mmol), 111f (198 mg, 0.40 mmol), Pd(dppf)Cl$_2$ (15 mg, 0.02 mmol), K$_3$PO$_4$ (170 mg, 0.8 mmol), sodium acetate (66 mg, 0.8 mmol), acetonitrile (5 mL), and water (0.8 mL). After three cycles of vacuum/argon flush, the mixture was heated at reflux for 2 h. It was then cooled to room temperature and filtered. The filtrate was concentrated under reduced pressure and the resulting residue was purified by silica-gel column chromatography eluting with 30:1 dichloromethane/methanol to afford 111g as a white solid (100 mg, 35%). MS: [M+H]+ 710.3

Example 111

(S)-6-tert-Butyl-2-(3-(5-(5-(2-ethyl-4-(oxetan-3-yl) piperazin-1-yl)pyridin-2-yl-amino)-1-methyl-6-oxo-1,6-dihydropyridin-3-yl)-5-fluoro-2-(hydroxymethyl)phenyl)-8-fluorophthalazin-1(2H)-one 111

To a solution of 111g (100 mg, 0.14 mmol) at 0° C. in methanol (5 mL) was added sodium borohydride (16.0 mg, 0.42 mmol). The mixture was stirred for 60 minutes. It was then quenched with water (1.0 mL) and concentrated. The residue was purified by reverse-phase prep-HPLC to afford 111 (32 mg, 32%). MS: [M+H]+ 712.3. $^1$H NMR (500 MHz, CDCl$_3$) δ 8.57 (d, J=2.0 Hz, 1H), 8.30 (d, J=2.0 Hz, 1H), 7.94 (s, 1H), 7.80 (s, 1H), 7.58 (s, 2H), 7.41 (d, J=2.0 Hz, 1H), 7.31-7.28 (m, 2H), 7.12 (dd, J=2.5, 8.5 Hz, 1H), 6.82 (d, J=9.0 Hz, 1H), 4.73-4.70 (m, 4H), 4.37 (s, 2H), 3.74-3.72 (m, 1H), 3.71 (s, 3H), 3.56-3.54 (m, 1H), 3.34-3.32 (m, 1H), 3.15-3.13 (m, 2H), 2.58-2.36 (m, 4H), 1.45 (s, 9H), 1.44-1.43 (m, 2H), 0.83 (t, J=7.5 Hz, 3H).

Example 112a (S)-2-(6-tert-Butyl-8-fluoro-1-oxophthalazin-2(1H)-yl)-4-(5-(5-(2-ethyl-4-(oxetan-3-yl)piperazin-1-yl) pyridin-2-ylamino)-1-methyl-6-oxo-1,6-dihydropyridin-3-yl)nicotinaldehyde 112a

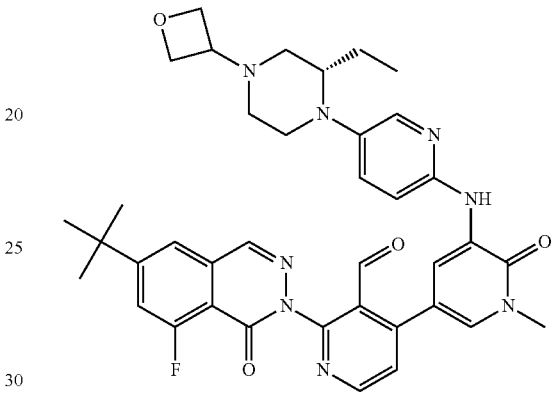

A 50-mL round bottom flask was charged with 2-(6-tert-butyl-8-fluoro-1-oxo-phthalazin-2(1H)-yl)-4-chloronicotinaldehyde 103b (150 mg, 0.43 mmol), (S)-3-(5-(2-ethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one (206 mg, 0.43 mmol), PdCl$_2$(dppf) (33 mg, 0.04 mmol), K$_3$PO$_4$ (202 mg, 0.86 mmol), NaOAc (71 mg, 0.86 mmol), and CH$_3$CN (10 mL), H$_2$O (2 mL). After three cycles of vacuum/argon flush, the mixture was heated at 100° C. for 3 h. It was then filtered and the filtrate was evaporated in vacuo. The residue was purified by flash column chromatography eluting with 1:3 petroleum/ethyl acetate to afford 112a as a yellow solid (146 mg, 49%). LCMS: [M+H]+ 693

Example 112

(S)-6-tert-Butyl-2-(4-(5-(5-(2-ethyl-4-(oxetan-3-yl) piperazin-1-yl)pyridin-2-ylamino)-1-methyl-6-oxo-1,6-dihydropyridin-3-yl)-3-(hydroxymethyl)pyridin-2-yl)-8-fluorophthalazin-1(2H)-one 112

A mixture of 112a (140 mg, 0.20 mmol), NaBH$_4$ (21 mg, 0.60) and CH$_3$OH (8 mL) was stirred at 25° C. for 1 h. Then the reaction mixture was quenched with water (10 mL), the mixture was extracted with CH$_2$Cl$_2$ (15 mL×2). The combined CH$_2$Cl$_2$ extract was concentrated under reduced pressure. The residue was purified with reverse-phase prep-HPLC to afford 112 (70 mg, 50%). LCMS: [M+H]+ 695. $^1$H NMR (500 MHz, DMSO) δ 8.50-8.60 (m, 2H), 8.44 (s, 1H), 7.90 (d, J=1.5, 1H), 7.82 (d, J=3.0, 1H), 7.75-7.78 (m, 1H), 7.51-7.53 (m, 1H), 7.45 (d, J=2.5, 1H), 7.33-7.35 (m, 1H), 7.22-7.24 (m, 1H), 4.47-4.59 (m, 2H), 4.36-4.45 (m, 4H), 3.60 (s, 3H), 3.46-3.50 (m, 1H), 3.38-3.41 (m, 3H), 3.14-3.17 (m, 1H), 2.96-3.00 (m, 1H), 2.60-2.64 (m, 1H), 2.50-2.55 (m, 1H), 2.14-2.17 (m, 1H), 2.06-2.10 (m, 1H), 1.66-1.69 (m, 1H), 1.39 (s, 9H), 1.21-1.28 (m, 1H), 0.77-0.80 (m, 3H)

Example 113a

5-Bromo-1-methyl-3-(pyrimidin-4-ylamino)pyridin-2(1H)-one 113a

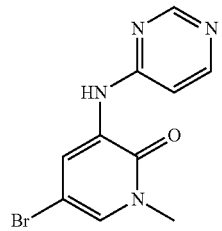 [SMILES: Cn1cc(Br)cc(Nc2ccncn2)c1=O]

A 100-mL single-neck round-bottomed flask equipped with a magnetic stirrer and nitrogen inlet was charged with 3,5-dibromo-1-methylpyridin-2(1H)-one (2.00 g, 21.0 mmol), 2-aminopyrimidine (5.61 g, 21.0 mmol), cesium carbonate (13.7 g, 42.1 mmol), DMF (5 mL) and 1,4-dioxane (70 mL). After bubbling nitrogen through the resulting suspension for 30 min, Xantphos (1.10 g, 1.89 mmol) and tris(dibenzylideneacetone)dipalladium(0) (963 mg, 1.05 mmol) were added. A reflux condenser was attached to the flask, and the reaction mixture was heated at 100° C. for 4 h. After this time, the mixture was cooled to room temperature and diluted with 90:10 methylene chloride/methanol (150 mL) and water (100 mL), and the layers were separated. The aqueous layer was extracted with 90:10 methylene chloride/methanol (50 mL), and the combined organic layers were washed with brine and dried over sodium sulfate. The drying agent was removed by filtration. The filtrate was concentrated under reduced pressure, and the resulting residue was purified by flush column chromatography (silica, 90:10 methylene chloride/methanol) to afford 113a in 58% yield (3.42 g) as an amorphous light green solid: mp 217-219° C.; $^1$H NMR (500 MHz, CDCl$_3$) δ 9.29 (s, 1H), 8.77 (s, 1H), 8.72 (d, J=2.5 Hz, 1H), 8.36 (d, J=6.0 Hz, 1H), 7.69 (d, J=2.5 Hz, 1H), 7.37 (dd, J=5.5, 1.0 Hz, 1H), 3.53 (s, 3H); MS (ESI+) m/z 281.0 (M+H).

Example 113b

1-Methyl-3-(pyrimidin-4-ylamino)-5-(4,4,5,5-tetramethyl-1,3,2-dioxaborolan-2-yl)pyridin-2(1H)-one 113b

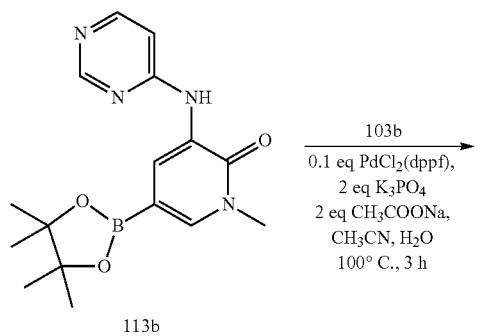

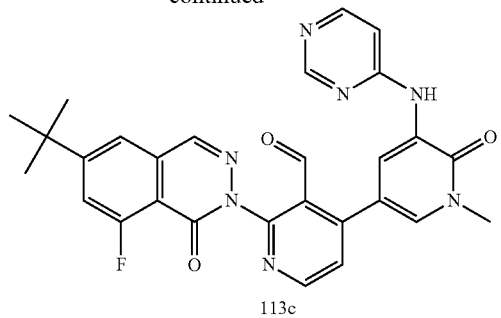

A 250-mL single-neck round-bottomed flask equipped with a magnetic stirrer and a condenser was charged with 113a (4.0 g, 14 mmol), X-phos (400 mg, 0.7 mmol), Pd2(dba)3 (635 mg, 0.7 mmol), potassium acetate (7.3 mg, 28 mmol), 4,4,4',4',5,5,5',5'-octamethyl-2,2'-bi(1,3,2-dioxaborolane) (10.6 g, 42 mmol), and 1,4-dioxane (100 mL). After three cycles of vacuum/argon flush, the reaction mixture was heated at 60° C. for 8 h. It was then cooled to room temperature and filtered. The filtrate was concentrated under reduced pressure and the resulting residue was purified by flush column chromatography eluting with 5:1 petroleum ether/ethyl acetate to afford 113b as a pale yellow solid (3.8 mg, 82%). MS: [M+H]$^+$ 329.5.

Example 113c 2-(6-tert-Butyl-8-fluoro-1-oxophthalazin-2(1H)-yl)-4-(1-methyl-6-oxo-5-(pyrimidin-4-ylamino)-1,6-dihydropyridin-3-yl)nicotinaldehyde 113c A 100-mL round-bottomed flask equipped with a reflux condenser was charged with 2-(6-tert-butyl-8-fluoro-1-oxophthalazin-2(1H)-yl)-4-chloronicotinaldehyde 103b (110 mg, 0.31 mmol), 113b (100 mg, 0.31 mmol), PdCl$_2$(dppf) (25 mg, 0.030 mmol), K$_3$PO$_4$ (241 mg, 0.93 mmol), NaAcO (76 mg, 0.93 mmol), acetonitrile (15 mL), and water (0.5 mL). After three cycles of vacuum/argon flush, the mixture was heated at 100° C. for 3 h. It was then filtered and the filtrate was evaporated under reduced pressure. The residue was purified with silica-gel column chromatography eluting with 1:20 methanol/dichloromethane to afford 113c as a red solid (80 mg, 51%). MS-ESI: [M+H]$^+$ 526.3

Example 113

6-tert-butyl-8-fluoro-2-[3-(hydroxymethyl)-4-[1-methyl-6-oxo-5-(pyrimidin-4-ylamino)-3-pyridyl]-2-pyridyl]phthalazin-1-one 113

A mixture of 113c (80 mg, 0.14 mmol), NaBH$_4$ (27 mg, 0.70 mmol), and methanol (10 mL) was stirred at room temperature for 0.5 h. The mixture was quenched with water (2 mL) and concentrated under reduced pressure. The residue was purified with reverse-phase prep-HPLC to afford 113 (57 mg, 71%). MS-ESI: [M+H]$^+$ 528.3. $^1$H NMR (500 MHz, DMSO-d$_6$) δ 9.26 (s, 1H), 8.76 (d, J=2.5 Hz, 1H), 8.67 (s, 1H), 8.59 (d, J=5.0 Hz, 1H), 8.54 (d, J=2.5 Hz, 1H), 8.31 (d, J=6.0 Hz, 1H), 7.90 (d, J=1.5 Hz, 1H), 7.79-7.76 (m, 1H), 7.69 (d, J=2.0 Hz 1H), 7.54 (d, J=5.0, Hz 1H), 7.34-7.32 (m, 1H), 4.94 (t, J=5.0 Hz, 1H), 4.42-4.40 (m, 2H), 3.62 (s, 3H), 1.39 (s, 9H).

Example 114a

5-Bromo-1-methyl-3-(2-methylpyrimidin-4-ylamino)pyridin-2(1H)-one 114a

Following the procedure in Example 113a, and starting with 2-methylpyrimidin-4-amine (2.0 g, 18.3 mmol) and 3,5-dibromo-1-methylpyridin-2(1H)-one (9.6 g, 36 mmol) afforded 114a as a yellow solid (2.3 g, 43.4%). MS: [M+H]$^+$ 295. $^1$H NMR (500 MHz, DMSO-d$_6$) δ 9.20 (s, 1H), 8.78 (s, 1H), 8.26 (d, J=4.5 Hz, 1H), 7.68 (s, 1H), 7.18 (d, J=4.5 Hz, 1H), 3.59 (s, 3H), 2.52 (s, 3H).

Example 114b

1-Methyl-3-(2-methylpyrimidin-4-ylamino)-5-(4,4,5,5-tetramethyl-1,3,2-dioxaborolan-2-yl)pyridin-2(1H)-one 114b

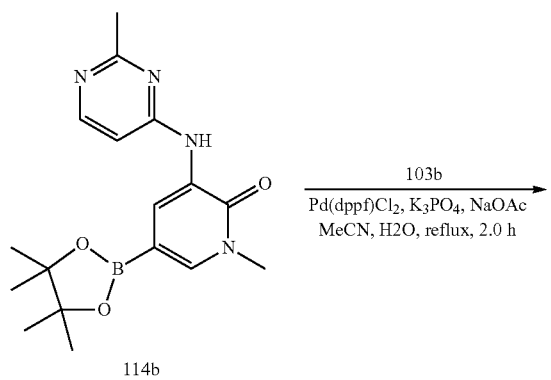

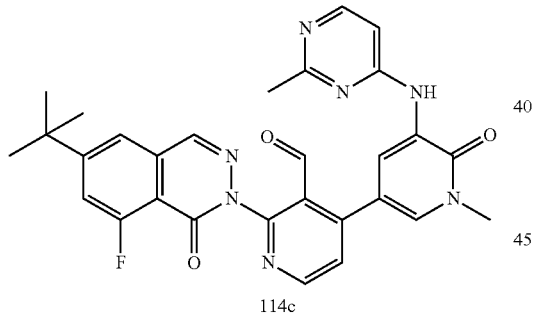

A 100-mL single-neck round-bottomed flask equipped with a magnetic stirrer and a reflux condenser was charged with bis(pinacolato) diboron (689 mg, 2.61 mmol), 1,4-dioxane (30 mL), 114a (307 mg, 1.04 mmol), Pd$_2$(dba)$_3$ (47 mg, 0.050 mmol), X-phos (48 mg, 0.10 mmol), and potassium acetate (305 mg, 3.12 mmol). The mixture was heated at 65° C. for 6 h. It was then filtered and the filtrate was evaporated in vacuo to afford 114b (300 mg, 84%) as a brown solid. MS: [M+H]$^+$ 342.2

Example 114c

2-(6-tert-Butyl-8-fluoro-1-oxophthalazin-2(1H)-yl)-4-(1-methyl-5-(2-methylpyrimidin-4-ylamino)-6-oxo-1,6-dihydropyridin-3-yl)nicotinaldehyde 114c A 50-mL single-neck round-bottomed flask equipped with a magnetic stirrer and a reflux condenser was charged with 114b (236 mg, 0.69 mmol), 2-(6-tert-butyl-8-fluoro-1-oxophthalazin-2(1H)-yl)-4-chloronicotinaldehyde 103b (250 mg, 0.69 mmol), PdCl$_2$(dppf) (29 mg, 0.035 mmol), K$_3$PO$_4$ (296 mg, 1.39 mmol), sodium acetate (114 mg, 1.39 mmol), acetonitrile (15 mL), and water (1 mL). The system was evacuated and refilled with N$_2$. The reaction mixture was heated at 100° C. for 2 h. It was then cooled to room temperature and filtered. The filtrate was concentrated under reduced pressure and the resulting residue was purified by silica-gel column chromatography eluting with 30:1 dichloromethane/methanol to afford 114c (134 mg, 36%) as a yellow solid. MS-ESI: [M+H]$^+$ 540.2.

Example 114

6-tert-butyl-8-fluoro-2-[3-(hydroxymethyl)-4-[1-methyl-5-[(2-methylpyrimidin-4-yl)amino]-6-oxo-3-pyridyl]-2-pyridyl]phthalazin-1-one 114

At 0° C., to a suspension of 2-(6-tert-butyl-8-fluoro-1-oxophthalazin-2(1H)-yl)-4-(1-methyl-5-(2-methylpyrimidin-4-ylamino)-6-oxo-1,6-dihydropyridin-3-yl)nicotinaldehyde 114c (130 mg, 0.24 mmol) in methanol (20 mL) was added sodium borohydride (27 mg, 0.72 mmol). The reaction mixture was stirred for 20 minutes and then quenched with water (10 mL). It was then concentrated under reduced pressure and the residue was extracted with dichloromethane (3×20 mL). The combined organic layer was dried and concentrated under reduced pressure. The residue was purified by reverse-phase prep-HPLC to afford 114 (20 mg, 15%) as a white solid. MS-ESI: [M+H]$^+$ 542.3. $^1$H NMR (500 MHz, CDCl$_3$) 8.97 (d, J=2.5 Hz, 1H), 8.71 (d, J=5.0 Hz, 1H, 8.36 (d, J=2.0 Hz, 1H), 8.28 (d, J=5.5 Hz, 1H), 8.09-8.06 (m, 1H), 7.86 (d, J=2.5 Hz, 1H), 7.60-7.56 (m, 3H), 6.61 (d, J=6.0 Hz, 1H), 4.54-4.43 (m, 2H), 4.16-4.13 (m, 1H), 3.75 (s, 3H), 2.62 (s, 3H), 1.46 (s, 9H).

Example 115a

5-Methyl-4,5,6,7-tetrahydrothiazolo[5,4-c]pyridin-2-amine 115a

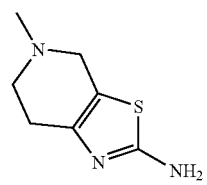

A solution of 1-methyl-4-piperidone (11.3 g, 100 mmol) in 2-propanol (80 mL) was heated to 50° C. To the solution were sequentially added a solution of cyanamide (4.2 g, 100 mmol) in 2-propanol (25 mL) and sulfur powder (3.2 g, 100 mmol). After a catalytic amount of pyrrolidine (1.3 mL) was added, the resultant mixture was stirred at 50° C. for 2 hours. The reaction mixture was allowed to cool to room temperature and stirred overnight. It was then cooled to or below 10° C. in an ice-water bath and stirred for 1 hour at the same temperature. The precipitated crystals were collected by filtration and washed with 2-propanol (20 mL). The wet crystals were dried in vacuo to afford 115a (10 g, 59%). MS: [M+H]$^+$ 170. $^1$H NMR (500 MHz, DMSO-$d_6$) δ 6.70 (s, 2H), 3.31 (s, 2H), 2.61 (t, J=5.5 Hz, 2H), 2.45 (m, 2H), 2.33 (s, 3H).

Example 115b

5-Bromo-1-methyl-3-(5-methyl-4,5,6,7-tetrahydrothiazolo[5,4-c]pyridin-2-ylamino)pyridin-2(1H)-one 115b

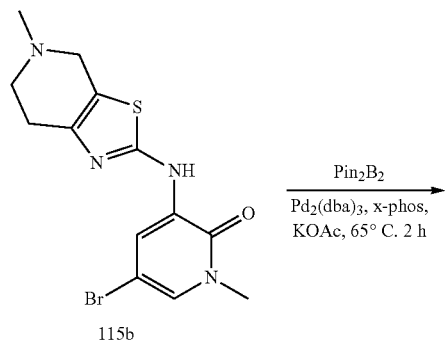

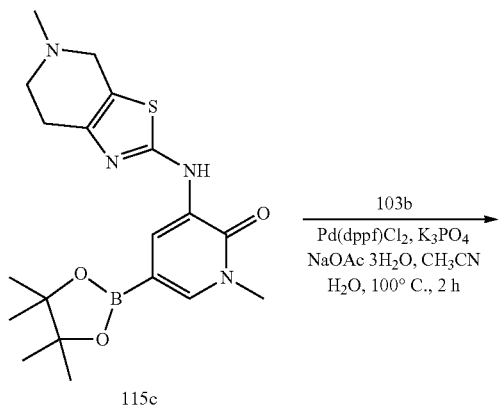

Following the procedures described for compound 113a and starting with 115a (4.0 g, 23.5 mmol) and 3,5-dibromo-1-methylpyridin-2(1H)-one (3.0 g, 17.8 mmol) afforded 115b as a yellow solid (2.8 g, 44%). MS: [M+H]$^+$ 357.

Example 115c

1-Methyl-3-(5-methyl-4,5,6,7-tetrahydrothiazolo[5,4-c]pyridin-2-ylamino)-5-(4,4,5,5-tetramethyl-1,3,2-dioxaborolan-2-yl)pyridin-2(1H)-one 115c Compound 115b (997 mg, 2.8 mmol) was dissolved in dioxane (50 mL), followed by additions of bis(pinacolato)diboron (3.0 g, 12.0 mmol), Pd$_2$(dba)$_3$ (128 mg, 0.14 mmol), X-phos (134 mg, 0.28 mmol), and potassium acetate (823 mg, 8.4 mmol). After three cycles of vacuum/argon flush, the mixture was heated at 65° C. for 2 h. The mixture was cooled to room temperature and filtered. The filtrate was concentrated under pressure and the residual was washed with petroleum ether (2×10 mL) to afford 115c as a yellow solid (968 mg, 86%), which was used in next step without further purification. MS-ESI: [M+H]$^+$ 403.2

Example 115d 2-(6-tert-Butyl-8-fluoro-1-oxophthalazin-2(1H)-yl)-4-(1-methyl-5-(5-methyl-4,5,6,7-tetrahydrothiazolo[5,4-c]pyridin-2-ylamino)-6-oxo-1,6-dihydropyridin-3-yl)nicotinaldehyde 115d A round-bottomed flask equipped with a reflux condenser was charged with 2-(6-tert-butyl-8-fluoro-1-oxophthalazin-2(1H)-yl)-4-chloronicotinaldehyde 103b (144 mg, 0.40 mmol), 115c (240 mg, 0.60 mmol), PdCl$_2$(dppf) (20 mg, 0.020 mmol), K$_3$PO$_4$ (180 mg, 0.80 mmol), sodium acetate trihydrate (120 mg, 0.80 mmol), and acetonitrile/water (15 mL/1 mL). After three cycles of vacuum/argon flush, the mixture was heated at 100° C. for 2 h. It was then cooled to room temperature and filtered. The filtrate was evaporated under reduced pressure. The residue was purified with silica-gel column chromatography eluting with 25:1 dichloromethane/methanol to afford 115d as a yellow solid (100 mg, 42%). MS-ESI: [M+H]$^+$ 600.3

Example 115

6-tert-butyl-8-fluoro-2-[3-(hydroxymethyl)-4-[1-methyl-5-[(5-methyl-6,7-dihydro-4H-thiazolo[5,4-c]pyridin-2-yl)amino]-6-oxo-3-pyridyl]-2-pyridyl]phthalazin-1-one 115

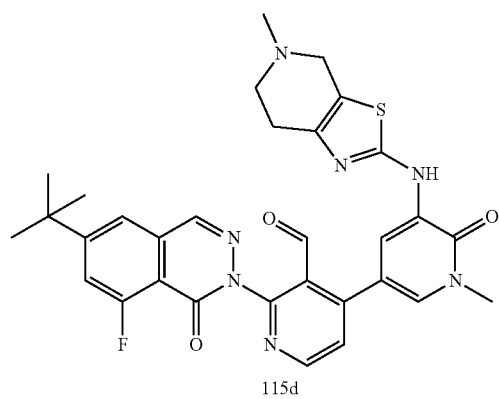

To a mixture of 115d (100 mg, 0.15 mmol) in methanol (6 mL) was added NaBH$_4$ (18 mg, 0.45 mmol). The mixture was stirred at 30° C. for 1 h and then quenched with water (10 mL). It was extracted with dichloromethane (3×30 mL) and the combined organic layer was concentrated under reduced pressure. The residue was purified by reverse-phase prep-HPLC to afford 115 (35 mg, 36%) as a white solid. MS-ESI: [M+H]$^+$ 602.2. $^1$H NMR (500 MHz, CDCl$_3$) δ 8.68 (d, J=5.0 Hz, 1H), 8.42 (d, J=2.5 Hz, 1H), 8.35 (d, J=2.5 Hz, 1H), 8.30 (s, 1H), 7.77 (d, J=2.0 Hz, 1H), 7.58-7.53 (m, 3H), 4.49-4.45 (m, 2H), 4.10 (bs, 1H), 3.73 (s, 3H), 3.58 (s, 2H), 2.83-2.79 (m, 4H), 2.52 (s, 3H), 1.45 (s, 9H).

Example 116a 6-tert-Butyl-2-(4-chloro-3-(hydroxymethyl)pyridin-2-yl)-8-fluorophthalazin-1(2H)-one 116a

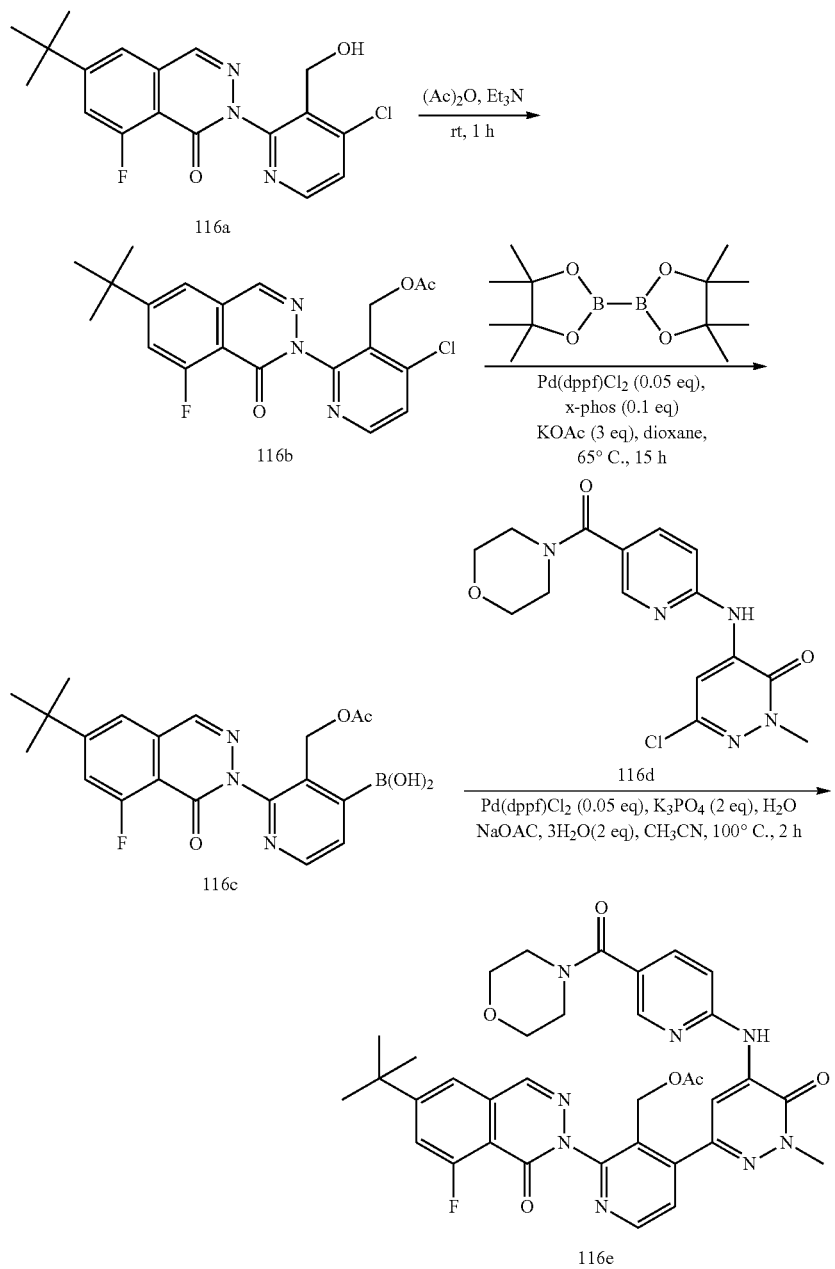

To a solution of 2-(6-tert-butyl-8-fluoro-1-oxophthalazin-2(1H)-yl)-4-chloronicotinaldehyde 103b (2.0 g, 5.5 mmol) in methanol (30 mL) was added NaBH$_4$ (700 mg, 16.5 mmol) at room temperature. The reaction mixture was stirred for 1 h and quenched with water (30 mL). It was then concentrated under reduced pressure and the residue was extracted with dichloromethane (3×30 mL). The combined organic phase was dried over anhydrous Na$_2$SO$_4$, filtered, and evaporated under reduced pressure to afford 116a as a white solid (1.8 g, 90%). MS: [M+H]$^+$ 362.3.

Example 116b (2-(6-tert-Butyl-8-fluoro-1-oxophthalazin-2(1H)-yl)-4-chloropyridin-3-yl)methyl Acetate 116b A 50-mL single-neck round-bottomed flask equipped with a magnetic stirrer was charged with 116a (1.6 g, 4.4 mmol), acetic anhydride (10 mL), and triethylamine (1 mL). The reaction mixture was stirred at room temperature for 1 h and concentrated under reduced pressure. The residue was purified by silica-gel column chromatography eluting with 30:1 dichloromethane/methanol to afford 116b as a brown solid (1.4 g, 82%). MS: [M+H]+ 404.3.

Example 116c 3-(Acetoxymethyl)-2-(6-tert-butyl-8-fluoro-1-oxophthalazin-2(1H)-yl)pyridin-4-ylboronic Acid 116c A 100-mL single-neck round-bottomed flask equipped with a magnetic stirrer and a reflux condenser was charged with 116b (1.0 g, 2.5 mmol), Pin$_2$B$_2$ (3.2 g, 12.5 mmol), Pd(dppf)Cl$_2$ (75 mg, 0.125 mmol), X-phos (75 mg, 0.25 mmol), potassium acetate (750 mg, 7.5 mmol), and dioxane (60 mL). After three cycles of vacuum/argon flush, the mixture was heated at 65° C. for 15 h. It was then cooled to room temperature and filtered. The filtrate was concentrated under reduced pressure and the resulting residue was washed with 3:1 petroleum ether/ethyl acetate (10 mL) to afford 116c as yellow solid (1.0 g, LCMS purity: 75%). MS: [M+H]+ 414.2.

Example 116d

6-Chloro-2-methyl-4-({5-[(morpholin-4-yl)carbonyl] pyridin-2-yl}amino)-2,3-dihydropyridazin-3-one 116d A 100-mL single-neck round-bottomed flask equipped with a magnetic stirrer and a reflux condenser was charged with 1,4-dioxane (40 mL), (6-aminopyridin-3-yl)(morpholino)methanone (2.07 g, 10.0 mmol), 4-bromo-6-chloro-2-methylpyridazin-3(2H)-one (3.35 g, 15.0 mmol), Pd$_2$(dba)$_3$ (915 mg, 1.0 mmol), XantPhos (578 mg, 1.0 mmol), and cesium carbonate (6.52 g, 20 mmol). After three cycles of vacuum/argon flush, the mixture was heated at 100° C. for 8 h. It was then cooled to room temperature and filtered. The solid was washed with dichloromethane (2×20 mL). The combined filtrate was dried over anhydrous Na$_2$SO$_4$ and concentrated under reduced pressure to afford 116d (2.45 g, 51%) as a yellow solid. MS: [M+H]+ 350.1

Example 116e (2-(6-tert-Butyl-8-fluoro-1-oxophthalazin-2(1H)-yl)-4-(1-methyl-5-(5-(morpholine-4-carbonyl)pyridin-2-ylamino)-6-oxo-1,6-dihydropyridazin-3-yl)pyridin-3-yl)methyl Acetate 116e A 50-mL round-bottomed flask equipped with a reflux condenser was charged with 116d (175 mg, 0.50 mmol), 3-(acetoxymethyl)-2-(6-tert-butyl-8-fluoro-1-oxophthalazin-2(1H)-yl)pyridin-4-ylboronic acid 116c (300 mg, 0.75 mmol), Pd(dppf)Cl$_2$ (25 mg, 0.025 mmol), K$_3$PO$_4$ (220 mg, 1.0 mmol), sodium acetate trihydrate (150 mg, 1.0 mmol), and acetonitrile/water (20/1 mL). After three cycles of vacuum/argon flush, the mixture was heated at 100° C. for 2 h. It was then filtered and the filtrate was evaporated under reduced pressure. The residue was purified by silica-gel column chromatography eluting with 25:1 dichloromethane/methanol to afford 116e as a yellow solid (150 mg, 45%). MS-ESI: [M+H]+ 683.3

Example 116

6-tert-butyl-8-fluoro-2-[3-(hydroxymethyl)-4-[1-methyl-5-[[5-(morpholine-4-carbonyl)-2-pyridyl] amino]-6-oxo-pyridazin-3-yl]-2-pyridyl]phthalazin-1-one 116

A mixture of 116e (150 mg, 0.20 mmol) and lithium hydroxide (85 mg, 2.0 mmol) in THF/i-propanol (5/3 mL) and water (2 mL) was stirred at 30° C. for 1 h. The mixture was evaporated under reduce pressure and the residue was extracted with ethyl acetate (3×20 mL). The combined ethyl acetate extract was concentrated under reduced pressure and the residue was purified by reverse-phase prep-HPLC to afford 116 (80 mg, 80%) as a white solid. MS-ESI: [M+H]+ 641.3. $^1$H NMR (500 MHz, CDCl$_3$) δ 8.78 (s, 1H), 8.75 (d, J=5.0 Hz, 1H), 8.47 (s, 1H), 8.45 (d, J=2.0 Hz, 1H), 8.34 (d, J=3.0 Hz, 1H), 7.79 (dd, J=2.0, 8.0 Hz, 1H), 7.64 (d, J=4.5 Hz, 1H), 7.57 (s, 1H), 7.52 (dd, J=1.5, 12.5 Hz, 1H), 7.02 (d, J=8.5 Hz, 1H), 4.57-4.55 (m, 2H), 3.94 (s, 3H), 3.81-3.75 (m, 6H), 1.64-1.62 (m, 2H), 1.44 (s, 9H).

Example 117a (S)-tert-Butyl 4-(6-(6-Chloro-2-methyl-3-oxo-2,3-dihydropyridazin-4-ylamino)pyridin-3-yl)-3-methylpiperazine-1-carboxylate 117a

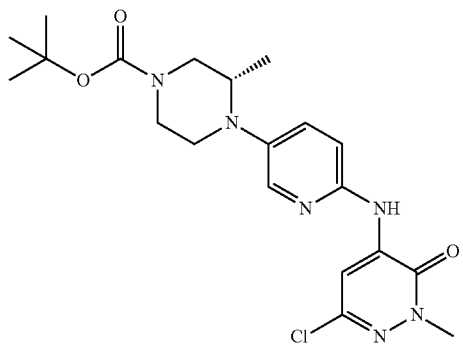 [SMILES: C[C@H]1CN(C(=O)OC(C)(C)C)CCN1c1ccc(Nc2cc(Cl)nn(C)c2=O)nc1]

A 250-mL single-neck round-bottomed flask equipped with a magnetic stirrer and a reflux condenser was charged with (S)-tert-butyl 4-(6-aminopyridin-3-yl)-3-methylpiperazine-1-carboxylate 105b (2.5 g, 8.5 mmol), 4-bromo-6-chloro-2-methylpyridazin-3(2H)-one (2.2 g, 10.0 mmol), XantPhos (240 mg, 0.40 mmol), tris(dibenzylideneacetone) dipalladium(0) (360 mg, 0.40 mmol), Cs$_2$CO$_3$ (5.5 g, 17 mmol), and 1,4-dioxane (100 mL). After three cycles of vacuum/argon flush, the mixture was heated at 100° C. for 2.5 h. It was then cooled to room temperature and filtered. The filtrate was concentrated under reduced pressure and the resulting residue was purified by silica-gel column chromatography eluting with dichloromethane/methanol (40:1 to 30:1) to afford 117a as a pale yellow solid (3.2 g, 86%). MS-ESI: [M+H]+ 435.1.

Example 117b (S)-6-Chloro-2-methyl-4-(5-(2-methylpiperazin-1-yl)pyridin-2-ylamino)pyridazin-3(2H)-one 117b A mixture of 117a (3.0 g, 6.9 mmol) and 4.0M HCl/ethanol (20 mL) was stirred at room temperature for 2 h. The mixture was then concentrated under reduced pressure to afford crude 117b as a yellow solid (2.5 g, 98%), which was used in the next step without further purification. MS-ESI: [M+H]+ 335.1.

Example 117c (S)-6-Chloro-2-methyl-4-(5-(2-methyl-4-(oxetan-3-yl)piperazin-1-yl)pyridin-2-ylamino)pyridazin-3 (2H)-one 117c A mixture of 117b (2.3 g, 6.8 mmol), oxetan-3-one (1.4 g, 20.0 mmol), NaBH$_3$CN (620 mg, 10 mmol), and zinc chloride (1.36 g, 10 mmol) in methanol (20 mL) was stirred at 50° C. for 3 hours. The mixture was added to water (40 mL) and concentrated under reduced pressure. The residue was extracted with dichloromethane three times. The combined organic layer was dried and concentrated under reduced pressure. The residue was purified by silica-gel column chromatography eluting with 50:1 dichloromethane/methanol to afford 117c (2.0 g, 75%). MS-ESI: [M+H]$^+$ 391.2.

Example 117d (S)-(2-(6-tert-Butyl-8-fluoro-1-oxophthalazin-2(1H)-yl)-4-(1-methyl-5-(5-(2-methyl-4-(oxetan-3-yl)piperazin-1-yl)pyridin-2-ylamino)-6-oxo-1,6-dihydropyridazin-3-yl)pyridin-3-yl)methyl Acetate 117d

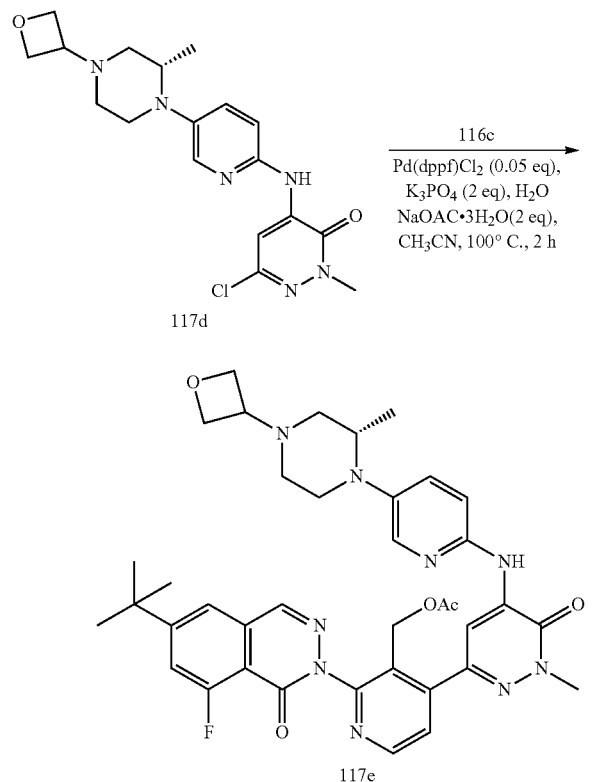

A round-bottomed flask equipped with a reflux condenser was charged with 117c (200 mg, 0.50 mmol), 3-(acetoxymethyl)-2-(6-tert-butyl-8-fluoro-1-oxophthalazin-2(1H)-yl)pyridin-4-yl-boronic acid 116c (300 mg, 0.75 mmol), Pd(dppf)Cl$_2$ (25 mg, 0.025 mmol), K$_3$PO$_4$ (220 mg, 1.0 mmol), sodium acetate trihydrate (150 mg, 1.0 mmol), and acetonitrile/water (20/1 mL). After three cycles of vacuum/argon flush, the mixture was heated at 100° C. for 2 h. It was then cooled to room temperature and filtered. The filtrate was evaporated under reduced pressure and the residue was purified with silica-gel column chromatography eluting with 25:1 dichloromethane/methanol to afford 117d as a yellow solid (110 mg, 42%). MS-ESI: [M+H]$^+$ 724.4

Example 117

6-tert-butyl-8-fluoro-2-[3-(hydroxymethyl)-4-[1-methyl-5-[[5-[(2S)-2-methyl-4-(oxetan-3-yl)piperazin-1-yl]-2-pyridyl]amino]-6-oxo-pyridazin-3-yl]-2-pyridyl]phthalazin-1-one 117

A mixture of 117d (110 mg, 0.15 mmol) and lithium hydroxide (65 mg, 1.5 mmol) in THF/i-propanol (5/3 mL) and water (2 mL) was stirred at 30° C. for 1 h. The mixture was evaporated under reduced pressure and the residue was extracted with ethyl acetate (2×20 mL). The combined ethyl acetate extract was concentrated under reduced pressure and the residue was purified by reverse-phase prep-HPLC to afford 117 (100 mg, 95%) as a yellow solid. MS-ESI: [M+H]$^+$ 682.4. $^1$H NMR (500 MHz, CDCl$_3$) δ 8.73 (d, J=5.0 Hz, 1H), 8.60 (s, 1H), 8.33 (d, J=2.5 Hz, 1H), 8.24 (s, 1H), 8.07 (s, 1H), 7.65 (d, J=5.0 Hz, 1H), 7.56-7.51 (m, 2H), 7.34 (s, 1H), 6.96 (d, J=9.0 Hz, 1H), 4.73-4.55 (m, 5H), 3.92 (m, 4H), 3.73-3.74 (m, 1H), 3.55-3.53 (m, 1H), 3.16-3.15 (m, 2H), 2.64-2.39 (m, 4H), 1.44 (s, 9H), 1.09-1.07 (m, 3H).

Example 118a

5-Bromo-1-methyl-3-(5-methyl-1H-pyrazol-3-ylamino)pyridin-2(1H)-one 118a

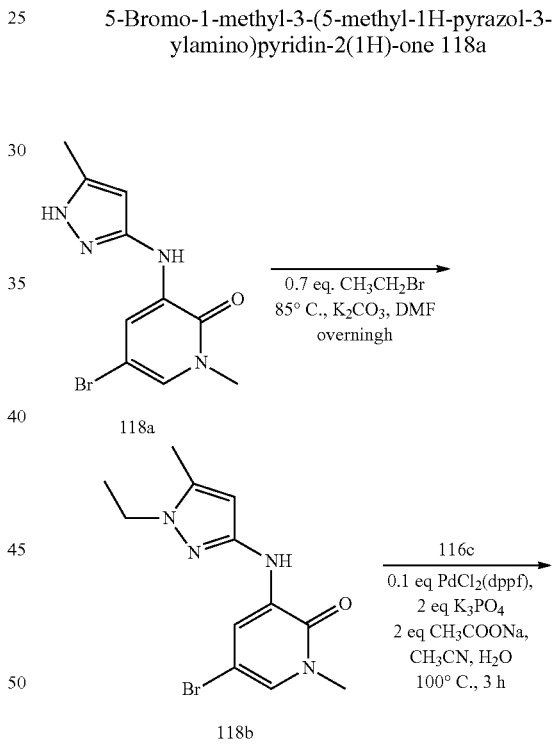

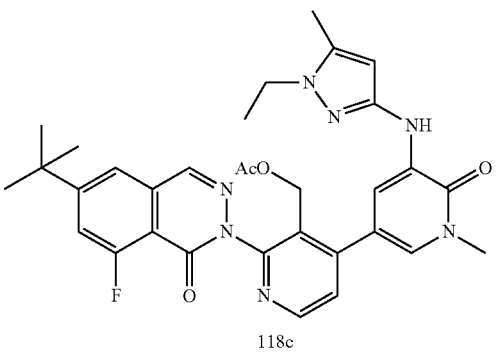

A 100-mL single-neck round-bottomed flask equipped with a magnetic stirrer and reflux condenser was charged with 1,4-dioxane (15 mL), 5-methyl-1H-pyrazol-3-amine (1 g, 10 mmol) (1), 3,5-dibromo-1-methylpyridin-2(1H)-one (4 g, 15 mmol) (2), and cesium carbonate (6.4 g, 20 mmol). Xantphos (400 mg, 0.8 mmol) and Pd$_2$(dba)$_3$ (700 mg, 0.8 mmol) were added, and the reaction mixture was heated at 100° C. for 5 h. After this time the reaction was cooled to room temperature and filtered. The filtrate was concentrated under reduced pressure and the residue was purified on flush column eluting with dichloromethane:methanol (20:1) to afford 118a (1.0 g, 35%). MS: [M+H]$^+$ 283.

Example 118b

5-Bromo-3-(1-ethyl-5-methyl-1H-pyrazol-3-ylamino)-1-methylpyridin-2(1H)-one 118b A 100-mL round-bottomed flask was charged with 118a (800 mg, 2.83 mmol), bromoethane (216 mg, 1.98 mmol), K$_2$CO$_3$ (780 mg, 5.66 mmol), and DMF (20 mL). The mixture was heated at 85° C. overnight. It was then filtered and the filtrate was evaporated in vacuo. The residue was purified by silica-gel column chromatography eluting with 1:20 methanol/dichloromethane to afford 118b as a red solid (298 mg, 37%). MS-ESI: [M+H]$^+$ 311.0. $^1$H NMR (500 MHz, DMSO-d$_6$) δ 8.28 (s, 1H), 7.99 (d, J=2.5 Hz, 1H), 7.35 (d, J=2.5 Hz, 1H), 5.85 (s, 1H), 3.98-3.94 (m, 2H), 3.48 (s, 3H), 2.19 (s, 3H), 1.27 (t, J=7.0 Hz, 3H).

Example 118c (2-(6-tert-Butyl-8-fluoro-1-oxophthalazin-2(1H)-yl)-4-(5-(1-ethyl-5-methyl-1H-pyrazol-3-ylamino)-1-methyl-6-oxo-1,6-dihydropyridin-3-yl)pyridin-3-yl) methyl Acetate 118c A 50-mL round-bottomed flask equipped with a reflux condenser was charged with 118b (103 mg, 0.33 mmol), 3-(acetoxymethyl)-2-(6-tert-butyl-8-fluoro-1-oxophthalazin-2(1H)-yl)pyridin-4-ylboronic acid 116c (136 mg, 0.33 mmol), PdCl$_2$(dppf) (27 mg, 0.033 mmol), K$_3$PO$_4$ (171 mg, 0.66 mmol), sodium acetate (54 mg, 0.66 mmol), acetonitrile (10 mL), and water (0.5 mL). After three cycles of vacuum/argon flush, the mixture was heated at 100° C. for 3 h. It was then filtered and the filtrate was in vacuo. The residue was purified by silica-gel column chromatography eluting with 1:20 methanol/dichloromethane to afford 118c as a yellow solid (80 mg, 41%). MS-ESI: [M+H]$^+$ 600.2

Example 118

6-tert-butyl-2-[4-[5-[(1-ethyl-5-methyl-pyrazol-3-yl)amino]-1-methyl-6-oxo-3-pyridyl]-3-(hydroxymethyl)-2-pyridyl]-8-fluoro-phthalazin-1-one 118

A mixture of 118c (80 mg, 0.13 mmol), lithium hydroxide (13 mg, 0.53 mmol), THF (6 mL), i-propanol (4 mL) and water (2 mL) was stirred at room temperature for 0.5 h. The mixture was concentrated under reduced pressure and diluted with water (5 mL). It was then extracted with dichloromethane (2×10 mL). The combined dichloromethane extract was concentrated under reduced pressure and the residue was purified with reverse-phase prep-HPLC to afford 118 (20 mg, 26%) as a white solid. MS-ESI: [M+H]$^+$ 558.3. $^1$H NMR (500 MHz, DMSO-d$_6$) δ 8.56 (d, J=5.0 Hz, 1H), 8.53 (d, J=2.5 Hz, 1H), 8.10 (s, 1H), 8.05 (d, J=2.5 Hz, 1H), 7.90 (d, J=2.0 Hz, 1H), 7.79-7.76 (m, 1H), 7.50 (d, J=5.0 Hz, 1H), 7.40 (d, J=2.5 Hz, 1H), 5.88 (s, 1H), 4.92 (t, J=5.0 Hz 1H), 4.46-4.45 (m, 2H), 3.91 (q, J=7.5 Hz, 2H), 3.59 (s, 3H), 2.19 (s, 3H), 1.40 (s, 9H), 1.27 (t, J=7.0 Hz, 3H).

Example 119a

5-Bromo-3-(1,5-dimethyl-1H-pyrazol-3-ylamino)-1-methylpyridin-2(1H)-one 119a

A solution of 5-bromo-1-methyl-3-(5-methyl-1H-pyrazol-3-ylamino)pyridin-2(1H)-one 118a (2.8 g, 9.9 mmol) in anhydrous DMF (10 mL) was treated with 60% dispersion of NaH in mineral oil (0.51 g, 13 mmol) while stirring under nitrogen. After the resulting effervescence ceased, the reaction was stirred for an additional 30 minutes. At this time the reaction was treated with iodomethane (0.98 g, 7.0 mmol) with continued stirring under nitrogen for 2 hours. Water (50 mL) was added slowly and the mixture was filtered. The filtrate was extracted with ethyl acetate (3×30 mL). The combined extract was concentrated under reduced pressure and the residue was purified by flush column chromatography eluting with 3:1 petroleum ether/ethyl acetate to afford 119a (0.70 g, 24%). MS: [M+H]$^+$ 297.

Example 119b (2-(6-tert-Butyl-8-fluoro-1-oxophthalazin-2(1H)-yl)-4-(5-(1,5-dimethyl-1H-pyrazol-3-ylamino)-1-methyl-6-oxo-1,6-dihydropyridin-3-yl)pyridin-3-yl) methyl Acetate 119b A 50-mL round-bottomed flask equipped with a reflux condenser was charged with 119a (180 mg, 0.50 mmol), 3-(acetoxymethyl)-2-(6-tert-butyl-8-fluoro-1-oxophthalazin-2(1H)-yl)pyridine-4-ylboronic acid 116c (207 mg, 0.50 mmol), Pd(dppf)Cl$_2$ (41 mg, 0.050 mmol), K$_3$PO$_4$ (212 mg, 1.0 mmol), sodium acetate (82 mg, 1.0 mmol), water (0.5 mL), and acetonitrile (10 mL). After three cycles of vacuum/ argon flush, the mixture was heated at reflux for 2 h. It was then cooled to room temperature and filtered. The filtrate was concentrated under reduced pressure and the resulting residue was purified by silica-gel column chromatography eluting with 30:1 dichloromethane/methanol to afford 119b as a white solid (175 mg, 60%). MS-ESI: [M+H]$^+$ 586.4

Example 119

6-tert-butyl-2-[4-[5-[(1,5-dimethylpyrazol-3-yl) amino]-1-methyl-6-oxo-3-pyridyl]-3-(hydroxymethyl)-2-pyridyl]-8-fluoro-phthalazin-1-one 119

A mixture of 119b (150 mg, 0.26 mmol) and lithium hydroxide (61.4 mg, 2.6 mmol) in i-propanol/THF (1:1, 4 mL) and water (1 mL) was stirred at 30° C. for 1 h. The mixture was evaporated in vacuo and the residue was diluted with water (5 mL). It was then extracted with ethyl acetate (2×10 mL). The combined ethyl acetate extract was concentrated under reduced pressure and the residue was purified by reverse-phase prep-HPLC to afford 119 (75.0 mg, 54%) as a white solid. MS-ESI: [M+H]$^+$ 544.3. $^1$H NMR (500 MHz, CDCl$_3$) δ 8.66 (d, J=5.0 Hz, 1H), 8.35 (d, J=2.0 Hz, 1H), 7.97 (d, J=2.0 Hz, 1H), 7.59-7.53 (m, 4H), 7.37 (s, 1H), 5.74 (s, 1H), 4.51 (s, 2H), 4.07 (s, 1H), 3.72 (s, 3H), 3.70 (s, 3H), 2.25 (s, 3H), 1.46 (s, 9H).

Example 120a

5-Bromo-1-methyl-3-(5-methylthiazol-2-ylamino) pyridin-2(1H)-one 120a

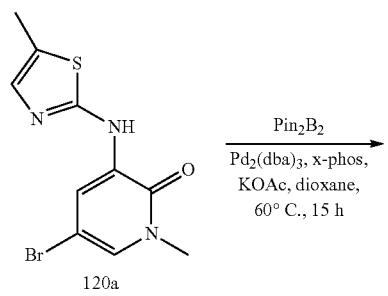

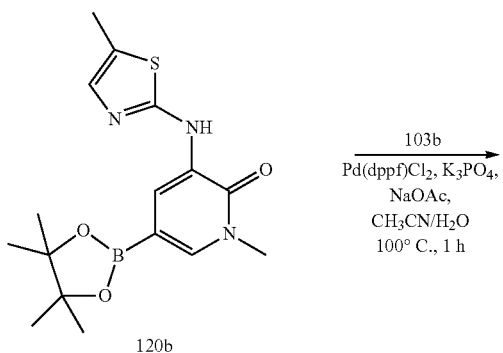

Example 120b

1-Methyl-3-(5-methylthiazol-2-ylamino)-5-(4,4,5,5-tetramethyl-1,3,2-dioxaborolan-2-yl)pyridin-2(1H)-one 120b

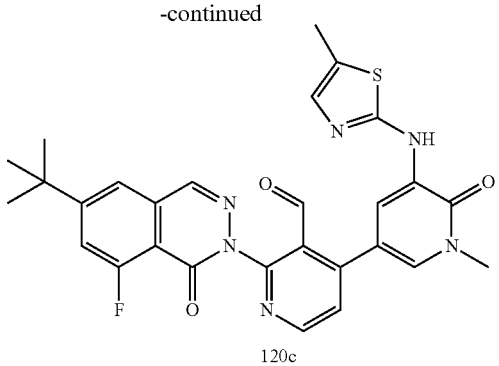

A 100-mL single-neck round-bottomed flask equipped with a magnetic stirrer and a reflux condenser was charged with 1,4-dioxane (50 mL), 5-methylthiazol-2-amine (2.28 g, 20.0 mmol), 3,5-dibromo-1-methylpyridin-2(1H)-one (5.34 g, 20.0 mmol) cesium carbonate (13.0 g, 40.0 mmol), xantphos (1.16 g, 2.0 mmol), and tris(dibenzylideneacetone)dipalladium(0) (916 mg, 1.0 mmol). The system was subjected to three cycles of vacuum/argon flush and heated at reflux for 5 h. It was then cooled to room temperature and filtered. The solid was washed with dichloromethane (3×50 mL). The combined filtrate was concentrated under reduced pressure and the residue was washed with acetonitrile (30 mL) to afford 120a (5 g, crude, 83%) as a yellow solid. MS-ESI: [M+H]$^+$ 300.1.

Example 120b

1-Methyl-3-(5-methylthiazol-2-ylamino)-5-(4,4,5,5-tetramethyl-1,3,2-dioxaborolan-2-yl)pyridin-2(1H)-one 120b A 250-mL round-bottomed flask equipped with a magnetic stirrer and a reflux condenser was charged with 120a (5.0 g, 16.6 mmol), Pin$_2$B$_2$ (21.1 g, 83.0 mmol), tris(dibenzylideneacetone)dipalladium(0) (760 mg, 0.83 mmol), x-phos (810 mg, 1.7 mmol), potassium acetate (4.9 g, 50 mmol), and 1,4-dioxane (80 mL). The reaction mixture was subjected to three cycles of vacuum/argon flush and heated at 65° C. for 3 h. It was then cooled to room temperature and filtered. The filtrate was concentrated under reduced pressure and the resulting residue was washed with petroleum ether to afford 120b (20.0 g, crude) as brown solid, which was used in next step without further purification. MS-ESI: [M+H]$^+$ 348.2

Example 120c 2-(6-tert-Butyl-8-fluoro-1-oxophthalazin-2(1H)-yl)-4-(1-methyl-5-(5-methylthiazol-2-ylamino)-6-oxo-1, 6-dihydropyridin-3-yl)nicotinaldehyde 120c A 25-mL single-neck round-bottomed flask equipped with a magnetic stirrer and a reflux condenser was charged with 120b (174 mg, 0.50 mmol), 2-(6-tert-butyl-8-fluoro-1-oxophthalazin-2(1H)-yl)-4-chloronicotinaldehyde 103b (180 mg, 0.50 mmol), K$_3$PO$_4$ (212 mg, 1.0 mmol), sodium acetate (82 mg, 1.0 mmol), 1,1'-bis(diphenylphosphino)ferrocenedichloropalladium(II) (18 mg, 0.025 mmol), acetonitrile (8 mL), and water (0.5 mL). The reaction mixture was subjected to three cycles of vacuum/argon flush and heated at 100° C. for 1 h. Analysis of the reaction mixture by LCMS showed complete conversion to the desired product. The reaction mixture was cooled to room temperature and filtered. The filtrate was concentrated under reduced pressure. The residue was diluted with dichloromethane (50 mL) and water (30 mL). The water layer was extracted with dichloromethane (2×30 mL). The combined organic extract was dried over $Na_2SO_4$, filtered, and concentrated under reduced pressure. The dark residue was purified by silica-gel column chromatography eluting with dichloromethane/methanol (80:1 to 30:1) to afford 120c (150 mg, 55%) as a yellow solid. MS-ESI: [M+H]$^+$ 545.3

Example 120

6-tert-butyl-8-fluoro-2-[3-(hydroxymethyl)-4-[1-methyl-5-[(5-methylthiazol-2-yl)amino]-6-oxo-3-pyridyl]-2-pyridyl]phthalazin-1-one 120

To a solution of 120c (98 mg, 0.18 mmol) in methanol/dichloromethane(3/3 mL) was added $NaBH_4$ (21 mg, 0.55 mmol) at room temperature. After the reaction was stirred for 1 h, LCMS indicated the reaction was complete. The mixture was quenched with water (5 mL) and concentrated under reduced pressure. The residue was extracted with dichloromethane (3×15 mL). The combined organic layer was washed with brine (20 mL), dried over $Na_2SO_4$, filtered, and concentrated under reduced pressure. The residue was purified by reverse-phase prep-HPLC to afford 120 (30 mg, 31%) as a white solid. MS-ESI: [M+H]$^+$ 546.7. $^1$H NMR (500 MHz, DMSO-$d_6$) δ 9.92 (s, 1H), 8.58 (d, J=5.5 Hz, 1H), 8.56 (d, J=2.5 Hz, 1H), 8.54 (d, J=2.0 Hz, 1H), 7.91 (d, J=2.0 Hz, 1H), 7.78 (d, J=13.0 Hz, 1H), 7.56 (d, J=2.0 Hz, 1H), 7.51 (d, J=5.0 Hz, 1H), 6.96 (d, J=1.0 Hz, 1H), 4.91 (bs, 1H), 4.42-4.41 (m, 2H), 3.60 (s, 3H), 2.28 (d, J=1.0 Hz, 3H), 1.40 (s, 9H).

Example 121a (2-(6-tert-Butyl-8-fluoro-1-oxophthalazin-2(1H)-yl)-4-(1-methyl-5-(5-methyl-1H-pyrazol-3-ylamino)-6-oxo-1,6-dihydropyridin-3-yl)pyridin-3-yl)methyl Acetate 121a

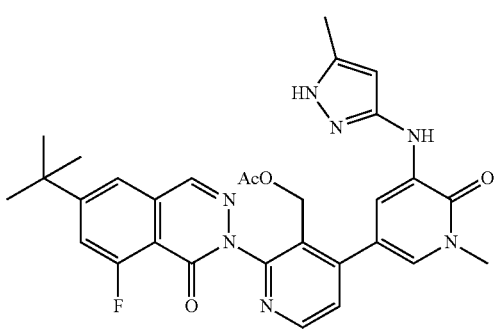

A 50-mL round-bottomed flask equipped with a reflux condenser was charged with 5-bromo-1-methyl-3-(5-methyl-1H-pyrazol-3-ylamino)pyridin-2(1H)-one 118a (142 mg, 0.50 mmol), 3-(acetoxymethyl)-2-(6-tert-butyl-8-fluoro-1-oxophthalazin-2(1H)-yl)pyridin-4-ylboronic acid 116c (310 mg, 0.75 mmol), Pd(dppf)Cl$_2$ (18 mg, 0.025 mmol), $K_3PO_4$ (212 mg, 1.0 mmol), sodium acetate (82 mg, 1.0 mmol), acetonitrile (10 mL), and water (0.2 mL). After three cycles of vacuum/argon flush, the mixture was heated at 100° C. for 2 h. It was then filtered and the filtrate was evaporated under reduced pressure. The residue was purified by silica-gel column chromatography eluting with 25:1 dichloromethane/methanol to afford 121a as a brown solid (100 mg, 35%). MS-ESI: [M+H]$^+$ 572.3

Example 121

6-tert-butyl-8-fluoro-2-[3-(hydroxymethyl)-4-[1-methyl-5-[(5-methyl-1H-pyrazol-3-yl)amino]-6-oxo-3-pyridyl]-2-pyridyl]phthalazin-1-one 121

A mixture of 121a (86 mg, 0.15 mmol) and lithium hydroxide (36 mg, 1.5 mmol) in THF/i-propanol (5:3, 8 mL) and water (2 mL) was stirred at 30° C. for 1 h. The mixture was evaporated under reduced pressure and the residue was diluted with water (5 mL). It was then extracted with ethyl acetate (2×10 mL). The combined ethyl acetate extract was concentrated under reduced pressure and the residue was purified by reverse-phase prep-HPLC to afford 121 (24 mg, 30%) as a white solid. MS-ESI: [M+H]$^+$ 530.3. $^1$H NMR (500 MHz, CDCl$_3$) δ 8.65 (d, J=5.0 Hz, 1H), 8.35 (d, J=2.0 Hz, 1H), 8.04 (d, J=2.5 Hz, 1H), 7.58-7.53 (m, 4H), 7.44 (s, 1H), 5.78 (s, 1H), 4.51-4.49 (m, 2H), 3.73 (s, 3H), 2.03 (s, 3H), 1.45 (s, 9H).

Example 122a

5-Bromo-3-(5-ethyl-1H-pyrazol-3-ylamino)-1-methylpyridin-2(1H)-one 122a

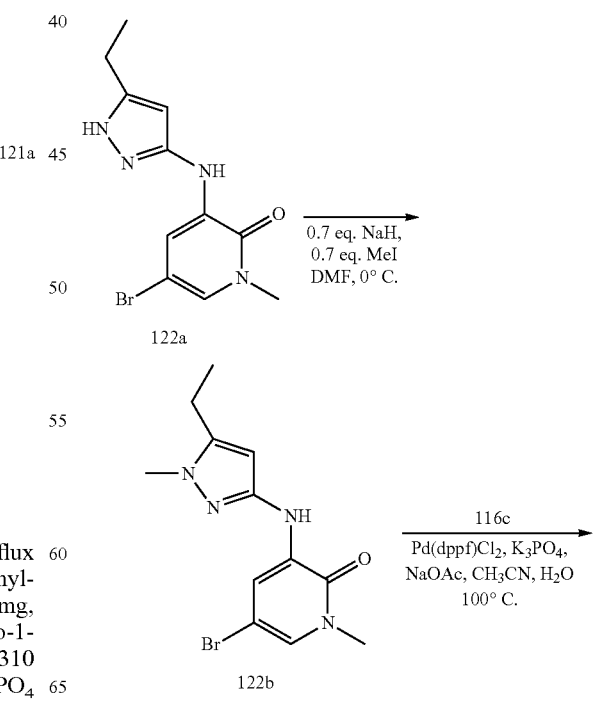

-continued

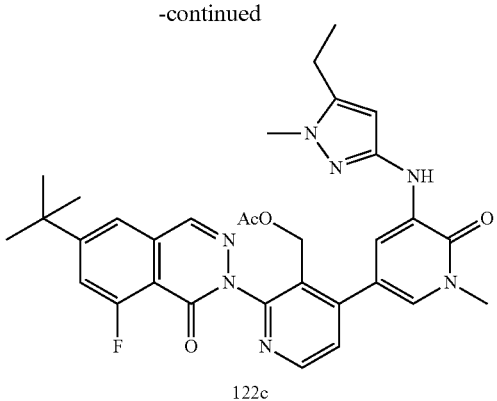

122c

A 100-mL single-neck round-bottomed flask equipped with a magnetic stirrer and a reflux condenser was charged with 1,4-dioxane (80 mL), 5-ethyl-1H-pyrazol-3-amine (3.33 g, 30.0 mmol), 3,5-dibromo-1-methylpyridin-2(1H)-one (9.6 g, 36 mmol), and cesium carbonate (19.5 g, 60 mmol). After bubbling nitrogen through the suspension for 10 minutes, Xantphos (1.73 mg, 3.0 mmol) and tris(dibenzylideneacetone)dipalladium(0) (1.36 mg, 1.5 mmol) were added. The system was subjected to three cycles of vacuum/argon flush and heated at reflux for 2 h. It was then filtered immediately. The solid was washed with dioxane (3×30 mL) and the combined filtrate was concentrated under reduced pressure. The residue was purified by silica-gel column chromatography eluting with petroleum ether/ethyl acetate (2:1 to 1:2) to afford 122a (3.8 g, 43%) as a red solid. MS-ESI: [M+H]$^+$ 297.0

Example 122b

5-Bromo-3-(5-ethyl-1-methyl-1H-pyrazol-3-ylamino)-1-methylpyridin-2(1H)-one 122b To a mixture of 122a (598 mg, 2.0 mmol) in DMF (10 mL) was added NaH (64 mg, 1.6 mmol) at 0° C. and the mixture was stirred for 0.5 h. To the mixture was added iodomethane (227 mg, 1.6 mmol) in DMF dropwise at 0° C. The mixture was stirred for 0.5 h and quenched with water (20 mL). It was then extracted with dichloromethane (3×30 mL). The combined extract was concentrated under reduced pressure and the residue was purified with silica-gel column chromatography eluting with petroleum ether/ethyl acetate (5:1 to 2:1) to afford 122b (360 mg, 58%) as a light yellow solid. MS-ESI: [M+H]$^+$ 311.1

Example 122c (2-(6-tert-Butyl-8-fluoro-1-oxophthalazin-2(1H)-yl)-4-(5-(5-ethyl-1-methyl-1H-pyrazol-3-ylamino)-1-methyl-6-oxo-1,6-dihydropyridin-3-yl)pyridin-3-yl) methyl Acetate 122c A 50-mL round-bottomed flask equipped with a reflux condenser was charged with 122b (310 mg, 1.0 mmol), 3-(acetoxymethyl)-2-(6-tert-butyl-8-fluoro-1-oxophthalazin-2 (1H)-yl)pyridin-4-ylboronic acid 116c (1.24 g, 3.0 mmol), K$_3$PO$_4$ (424 mg, 2.0 mmol), sodium acetate (164 mg, 2.0 mmol), 1,1'-bis(diphenylphosphino)ferrocenedichloropalladium(II) (73 mg, 0.10 mmol), acetonitrile (10 mL), and water (0.5 mL). The system was subject to three cycles of vacuum/nitrogen flush and heated at 100° C. under N$_2$ protection for 2.5 h. The reaction mixture was cooled to room temperature and concentrated under reduced pressure. The residue was diluted with dichloromethane (50 mL) and water (50 mL). The aqueous layer was separated and extracted with dichloromethane (3×20 mL). The combined organic layer was dried over Na$_2$SO$_4$, filtered, and concentrated under reduced pressure. The dark residue was purified with silica-gel column chromatography eluting with 60:1 dichloromethane/methanol to afford 122c (150 mg, 25%) as a yellow oil. MS-ESI: [M+H]$^+$ 600.0

Example 122

6-tert-butyl-2-[4-[5-[(5-ethyl-1-methyl-pyrazol-3-yl)amino]-1-methyl-6-oxo-3-pyridyl]-3-(hydroxymethyl)-2-pyridyl]-8-fluoro-phthalazin-1-one 122

To a solution of 122c (150 mg, 0.25 mmol) in THF/i-propanol/water (2.5/1/0.5 mL) was added lithium hydroxide (70 mg, 2.5 mmol) at 35° C. After the reaction was stirred for 3 h, LCMS indicated the reaction was completed. The mixture was poured into water (15 mL) and extracted with dichloromethane (3×20 mL). The combined organic layer was washed with brine (30 mL), dried over Na$_2$SO$_4$, filtered, and concentrated under reduced pressure. The residue solid was purified by reverse-phase prep-HPLC to afford 122 (49 mg, 35%) as a white solid. MS-ESI: [M+H]$^+$ 557.8. $^1$H NMR (500 MHz, CDCl$_3$) δ 8.59 (d, J=5.0 Hz, 1H), 8.51 (d, J=2.5 Hz, 1H), 7.92 (d, J=2.0 Hz, 1H), 7.88 (d, J=1.5 Hz, 1H), 7.73 (m, 1H), 7.64 (d, J=5.0 Hz, 1H), 7.41 (d, J=1.5 Hz, 1H), 5.92 (s, 1H), 4.59 (s, 2H), 3.72 (s, 3H), 3.68 (s, 3H), 2.64 (m, 2H), 1.47 (s, 9H), 1.27 (t, J=2.5, 3H)

Example 123a

1-Ethyl-4-nitro-1H-pyrazole 123a

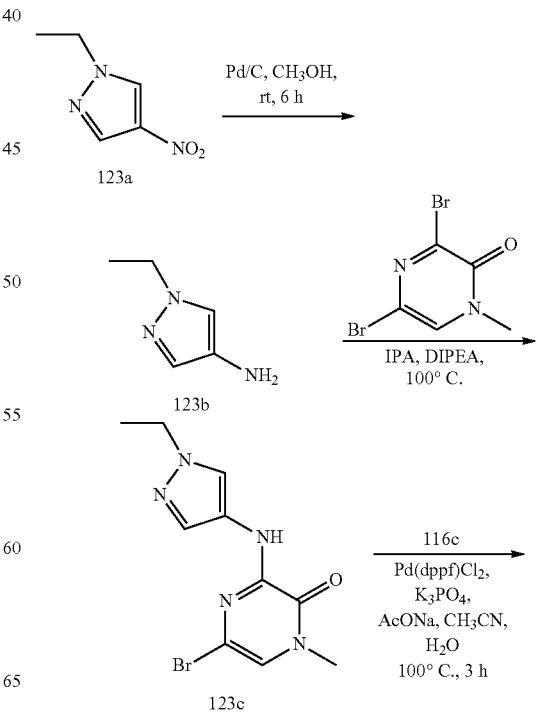

-continued

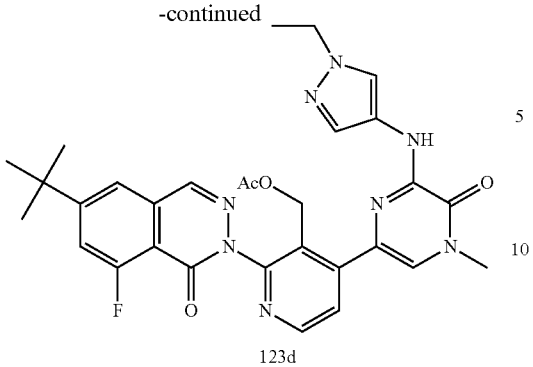

123d

To a solution of 4-nitro-1H-pyrazole (5.0 g, 44.2 mmol) in anhydrous DMF (100 mL) was NaH (60% in oil) (1.94 g, 48.6 mmol) while being stirred at −25° C. under nitrogen. The mixture was stirred for 30 min before bromoethane (5.30 g, 48.6 mmol) was added. The mixture was continued to stir under nitrogen at −25° C. for 6 h. The solution was diluted with ethyl acetate (100 mL), washed with water (2×50 mL) and brine solution (50 mL), dried over magnesium sulfate, and filtered. The filtrate was concentrated under reduced pressure to afford crude 123a (5.0 g, 80%), which was used in next step without further purification. MS-ESI: [M+H]$^+$ 142.0

Example 123b

1-Ethyl-1H-pyrazol-4-amine 123b

A 100-mL single-neck round-bottomed flask was purged with hydrogen and charged with 123a (4.5 g, 31.9 mmol), 10% palladium on carbon (10% wet, 2.0 g), and methanol (50 mL). The mixture was stirred at room temperature for 6 h. The catalyst was removed by filtration through a pad of CELITE® and the filtrate was concentrated under reduced pressure to afford 123b (3.3 g, 93%). MS-ESI: [M+H]$^+$ 112.0

Example 123c

5-Bromo-3-(1-ethyl-1H-pyrazol-4-ylamino)-1-methylpyrazin-2(1H)-one 123c

A 100-mL single-neck round-bottomed flask equipped with a magnetic stirrer and reflux condenser was charged with 123b (500 mg, 4.5 mmol), 3,5-dibromo-1-methylpyrazin-2 (1H)-one (2.40 g, 9.0 mmol), DIPethyl acetate (3 mL), and isopropanol (50 mL). The mixture was heated at 100° C. for 2 h. It was then cooled to room temperature and filtered. The filtrate was concentrated under reduced pressure to afford 123c (802 mg, 60%) as a white solid. MS-ESI: [M+H]$^+$ 298.0

Example 123d (2-(6-tert-Butyl-8-fluoro-1-oxophthalazin-2(1H)-yl)-4-(6-(1-ethyl-1H-pyrazol-4-ylamino)-4-methyl-5-oxo-4,5-dihydropyrazin-2-yl)pyridin-3-yl)methyl Acetate 123d A 50-mL round-bottomed flask equipped with a magnetic stirrer and a reflux condenser was charged with 123c (151 mg, 0.51 mmol), 3-(acetoxymethyl)-2-(6-tert-butyl-8-fluoro-1-oxophthalazin-2(1H)-yl)pyridin-4-ylboronic acid 116c (206 mg, 0.50 mmol), PdCl$_2$(dppf) (22 mg, 0.030 mmol), K$_3$PO$_4$ (216 mg, 1.02 mmol), sodium acetate (84 mg, 1.02 mmol), acetonitrile (10 mL), and water (0.5 mL). After three cycles of vacuum/argon flush, the mixture was heated at 100° C. for 3 h. It was then filtered and the filtrate was evaporated under reduced pressure. The residue was purified by silica-gel column chromatography eluting with 1:3 petroleum/ethyl acetate to afford 123d as a yellow solid (158 mg, 53%). MS-ESI: [M+H]$^+$ 587.2

Example 123

6-tert-butyl-2-[4-[6-[(1-ethylpyrazol-4-yl)amino]-4-methyl-5-oxo-pyrazin-2-yl]-3-(hydroxymethyl)-2-pyridyl]-8-fluoro-phthalazin-1-one 123

A mixture of 123d (152 mg, 0.26 mmol) and lithium hydroxide (61 mg, 2.56 mmol) in i-propanol/THF (1:1, 10 mL) and water (3 mL) was stirred at room temperature for 1 h. The mixture was evaporated under reduced pressure and the residue was extracted with ethyl acetate (2×10 mL). The combined ethyl acetate extract was concentrated under reduced pressure and the residue was purified by reverse-phase prep-HPLC to afford 123 (55 mg, 39%) as a yellow solid. MS-ESI: [M+H]$^+$ 545.2. $^1$H NMR (500 MHz, DMSO-d$_6$) δ 9.72 (s, 1H), 8.58 (d, J=5.0 Hz, 1H), 8.54 (d, J=2.5 Hz, 1H), 8.18 (s, 1H), 7.90 (d, J=2.0 Hz, 1H), 7.80-7.75 (m, 1H), 7.74 (s, 1H), 7.71 (d, J=5.0 Hz, 1H), 7.51 (s, 1H), 4.90 (t, J=5.0 Hz, 1H), 4.61-4.53 (m, 2H), 4.09 (q, J=7.5 Hz, 2H), 3.54 (s, 3H), 1.41 (s, 9H), 1.35 (t, J=6.0 Hz, 3H).

Example 124a (3-Nitro-1H-pyrazol-5-yl)methanol 124a

A 3-L three-neck round-bottomed flask equipped with a mechanical stirrer, addition funnel and nitrogen inlet was purged with nitrogen and charged with 3-nitropyrazole-5-carboxylic acid (28.0 g, 178 mmol) and THF (420 mL) and cooled to −5° C. using an ice/acetone bath. Borane-THF complex solution (1.0 M, 535 mL, 535 mmol) was added at a rate that maintained the internal reaction temperature below 5° C. After the addition was complete the cooling bath was removed and the reaction was stirred at room temperature for 18 h. After this time the reaction was cooled to −5° C. using an ice/acetone bath, water (70 mL) and 4N hydrochloric acid (70 mL) was added and the reaction was stirred at reflux for 1 h in order to destroy the borane complex with pyrazole. The reaction was cooled to room temperature and concentrated under reduced pressure to a volume of approximately 30 mL. Ethyl acetate (175 mL) was added and the mixture stirred for 15 min. The aqueous layer was separated and extracted with ethyl acetate (4×200 mL). The combined organic layers were washed with saturated aqueous sodium bicarbonate (2×50 mL), brine (50 mL) and dried over sodium sulfate, the drying agent was removed by filtration, and the filtrate concentrated under reduced pressure to afford 124a in a 94% yield (24.0 g) as a light yellow solid: $^1$H NMR (300 MHz, DMSO-d$_6$) δ 13.90 (br s, 1H), 6.87 (s, 1H), 5.58 (t, 1H, J=5.4 Hz), 4.53 (d, 2H, J=5.1 Hz); MS (ESI+) m/z 144.0 (M+H)

Example 124b (1-(2-Bromoethyl)-3-nitro-1H-pyrazol-5-yl)methanol 124b

A 1-L three-necked round-bottomed flask equipped with a mechanical stirrer and thermoregulator was purged with nitrogen and charged with 124a (25.0 g, 175 mmol), DMF (250 mL), and cesium carbonate (70.0 g, 215 mmol) was heated at 104° C. for 5 min. The reaction mixture was then cooled to 0° C. using an ice/acetone bath and dibromoethane (329 g, 1.75 mol) was added portionwise (no exotherm). The reaction was stirred at 0° C. for 1 then at room temperature for 4 h. After this time a solution of $KH_2PO4$ (40 g) in water (400 mL) was added slowly. The reaction mixture was stirred at room temperature for 30 min. Ethyl acetate (450 mL) was added and the aqueous layer was separated and extracted with ethyl acetate (2×100 mL). The combined organic layers were washed with water (200 mL), brine (200 mL), dried over sodium sulfate, and the drying agent was removed by filtration. The filtrate was concentrated under reduced pressure to afford an 86% yield (37.5 g) of crude 124b as an orange oil: $^1H$ NMR (300 MHz, $CDCl_3$) δ 6.85 (s, 1H), 4.82 (d, 2H, J=5.4 Hz), 4.66 (t, 2H, J=6.3 Hz), 3.83 (t, 2H, J=6.3 Hz); MS (ESI+) m/z 249.9 (M+H).

Example 124c 1-(2-Bromoethyl)-5-(bromomethyl)-3-nitro-1H-pyrazole 124c

A 500-mL three-necked round-bottomed flask equipped with a magnetic stirrer, nitrogen inlet and reflux condenser was purged with nitrogen and charged with 124b (37.0 g, 148 mmol) and chloroform (160 mL). The reaction was cooled to −5° C. using an ice/acetone bath and phosphorous tribromide (40.0 g, 148 mmol) was added portionwise. The cooling bath was removed and the reaction stirred at reflux for 2 h. After this time, the reaction was cooled to −5° C. and saturated aqueous sodium bicarbonate (250 mL) was added until a pH of 8.5 was reached. The mixture was extracted with ethyl acetate (3×150 mL) and the combined organic layers were washed with saturated aqueous sodium carbonate (2×50 mL), brine (75 mL), dried over sodium sulfate and the drying agent was removed by filtration. The filtrate was concentrated under reduced pressure to afford a yellow residue that was dissolved with gentle heating in methylene chloride (60 mL). Hexanes (approximately 20 mL) was added and the solution became cloudy. The mixture was heated until a solid precipitate formed, methylene chloride (9 mL) was added and the solution became clear. The solution was left to cool to room temperature and after 4 h the resulting crystals were collected by vacuum filtration. The filter cake was washed with a ice cold 1:2 mixture of methylene chloride:hexanes (2×20 mL) to afford 1-(2-bromoethyl)-5-(bromomethyl)-3-nitro-1H-pyrazole (19.7 g). The combined filtrates were evaporated and the procedure was performed again to afford an additional 9.70 g of 1-(2-bromoethyl)-5-(bromo-methyl)-3-nitro-1H-pyrazole. The solids were combined and dried under high vacuum for 18 h to afford a 57% yield (26.0 g) of 124c as white crystals: mp 95-97° C.; $^1H$ NMR (300 MHz, $CDCl_3$) δ 6.93 (s, 1H), 4.63 (t, 2H, J=6.0 Hz), 4.54 (s, 2H), 3.86 (t, 2H, J=6.0 Hz).

Example 124d

2-Nitro-4,5,6,7-tetrahydropyrazolo[1,5-a]pyrazine 124d

A 250-mL single-neck round-bottomed flask equipped with a magnetic stirrer was charged with 124c (3.0 g, 9.64 mmol) in THF (35 mL) and aqueous ammonia (135 mL, 25-28%). The mixture was stirred at room temperature for 72 h under nitrogen. The reaction mixture was then concentrated under reduced pressure and the resulting residue was partitioned between ethyl acetate (100 mL) and water (100 mL). The aqueous layer was extracted with ethyl acetate (2×50 mL). The combined organic layer was washed with 10% potassium carbonate (2×100 mL), brine (200 mL), and dried over sodium sulfate. The drying agent was removed by filtration, and the filtrate was concentrated under reduced pressure to afford 124d as a yellow solid (1.23 g, 76%). MS: $[M+H]^+$ 169

Example 124e 1-(2-Nitro-6,7-dihydropyrazolo[1,5-a]pyrazin-5 (4H)-yl)ethanone 124e To a solution of 124d (672 mg, 4.0 mmol) in dichloromethane (20 mL) was added acetyl chloride (936 mg, 12.0 mmol) and $K_2CO_3$ (1104 mg, 8.0 mmol). The mixture was stirred overnight. It was then filtered and the filtrate was concentrated under reduced pressure. The resulting residue was purified by silica-gel column chromatography eluting with 100:1 dichloromethane/methanol to afford 124e as white solid (500 mg, 60%). MS: $[M+H]^+$ 211.2

Example 124f 1-(2-Amino-6,7-dihydropyrazolo[1,5-a]pyrazin-5 (4H)-yl)ethanone 124f A 50-mL single-neck round-bottomed flask was purged with nitrogen and charged with 124e (492 mg, 2.34 mmol), 10% palladium on carbon (50% wet, 234 mg), and methanol (20 mL). The mixture was evacuated, charged with hydrogen gas, and stirred at room temperature for 2 h. The hydrogen was then evacuated and nitrogen was charged into the flask. The catalyst was removed by filtration through a pad of CELITE® and the filtrate was concentrated under reduced pressure to afford 124f (380 mg, 80%). MS: $[M+H]^+$ 181.1

Example 124g 3-(5-Acetyl-4,5,6,7-tetrahydropyrazolo[1,5-a]pyrazin-2-ylamino)-5-bromo-1-methylpyridin-2(1H)-one 124g A 50-mL single-neck round-bottomed flask equipped with a magnetic stirrer and a reflux condenser was charged with 124f (270 mg, 1.5 mmol), 1,4-dioxane (20 mL), $Pd_2(dba)_3$ (137 mg, 0.15 mmol), XantPhos (173 mg, 0.30 mmol), and cesium carbonate (978 mg, 3.0 mmol). After three cycles of vacuum/argon flush, the mixture was heated at 100° C. for 6 h. After this time the reaction was cooled to room temperature. It was then filtered and the filtrate was evaporated in vacuo. The residue was purified by silica-gel column chromatography eluting with 50:1 dichloromethane/methanol to afford 124g (540 mg, 89%) as a yellow solid. MS: $[M+H]^+$ 368.0

Example 124h 3-(5-Acetyl-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 124h A 50-mL single-neck round-bottomed flask equipped with a magnetic stirrer and a reflux condenser was charged with 124g (365 mg, 1.0 mmol), $Pin_2B_2$ (1.26 g, 5.0 mmol), $Pd_2$(dba)$_3$ (91 mg, 0.10 mmol), X-phos (92 mg, 0.20 mmol), potassium acetate (294 mg, 3.0 mmol), and dioxane (10 mL). After three cycles of vacuum/argon flush, the mixture was heated at 60° C. for 16 h. It was then cooled to room temperature and filtered. The filtrate was concentrated under reduced pressure and the residue was purified by silica-gel column chromatography eluting with 50:1 methylene chloride/methanol to afford 124h as a brown solid (330 mg, 80%). MS: [M+H]$^+$ 414.2

Example 124i 4-(5-(5-Acetyl-4,5,6,7-tetrahydropyrazolo[1,5-a]pyrazin-2-ylamino)-1-methyl-6-oxo-1,6-dihydropyridin-3-yl)-2-(6-tert-butyl-8-fluoro-1-oxophthalazin-2(1H)-yl)nicotinaldehyde 124i

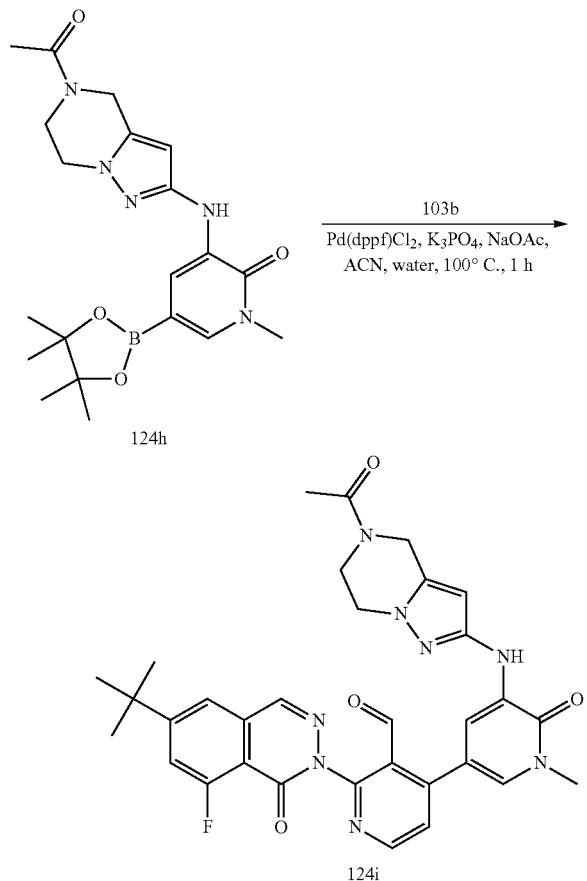

Following the procedure described in Example 123d, and starting with 2-(6-tert-butyl-8-fluoro-1-oxophthalazin-2(1H)-yl)-4-chloronicotinaldehyde 103b (200 mg, 0.57 mmol) and 124h (343 mg, 0.83 mmol), 124i was obtained as a yellow solid (300 mg, 86%). MS-ESI: [M+H]$^+$ 611.3

Example 124

2-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-6-tert-butyl-8-fluoro-phthalazin-1-one 124

Following the procedure in Example 120, and starting with 124i (200 mg, 0.33 mmol), 124 was obtained as a white solid (54 mg, 27%). MS-ESI: [M+H]$^+$ 613.3. $^1$H NMR (500 MHz, DMSO-d$_6$, T=80° C.) δ 8.53 (d, J=8.0 Hz, 1H), 8.47 (d, J=5.0 Hz, 1H), 7.94-7.92 (m, 2H), 7.84 (d, J=2.0 Hz, 1H), 7.67 (dd, J=2.5, 22.0 Hz, 1H), 7.46 (d, J=8.5 Hz, 1H), 7.34 (d, J=4.0 Hz, 1H), 5.98 (s, 1H), 4.63-4.57 (m, 3H), 4.44 (d, J=8.0 Hz, 2H), 3.98 (bs, 2H), 3.89-3.86 (m, 2H), 3.58 (s, 3H), 2.08 (s, 3H), 1.41 (s, 9H).

Example 125a

5-Bromo-1-methyl-3-(5-methyloxazol-2-ylamino)pyridin-2(1H)-one 125a

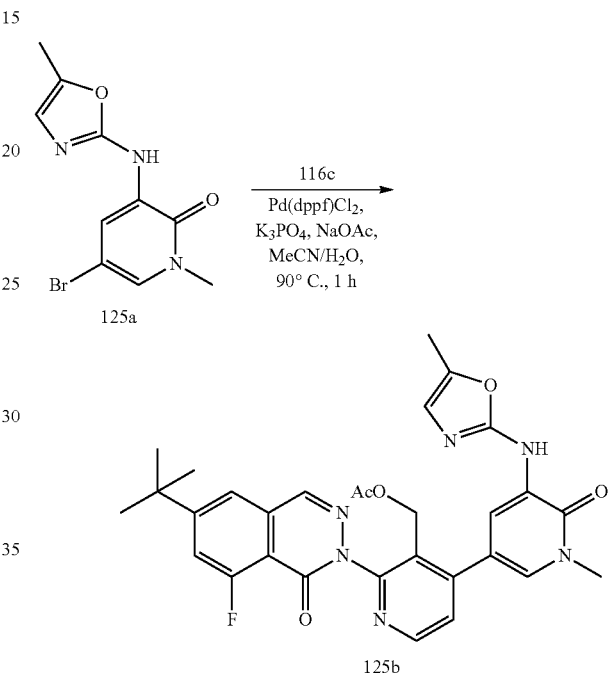

A 100-mL single-neck round-bottomed flask equipped with a magnetic stirrer and a reflux condenser was charged with 5-methyloxazol-2-amine (276 mg, 2.82 mmol), 3,5-dibromo-1-methylpyridin-2(1H)-one (753 mg, 2.82 mmol), tris-(dibenzylideneacetone)dipalladium(0) (256 mg, 0.28 mmol), XantPhos (324 mg, 0.56 mmol), Cs$_2$CO$_3$ (1.8 g, 5.64 mmol), and 1,4-dioxane (30 mL). After three cycles of vacuum/argon flush, the mixture was heated at 92° C. for 3 hrs. It was then cooled to room temperature and filtered. The filtrate was concentrated under reduced pressure and the resulting residue was purified by silica-gel column chromatography eluting with 100:1 dichloromethane/methanol to afford 125a as a white solid (702 mg, 88%). MS-ESI: [M+H]$^+$ 284.1.

Example 125b (2-(6-tert-Butyl-8-fluoro-1-oxophthalazin-2(1H)-yl)-4-(1-methyl-5-(5-methyloxazol-2-ylamino)-6-oxo-1,6-dihydropyridin-3-yl)pyridin-3-yl)methyl Acetate 125b A 50-mL single-neck round-bottomed flask equipped with a magnetic stirrer and a reflux condenser was charged with 125a (150 mg, 0.53 mmol), 3-(acetoxymethyl)-2-(6-tert-butyl-8-fluoro-1-oxophthalazin-2(1H)-yl)pyridin-4-ylboronic acid 116c (438 mg, 1.06 mmol), Pd(dppf)Cl$_2$ (39 mg, 0.053 mmol), K$_3$PO$_4$ (225 mg, 1.06 mmol), sodium acetate (87 mg, 1.06 mmol), water (0.5 mL), and acetonitrile (10 mL). After three cycles of vacuum/argon flush, the mixture was heated at 90° C. for 1 h. It was then cooled to room temperature and filtered. The filtrate was concentrated under reduced pressure and the resulting residue was purified by silica-gel column chromatography eluting with dichloromethane/methanol (100:1 to 50:1) to afford 125b as a yellow solid (120 mg, 40%). MS-ESI: [M+H]$^+$ 573.3.

Example 125

6-tert-butyl-8-fluoro-2-[3-(hydroxymethyl)-4-[1-methyl-5-[(5-methyloxazol-2-yl)amino]-6-oxo-3-pyridyl]-2-pyridyl]phthalazin-1-one 125

A mixture of 125b (114 mg, 0.20 mmol) and lithium hydroxide (120 mg, 5.0 mmol) in i-propanol/THF/water (2:2:1, 10 mL) was stirred at 35° C. for 30 mins. The mixture was concentrated under reduced pressure and the residue was diluted with water (5 mL). The resulting mixture was extracted with dichloromethane three times. The combined organic layer was then concentrated under reduced pressure and the resulting residue was purified by reverse-phase prep-HPLC to afford 125 (52 mg, 49%). MS-ESI: [M+H]$^+$ 530.9. $^1$H NMR (500 MHz, DMSO-d$_6$) δ 9.25 (s, 1H), 8.57 (d, J=5.0 Hz, 1H), 8.53 (d, J=3.0 Hz, 1H), 8.25 (d, J=2.5 Hz, 1H), 7.90 (d, J=1.0 Hz, 1H), 7.78 (dd, J=1.0, 13.0 Hz, 1H), 7.61 (d, J=2.0 Hz, 1H), 7.50 (d, J=5.0 Hz, 1H), 6.64 (d, J=1.5 Hz, 1H), 4.92 (bs, 1H), 4.40 (d, J=7.0 Hz, 2H), 3.60 (s, 3H), 2.22 (s, 3H), 1.39 (s, 9H).

Example 126a

3-Cyclopropyl-3-oxopropanenitrile 126a

To a solution of acetonitrile (0.34 mL, 6.58 mmol) in THF (3 mL) at −78° C. under N$_2$ protection was added lithium di-i-propylamide (3.3 mL, 2M in THF, 6.58 mmol) dropwise. The reaction mixture was stirred at −78° C. for 3 h. Then ethyl cyclopropanecarboxylate (0.50 g, 4.38 mmol) in THF (2 mL) was added and the mixture was allowed to warm to room temperature for a period of 1 h. Water (2 mL) was added and the solvent was removed under reduced pressure. Dichloromethane (2 mL) was added and the pH of the mixture was adjusted to 5 with 2N HCl. It was then extracted with dichloromethane (5 mL×2). The combined organic layer was dried over Na$_2$SO$_4$ and concentrated to afford 126a as a yellow oil, which was used in the next step without further purification.

Example 126b

3-Cyclopropyl-1H-pyrazol-5-amine 126b

To a solution of 126a (477 mg, 4.38 mmol) in methanol (5 mL) was added hydrazine hydrate (5 mL, 80%). The reaction mixture was heated at 75° C. for 15 h. The methanol was removed under reduced pressure and the residue was extracted with dichloromethane (2×8 mL). The combined extract was dried over Na$_2$SO$_4$ and concentrated. The residue was purified by flash column eluting with 100:1 dichloromethane/methanol to afford 126b as a yellow oil (250 mg, 46%, over two steps). MS: [M+H]$^+$ 124.

Example 126c tert-Butyl 5-Amino-3-cyclopropyl-1H-pyrazole-1-carboxylate 126c

To a mixture of 126b (0.25 g, 2.0 mmol) and K$_2$CO$_3$ (0.828 g, 6.0 mmol) in THF (5 mL) was added (Boc)$_2$O (0.436 g, 2.0 mmol) in THF (5 mL). The reaction mixture was stirred at room temperature for 15 h. It was then filtered and the filtrate was concentrated under reduced pressure. The residue was purified by flash column eluting with 6:1 petroleum ether/ethyl acetate to afford 126c as a white solid (240 mg, 54%). MS: [M-Boc]$^+$ 124.

Example 126d

5-Bromo-3-(3-cyclopropyl-1H-pyrazol-5-ylamino)-1-methylpyridin-2(1H)-one 126d

A 100-mL single-neck round-bottomed flask equipped with a magnetic stirrer and a reflux condenser was charged with 1,4-dioxane (15 mL), 126c (455 mg, 1.95 mmol), 3,5-dibromo-1-methylpyridin-2(1H)-one (0.40 g, 1.5 mmol), and cesium carbonate (1.22 g, 3.75 mmol). After bubbling nitrogen through the resulting mixture for 30 minutes, XantPhos (87 mg, 0.15 mmol) and tris(dibenzylideneacetone)dipalladium(0) (70 mg, 0.075 mmol) were added. The reaction mixture was refluxed for 15 h. After this time the reaction was cooled to room temperature and filtered. The filtrate was partitioned between ethyl acetate (30 mL) and water (30 mL). The aqueous layer was separated and extracted with ethyl acetate (2×50 mL). The combined organic layer was washed with brine (50 mL) and dried over sodium sulfate. The drying agent was removed by filtration and the filtrate was concentrated under reduced pressure. The residue was purified on silica-gel column eluting with 50:1 dichloromethane/methanol to afford 126d as a yellow solid (320 mg, 70%). MS: [M+H]$^+$ 309. $^1$H NMR (500 MHz, DMSO-d$_6$) δ 11.85 (s, 1H), 8.23 (s, 1H), 8.02 (d, J=2.5 Hz, 1H), 7.35 (d, J=2.5 Hz, 1H), 5.77 (d, J=2.0 Hz, 1H), 3.46 (s, 3H), 1.84-1.82 (m, 1H), 0.92-0.90 (m, 2H), 0.65-0.64 (m, 2H).

Example 126e 5-(3-Cyclopropyl-1H-pyrazol-5-ylamino)-1-methyl-6-oxo-1,6-dihydropyridin-3-ylboronic Acid 126e A 50-mL single-neck round-bottomed flask equipped with a magnetic stirrer and a reflux condenser was charged with 126d (205 mg, 0.665 mmol), 4,4,4',4',5,5,5',5'-octamethyl-2,2'-bi(1,3,2-dioxaborolane) (1.0 g, 4.0 mmol), dioxane (16 mL), PdCl$_2$(dppf) (54.3 mg, 0.066 mmol), and potassium acetate (0.39 mg, 4.0 mmol). After bubbling argon through the resulting mixture for 30 minutes, it was stirred at 105° C. for 4 h under argon atmosphere. It was then cooled to room temperature and filtered. The filtrate was evaporated under reduced pressure to afford crude 126e, which was used without further purification. MS: [M+H]+ 275.

Example 126f

5-Bromo-3-(5-cyclopropyl-1-methyl-1H-pyrazol-3-ylamino)-1-methylpyridine-2(1H)-one 126f

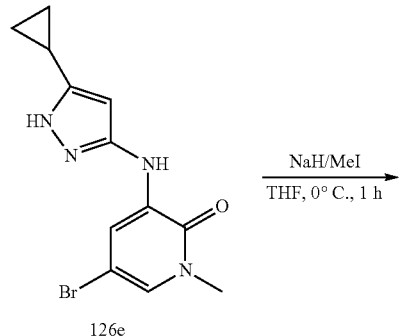

At 0° C., to a solution of 126e (500 mg, 1.6 mmol) in DMF (6 mL) was added NaH (60% in oil) (80 mg, 2.0 mmol). The reaction mixture was stirred at 0° C. for 1 h. Iodomethane (213 mg, 1.5 mmol) was introduced and the resulting mixture was stirred at room temperature for another 2 h. Then water (10 mL) was added to the mixture. The resulting suspension was filtered, washed with water, and dried in vacuo to afford 126f as a white solid (350 mg, 68%). MS-ESI: [M+H]+ 323.1.

Example 126g (2-(6-tert-Butyl-8-fluoro-1-oxophthalazin-2(1H)-yl)-4-(5-(5-cyclopropyl-1-methyl-1H-pyrazol-3-ylamino)-1-methyl-6-oxo-1,6-dihydropyridin-3-yl)pyridin-3-yl)methyl Acetate 126g A sealed tube equipped with a magnetic stirrer was charged with 126f (200 mg, 0.62 mmol), (2-(6-tert-butyl-8-fluoro-1-oxophthalazin-2(1H)-yl)-4-(4,4,5,5-tetramethyl-1,3,2-dioxaborolan-2-yl)pyridin-3-yl)methyl acetate 116c (268 mg, 0.65 mmol), Pd(dppf)Cl₂ (18 mg, 0.025 mmol), sodium acetate (74 mg, 0.90 mmol), K₃PO₄ (191 mg, 0.90 mmol), and acetonitrile/water (5 mL/0.5 mL). After three cycles of vacuum/argon flush, the mixture was heated at 100° C. for 2.0 h. It was then cooled to room temperature and filtered. The filtrate was evaporated under reduced pressure. The residue was purified by silica-gel column chromatography eluting with 10:1 dichloromethane/methanol to afford 126g (100 mg, 26%) as a brown solid. MS-ESI: [M+H]+ 612.3.

Example 126

6-tert-butyl-2-[4-[5-[(5-cyclopropyl-1-methyl-pyrazol-3-yl)amino]-1-methyl-6-oxo-3-pyridyl]-3-(hydroxymethyl)-2-pyridyl]-8-fluoro-phthalazin-1-one 126

A mixture of 126g (100 mg, 0.16 mmol) and lithium hydroxide (72 mg, 3.0 mmol) in i-propanol/THF (1:1, 4 mL) and water (1 mL) was stirred at 50° C. for 2 h. The mixture was evaporated under reduced pressure. The residue was purified by reverse-phase Combiflash to afford 126 (32 mg, 35%) as a white solid. MS-ESI: [M+H]+ 570.3. ¹H NMR (500 MHz, DMSO-d₆) δ 8.63 (d, J=5.0 Hz, 1H), 8.33 (d, J=2.0 Hz, 1H), 7.94 (d, J=1.5 Hz, 1H), 7.56-7.55 (m, 2H), 7.53-7.51 (m, 2H), 7.33 (s, 1H), 5.53 (s, 1H) 4.49-4.48 (m, 2H), 4.04-4.02 (m, 1H), 3.79 (s, 3H), 3.69 (s, 3H), 1.69-1.65 (m, 1H), 1.43 (s, 9H), 0.97-0.94 (m, 2H), 0.68-0.65 (m, 2H).

Example 127a

6-Chloro-2-methyl-4-(5-methyl-1H-pyrazol-3-ylamino)pyridazin-3(2H)-one 127a

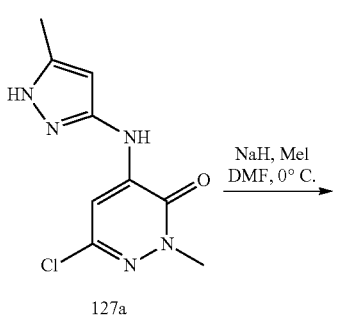

-continued

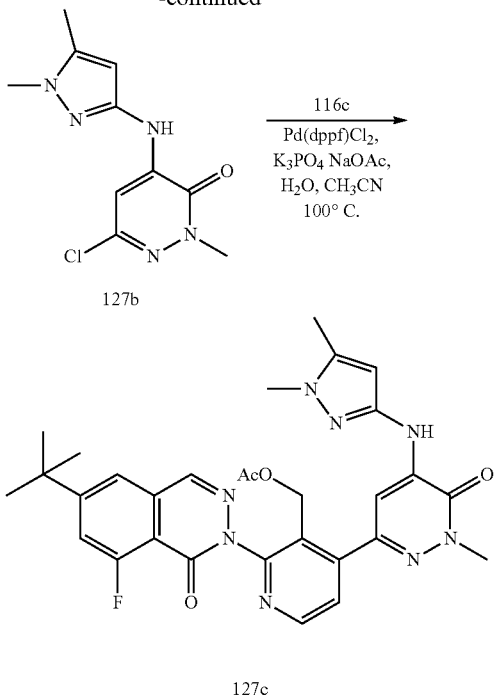

127b

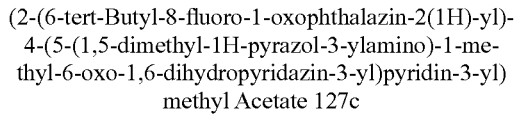

127c

A 100-mL single-neck round-bottomed flask equipped with a magnetic stirrer and a reflux condenser was charged with 1,4-dioxane (20 mL), 5-ethyl-1H-pyrazol-3-amine (971 mg, 10.0 mmol), 4-bromo-6-chloro-2-methylpyridazin-3(2H)-one (2.46 g, 11.0 mmol), and cesium carbonate (6.52 g, 20.0 mmol). After bubbling nitrogen through the suspension for 10 minutes, xantphos (1.74 g, 3.0 mmol) and tris(dibenzylideneacetone)dipalladium(0) (1.37 g, 1.5 mmol) were added. The system was subjected to three cycles of vacuum/argon flush and heated at reflux for 2 h. It was then filtered immediately when the reaction mixture was still hot. The solid was washed with dioxane (3×30 mL) and the combined filtrate was concentrated under reduced pressure. The residue was purified by silica-gel chromatography eluting with 6:1 petroleum ether/ethyl acetate to afford 127a (1.8 g, 75%) as a yellow solid. MS-ESI: [M+H]$^+$ 239.9

Example 127b

6-Chloro-4-(1,5-dimethyl-1H-pyrazol-3-ylamino)-2-methylpyridazin-3(2H)-one 127b

To a mixture of 127a (480 mg, 2.0 mmol) in anhydrous DMF (10 mL) was added NaH (purity 60%) (64 mg, 1.6 mmol) at 0° C. and the resulting mixture was stirred for 0.5 h. To the mixture was added iodomethane (227 mg, 1.6 mmol) in DMF (5 mL) dropwise at 0° C. The reaction mixture was stirred for additional 1.5 h and quenched with water (20 mL). It was then extracted with dichloromethane (3×20 mL) and the combined organic layer was evaporated under reduced pressure. The residue was purified by reverse-phase Combi-flush (A: 2% aqueous NH$_4$HCO$_3$, B: acetonitrile) to afford 127b (120 mg, 24%) as a light yellow solid. MS-ESI: [M+H]$^+$ 254.3

Example 127c (2-(6-tert-Butyl-8-fluoro-1-oxophthalazin-2(1H)-yl)-4-(5-(1,5-dimethyl-1H-pyrazol-3-ylamino)-1-methyl-6-oxo-1,6-dihydropyridazin-3-yl)pyridin-3-yl)methyl Acetate 127c A 50-mL single-neck round-bottomed flask equipped with a magnetic stirrer and a reflux condenser was charged with 127b (120 mg, 0.47 mmol,), (2-(6-tert-butyl-8-fluoro-1-oxophthalazin-2(1H)-yl)-4-(4,4,5,5-tetramethyl-1,3,2-dioxaborolan-2-yl)pyridin-3-yl)methyl acetate 116c (536 mg, 1.3 mmol), Pd(dppf)Cl$_2$ (34 mg, 0.047 mmol), K$_3$PO$_4$ (199 mg, 0.94 mmol), sodium acetate (77 mg, 0.94 mmol), acetonitrile (10 mL), and water (0.2 mL). After three cycles of vacuum/argon flush, the mixture was heated at 100° C. for 2 h. It was then cooled to room temperature and filtered. The filtrate was concentrated under reduced pressure and the resulting residue was purified by silica-gel column chromatography eluting with dichloromethane/methanol (100:1 to 30:1) to afford 127c (180 mg, 65%) as a black oil. MS-ESI: [M+H]$^+$ 587.1

Example 127

6-tert-butyl-2-[4-[5-[(1,5-dimethylpyrazol-3-yl)amino]-1-methyl-6-oxo-pyridazin-3-yl]-3-(hydroxymethyl)-2-pyridyl]-8-fluoro-phthalazin-1-one 127

To a solution of 127c (176 mg, 0.30 mmol) in propan-2-ol (4 mL), tetrahydrofuran (4 mL), and water (1.0 mL) was added lithium hydroxide (72 mg, 3.0 mmol). The mixture was stirred at 30° C. for 2 h. It was then evaporated under reduced pressure and the residue was purified by reverse-phase prep-HPLC to afford 127 (30 mg, 18%) as a white solid. MS-ESI: [M+H]$^+$ 544.8. $^1$H NMR (500 MHz, MeOD) δ 8.66 (d, J=5.0 Hz, 1H), 8.51 (d, J=2.5 Hz, 1H), 7.88 (s, 1H), 7.88 (s, 1H), 7.76-7.72 (m, 2H), 5.97 (s, 1H), 4.68 (s, 2H), 3.89 (s, 3H), 3.75 (s, 3H), 2.29 (s, 3H), 1.47 (s, 9H)

Example 128a

5-Methyl-2-nitro-4,5,6,7-tetrahydropyrazolo[1,5-a]pyrazine 128a

A 1-L single-neck round-bottomed flask equipped with a magnetic stirrer and nitrogen inlet was charged with THF (350 mL), 124c (10.0 g, 32.2 mmol), 2M methylamine solution in THF (113 mL, 225 mmol) and stirred at room temperature for 72 h. After this time the reaction was concentrated to dryness under reduced pressure, and the resulting solid was stirred with a mixture of ethyl acetate (75 mL) and 10% aqueous potassium carbonate (75 mL). The aqueous layer was separated and extracted with ethyl acetate (2×75 mL). The combined organic extracts were washed with 10% aqueous potassium carbonate (75 mL), followed by brine (50 mL) and dried over sodium sulfate. The drying agent was removed by filtration, and the filtrate concentrated under reduced pressure to afford 128a in 97% yield (5.70 g) as a yellow solid. $^1$H NMR (300 MHz, CDCl$_3$) δ 6.62 (s, 1H), 4.28 (t, 2H, J=5.4 Hz), 3.67 (s, 2H), 2.95 (t, 2H, J=5.4 Hz), 2.52 (s, 3H); MS (ESI+) m/z 183.0 (M+H)

Example 128b

5-Methyl-4,5,6,7-tetrahydropyrazolo[1,5-a]pyrazin-2-amine 128b

A 500-mL Parr reactor bottle was purged with nitrogen and charged with 10% palladium on carbon (50% wet, 800 mg dry weight) and a solution of 128a (4.00 g, 2.20 mmol) in ethanol (160 mL). The bottle was attached to Parr hydrogenator, evacuated, charged with hydrogen gas to a pressure of 45 psi and shaken for 2 h. After this time, the hydrogen was evacuated, and nitrogen was charged into the bottle. CELITE® 521 (1.0 g) was added, and the mixture was filtered through a pad of CELITE® 521. The filter cake was washed with ethanol (2×75 mL), and the combined filtrates were concentrated to dryness under reduced pressure to afford a 99% yield of 128b (3.31 g) as an orange solid. $^1$H NMR (300 MHz, CDCl$_3$) δ 5.34 (s, 1H), 3.98 (t, 2H, J=5.4 Hz), 3.52 (s, 3H), 2.84 (t, 2H, J=5.7 Hz), 2.45 (s, 3H); MS (ESI+) m/z 153.1 (M+H)

Example 128c

5-Bromo-1-methyl-3-(5-methyl-4,5,6,7-tetrahydro-pyrazolo[1,5-a]pyrazin-2-ylamino)pyridin-2(1H)-one 128c A sealed tube equipped with a magnetic stirrer was charged with 128b (1.02 g, 6.7 mmol), 3,5-dibromo-1-methylpyridin-2(1H)-one (2.15 g, 8.1 mmol), Pd$_2$(dba)$_3$ (610 mg, 0.67 mmol), 2,2-bis(diphenylphosphino)-1,1-binaphthyl (775 mg, 1.34 mmol), cesium carbonate (4.37 g, 13.6 mmol), and 1,4-dioxane (30 mL). After three cycles of vacuum/argon flush, the mixture was heated at 110° C. for 2 h. It was then filtered and the filtrate was evaporated in vacuo. The residue was purified by silica gel column chromatography eluting with dichloromethane/methanol (15:1, V/V) to afford 128c (380 mg, 14%) as a white solid. LCMS: [M+H]$^+$ 338

Example 128d

1-Methyl-3-(5-methyl-4,5,6,7-tetrahydropyrazolo[1,5-a]pyrazin-2-ylamino)-5-(4,4,5,5-tetramethyl-1,3,2-dioxaborolan-2-yl)pyridin-2(1H)-one 128d A 100-mL single-neck round-bottomed flask equipped with a magnetic stirrer and a condenser was charged with 128c (1.0 g, 3 mmol), Pin$_2$B$_2$ (3.8 g, 15 mmol), Pd(dppf)Cl$_2$ (137 mg, 0.15 mmol), X-phos (143 mg, 0.3 mmol), potassium acetate (88 mg, 9 mmol), and 1,4-dioxane (50 mL). After three cycles of vacuum/argon flush, the reaction mixture was heated at 60° C. for 15 h. It was then cooled to room temperature and filtered. The filtrate was concentrated under reduced pressure and the resulting residue was washed with petroleum ether to afford 128d as a yellow solid (0.87 g, 75%). MS: [M+H]$^+$ 386

Example 128e

2-(6-tert-Butyl-8-fluoro-1-oxophthalazin-2(1H)-yl)-4-(1-methyl-5-(5-methyl-4,5,6,7-tetrahydropyrazolo[1,5-a]pyrazin-2-ylamino)-6-oxo-1,6-dihydropyridin-3-yl)nicotinaldehyde 128e

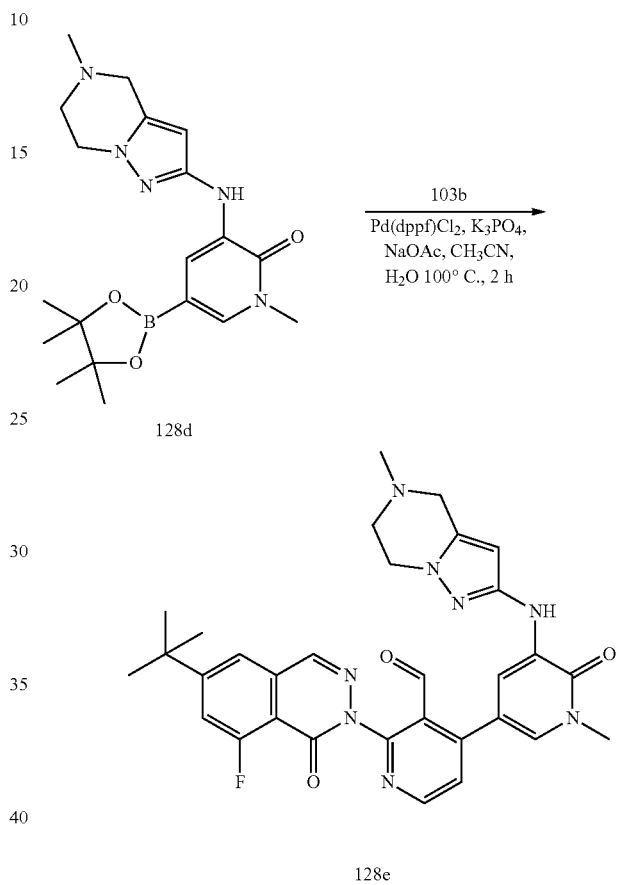

A 25-mL round-bottomed flask equipped with a reflux condenser was charged with 128d (193 mg, 0.50 mmol), 2-(6-tert-butyl-8-fluoro-1-oxophthalazin-2(1H)-yl)-4-chloronicotinaldehyde 103b (180 mg, 0.50 mmol), 1,1'-bis(diphenylphosphino)ferrocenedichloropalladium(II) (17 mg, 0.025 mmol), K$_3$PO$_4$ (212 mg, 1.0 mmol), sodium acetate (82 mg, 1.0 mmol), acetonitrile (6 mL), and water (0.5 mL). After three cycles of vacuum/argon flush, the mixture was heated at 100° C. for 1 h. Analysis of the reaction mixture by LCMS showed completed conversion to the desired product. The reaction mixture was cooled to room temperature and concentrated under reduced pressure. The residue was diluted with dichloromethane (20 mL) and water (10 mL). The aqueous layer was separated and extracted with dichloromethane (3×10 mL). The combined organic layer was dried over Na$_2$SO$_4$ and filtered. The filtrate was concentrated under reduced pressure. The dark residue was purified by silica-gel column chromatography eluting with dichloromethane/methanol (80:1 to 30:1) to afford 128e (190 mg, 65%) as a yellow solid. MS-ESI: [M+H]$^+$ 583.3

Example 128

6-tert-butyl-8-fluoro-2-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]phthalazin-1-one 128

To a solution of 128e (158 mg, 0.27 mmol) in methanol/dichloromethane (5/5 mL) was added NaBH$_4$ (31 mg, 0.82 mmol) at room temperature. After the reaction was stirred for 1 h, LCMS indicated the reaction was complete. The reaction was quenched with water (10 mL) and concentrated under reduced pressure. The residue was extracted with dichloromethane (3×20 mL). The combined organic layer was washed with brine (30 mL), dried over Na$_2$SO$_4$, filtered, and concentrated under reduced pressure. The residue was purified by reverse-phase prep-HPLC to afford 128 (95 mg, 60%) as a white solid. MS-ESI: [M+H]$^+$ 585.3. $^1$H NMR (500 MHz, CDCl$_3$) δ 8.66 (d, J=5.0 Hz, 1H), 8.35 (d, J=2.0 Hz, 1H), 8.00 (d, J=2.5 Hz, 1H), 7.58-7.54 (m, overlap, 4H), 7.44 (s, 1H), 5.70 (s, 1H), 4.52-4.39 (m, 2H), 4.10-4.09 (m, 3H), 3.70 (s, 3H), 3.59 (s, 2H), 2.88-2.86 (m, 2H), 2.47 (s, 3H), 1.43 (s, 9H).

Example 129a

5-Bromo-1-methyl-3-(5-methylisoxazol-3-ylamino)pyridin-2(1H)-one 129a

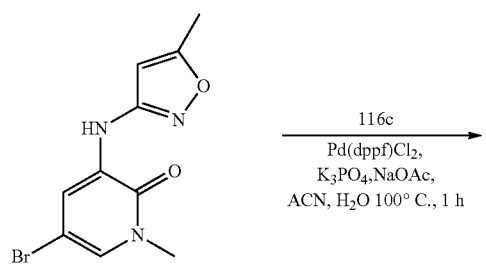

A 100-mL single-neck round-bottomed flask equipped with a magnetic stirrer and a reflux condenser was charged with 5-methylisoxazol-3-amine (1.0 g, 10.2 mmol), 3,5-dibromo-1-methylpyridin-2(1H)-one (4.09 g, 15.3 mmol), Pd$_2$(dba)$_3$ (467 mg, 0.51 mmol), Xantphos (598 mg, 1.02 mmol), Cs$_2$CO$_3$ (6.65 g, 20.4 mmol), and dioxane (50 mL). After three cycles of vacuum/argon flush, the reaction mixture was heated at 100° C. for 3 h. Analysis of the reaction mixture by LCMS showed completed conversion to the desired product. It was filtered when the mixture was still hot. The filtrate was cooled to room temperature and the resulting precipitate was collected by filtration to afford 129a (1.6 g, 55%) as a yellow solid. MS-ESI: [M+H]$^+$ 284.1

Example 129b (2-(6-tert-Butyl-8-fluoro-1-oxophthalazin-2(1H)-yl)-4-(1-methyl-5-(5-methylisoxazol-3-ylamino)-6-oxo-1,6-dihydropyridin-3-yl)pyridin-3-yl)methyl Acetate 129b A 50-mL single-neck round-bottomed flask equipped with a magnetic stirrer and a reflux condenser was charged with 3-(acetoxymethyl)-2-(6-tert-butyl-8-fluoro-1-oxophthalazin-2(1H)-yl)pyridin-4-ylboronic acid 116c (438 mg, 1.06 mmol), 129a (150 mg, 0.60 mmol), Pd(dppf)Cl$_2$ (19 mg, 0.026 mmol), K$_3$PO$_4$ (224 mg, 1.06 mmol), sodium acetate (87 mg, 1.06 mmol), water (5 drops), and acetonitrile (10 mL). After three cycles of vacuum/argon flush, the reaction mixture was heated at 100° C. for 1 h. Analysis of the reaction mixture by LCMS showed complete conversion to the desired product. The mixture was cooled down to room temperature and filtered. The filtrate was concentrated under reduced pressure to afford 129b (300 mg, 87%) as a dark oil, which was used in next step without further purification. MS-ESI: [M+H]$^+$ 573.3

Example 129

6-tert-butyl-8-fluoro-2-[3-(hydroxymethyl)-4-[1-methyl-5-[(5-methylisoxazol-3-yl)amino]-6-oxo-3-pyridyl]-2-pyridyl]phthalazin-1-one 129

To a solution of 129b (280 mg, 0.49 mmol) in THF (4 mL), i-propanol (4 mL), and water (2 mL) was added lithium hydroxide (24 mg, 0.98 mmol). The reaction mixture was stirred at room temperature for 1 h. It was concentrated under reduced pressure and the residue was purified by reverse-phase prep-HPLC to afford 129 as a white solid (85 mg, 33%). MS-ESI: [M+H]$^+$ 531.3. $^1$H NMR (500 MHz, DMSO-d$_6$) δ 9.03 (s, 1H), 8.58 (d, J=5.0 Hz, 1H), 8.54 (d, J=3.0 Hz, 1H), 7.99 (d, J=2.0 Hz, 1H), 7.91 (d, J=1.0 Hz, 1H), 7.78 (dd, J=1.0, 13.0 Hz, 1H), 7.56 (d, J=2.0 Hz, 1H), 7.51 (d, J=5.0 Hz,

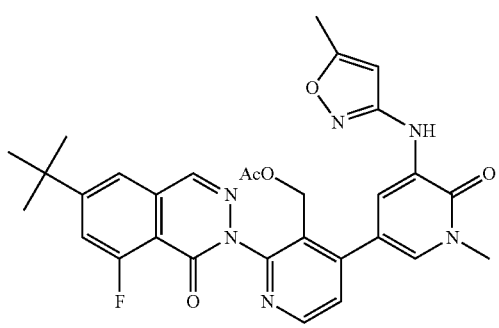

1H), 6.26 (s, 1H), 4.92 (s, 1H), 4.43 (d, J=6.0 Hz, 2H), 3.61 (s, 3H), 2.32 (s, 3H), 1.40 (s, 9H).

Example 130a

5-Bromo-1-methyl-3-(1-methyl-1H-imidazol-4-ylamino)pyridin-2(1H)-one 130a

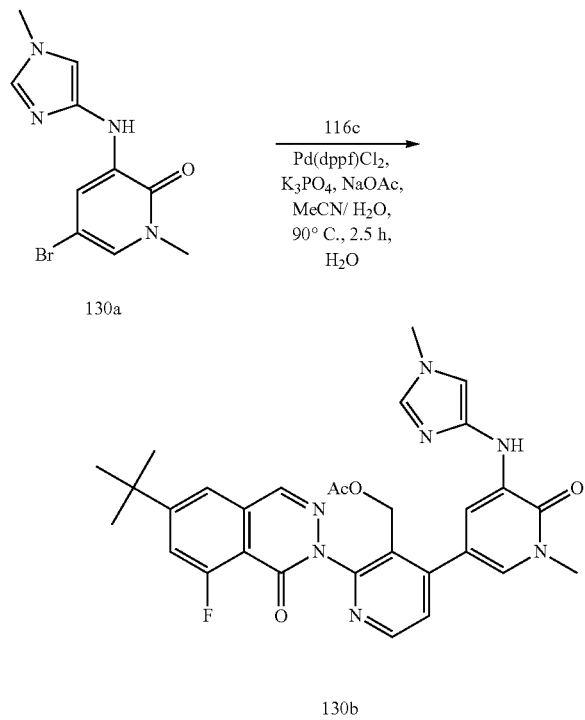

A 100-mL single-neck round-bottomed flask equipped with a magnetic stirrer and a reflux condenser was charged with 1,4-dioxane (50 mL), 1-methyl-1H-imidazol-4-amine (1.1 g, 11.3 mmol), 3,5-dibromo-1-methylpyridin-2(1H)-one (3.0 g, 11.3 mmol), Pd$_2$(dba)$_3$ (1.0 g, 1.13 mmol), XantPhos (1.3 g, 2.26 mmol), and cesium carbonate (7.3 g, 22.6 mmol). After three cycles of vacuum/argon flush, the mixture was heated at 92° C. for 4.5 hrs. It was then cooled to room temperature and filtered. The filtrate was concentrated under reduced pressure and the resulting residue was purified by silica-gel column chromatography eluting with dichloromethane/methanol (100:1 to 50:1) to afford 130a (2.4 g, 76%) as a yellow solid. MS-ESI: [M+H]$^+$ 283.1

Example 130b (2-(6-tert-Butyl-8-fluoro-1-oxophthalazin-2(1H)-yl)-4-(1-methyl-5-(1-methyl-1H-imidazol-4-ylamino)-6-oxo-1,6-dihydropyridin-3-yl)pyridin-3-yl)methyl Acetate 130b A 50-mL round-bottomed flask equipped with a magnetic stirrer was charged with 130a (150 mg, 0.53 mmol), 3-(acetoxymethyl)-2-(6-tert-butyl-8-fluoro-1-oxophthalazin-2 (1H)-yl)pyridin-4-ylboronic acid 116c (438 mg, 1.06 mmol), PdCl$_2$(dppf) (43 mg, 0.053 mmol), K$_3$PO$_4$ (225 mg, 1.06 mmol), sodium acetate (87 mg, 1.06 mmol), acetonitrile (10 mL), and water (0.2 mL). After bubbling nitrogen into the mixture for 10 minutes, a reflux condenser was attached to the flask and the reaction mixture was heated at 90° C. for 2.5 h. It was then cooled to room temperature and filtered. The filtrate was evaporated under reduced pressure and the resulting residue was purified by silica-gel column chromatography eluting with dichloromethane/methanol (50:1 to 20:1) to afford 130b as a yellow solid (120 mg, 40%). MS-ESI: [M+H]$^+$ 572.3.

Example 130

6-tert-butyl-8-fluoro-2-[3-(hydroxymethyl)-4-[1-methyl-5-[(1-methylimidazol-4-yl)amino]-6-oxo-3-pyridyl]-2-pyridyl]phthalazin-1-one 130

A mixture of 130b (100 mg, 0.18 mmol) and lithium hydroxide hydrate (189 mg, 4.5 mmol) in i-propanol/THF/water (2:2:1, 10 mL) was stirred at 35° C. for 30 min. The mixture was evaporated under reduced pressure and the residue was added water (5 mL). It was then extracted with dichloromethane (3×10 mL). The combined extract was concentrated under reduced pressure and the residue was purified by reverse-phase prep-HPLC to afford 130 (41.1 mg, 44.4%) as white solid. MS-ESI: [M+H]$^+$ 530.3. $^1$H NMR (500 MHz, DMSO-d$_6$) δ 8.56-8.53 (m, 2H), 7.90 (d, J=2.0 Hz, 1H), 7.78 (dd, J=2.0, 12.5 Hz, 1H), 7.61 (s, 1H), 7.51 (d, J=5.0 Hz, 1H), 7.41-7.39 (m, 2H), 7.37 (d, J=2.0 Hz, 1H), 6.97 (d, J=1.5 Hz, 1H), 5.04-5.02 (m, 1H), 4.41-4.39 (m, 2H), 3.59 (s, 3H), 3.58 (s, 3H), 1.39 (s, 9H).

Example 131a

2-Nitro-6,7-dihydro-4H-pyrazolo[5,1-c][1,4]oxazine 131a

A 250-mL single-neck round-bottomed flask equipped with a magnetic stirrer and reflux condenser was charged with 1-(2-bromoethyl)-5-(bromomethyl)-3-nitro-1H-pyrazole 124c (3.00 g, 9.59 mmol) and 4M aqueous hydrobromic acid (120 mL), and the resulting mixture was heated at reflux for 24 h. After this time, the reaction mixture was concentrated under reduced pressure to approximately 6 mL volume, and the residue was stirred in 2M aqueous sodium hydroxide (40 mL) for 2 h. After this time methylene chloride was added (40 mL) and the mixture was stirred for 15 min. The aqueous layer was separated and extracted with methylene chloride (2×50 mL). The combined organic extracts were washed with brine (100 mL) and dried over sodium sulfate. The drying agent was removed by filtration and the filtrate concentrated under reduced pressure to afford a 62% yield (1.01 g) of 131a as a white solid: mp 110-112° C.; $^1$H NMR (300 MHz, CDCl$_3$) 6.68 (s, 1H), 4.87 (s, 2H), 4.28 (t, 2H, J=5.4 Hz), 4.20 (t, 2H, J=5.1 Hz); MS (ESI+) m/z 170.0 (M+H).

Example 131b 6,7-Dihydro-4H-pyrazolo[5,1-c][1,4]oxazin-2-amine 131b

A 500-mL Parr hydrogenation bottle was purged with nitrogen and charged with 131a (1.01 g, 5.92 mmol), 10% palladium on carbon (50% wet, 125 mg dry weight) and ethanol (50 mL). The bottle was evacuated, charged with hydrogen gas to a pressure of 25 psi and shaken for 2 h on a Parr hydrogenation apparatus. The hydrogen was then evacuated and nitrogen charged to the bottle. The catalyst was removed by filtration through a pad of CELITE® 521 and the filtrate concentrated under reduced pressure. The resulting residue was purified by column chromatography using 400 cc of silica gel and eluting with 3% methanol in methylene chloride. The fractions were collected to afford, after concentrating under reduced pressure, a 73% yield (601 mg) of 131b as a yellow solid: mp 74-76° C. $^1$H NMR (300 MHz, CDCl$_3$) δ 5.37 (s, 1H), 4.72 (s, 2H), 4.07 (t, 2H, J=5.1 Hz), 3.98 (t, 2H, J=5.1 Hz), 3.57 (br s, 2H); MS (ESI+) m/z 140.4 (M+H).

Example 131c

5-Bromo-3-(6,7-dihydro-4H-pyrazolo[5,1-c][1,4]oxazin-2-ylamino)-1-methylpyridin-2(1H)-one 131c A 50-mL three-neck round-bottomed flask equipped with a magnetic stirrer, reflux condenser and nitrogen inlet was charged with 1,4-dioxane (20 mL), 131b (600 mg, 4.31 mmol), 3,5-dibromo-1-methylpyridine-2(1H)-one (1.44 g, 5.40 mmol) and cesium carbonate (3.08 g, 9.48 mmol). After bubbling nitrogen through the resulting solution for 30 min, Xantphos (300 mg, 0.52 mmol) and tris(dibenzylideneacetone)dipalladium(0) (320 mg, 0.35 mmol) were added, and the reaction mixture was heated at reflux for 2 h. After this time the reaction was cooled to room temperature, partitioned between ethyl acetate (75 mL) and water (75 mL) and filtered. The aqueous layer was separated and extracted with ethyl acetate (2×25 mL). The organic layers were combined and washed with brine (50 mL) and dried over sodium sulfate. The drying agent was removed by filtration and the filtrate concentrated under reduced pressure. The resulting residue was purified by column chromatography using 500 cc of silica gel and eluting with 1% methanol in methylene chloride. The fractions were collected to afford, after concentrating under reduced pressure, a 31% yield (433 mg) of 131c as a green solid: mp 195-197° C.; $^1$H NMR (300 MHz, CDCl$_3$) 7.92 (d, 1H, J=2.4 Hz), 7.44 (s, 1H), 6.90 (d, 1H, J=2.4 Hz), 5.65 (s, 1H), 4.80 (s, 2H), 4.13 (s, 2H), 3.61 (s, 5H); MS (ESI+) m/z 324.9 (M+H).

Example 131d 3-(6,7-Dihydro-4H-pyrazolo[5,1-c][1,4]oxazin-2-ylamino)-1-methyl-5-(4,4,5,5-tetramethyl-1,3,2-dioxaborolan-2-yl)pyridin-2(1H)-one 131d A 250-mL round bottomed flask equipped with a magnetic stirrer and a reflux condenser was charged with the mixture of 131c (1.3 g, 4.0 mmol), bis(pinacolato)diboron (2.03 g, 8.0 mmol), PdCl$_2$(dppf) (439 mg, 0.60 mmol), potassium acetate (784 mg, 8.0 mmol), and 1,4-dioxane (60 mL). After bubbling nitrogen through the mixture for 30 minutes, it was heated at reflux for 15 h. The mixture was cooled to room temperature upon completion of the reaction and filtered. The solid was washed with ethyl acetate (100 mL). The combined filtrate was evaporated under reduced pressure and the residue was purified by silica-gel column chromatography eluting with 30:1 dichloromethane/methanol to afford 131d (446 mg, 30%). MS: [M+H]$^+$ 373.

Example 131e 2-(6-tert-Butyl-8-fluoro-1-oxophthalazin-2(1H)-yl)-4-(5-(6,7-dihydro-4H-pyrazolo[5,1-c][1,4]oxazin-2-ylamino)-1-methyl-6-oxo-1,6-dihydropyridin-3-yl)nicotinaldehyde 131e

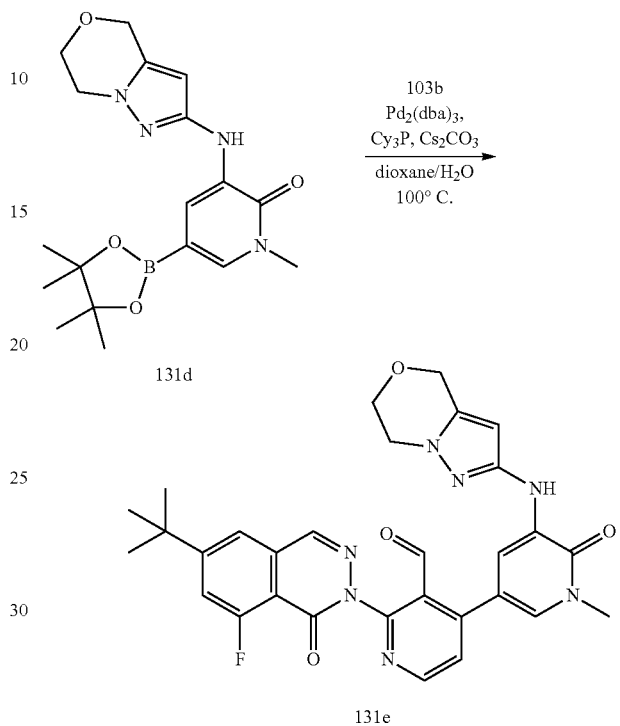

A 50-mL round-bottomed flask equipped with a reflux condenser was charged with 2-(6-tert-butyl-8-fluoro-1-oxophthalazin-2(1H)-yl)-4-chloronicotinaldehyde 103b (216 mg, 1 eq., 0.60 mmol), 131d (446 mg, 2 eq., 1.2 mmol), Pd$_2$(dba)$_3$ (55 mg, 0.1 eq., 0.060 mmol), Cy$_3$P (67 mg, 0.4 eq., 0.24 mmol), Cs$_2$CO$_3$ (395 mg, 2 eq., 1.2 mmol), water (0.5 mL), and dioxane (10 mL). After three cycles of vacuum/N$_2$ flush, the reaction mixture was stirred at 100° C. for 2 hrs. It was then cooled to room temperature and filtered. The filtrate was evaporated under reduced pressure and the resulting residue was purified by silica-gel column chromatography eluting with 4:1 petroleum ether/ethyl acetate to afford 131e (272 mg, 80%) as a brown solid. MS-ESI: [M+H]$^+$ 569.8

Example 131

6-tert-butyl-2-[4-[5-(6,7-dihydro-4H-pyrazolo[5,1-c][1,4]oxazin-2-ylamino)-1-methyl-6-oxo-3-pyridyl]-3-(hydroxymethyl)-2-pyridyl]-8-fluoro-phthalazin-1-one 131

A 50-mL single-neck round-bottomed flask equipped with a magnetic stirrer was charged with 131e (220 mg, 1.0 eq., 0.39 mmol), NaBH$_4$ (73 mg, 5.0 eq., 1.90 mmol), and methanol (10 mL). The mixture was stirred at room temperature for 1 h and quenched with water (5 mL). It was then concentrated under reduced pressure and resulting residue was extracted with dichloromethane (3×10 mL). The combined organic layer was concentrated under reduced pressure and the residue was purified by reverse-phase prep-HPLC to afford 131 (105 mg, 47%). MS-ESI: [M+H]$^+$ 571.8. $^1$H NMR (500 MHz, CDCl₃) δ 8.66 (d, J=5.0 Hz, 1H), 8.35 (d, J=2.5 Hz, 1H), 8.03 (d, J=2.5 Hz, 1H), 7.59-7.53 (m, 4H), 7.48 (s, 1H), 5.73 (s, 1H), 4.81 (s, 2H), 4.51 (bs, 2H), 4.12-4.05 (m, overlap, 5H), 3.73 (s, 3H), 1.46 (s, 9H).

Example 132a (R)-(6-Aminopyridin-3-yl)(3-methylmorpholino) methanone 132a

To a solution of (R)-3-methylmorpholine (2.02 g, 20 mmol) in ethanol (25 mL) was added 1-ethyl-3-(3-dimethylaminopropyl) carbodiimide (EDCI) (3.33 g, 17.4 mmol), hydroxybenzotriazole (HOBt) (2.35 g, 17.4 mmol), and 6-aminonicotinic acid (2.0 g, 14.5 mmol). After stirring for 18 h at room temperature, the reaction suspension was filtered and the filtrate was concentrated under reduced pressure. The residue was purified by silica-gel column chromatography eluting with 3:1 ethyl acetate/petroleum ether to afford 132a as a white solid (1.6 g, 36%). MS-ESI: [M+H]⁺ 222.3.

Example 132b (R)-5-Bromo-1-methyl-3-(5-(3-methylmorpholine-4-carbonyl)pyridin-2-ylamino)pyridin-2(1H)-one 132b A 100-mL single-neck round-bottomed flask equipped with a magnetic stirrer and a reflux condenser was charged with 132a (332 mg, 1.5 mmol), 3,5-dibromo-1-methylpyridin-2(1H)-one (H-001) (480 mg, 1.8 mmol), and cesium carbonate (978 mg, 3.0 mmol). After bubbling nitrogen through the suspension for 3 minutes, Xantphos (87 mg, 0.15 mmol) and tris(dibenzylideneacetone)dipalladium(0) (69 mg, 0.075 mmol) were added. The system was subjected to three cycles of vacuum/argon flush and heated at reflux for 2.5 h. It was then cooled to room temperature and filtered. The solid was washed with dichloromethane (2×50 mL) and the combined filtrate was concentrated under reduced pressure. The residue was purified by silica-gel column chromatography eluting with petroleum ether/ethyl acetate (2:1 to 1:2) to afford 132b (430 mg, 70%) as a yellow solid. MS-ESI: [M+H]⁺ 407.3

Example 132c (R)-1-Methyl-5-(5-(3-methylmorpholine-4-carbonyl)pyridin-2-ylamino)-6-oxo-1,6-dihydropyridin-3-ylboronic Acid 132c

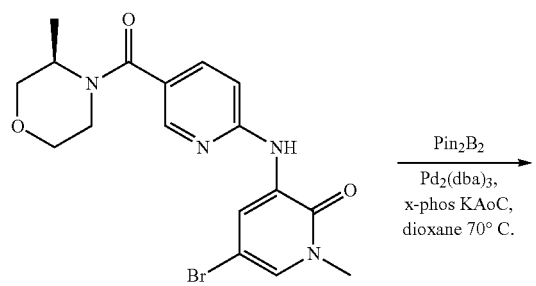

132b

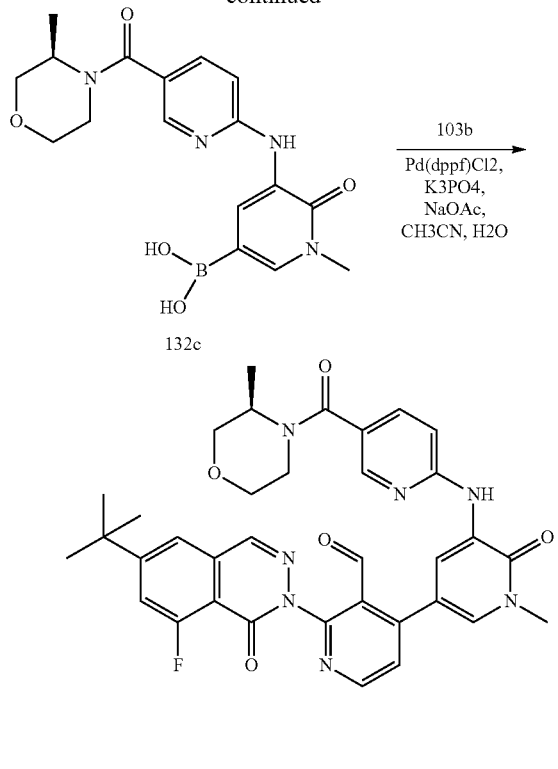

132d

A 100-mL round-bottomed flask equipped with a reflux condenser was charged with 132b (580 mg. 1.42 mmol), bis(pinacolato)diboron (1.2 g, 4.5 mmol), Pd₂(dba)₃ (137 mg, 0.15 mmol), X-phos (71 mg, 0.15 mmol), potassium acetate (294 mg, 3.0 mmol), and 1,4-dioxane (20 mL). After three cycles of vacuum/argon flush, the mixture was heated at 70° C. for 2 h. Then it was filtered and the filtrate was evaporated under reduced pressure. The residue was washed with petroleum ether to afford 132c (500 mg, 94%) as a white solid, which was used in the next step without further purification. MS-ESI: [M+H]⁺ 373.1

Example 132d (R)-2-(6-tert-Butyl-8-fluoro-1-oxophthalazin-2(1H)-yl)-4-(1-methyl-5-(5-(3-methylmorpholine-4-carbonyl)pyridin-2-ylamino)-6-oxo-1,6-dihydropyridin-3-yl)nicotinaldehyde 132d A 25-mL single-neck round-bottomed flask equipped with a magnetic stirrer and a reflux condenser was charged with 132c (260 mg, 0.70 mmol), 2-(6-tert-butyl-8-fluoro-1-oxophthalazin-2(1H)-yl)-4-chloronicotin-aldehyde 103b (180 mg, 0.50 mmol), K₃PO₄ (297 mg, 1.4 mmol), sodium acetate (114 mg, 1.4 mmol), 1,1'-bis(diphenylphosphino)ferrocene-dichloropalladium(II) (57 mg, 0.070 mmol), and acetonitrile/water (10/0.2 mL). After three cycles of vacuum/N₂ flush, the mixture was heated at 100° C. 1.5 h. Analysis of the reaction mixture by LCMS showed complete conversion to the desired product. The reaction mixture was cooled to room temperature and concentrated under reduced pressure. The residue was diluted with dichloromethane (20 mL) and water (20 mL). The aqueous layer was separated and extracted with dichloromethane (3×20 mL). The combined organic layer was dried over Na₂SO₄, filtered, and concentrated under reduced pressure. The dark residue was purified by silica-gel column chromatography eluting with 60:1 dichloromethane/methanol to afford 132d (120 mg, 37%) as a yellow solid. MS-ESI: [M+H]+ 652.3

Example 132

6-tert-butyl-8-fluoro-2-[3-(hydroxymethyl)-4-[1-methyl-5-[[5-[(3R)-3-methylmorpholine-4-carbonyl]-2-pyridyl]amino]-6-oxo-3-pyridyl]-2-pyridyl]phthalazin-1-one 132

A solution of 132d (120 mg, 0.18 mmol) in methanol/dichloromethane (4/4 mL) was added NaBH₄ (15 mg, 0.60 mmol). The mixture was stirred at room temperature for 1 h and quenched with water (2 mL). It was then evaporated under reduced pressure and the residue was purified by reverse-phase prep-HPLC to afford 132 (60 mg, 50%) as a white solid. MS-ESI: [M+H]+ 654.3. ¹H NMR (500 MHz, MeOD-d₄) δ 8.94 (d, J=2.5 Hz, 1H), 8.61 (d, J=5.0 Hz, 1H), 8.51 (d, J=2.5 Hz, 1H), 8.35 (d, J=2.0 Hz, 1H) 7.88 (d, J=1.5 Hz, 1H), 7.75 (d, J=1.5 Hz, 1H), 7.72-7.69 (m, 1H), 7.65 (d, J=5.0 Hz, 1H), 7.61 (d, J=2.5 Hz, 1H), 7.13 (d, J=7.5 Hz, 1H), 4.62-4.58 (m, 2H), 4.36-4.31 (m, 1H), 3.61-3.84 (m, 2H), 3.71-3.67 (m, overlap, 5H), 3.56-3.47 (m, 2H), 1.47 (s, 9H), 1.39 (d, J=7.0 Hz, 3H).

Example 133a

5-(2-Methoxyethyl)-2-nitro-4,5,6,7-tetrahydropyrazolo[1,5-a]pyrazine 133a

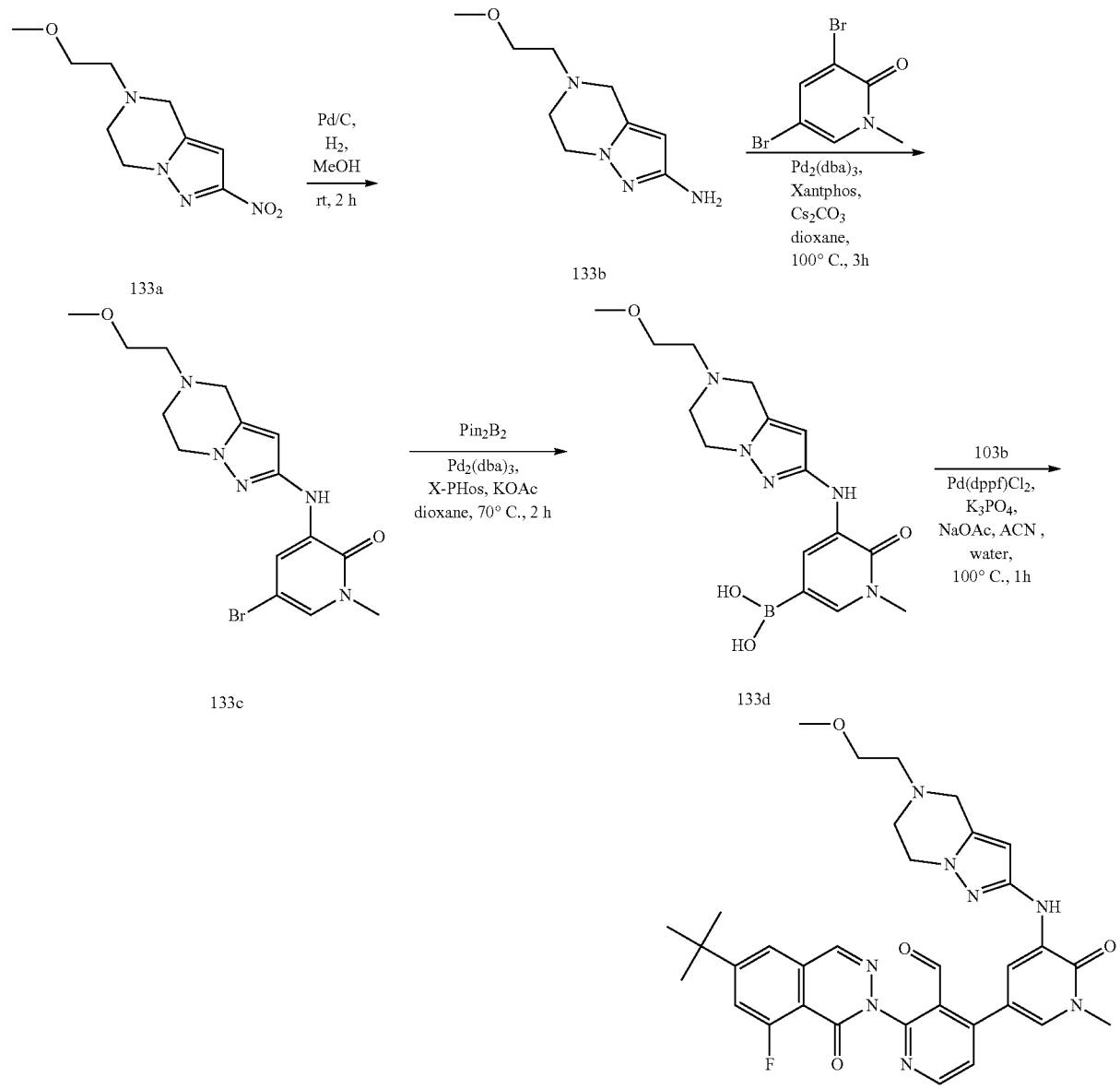

To a solution of 2-nitro-4,5,6,7-tetrahydropyrazolo[1,5-a]pyrazine 124d (190 mg, 1.13 mmol) in acetonitrile (10 mL) was added $K_2CO_3$ (311.9 mg, 2.26 mmol) and 1-bromo-2-methoxyethane (188.3 mg, 1.36 mmol). The reaction mixture was heated at 80° C. for 17 h under microwave irradiation. Analysis of the reaction mixture by LCMS showed complete conversion to the desired product. The mixture was cooled to room temperature and filtered. The filtrate was concentrated under reduced pressure to afford 133a as a white solid (230 mg, 90%), which was used in the next step without further purification. MS-ESI: [M+H]$^+$ 227.0

Example 133b 5-(2-Methoxyethyl)-4,5,6,7-tetrahydropyrazolo[1,5-a]pyrazin-2-amine 133b To a solution of 133a (286 mg, 1.26 mmol) in methanol (10 mL) was added Pd/C (28.6 mg). The system was evacuated and then refilled with $H_2$. After stirring at room temperature for 2 h, the mixture was filtered off. The filtrate was concentrated under reduced pressure to afford 133b as a yellow solid (240 mg, 97%), which was used in the next step without further purification. MS-ESI: [M+H]$^+$ 197.0

Example 133c

5-Bromo-3-(5-(2-methoxyethyl)-4,5,6,7-tetrahydropyrazolo[1,5-a]pyrazin-2-ylamino)-1-methylpyridin-2(1H)-one 133c A 100-mL round-bottomed flask equipped with a magnetic stirrer and a reflux condenser was charged with 133b (230 mg, 1.17 mmol), 3,5-dibromo-1-methylpyridin-2(1H)-one (468.4 mg, 1.76 mmol), $Pd_2(dba)_3$ (53.5 mg, 0.0585 mmol), Xantphos (67.6 mg, 0.117 mmol), $Cs_2CO_3$ (762.8 mg, 2.34 mmol), and dioxane (20 mL). After three cycles of vacuum/$N_2$ flush, the mixture was heated at 100° C. for 3 h. Analysis of the reaction mixture by LCMS showed complete conversion to the desired product. It was cooled to room temperature and filtered. The filtrate was concentrated under reduced pressure. The residue was purified by silica-gel column chromatography eluting with 40:1 dichloromethane/methanol to afford 133c as a dark solid (380 mg, 85%). MS-ESI: [M+H]$^+$ 382.2

Example 133d 3-(5-(2-Methoxyethyl)-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 133d A 50-mL single-neck round-bottomed flask equipped with a magnetic stirrer and a reflux condenser was charged with 133c (330 mg, 0.86 mmol), $Pin_2B_2$ (329 mg, 1.30 mmol), $Pd_2(dba)_3$ (40 mg, 0.043 mmol), X-phos (41 mg, 0.086 mmol), potassium acetate (169 mg, 1.726 mmol), and dioxane (10 mL). After three cycles of vacuum/$N_2$ flush, the mixture was heated at 70° C. for 2 h. Analysis of the reaction mixture by LCMS showed complete conversion to the desired product. It was cooled to room temperature and filtered. The filtrate was concentrated under reduced pressure. The residue was washed with petroleum ether to afford 133d as a dark oil (240 mg, 80%), which was used in the next step without further purification. MS-ESI: [M+H]$^+$ 348.3

Example 133e 2-(6-tert-Butyl-8-fluoro-1-oxophthalazin-2(1H)-yl)-4-(5-(5-(2-methoxyethyl)-4,5,6,7-tetrahydropyrazolo[1,5-a]pyrazin-2-ylamino)-1-methyl-6-oxo-1,6-dihydropyridin-3-yl)nicotinaldehyde 133e A 25-mL round-bottomed flask equipped with a reflux condenser was charged with 2-(6-tert-butyl-8-fluoro-1-oxophthalazin-2(1H)-yl)-4-chloronicotinaldehyde 103b (100 mg, 0.28 mmol), 133d (144.4 mg, 0.42 mmol), Pd(dppf)Cl$_2$ (11.3 mg, 0.0139 mmol), $K_3PO_4$ (117.8 mg, 0.556 mmol), sodium acetate (45.6 mg, 0.556 mmol), acetonitrile (10 mL), and water (3 drops). After three cycles of vacuum/$N_2$ flush, the mixture was heated at 100° C. for 1 h under $N_2$ protection. Analysis of the reaction mixture by LCMS showed complete conversion to the desired product. It was cooled to room temperature and filtered. The filtrate was concentrated under reduced pressure. The residue was purified by silica-gel column chromatography eluting with 40:1 dichloromethane/methanol to afford 133e as a yellow solid (140 mg, 80%). MS-ESI: [M+H]$^+$ 627.3

Example 133

6-tert-butyl-8-fluoro-2-[3-(hydroxymethyl)-4-[5-[[5-(2-methoxyethyl)-6,7-dihydro-4H-pyrazolo[1,5-a]pyrazin-2-yl]amino]-1-methyl-6-oxo-3-pyridyl]-2-pyridyl]phthalazin-1-one 133

To a solution of 133e (180 mg, 0.287 mmol) in dichloromethane (5 mL) and methanol (5 mL) was added NaBH$_4$ (21.7 mg, 0.574 mmol). After stirring at room temperature for 1 h, it was quenched with aqueous NH$_4$Cl (5 mL) and concentrated under reduced pressure. The residue was extracted with dichloromethane (3×20 mL) The combined organic layer was washed with brine, dried over Na$_2$SO$_4$, concentrated under reduced pressure, and purified by reverse-phase prep-HPLC to afford 133 (50 mg, 27%) as a white solid. MS-ESI: [M+H]$^+$ 629.3. $^1$H NMR (500 MHz, DMSO-d$_6$) δ 8.57 (d, J=5.5 Hz, 1H), 8.54 (d, J=2.5 Hz, 1H), 8.22 (s, 1H), 8.04 (d, J=2.5 Hz, 1H), 7.90 (d, J=1.5 Hz, 1H), 7.78 (dd, J=1.5, 13.5 Hz, 1H), 7.51 (d, J=5.5 Hz, 1H), 7.39 (d, J=2.0 Hz, 1H), 5.89 (s, 1H), 4.90-4.88 (m, 1H), 4.42 (s, 2H), 3.92 (t, J=5.5 Hz, 2H), 3.61 (s, 2H), 3.59 (s, 3H), 3.50 (t, J=5.0 Hz, 2H), 3.25 (s, 3H), 2.90 (t, J=5.5 Hz, 2H), 2.67 (t, J=5.0 Hz, 2H), 1.40 (s, 9H).

Example 134a

2-Nitro-5-(2,2,2-trifluoroethyl)-4,5,6,7-tetrahydropyrazolo[1,5-a]pyrazine 134a

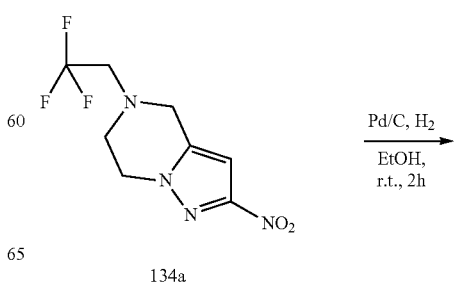

134a

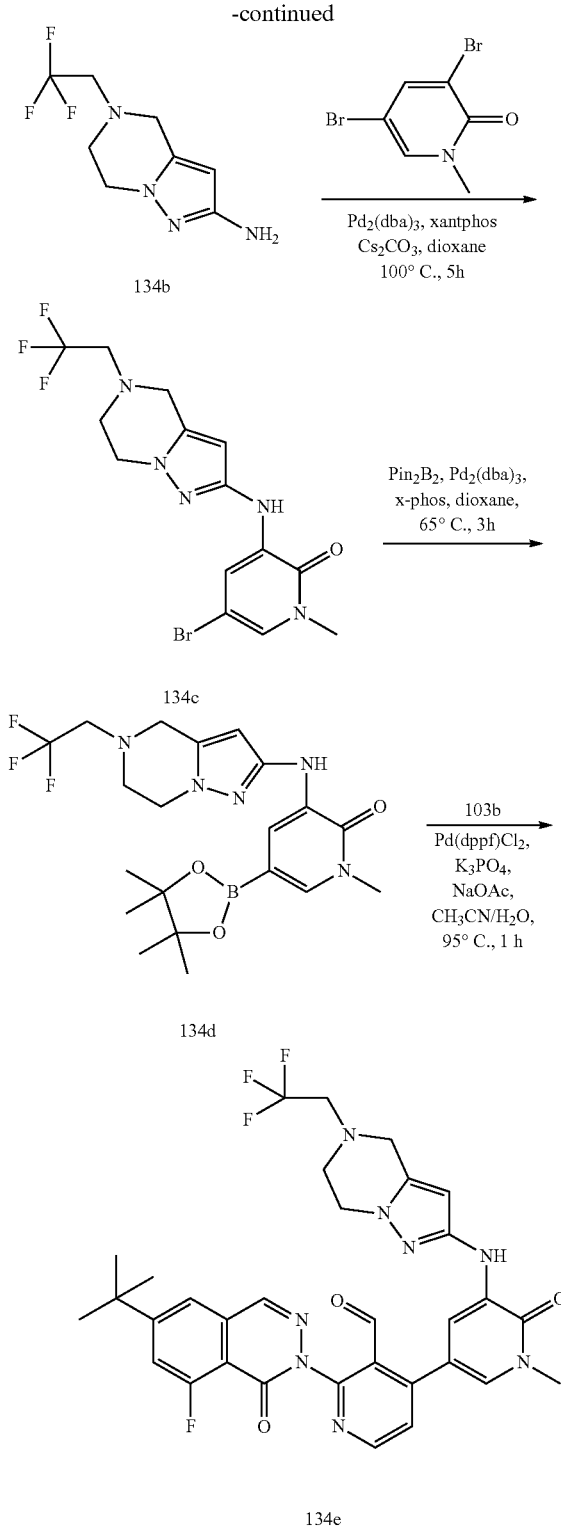

trated under reduced pressure and the residue was purified by silical-gel column chromatography eluting with 50:1 dichloromethane/methanol to afford 134a (392 mg, 78%) as a yellow solid. MS-ESI: [M+H]$^+$ 250.9

Example 134b 5-(2,2,2-Trifluoroethyl)-4,5,6,7-tetrahydropyrazolo[1,5-a]pyrazin-2-amine 134b To a solution of 134a (390 mg, 1.56 mmol) in ethanol (20 mL) was added Pd/C (about 200 mg). The reaction was charged with hydrogen gas (via balloon) and stirred at room temperature for 2 h. After reaction was complete, the mixture was filtered through a plug of CELITE®. The filtrate was concentrated under reduced pressure to afford 134b as a yellow solid (308 mg, 90%), which was used in the next step without further purification. MS-ESI: [M+H]$^+$ 221.1

Example 134c

5-Bromo-1-methyl-3-(5-(2,2,2-trifluoroethyl)-4,5,6,7-tetrahydropyrazolo[1,5-a]pyrazin-2-ylamino)pyridin-2(1H)-one 134c A 100-mL round-bottomed flask equipped with a reflux condenser was charged with 134b (300 mg, 1.36 mmol), 3,5-dibromo-1-methylpyridin-2(1H)-one (364 mg, 1.36 mmol), cesium carbonate (887 mg, 2.7 mmol), and 1,4-dioxane (20 mL). After bubbling nitrogen through the suspension for 10 minutes, xantphos (78 mg, 0.136 mmol) and Pd$_2$(dba)$_3$ (62 mg, 0.068 mmol) were added. The system was subjected to three cycles of vacuum/argon flush and heated at reflux for 5 h. It was then cooled to room temperature and filtered. The solid was washed with dichloromethane (30 mL). The combined filtrate was concentrated under reduced pressure. The solid residue was purified by silica-gel column chromatography eluting with dichloromethane/methanol (80/1 to 30/1) to afford 134c (420 mg, 76%) as a yellow solid. MS-ESI: [M+H]$^+$ 406.0

Example 134d

1-Methyl-5-(4,4,5,5-tetramethyl-1,3,2-dioxaborolan-2-yl)-3-(5-(2,2,2-trifluoro-ethyl)-4,5,6,7-tetrahydropyrazolo[1,5-a]pyrazin-2-ylamino)pyridin-2(1H)-one 134d A 50-mL single-neck round-bottomed flask equipped with a magnetic stirrer and a reflux condenser was charged with 134c (400 mg, 0.98 mmol), Pin$_2$B$_2$ (750 mg, 2.96 mmol), Pd$_2$(dba)$_3$ (45 mg, 0.05 mmol), x-phos (48 mg, 0.1 mmol), potassium acetate (294 mg, 3.0 mmol), and 1,4-dioxane (15 mL). The reaction mixture was subjected to three cycles of vacuum/argon flush and heated at 65° C. for 3 h. It was then cooled to room temperature and filtered. The filtrate was concentrated under reduced pressure. The resulting residue was washed with petroleum ether to afford 134d (400 mg, 90%) as a brown solid, which was used in the next step without further purification. MS-ESI: [M+H]$^+$ 453.9

Example 134e 2-(6-tert-Butyl-8-fluoro-1-oxophthalazin-2(1H)-yl)-4-(1-methyl-6-oxo-5-(5-(2,2,2-trifluoroethyl)-4,5,6,7-tetrahydropyrazolo[1,5-a]pyrazin-2-ylamino)-1,6-dihydropyridin-3-yl)nicotinaldehyde 134e A 25-mL round-bottomed flask equipped with a reflux condenser was charged with 134d (200 mg, 0.44 mmol), A sealed tube equipped with a magnetic stirrer was charged with 1-(2-bromoethyl)-5-(bromomethyl)-3-nitro-1H-pyrazole 124c (632 mg, 2.0 mmol), 2,2,2-trifluoroethanamine (594 mg, 6.0 mmol), and DMSO (5 mL), and heated at 120° C. for 2 h. The mixture was cooled to room temperature and diluted with water (20 mL). The resulting mixture was extracted with ethyl acetate (3×20 mL). The combiner organic layer was dried and filtered. The filtrate was concen- 2-(6-tert-butyl-8-fluoro-1-oxophthalazin-2(1H)-yl)-4-chloronicotinaldehyde 103b (159 mg, 0.44 mmol), K₃PO₄ (186 mg, 0.88 mmol), sodium acetate (72 mg, 0.88 mmol), 1,1'-bis(diphenylphosphino)ferrocenedichloropalladium(II) (16 mg, 0.022 mmol), and acetonitrile/water (8/0.2 mL). After three cycles of vacuum/N₂ flush, the mixture was heated at 100° C. for 1 h under N₂ protection. Analysis of the reaction mixture by LCMS showed complete conversion to the desired product. The reaction mixture was cooled to room temperature and diluted with dichloromethane (30 mL) and water (15 mL). The water layer was separated and extracted with dichloromethane (2×15 mL). The combined organic extract was dried over Na₂SO₄, filtered, and concentrated under reduced pressure. The dark residue was purified by silica-gel column chromatography eluting with dichloromethane/methanol (80/1 to 30/1) to afford 134e (128 mg, 45%) as a yellow solid. MS-ESI: [M+H]⁺ 651.3

Example 134

6-tert-butyl-8-fluoro-2-[3-(hydroxymethyl)-4-[1-methyl-6-oxo-5-[[5-(2,2,2-trifluoroethyl)-6,7-dihydro-4H-pyrazolo[1,5-a]pyrazin-2-yl]amino]-3-pyridyl]-2-pyridyl]phthalazin-1-one 134

To a solution of 134e (110 mg, 0.169 mmol) in methanol/dichloromethane(4/4 mL) was added NaBH₄ (19 mg, 0.51 mmol) at room temperature. After the reaction was stirred for 1 h, LCMS indicated the reaction was complete. The mixture was quenched with water (20 mL) and extracted with dichloromethane (3×30 mL). The combined organic layer was washed with brine (20 mL), dried over Na₂SO₄, filtered, and concentrated under reduced pressure. The residue was purified by reverse-phase prep-HPLC to afford 134 (50 mg, 45%) as a white solid. MS-ESI: [M+H]⁺ 653.3. ¹H NMR (500 MHz, CDCl₃) δ 8.66 (d, J=5.0 Hz, 1H), 8.35 (d, J=2.5 Hz s, 1H), 8.00 (d, J=2.5 Hz, 1H), 7.59-7.58 (m, 1H), 7.56-7.55 (m, 1H), 7.53-7.52 (m, 2H), 7.45 (s, 1H), 5.73 (s, 1H), 4.51-4.49 (m, 2H), 4.11-4.08 (m, 2H), 4.05-4.03 (m, 1H), 3.94 (s, 2H), 3.73 (s, 3H), 3.24-3.18 (m, 4H), 1.45 (s, 9H).

Example 135a 5-(2,2-Difluoroethyl)-2-nitro-4,5,6,7-tetrahydropyrazolo[1,5-a]pyrazine 135a

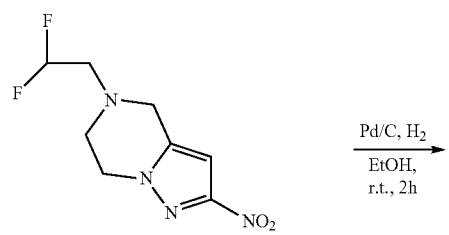

135a

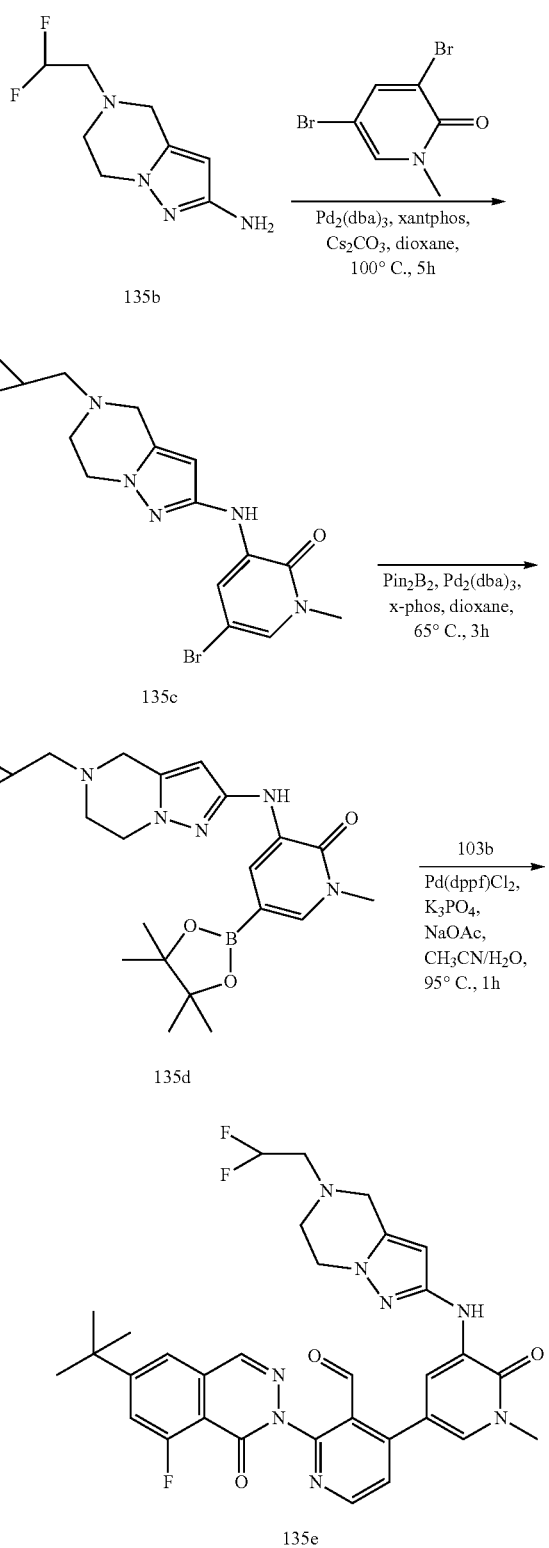

A sealed tube equipped with a magnetic stirrer was charged with 1-(2-bromoethyl)-5-(bromomethyl)-3-nitro-1H-pyrazole 124c (632 mg, 2.0 mmol), 2,2-difluoroethanamine (486 mg, 6.0 mmol), and DMSO (5 mL). It was heated at 120° C. for 2 h. The mixture was cooled to room temperature and diluted with water (20 mL). The resulting mixture was extracted with ethyl acetate (3×20 mL). The combiner organic layer was dried and filtered. The filtrate was concentrated under reduced pressure and the residue was purified by silica-gel column chromatography eluting with 50:1 dichloromethane/methanol to afford 135a (371 mg, 80%) as a yellow solid. MS-ESI: [M+H]$^+$ 233.2

Example 135b 5-(2,2-Difluoroethyl)-4,5,6,7-tetrahydropyrazolo[1,5-a]pyrazin-2-amine 135b A solution of 135a (370 mg, 1.59 mmol) in ethanol (20 mL) was added Pd/C (about 200 mg). The reaction was charged with hydrogen gas (via balloon) and stirred at room temperature for 2 h. After reaction was complete, the mixture was filtered through a plug of CELITE®. The filtrate was concentrated reduced pressure to afford 135b as a yellow solid (293 mg, 91%), which was used in the next step without further purification. MS-ESI: [M+H]$^+$ 203.2

Example 135c

5-Bromo-3-(5-(2,2-difluoroethyl)-4,5,6,7-tetrahydropyrazolo[1,5-a]pyrazin-2-ylamino)-1-methylpyridin-2(1H)-one 135c A 50-mL round-bottomed flask equipped with a reflux condenser was charged with 135b (290 mg, 1.43 mmol), 3,5-dibromo-1-methylpyridin-2(1H)-one (383 mg, 1.43 mmol), cesium carbonate (932 mg, 2.86 mmol), and 1,4-dioxane (20 mL). After bubbling nitrogen through the suspension for 10 minutes, xantphos (82 mg, 0.143 mmol) and Pd$_2$(dba)$_3$ (65 mg, 0.072 mmol) were added. The system was subjected to three cycles of vacuum/argon flush and heated at reflux for 5 h. It was then cooled to room temperature and filtered. The solid was washed with dichloromethane (30 mL). The combined organic filtrate was concentrated under reduced pressure. The residue was purified by silica-gel column chromatography eluting with dichloromethane/methanol (80/1 to 30/1) to afford 135c (400 mg, 72%) as a yellow solid. MS-ESI: [M+H]$^+$ 387.8

Example 135d 3-(5-(2,2-Difluoroethyl)-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 135d A 50-mL single-neck round-bottomed flask equipped with a magnetic stirrer and a reflux condenser was charged with 135c (400 mg, 1.03 mmol), Pin$_2$B$_2$ (785 mg, 3.1 mmol), Pd$_2$(dba)$_3$ (45 mg, 0.050 mmol), X-phos (48 mg, 0.10 mmol), potassium acetate (294 mg, 3.0 mmol), and 1,4-dioxane (20 mL). The reaction mixture was subjected to three cycles of vacuum/argon flush and heated at 65° C. for 3 h. It was then cooled to room temperature and filtered. The filtrate was concentrated under reduced pressure. The resulting residue was washed with petroleum ether to afford 135d (412 mg, 92%) as a brown solid, which was used in next step without further purification. MS-ESI: [M+H]$^+$ 436.0

Example 135e 2-(6-tert-Butyl-8-fluoro-1-oxophthalazin-2(1H)-yl)-4-(5-(5-(2,2-difluoroethyl)-4,5,6,7-tetrahydropyrazolo[1,5-a]pyrazin-2-ylamino)-1-methyl-6-oxo-1,6-dihydropyridin-3-yl)nicotinaldehyde 135e A 25-mL round-bottomed flask equipped with a reflux condenser was charged with 135d (200 mg, 0.46 mmol), 2-(6-tert-butyl-8-fluoro-1-oxophthalazin-2(1H)-yl)-4-chloronicotinaldehyde 103b (166 mg, 0.46 mmol), K$_3$PO$_4$ (195 mg, 0.92 mmol), sodium acetate (75 mg, 0.92 mmol), 1,1'-bis(diphenylphosphino)ferrocenedichloropalladium(II) (17 mg, 0.023 mmol), and acetonitrile/water (8/0.2 mL). After three cycles of vacuum/N$_2$ flush, the mixture was heated at 100° C. for 1 h. Analysis of the reaction mixture by LCMS showed complete conversion to the desired product. The reaction mixture was cooled to room temperature and diluted with dichloromethane (30 mL) and water (15 mL). The water layer was extracted with dichloromethane (2×15 mL). The combined organic extract was dried over Na$_2$SO$_4$, filtered, and concentrated under reduced pressure. The dark residue was purified by silica-gel column chromatography eluting with dichloromethane/methanol (80/1 to 30/1) to afford 135e (110 mg, 38%) as a yellow solid. MS-ESI: [M+H]$^+$ 633.3

Example 135

6-tert-butyl-2-[4-[5-[[5-(2,2-difluoroethyl)-6,7-dihydro-4H-pyrazolo[1,5-a]pyrazin-2-yl]amino]-1-methyl-6-oxo-3-pyridyl]-3-(hydroxymethyl)-2-pyridyl]-8-fluoro-phthalazin-1-one 135

To a solution of 135e (100 mg, 0.158 mmol) in methanol/dichloromethane(4/4 mL) was added NaBH$_4$ (18 mg, 0.475 mmol) at room temperature. After the reaction was stirred for 1 h, LCMS indicated the reaction was complete. The reaction mixture was quenched with water (20 mL) and extracted with dichloromethane (3×20 mL). The combined organic layer was washed with brine (20 mL), dried over Na$_2$SO$_4$, filtered, and concentrated under reduced pressure. The residue was purified by reverse-phase prep-HPLC to afford 135 (60 mg, 60%) as a white solid. MS-ESI: [M+H]$^+$ 635.3. $^1$H NMR (500 MHz, CDCl$_3$) δ 8.66 (d, J=5.0 Hz, 1H), 8.35 (d, J=2.5 Hz, 1H), 8.00 (d, J=2.5 Hz, 1H), 7.59-7.58 (m, 1H), 7.56-7.55 (m, 1H), 7.53-7.52 (m, 2H), 7.45 (s, 1H), 6.07-5.83 (m, 1H), 5.72 (s, 1H), 4.51-4.49 (m, 2H), 4.11-4.08 (m, 2H), 4.05-4.03 (m, 1H), 3.94 (s, 2H), 3.73 (s, 3H), 3.13-3.10 (m, 2H), 3.00-2.94 (m, 2H), 1.45 (s, 9H).

Example 136a (S)-(6-Aminopyridin-3-yl)(3-methylmorpholino)methanone 136a

To a solution of (S)-3-methylmorpholine (1.5 g, 15.0 mmol) in ethanol (20 mL) was added EDCI (3.33 g, 17.4 mmol), HOBt (2.35 g, 17.4 mmol), and 6-aminonicotinic acid (2.07 g, 15.0 mmol) at room temperature. After stirring for 18 h, the resulting suspension was filtered. The solid was purified by silica-gel column chromatography eluting with 2:1 petroleum ether/ethyl acetate to straight ethyl acetate to afford 136a (1.0 g, 30%) as a white solid. MS-ESI: 222.3 (M+H)$^+$.

Example 136b (S)-5-Bromo-1-methyl-3-(5-(3-methylmorpholine-4-carbonyl)pyridine-2-ylamino)pyridin-2(1H)-one 136b

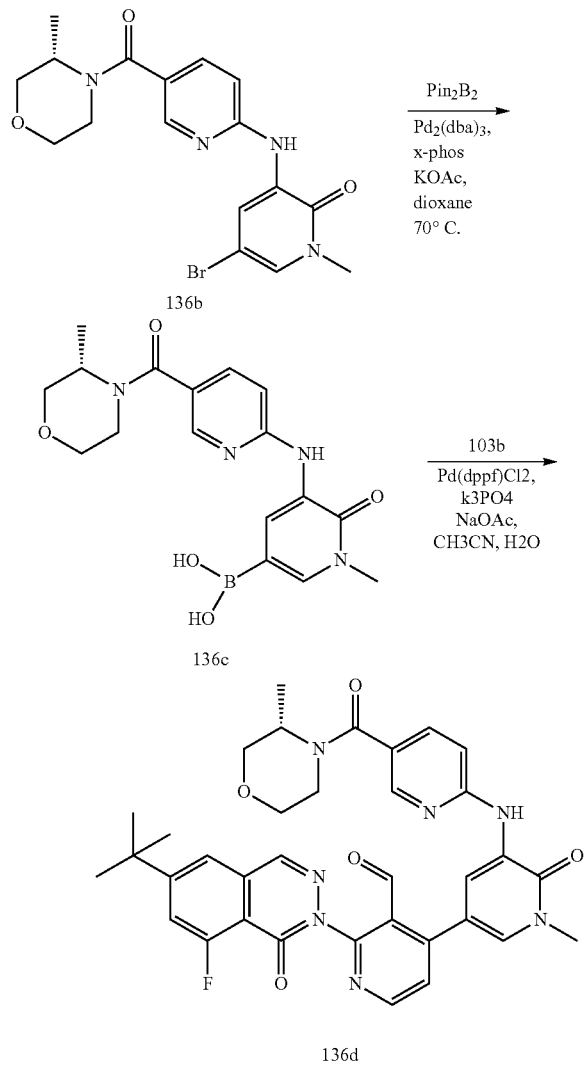

A 50-mL single-neck round-bottomed flask equipped with a magnetic stirrer and a reflux condenser was charged with 136a (222 mg, 1.0 mmol), 3,5-dibromo-1-methylpyridin-2(1H)-one (320 mg, 1.2 mmol), cesium carbonate (652 mg, 2 mmol), and 1,4-dioxane (10 mL). After bubbling nitrogen through the suspension for 10 minutes, Xantphos (58 mg, 0.10 mmol) and tris(dibenzylideneacetone)dipalladium(0) (46 mg, 0.050 mmol) were added. The system was subjected to three cycles of vacuum/argon flush and heated at reflux for 2.5 h. It was then cooled to room temperature and filtered. The solid was washed with dichloromethane (2×30 mL) and the combined filtrate was concentrated under reduced pressure. The residue was purified by silica-gel column chromatography eluting with petroleum ether/ethyl acetate (2:1 to 1:2) to afford 136b (280 mg, 69%) as a yellow solid. MS-ESI: [M+H]+ 407.3

Example 136c (S)-1-Methyl-5-(5-(3-methylmorpholine-4-carbonyl)pyridin-2-ylamino)-6-oxo-1,6-dihydropyridin-3-ylboronic Acid 136c A 100-mL round-bottomed flask equipped with a reflux condenser was charged with 136b (600 mg, 1.5 mmol), bis(pinacolato)diboron (1.2 g, 4.5 mmol), Pd$_2$(dba)$_3$ (137 mg, 0.15 mmol), X-phos (71 mg, 0.15 mmol), potassium acetate (294 mg, 3.0 mmol), and 1,4-dioxane (20 mL). After three cycles of vacuum/argon flush, the mixture was heated at 70° C. for 2 h. It was then filtered and the filtrate was evaporated under reduced pressure. The residue was washed with petroleum ether to afford 136c (520 mg, 93%) as a white solid, which was used directed without further purification. MS-ESI: [M+H]+ 373.1

Example 136d (S)-2-(6-tert-Butyl-8-fluoro-1-oxophthalazin-2(1H)-yl)-4-(1-methyl-5-(5-(3-methylmorpholine-4-carbonyl)pyridin-2-ylamino)-6-oxo-1,6-dihydropyridin-3-yl)nicotinaldehyde 136d A 100-mL single-neck round-bottomed flask equipped with a magnetic stirrer and a reflux condenser was charged with 136c (260 mg, 0.70 mmol), 2-(6-tert-butyl-8-fluoro-1-oxophthalazin-2(1H)-yl)-4-chloronicotinaldehyde 103b (180 mg, 0.50 mmol), K$_3$PO$_4$ (297 mg, 1.4 mmol), sodium acetate (114 mg, 1.4 mmol), 1,1'-bis(diphenylphosphino)ferrocenedichloropalladium(II) (57 mg, 0.07 mmol), and acetonitrile/water (10/0.2 mL). After three cycles of vacuum/N$_2$ flush, the mixture was heated at 100° C. for 1.5 h. Analysis of the reaction mixture by LCMS showed complete conversion to the desired product. The reaction mixture was cooled to room temperature and concentrated under reduced pressure. The residue was diluted with dichloromethane (20 mL) and water (10 mL). The aqueous layer was separated and extracted with dichloromethane (3×20 mL). The combined organic layers was dried over Na$_2$SO$_4$, filtered, and concentrated under reduced pressure. The dark residue was purified by silica-gel column chromatography eluting with 60:1 dichloromethane/methanol to afford 136d (140 mg, 43%) as a yellow solid. MS-ESI: [M+H]+ 652.3

Example 136

6-tert-butyl-8-fluoro-2-[3-(hydroxymethyl)-4-[1-methyl-5-[[5-[(3S)-3-methylmorpholine-4-carbonyl]-2-pyridyl]amino]-6-oxo-3-pyridyl]-2-pyridyl]phthalazin-1-one 136

A solution of 136d (140 mg, 0.21 mmol) in methanol/dichloromethane (4/4 mL) was added NaBH$_4$ (16 mg, 0.63 mmol). The mixture was stirred at room temperature for 1 h and quenched with water (2 mL). It was then evaporated under reduced pressure and the residue was purified by reverse-phase prep-HPLC to afford 136 (40 mg, 28%) as a white solid. MS-ESI: [M+H]+ 654.3. $^1$H NMR (500 MHz, DMSO-d$_6$) δ 9.00 (s, 1H), 8.77 (d, J=8.0 Hz, 1H), 8.57 (d, J=5.0 Hz, 1H), 8.53 (d, J=2.5 Hz, 1H), 8.25 (d, J=2.5 Hz, 1H), 7.90 (d, J=1.5 Hz, 1H), 7.78 (d, J=1.0 Hz, 1H), 7.65-7.63 (m, 1H), 7.59 (d, J=2.5 Hz, 1H), 7.53 (d, J=5.0 Hz, 1H), 7.37 (d, J=8.5 Hz, 1H), 4.91-4.89 (m, 1H), 4.45-4.39 (m, 2H), 4.17-4.13 (m, 1H), 3.79-3.67 (m, 2H), 3.58-3.53 (m, overlap, 5H), 3.41-3.36 (m, 1H), 3.29-3.25 (m, 1H), 1.39 (s, 9H), 1.22 (d, J=7.5 Hz, 3H).

Example 138a (S)-tert-Butyl 4-(6-(5-Chloro-2-methoxypyridin-3-ylamino)pyridin-3-yl)-3-methylpiperazine-1-carboxylate 138a

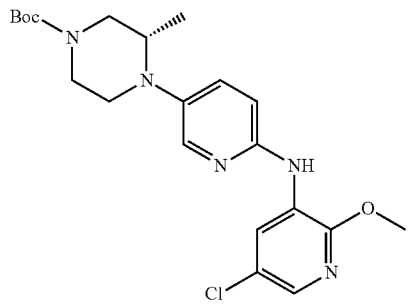 [SMILES: COc1ncc(Cl)cc1Nc1ccc(N2CCN(C(=O)OC(C)(C)C)C[C@@H]2C)cn1]

A 100-mL single-neck round-bottomed flask equipped with a magnetic stirrer and a reflux condenser was charged with 1,4-dioxane (40 mL), (S)-tert-butyl 4-(6-amino pyridin-3-yl)-3-methylpiperazine-1-carboxylate 105b (2.04 g, 7.0 mmol), 3-bromo-5-chloro-2-methoxypyridine (2.8 g, 12.6 mmol), $Pd_2(dba)_3$ (640 mg, 0.70 mmol), XantPhos (404.6 mg, 0.70 mmol), and cesium carbonate (4.56 g, 14.0 mmol). After three cycles of vacuum/argon flush, the mixture was heated at 100° C. for 4 h. After this time the reaction was cooled to room temperature. It was then filtered and the filtrate was evaporated under reduced pressure. The residue was purified by silica-gel column chromatography eluting with 1:3 ethyl acetate/petroleum ether to afford 138a (1.7 g, 57%) as a yellow solid. MS-ESI: $[M+H]^+$ 434.2

Example 138b (S)-5-Chloro-3-(5-(2-methylpiperazin-1-yl)pyridin-2-ylamino)pyridin-2(1H)-one 138b A solution of 138a (1.0 g, 2.3 mmol) in dioxane/HCl (30 mL) was stirred at 100° C. for 2 h. It was then evaporated under reduced pressure to afford 138b (1.48 g, crude) as a yellow solid. MS-ESI: $[M+H]^+$ 320.3

Example 138c (S)-5-Chloro-3-(5-(2-methyl-4-(oxetan-3-yl)piperazin-1-yl)pyridin-2-ylamino)pyridin-2(1H)-one 138c

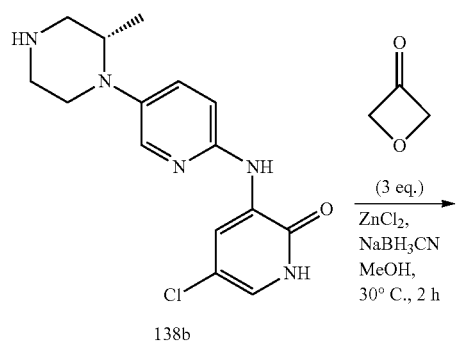

To a solution of 138b (1.0 g, 3.1 mmol) in methanol (35 mL) was added oxetan-3-one (669.6 mg, 9.3 mmol), $NaBH_3CN$ (585.9 mg, 9.3 mmol), and $ZnCl_2$ (1.26 g, 9.3 mmol). The reaction was stirred at 30° C. for 2 h. The mixture was evaporated under reduced pressure and the residue diluted with water (20 mL). It was then extracted with dichloromethane (3×30 mL). The combined dichloromethane extract was concentrated under reduced pressure and the residue was purified by silica-gel column chromatography eluting with 40:1 ethyl acetate/methanol to afford 138c (291 mg, 25%) as a red solid. MS-ESI: $[M+H]^+$ 376.3

Example 138

(S)-6-tert-Butyl-8-fluoro-2-(3-(hydroxymethyl)-4-(5-(5-(2-methyl-4-(oxetan-3-yl)piperazin-1-yl)pyridin-2-ylamino)-6-oxo-1,6-dihydropyridin-3-yl)pyridin-2-yl) phthalazin-1(2H)-one 138

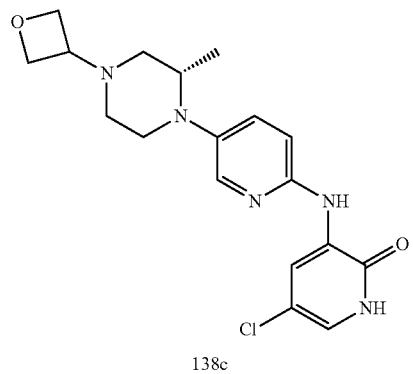

A sealed tube equipped with a magnetic stirrer was charged with 138c (150 mg, 0.40 mmol), 3-(acetoxymethyl)-2-(6-tert-butyl-8-fluoro-1-oxophthalazin-2(1H)-yl)pyridin-4-ylboronic acid 116c (495.6 mg, 1.2 mmol), $Pd_2(dba)_3$ (36.6 mg, 0.040 mmol), $P(cy)_3$ (44.6 mg, 0.16 mmol), $Cs_2CO_3$ (391.2 mg, 1.2 mmol), dioxane (8 mL), and water (0.2 mL). After three cycles of vacuum/argon flush, the mixture was heated at 120° C. for 4 h. After this time the reaction was cooled to room temperature. It was then filtered and the filtrate was evaporated under reduced pressure. The residue was purified by silica-gel column chromatography eluting with 40:1 ethyl acetate/methanol and further purified by reverse-phase prep-HPLC to afford 138 (48 mg, 18%) as a yellow solid. MS-ESI: $[M+H]^+$ 667.3. $^1H$ NMR (500 MHz, DMSO-$d_6$) δ 12.05 (s, 1H), 8.65 (d, J=2.0 Hz, 1H), 8.57 (d, J=5.0 Hz, 1H), 8.55 (d, J=3.0 Hz, 1H), 8.44 (s, 1H), 7.91 (d, J=2.0 Hz, 1H), 7.87 (d, J=2.5 Hz, 1H), 7.79 (dd, J=1.0 Hz, 13.0 Hz, 1H), 7.54 (d, J=5.0 Hz, 1H), 7.39 (dd, J=2.5 Hz, 9.0 Hz, 1H), 7.26-7.23 (m, 2H), 4.97-4.95 (m, 1H), 4.58-4.54 (m, 2H), 4.48-4.46 (m, 1H), 4.43-4.41 (m, 1H), 4.38-4.37 (m, 2H), 3.69-3.68 (m, 1H), 3.41-3.39 (m, 1H), 3.11-3.09 (m, 1H), 2.97-2.93 (m, 1H), 2.56-2.54 (m, 1H), 2.35-2.32 (m, 2H), 2.21-2.17 (m, 1H), 1.40 (s, 9H), 0.94 (d, J=6.5 Hz, 3H),

Example 139a

(3-Nitro-1H-pyrazol-5-yl)methanol 139a

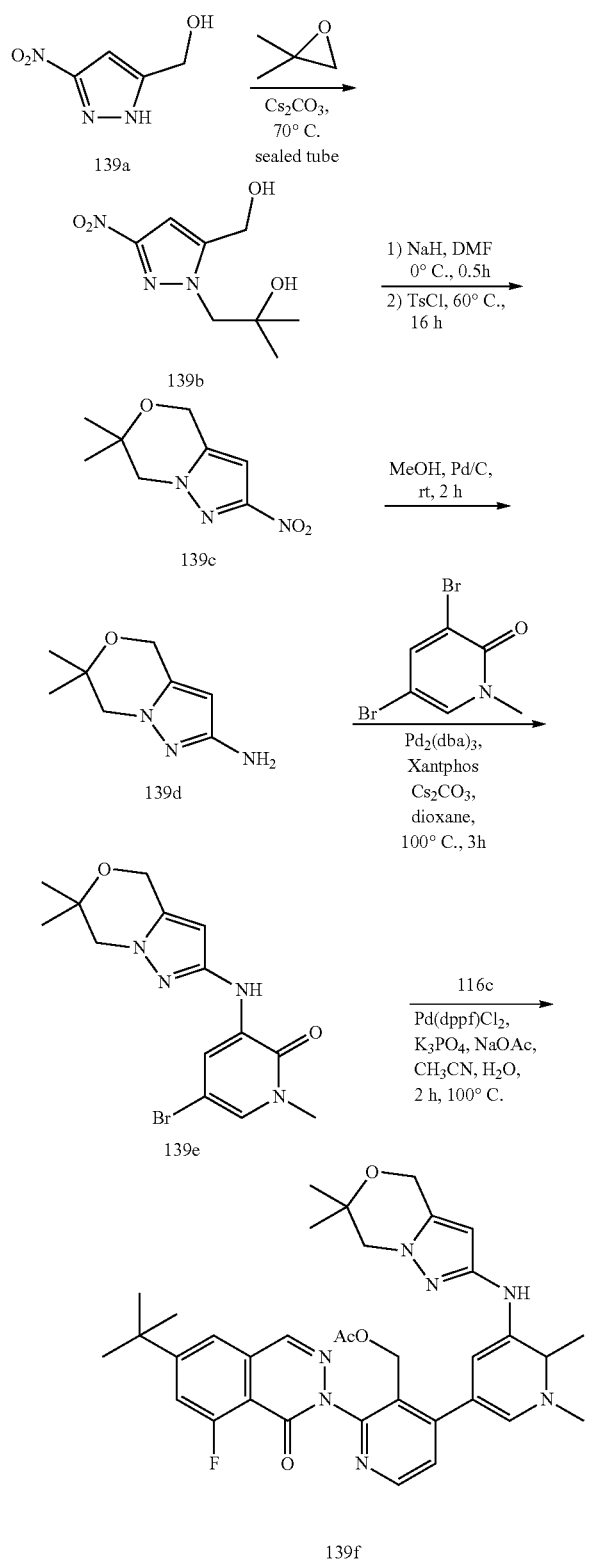

A mixture of 3-nitro-1H-pyrazole-5-carboxylic acid (4.71 g, 30 mmol), BH$_3$/THF (75 mL, 1 mol/L, 75 mmol) was stirred at 60° C. for 2 h. The mixture was cooled to room temperature and 4M HCl (19 mL, 75 mmol) was added. It was stirred at 70° C. for 2 h. After cooling down to room temperature, the mixture was concentrated under reduced pressure. The residue was partitioned between ethyl acetate and brine (100:100 mL). The aqueous phase was extract with ethyl acetate (4×50 mL). The combined organic layer was dried on Na$_2$SO$_4$ and evaporated under reduced pressure. The residue was purified by silica-gel column chromatography eluting with petroleum ether/ethyl acetate (5:1 to 1:1) to afford 139a (3.5 g, 79%) as a white solid. MS-ESI: [M+H]$^+$ 144.2

Example 139b

1-(5-(Hydroxymethyl)-3-nitro-1H-pyrazol-1-yl)-2-methylpropan-2-ol 139b

A sealed tube was charged with 139a (2.145 g, 15 mmol), Cs$_2$CO$_3$ (978 mg, 3.0 mmol), and 2,2-dimethyloxirane (15 mL). The mixture was stirred at 70° C. for 3 h. After cooled to room temperature, the mixture was concentrated under reduced pressure. The residue was purified by silica-gel column chromatography eluting with petroleum ether/ethyl acetate (5:1 to 1:1) to afford 139b (1.2 g, 38%) as a white solid. MS-ESI: [M+H]$^+$ 216.2

Example 139c

6,6-Dimethyl-2-nitro-6,7-dihydro-4H-pyrazolo[5,1-c][1,4]oxazine 139c

To a solution of 139b (1.1 g, 5.1 mmol) in DMF (10 mL), was added NaH (60 percent dispersion in mineral oil, 246 mg, 6.14 mmol) at 0° C. The resulting suspension was stirred for 30 min, followed by the addition of p-toluenesulfonyl chloride (1169 mg, 6.14 mmol). The mixture was stirred at 60° C. overnight. After cooling to room temperature, saturated ammonium chloride solution was added and the mixture was extracted with dichloromethane. The combined organic layer was washed with brine, dried over Na$_2$SO$_4$, and evaporated under reduced pressure. The residue was purified by silica-gel column chromatography eluting with petroleum ether/ethyl acetate gradient (9:1 to 2:1) to afford 139c (228 mg, 22%). MS-ESI: [M+H]$^+$ 198.3

Example 139d

6,6-Dimethyl-6,7-dihydro-4H-pyrazolo[5,1-c][1,4]oxazin-2-amine 139d

A 50-mL single-neck round-bottomed flask was purged with nitrogen and charged with 139c (0.21 g, 1.25 mmol), 10% palladium on carbon (50% wet, 125 mg), and methanol (10 mL). The mixture was evacuated, charged with hydrogen gas, and stirred at room temperature for 2 h. The hydrogen was then evacuated and nitrogen was charged into the flask. The catalyst was removed by filtration through a pad of CELITE® and the filtrate was concentrated under reduced pressure to afford 139d (167 mg, 93%). MS-ESI: [M+H]$^+$ 168.1

Example 139e

5-Bromo-3-(6,6-dimethyl-6,7-dihydro-4H-pyrazolo
[5,1-c][1,4]oxazin-2-ylamino)-1-methylpyridin-2
(1H)-one 139e A 100-mL round-bottomed flask equipped with a reflux condenser was charged with 1,4-dioxane (10 mL), 139d (167 mg, 1.0 mmol), 3,5-dibromo-1-methylpyridin-2(1H)-one (320 mg, 1.2 mmol), Pd$_2$(dba)$_3$ (91 mg, 0.10 mmol), XantPhos (116 mg, 0.20 mmol), and cesium carbonate (652 mg, 2.0 mmol). After three cycles of vacuum/argon flush, the mixture was heated at 100° C. for 3 h. It was then filtered and the filtrate was evaporated under reduced pressure. The residue was purified by silica-gel column chromatography eluting with 100:1 dichloromethane/methanol to afford 139e (210 mg, 60%) as a yellow solid. MS-ESI: [M+H]$^+$ 352.9

Example 139f (2-(6-tert-Butyl-8-fluoro-1-oxophthalazin-2(1H)-yl)-
4-(5-(6,6-dimethyl-6,7-dihydro-4H-pyrazolo[5,1-c]
[1,4]oxazin-2-ylamino)-1-methyl-6-oxo-1,6-dihydro-
pyridin-3-yl)pyridin-3-yl)methyl Acetate 139f A 25-mL single-neck round-bottomed flask equipped with a magnetic stirrer and a reflux condenser was charged with 139e (177 mg, 0.50 mmol), 3-(acetoxymethyl)-2-(6-tert-butyl-8-fluoro-1-oxophthalazin-2(1H)-yl)pyridin-4-ylboronic acid 116c (207 mg, 0.50 mmol), Pd(dppf)Cl$_2$ (41 mg, 0.050 mmol), sodium acetate (82 mg, 1.0 mmol), K$_3$PO$_4$.trihydrate (266 mg, 1.0 mmol), water (6 drops), and acetonitrile (5 mL). After three cycles of vacuum/argon flush, the mixture was heated at 100° C. for 2 h. It was then filtered and the filtrate was evaporated under reduced pressure. The residue was purified by silica-gel column chromatography eluting with 50:1 dichloromethane/methanol to afford 139f (161 mg, 50%) as a brown solid. MS-ESI: [M+H]$^+$ 642.3

Example 139

6-tert-butyl-2-[4-[5-[(6,6-dimethyl-4,7-dihydropyrazolo[5,1-c][1,4]oxazin-2-yl)amino]-1-methyl-6-oxo-3-pyridyl]-3-(hydroxymethyl)-2-pyridyl]-8-fluorophthalazin-1-one 139

A mixture of 139f (160 mg, 0.25 mmol) and lithium hydroxide (60 mg, 2.5 mmol) in i-propanol/THF (1:1, 4 mL) and water (1 mL) was stirred at 30° C. for 1 h. The mixture was evaporated under reduced pressure and the residue was diluted with water (5 mL). It was then extracted with ethyl acetate (3×10 mL). The combined ethyl acetate extract was concentrated under reduced pressure and the residue was purified by reverse-phase prep-HPLC to afford 139 (60 mg, 40%) as a light yellow solid. MS-ESI: [M+H]$^+$ 599.8. $^1$H NMR (500 MHz, DMSO-d$_6$) δ 8.57 (d, J=5.0 Hz, 1H), 8.54 (d, J=2.5 Hz, 1H), 8.34 (s, 1H), 8.08 (d, J=2.5 Hz, 1H), 7.90 (d, J=1.5 Hz, 1H), 7.79-7.76 (m, 1H), 7.51 (d, J=5.0 Hz, 1H), 7.39 (d, J=2.0 Hz, 1H), 5.95 (s, 1H), 4.92 (bs, 1H), 4.73 (s, 2H), 4.42 (s, 2H), 3.80 (s, 2H), 3.60 (s, 3H), 1.40 (s, 9H), 1.26 (s, 6H).

Example 140a

5-Bromo-1-methyl-3-(1-methyl-1H-pyrazol-3-ylamino)pyridin-2(1H)-one 140a

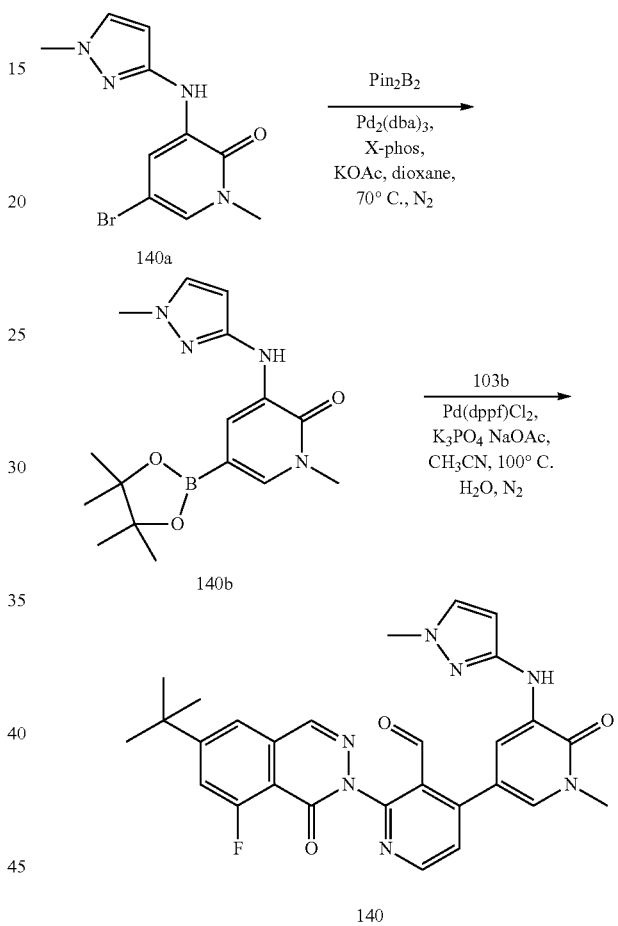

A 250-mL single-neck round-bottomed flask equipped with a magnetic stirrer and a reflux condenser was charged with 1,4-dioxane (100 mL), 1-methyl-1H-pyrazol-3-amine (970 mg, 10.0 mmol), 3,5-dibromo-1-methylpyridin-2-(1H)-one (2.9 g, 11 mmol), and cesium carbonate (6.5 g, 20.0 mmol). After bubbling nitrogen through the suspension for 10 minutes, tris(dibenzylideneacetone)dipalladium(0) (457 mg, 0.50 mmol) and Xantphos (587 mg, 1.0 mmol) were added. The system was subjected to three cycles of vacuum/argon flush and heated at reflux for 2 h. It was then cooled to room temperature and filtered. The solid was washed with dichloromethane (2×50 mL) and the combined organic filtrate was concentrated. The residue was purified by silica-gel column chromatography eluting with 30:1 dichloromethane/methanol to afford 140a as a yellow solid (900 mg, 32%). MS-ESI: [M+H]$^+$ 283.1

Example 140b

1-Methyl-3-(1-methyl-1H-pyrazol-3-ylamino)-5-(4,4,5,5-tetramethyl-1,3,2-dioxaborolan-2-yl)pyridin-2(1H)-one 140b A 100-mL round-bottomed flask equipped with a reflux condenser was charged with 140a (564 mg, 2.0 mmol), bis(pinacolato) diboron (1.5 g, 6.0 mmol), $Pd_2(dba)_3$ (183 mg, 0.20 mmol), X-phos (95 mg, 0.20 mmol), potassium acetate (392 mg, 4.0 mmol), and 1,4-dioxane (20 mL). After three cycles of vacuum and argon flush, the mixture was heated at 70° C. for 2 h. Then it was cooled to room temperature and filtered. The filtrate was evaporated under reduced pressure. The residue was washed with petroleum ether to afford 140b (600 mg, 91%) as a brown solid, which was used without further purification. MS-ESI: $[M+H]^+$ 331.0

Example 140c 2-(6-tert-Butyl-8-fluoro-1-oxophthalazin-2(1H)-yl)-4-(1-methyl-5-(1-methyl-1H-pyrazol-3-ylamino)-6-oxo-1,6-dihydropyridin-3-yl)nicotinaldehyde 140c A 50-mL round-bottomed flask equipped with a reflux condenser was charged with 2-(6-tert-butyl-8-fluoro-1-oxophthalazin-2(1H)-yl)-4-chloronicotinaldehyde 103b (359 mg, 1.0 mmol), 140b (660 mg, 2.0 mmol), $K_3PO_4$ (424 mg, 2.0 mmol), 1,1'-bis(diphenylphosphino)ferrocenedichloropalladium(II) (82 mg, 0.10 mmol), sodium acetate (164 mg, 2.0 mmol), and acetonitrile/water (15/0.2 mL). After three cycles of vacuum/$N_2$ flush, the mixture was heated at 100° C. for 1.5 h. The mixture was cooled to room temperature and concentrated under reduced pressure. The residue was diluted with dichloromethane (30 mL) and water (30 mL). The organic layer was separated and the aqueous extracted with dichloromethane (3×20 mL). The combined organic layer was dried over $Na_2SO_4$, filtered, and concentrated under reduced pressure. The dark residue was purified by silica-gel column chromatography eluting with dichloromethane/methanol (80/1 to 50/1) to afford 140c (280 mg, 53%) as yellow solid. MS-ESI: $[M+H]^+$ 528.1

Example 140

6-tert-butyl-8-fluoro-2-[3-(hydroxymethyl)-4-[1-methyl-5-[(1-methylpyrazol-3-yl)amino]-6-oxo-3-pyridyl]-2-pyridyl]phthalazin-1-one 140

To a solution of 140c (270 mg, 0.50 mmol) in THF (5 mL), propan-2-ol (5 mL), and water (2 mL) was added lithium hydroxide (36 mg, 1.5 mmol). The reaction mixture was stirred at room temperature for 1 h and concentrated under reduced pressure. The residue was diluted with dichloromethane (20 mL) and water (10 mL). The organic layer was separated and the aqueous layer was extracted with dichloromethane (3×15 mL). The combined organic layer was washed with brine and concentrated under reduced pressure. The residue was purified by reverse-phase prep-HPLC to afford 140 (53 mg, 20%) as a white solid. MS-ESI: $[M+H]^+$ 530.3. $^1$H NMR (500 MHz, DMSO-$d_6$) δ 8.56 (d, J=5.0 Hz, 1H), 8.53 (d, J=2.0 Hz, 1H), 8.21 (s, 1H), 8.03 (d, J=2.5 Hz, 1H), 7.89 (s, 1H), 7.78-7.5 (m, 1H), 7.51-7.48 (m, 2H), 7.39 (d, J=2.5 Hz, 1H), 6.07 (d, J=2.0 Hz, 1H), 4.91 (s, 1H), 4.42 (s, 2H), 3.71 (s, 3H), 3.58 (s, 3H), 1.39 (s, 9H)

Example 141a

6-Chloro-2-methyl-4-(5-methylisoxazol-3-ylamino)pyridazin-3(2H)-one 141a

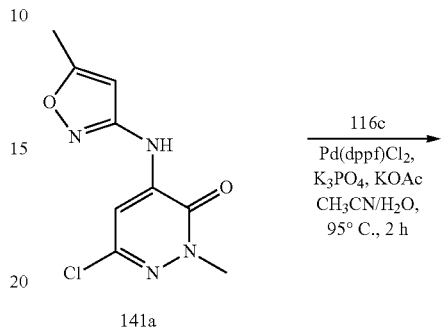

A 100-mL single-neck round-bottomed flask equipped with a magnetic stirrer and a reflux condenser was charged with 1,4-dioxane (40 mL), 5-methylisoxazol-3-amine (559 mg, 5.7 mmol), 4-bromo-6-chloro-2-methylpyridazin-3(2H)-one (1.89 g, 8.55 mmol), $Pd_2(dba)_3$ (521 mg, 0.57 mmol), XantPhos (329 mg, 0.57 mmol), and cesium carbonate (3.72 g, 11.4 mmol). After three cycles of vacuum/argon flush, the mixture was heated at 100° C. for 3 h. Then the mixture was cooled to 80° C. and filtered. The filtrate was cooled to room temperature. It was then filtered to afford 141a (600 mg, 44%) as a yellow solid. MS-ESI: $[M+H]^+$ 241.0

Example 141b (2-(6-tert-Butyl-8-fluoro-1-oxophthalazin-2(1H)-yl)-4-(1-methyl-5-(5-methylisoxazol-3-ylamino)-6-oxo-1,6-dihydropyridazin-3-yl)pyridin-3-yl)methyl Acetate 141b

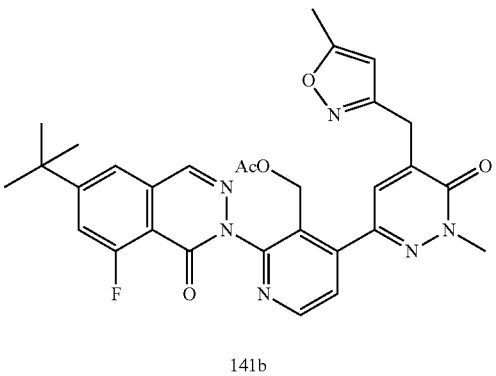

A 100-mL single-neck round-bottomed flask equipped with a magnetic stirrer and a reflux condenser was charged with 141a (288 mg, 1.2 mmol), 3-(acetoxymethyl)-2-(6-tert-butyl-8-fluoro-1-oxo-phthalazin-2(1H)-yl)pyridin-4-ylboronic acid 116c (1.49 g, 3.6 mmol), $Pd(dppf)Cl_2$ (99 mg, 0.12 mmol), potassium acetate (235 mg, 2.4 mmol), $K_3PO_4$ (523 mg, 2.4 mmol), acetonitrile (20 mL), and water (10 drops). After three cycles of vacuum/argon flush, the mixture was heated at 95° C. for 2 h. It was then filtered and the filtrate was concentrated under reduced pressure. The residue was purified by silica-gel column chromatography eluting with 1:1 ethyl acetate/petroleum ether to afford 141b (220 mg, 32%) as a yellow solid. MS-ESI: [M+H]+ 574.2

Example 141

6-tert-butyl-8-fluoro-2-[3-(hydroxymethyl)-4-[1-methyl-5-[(5-methylisoxazol-3-yl)amino]-6-oxo-pyridazin-3-yl]-2-pyridyl]phthalazin-1-one 141

A mixture of 141a (117.3 mg, 0.20 mmol) and lithium hydroxide monohydrate (84 mg, 2.0 mmol) in i-propanol/THF (1:1, 8 mL) and water (1 mL) was stirred at 35° C. for 0.5 h. The mixture was concentrated under reduced pressure. The residue was partitioned between water (10 mL) and dichloromethane (10 mL). The aqueous phase was extracted with dichloromethane (3×10 mL). The combined organic layer was concentrated under reduced pressure and the residue was purified by reverse-phase prep-HPLC to afford 141 (70 mg, 66%) as a pale yellow solid. MS-ESI: [M+H]+ 532.2. $^1$H NMR (500 MHz, DMSO-$d_6$) δ 9.92 (s, 1H), 8.65 (d, J=5.5 Hz, 1H), 8.55 (d, J=2.5 Hz, 1H), 7.90 (d, J=1.5 Hz, 1H), 7.85 (s, 1H), 7.80-7.77 (m, 1H), 7.62 (d, J=5.0 Hz, 1H), 6.33 (s, 1H), 4.85 (s, 1H), 4.56-4.53 (m, 1H), 4.45-4.42 (m, 1H), 3.80 (s, 3H), 2.36 (s, 3H), 1.40 (s, 9H).

Example 142a

3-Bromo-5-iodopyridin-2-ol 142a

A 100-mL single-neck round-bottomed flask equipped with a magnetic stirrer was charged with acetonitrile (50 mL), TFA (10 mL), 3-bromopyridin-2-ol (4.0 g, 11.56 mmol), N-iodosuccinimide (5.2 g, 11.56 mmol). The mixture was stirred at room temperature for 15 h. The mixture was diluted with water (100 mL) and resulting white solid was collected by filtration to afford 142a (6.6 g, 96%) as a white solid. MS-ESI: [M+H]+ 300

Example 142b

3-Bromo-5-iodo-1-methylpyridin-2(1H)-one 142b

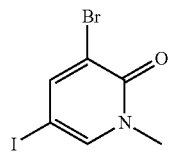

A 100-mL single-neck round-bottomed flask equipped with a magnetic stirrer was charged with DMF (50 mL), 142a (6.0 g, 20.0 mmol), CH$_3$I (4.26 g, 30.0 mmol), and K$_2$CO$_3$ (5.52 g, 40.0 mmol). The mixture was stirred at room temperature for 2 h and diluted with water (200 mL). The resulting white solid was collected by filtration to afford 142b (5.97 g, 95%) as a white solid. MS-ESI: [M+H]+ 314

Example 142c (4-(5-Bromo-1-methyl-6-oxo-1,6-dihydropyridin-3-yl)-2-(6-tert-butyl-8-fluoro-1-oxophthalazin-2(1H)-yl)pyridin-3-yl)methyl acetate 142c

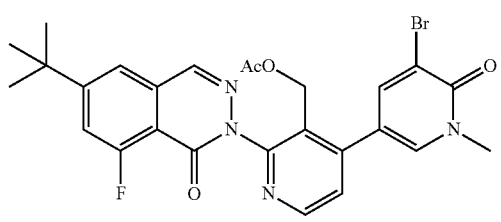 [SMILES: CC(=O)OCc1c(-c2cc(Br)c(=O)n(C)c2)ccnc1-n1ncc2cc(C(C)(C)C)cc(F)c2c1=O]

A 50-mL single-neck round-bottomed flask equipped with a magnetic stirrer and a reflux condenser was charged with 142b, (1.37 g, 4.38 mmol, 1.0 eq.), 3-(acetoxymethyl)-2-(6-tert-butyl-8-fluoro-1-oxophthalazin-2(1H)-yl)pyridine-4-yl-boronic acid 116c (2.07 mg, 5.0 mmol), Pd(dppf)Cl$_2$ (179 mg, 0.219 mmol, 0.050 eq.), sodium acetate (718 mg, 8.76 mmol, 2.0 eq.), K$_3$PO$_4$ (1.86 g, 8.76 mmol, 2.0 eq.), acetonitrile (20 mL), and water (1 mL). After three cycles of vacuum/argon flush, the mixture was heated at 30° C. for 2 h. It was then cooled to room temperature and filtered. The filtrate was concentrated under reduced pressure and the resulting residue was purified by silica-gel column chromatography eluting with 100:1 dichloromethane/ethanol to afford 142c (800 mg, 32%) as a yellow solid. MS-ESI: [M+H]+ 555.2. $^1$H NMR (500 MHz, DMSO-$d_6$) δ 8.66 (d, J=5.0 Hz, 1H), 8.56 (d, J=2.5 Hz, 1H), 8.14 (d, J=2.5 Hz, 1H), 8.08 (d, J=2.0 Hz, 1H), 7.91 (d, J=1.5 Hz, 1H), 7.82-7.79 (m, 1H), 7.62 (d, J=6.5 Hz, 1H), 5.02 (s, 2H), 3.59 (s, 3H), 1.78 (s, 3H), 1.40 (s, 9H).

Example 142d (2-(6-tert-butyl-8-fluoro-1-oxophthalazin-2(1H)-yl)-4-(5-(1-ethyl-1H-pyrazol-3-ylamino)-1-methyl-6-oxo-1,6-dihydropyridin-3-yl)pyridin-3-yl)methyl acetate 142d

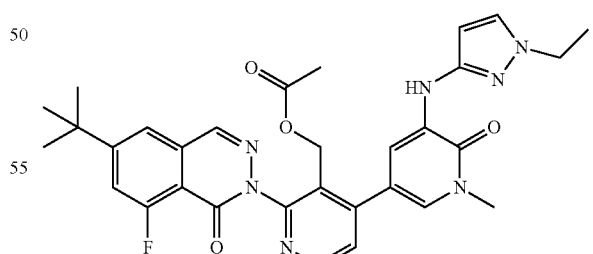

Into a 1-dram vial was added 142c (40 mg, 0.074 mmol), 1-ethyl-1H-pyrazol-3-amine (1.2 equiv), cesium carbonate (1.5 equiv), Xantphos (10 mol %) and tris(dibenzylideneacetone) dipalladium(0) (5 mol %) in dry 1,4-dioxane (0.2 M). The reaction was then stirred at 80° C. for 3 hours. After cooling to room temperature, the reaction was then diluted with dichloromethane (3 mL) and washed with water (2×3 mL). The organic layer was dried over magnesium sulfate, filtered and concentrated in vacuo. The crude product 142d was then carried on to the subsequent step without purification.

Example 142

6-tert-butyl-2-[4-[5-[(1-ethylpyrazol-3-yl)amino]-1-methyl-6-oxo-3-pyridyl]-3-(hydroxymethyl)-2-pyridyl]-8-fluoro-phthalazin-1-one 142

Into a 1 dram vial was added 142d (1 equiv) in a 4:1 mixture of THF and water (1 mL) Lithium hydroxide (1.5 equiv) was then added to the mixture and the reaction was stirred at room temperature for 16 hours. The reaction was then diluted with dichloromethane (3 mL) and washed with water (2×3 mL). The organic layer was collected, dried over magnesium sulfate, filtered, and concentrated in vacuo. The crude material was purified by reverse-phase chromatography to give 142 (7.6 mg, 19% yield). $^1$H NMR (400 MHz, DMSO-d6) δ 8.55 (s, 1H), 8.52 (d, J=2.5 Hz, 1H), 8.16 (s, 1H), 8.06 (d, J=2.5 Hz, 1H), 7.89 (m, 1H), 7.75 (dd, J=13.1, 1.9 Hz, 1H), 7.53 (d, J=2.2 Hz, 1H), 7.51 (d, J=12.6 Hz, 1H), 7.40 (d, J=2.1 Hz, 1H), 6.07 (s, 1H), 4.46 (br s 1H), 4.00 (q, J=7.2 Hz, 2H), 3.60 (s, 3H), 3.17 (s, 2H), 1.39 (s, 9H), 1.34 (t, J=7.2 Hz, 3H). ES-MS m/z 544.3 [M+1].

Example 143

6-tert-butyl-8-fluoro-2-[3-(hydroxymethyl)-4-[5-[[5-(methoxymethyl)-1-methyl-pyrazol-3-yl]amino]-1-methyl-6-oxo-3-pyridyl]-2-pyridyl]phthalazin-1-one 143

Following the procedures of Example 142, and substituting 5-(methoxymethyl)-1-methyl-1H-pyrazol-3-amine for 1-ethyl-1H-pyrazol-3-amine, 143 was prepared (11.2 mg, 54% yield). $^1$H NMR (400 MHz, DMSO-d6) δ 8.56 (d, J=5.0 Hz, 1H), 8.53 (d, J=2.5 Hz, 1H), 8.19 (s, 1H), 8.03 (d, J=2.4 Hz, 1H), 7.89 (d, J=1.8 Hz, 1H), 7.76 (dd, J=13.2, 1.7 Hz, 1H), 7.50 (d, J=5.0 Hz, 1H), 7.39 (d, J=2.4 Hz, 1H), 6.11 (s, 1H), 4.43 (d, J=5.4 Hz, 2H), 4.38 (s, 2H), 3.66 (s, 3H), 3.59 (s, 3H), 3.26 (s, 3H), 1.39 (s, 9H). ES-MS m/z 574.3 [M+1].

Example 144

6-tert-butyl-8-fluoro-2-[3-(hydroxymethyl)-4-[1-methyl-5-[[1-methyl-5-(pyrrolidine-1-carbonyl)pyrazol-3-yl]amino]-6-oxo-3-pyridyl]-2-pyridyl]phthalazin-1-one 144

Following the procedures of Example 142, and substituting (3-amino-1-methyl-1H-pyrazol-5-yl)(pyrrolidin-1-yl)methanone for 1-ethyl-1H-pyrazol-3-amine, 144 was prepared (14.6 mg, 65% yield). $^1$H NMR (400 MHz, DMSO-d$_6$) δ 8.59-8.50 (m, 2H), 8.28 (s, 1H), 8.04 (d, J=2.3 Hz, 1H), 7.89 (d, J=1.8 Hz, 1H), 7.76 (dd, J=13.1, 1.7 Hz, 1H), 7.51 (d, J=5.1 Hz, 1H), 7.42 (d, J=2.3 Hz, 1H), 6.46 (s, 1H), 4.87 (t, J=5.1 Hz, 1H), 4.47-4.40 (m, 2H), 3.79 (s, 3H), 3.60 (s, 3H), 3.48 (dd, J=19.0, 6.7 Hz, 4H), 1.91-1.82 (m, 4H), 1.39 (s, 9H). ES-MS m/z 627.4 [M+1].

Example 145

6-tert-butyl-2-[4-[5-[[1-(2,2-difluoroethyl)-5-methyl-pyrazol-3-yl]amino]-1-methyl-6-oxo-3-pyridyl]-3-(hydroxymethyl)-2-pyridyl]-8-fluoro-phthalazin-1-one 145

Following the procedures of Example 142, and substituting 1-(2,2-difluoroethyl)-5-methyl-1H-pyrazol-3-amine for 1-ethyl-1H-pyrazol-3-amine, 145 was prepared (11 mg, 26% yield). $^1$H NMR (400 MHz, DMSO-d6) δ 8.55 (d, J=5.0 Hz, 1H), 8.52 (d, J=2.7 Hz, 1H), 8.20 (s, 1H), 8.11 (d, J=2.4 Hz, 1H), 7.90 (d, J=1.6 Hz, 1H), 7.75 (dd, J=13.1, 1.8 Hz, 1H), 7.50 (d, J=5.0 Hz, 1H), 7.42 (d, J=2.4 Hz, 1H), 5.97 (s, 1H), 4.88 (t, J=5.0 Hz, 1H), 4.46-4.33 (m, 5H), 3.59 (s, 3H), 2.21 (s, 3H), 1.39 (s, 9H). ES-MS m/z 594.3 [M+1].

Example 146a

Ethyl 2-(5-(Hydroxymethyl)-3-nitro-1H-pyrazol-1-yl)acetate 146a

A 100-mL single-neck round-bottomed flask equipped with a magnetic stirrer was charged with acetonitrile (30 mL), (3-nitro-1H-pyrazol-5-yl)methanol (1.43 g, 10.0 mmol), Cs$_2$CO$_3$ (490 mg, 1.5 mmol), and ethyl 2-bromoacetate (2.00 g, 12 mmol). The mixture was stirred at 40° C. for 5 h. It was then cooled to room temperature and filtered. The filtrate was concentrated under reduced pressure and the residue was purified by silica-gel column chromatography eluting with 30:1 dichloromethane/methanol to afford 146a (1.65 g, 72%) as a yellow solid. MS-ESI: [M+H]$^+$ 229.9

Example 146b

Ethyl 2-(5-(Chloromethyl)-3-nitro-1H-pyrazol-1-yl)acetate 146b

To a mixture of 146a (1.50 g, 6.55 mmol) in CHCl$_3$ (60 mL) cooled at 0° C. was slowly added SOCl$_2$ (2.34 g, 19.6 mmol) while maintaining the internal temperature below 5° C. This reaction mixture was warmed to 50° C. and stirred at this temperature for 3 h. It was then cooled to 0° C. and quenched with water. The organic layer was separated and evaporated under reduced pressure. The residue was purified by silica-gel column chromatography eluting with 30:1 dichloromethane/methanol to afford 146b (1.1 g, 68%) as a yellow solid. MS-ESI: [M+H]$^+$ 247.9

Example 146c

5-Methyl-2-nitro-4,5-dihydropyrazolo[1,5-a]pyrazin-6(7H)-one 146c

To a solution of 146b (1.0 g, 4.0 mmol) in dichloromethane (30 mL) was added a solution of CH$_3$NH$_2$ (1.07 g, 12.0 mmol, 35% in methanol). This reaction mixture was stirred at room temperature for 3 h and diluted with water (30 mL). The organic layer was separated, dried over Na$_2$SO$_4$, and concentrated under reduced pressure. The residual was purified by silica-gel column chromatography eluting with 30:1 dichloromethane/methanol to afford 146c (450 mg, 57%) as a yellow solid. MS-ESI: [M+H]$^+$ 196.9

Example 146d

2-Amino-5-methyl-4,5-dihydropyrazolo[1,5-a]pyrazin-6(7H)-one 146d

A solution of 146c (450 mg, 2.3 mmol) in ethanol (30 mL) was added Pd/C (10%, 400 mg). The reaction was charged with hydrogen gas (via balloon) and stirred at room temperature for 2 h. After reaction was complete, the mixture was filtered through a plug of CELITE® and the filtrate was concentrated under reduced pressure to afford 146d as a yellow solid (320 mg, 84%), which was used without further purification in the next step. MS-ESI: [M+H]$^+$ 167.1

Example 146e 2-(5-Bromo-1-methyl-2-oxo-1,2-dihydropyridin-3-ylamino)-5-methyl-4,5-dihydropyrazolo[1,5-a]pyrazin-6(7H)-one 146e A 100-mL round-bottomed flask equipped with a magnetic stirrer and a reflux condenser was charged with 146d (300 mg, 1.8 mmol), 3,5-dibromo-1-methylpyridin-2(1H)-one (482 mg, 1.8 mmol), cesium carbonate (1.17 g, 3.6 mmol), and 1,4-dioxane (20 mL). After bubbling nitrogen through the suspension for 10 minutes, xantphos (104 mg, 0.18 mmol) and tris(dibenzylideneacetone)dipalladium(0) (82 mg, 0.090 mmol) were added. The system was subjected to three cycles of vacuum/argon flush and heated at reflux for 5 h. It was then cooled to room temperature and filtered. The solid was washed with dichloromethane (2×30 mL). The combined filtrate was concentrated under reduced pressure. The residue was purified by silica-gel column chromatography eluting with dichloromethane/methanol (80/1 to 30/1) to afford 146e (390 mg, 61%) as a yellow solid.

Example 146f (2-(6-tert-Butyl-8-fluoro-1-oxophthalazin-2(1H)-yl)-4-(1-methyl-5-(5-methyl-6-oxo-4,5,6,7-tetrahydropyrazolo[1,5-a]pyrazin-2-ylamino)-6-oxo-1,6-dihydropyridin-3-yl)pyridin-3-yl)methyl Acetate 146f

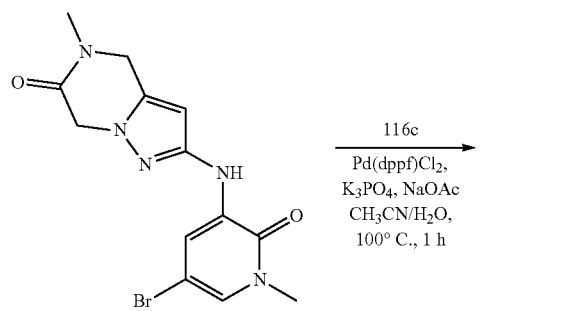

146e

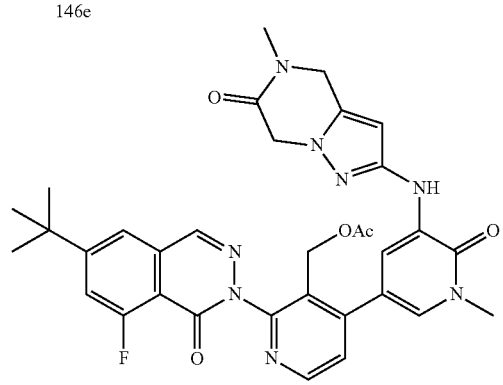

146f

A 25-mL round-bottomed flask equipped with a reflux condenser was charged with 3-(acetoxymethyl)-2-(6-tert-butyl-8-fluoro-1-oxophthalazin-2(1H)-yl)pyri-din-4-ylboronic acid 116c (165 mg, 0.40 mmol), 146e (141 mg, 0.40 mmol), K$_3$PO$_4$ (170 mg, 0.80 mmol), sodium acetate (66 mg, 0.80 mmol), Pd(dppf)Cl$_2$ (15 mg, 0.020 mmol), and acetonitrile/water (8/0.2 mL). The mixture was subjected to three cycles of vacuum/nitrogen flush and heated at 100° C. under N$_2$ protection for 1 h. Analysis of the reaction mixture by LCMS showed complete conversion to the desired product. The reaction mixture was cooled to room temperature and concentrated under reduced pressure. The residue was diluted with dichloromethane (30 mL) and water (30 mL). The organic layer was separated and the water layer was extracted with dichloromethane (2×30 mL). The combined organic extract was dried over Na$_2$SO$_4$, filtered, and concentrated under reduced pressure. The dark residue was purified by silica-gel column chromatography eluting with dichloromethane/methanol (80/1 to 30/1) to afford 146f (115 mg, 45%) as a yellow solid. MS-ESI: [M+H]$^+$ 641.4

Example 146

6-tert-butyl-8-fluoro-2-[3-(hydroxymethyl)-4-[1-methyl-5-[(5-methyl-6-oxo-4,7-dihydropyrazolo[1,5-a]pyrazin-2-yl)amino]-6-oxo-3-pyridyl]-2-pyridyl]phthalazin-1-one 146

To a solution of 146f (110 mg, 0.172 mmol) in THF/i-propanol/water (4/2/2 mL) was added lithium hydroxide (21 mg, 0.86 mmol). The mixture was stirred at 30° C. for 1 h. After the reaction was complete, the mixture was concentrated under reduced pressure. The residue was diluted with water (10 mL) and extracted with ethyl acetate (3×20 mL). The combined organic layer was dried and concentrated under reduced pressure. The residue was purified by reverse-phase prep-HPLC to afford 146 as a white solid (45 mg, 44%). MS-ESI: [M+H]$^+$ 599.2. $^1$H NMR (500 MHz, DMSO-d$_6$) δ 8.57 (d, J=5.0 Hz, 1H), 8.54 (d, J=2.5 Hz, 1H), 8.41 (s, 1H), 8.08 (d, J=2.5 Hz, 1H), 7.91 (d, J=1.5 Hz, 1H), 7.78 (d, J=13.0 Hz, 1H), 7.51 (d, J=5.0 Hz, 1H), 7.42 (d, J=2.5 Hz, 1H), 6.08 (s, 1H), 4.91-4.89 (m, 1H), 4.62 (s, 2H), 4.57 (s, 2H), 4.45-4.43 (m, 2H), 3.61 (s, 3H), 2.98 (s, 3H), 1.40 (s, 9H).

Example 147a 1-(6-Nitropyridin-3-yl)azetidin-3-ol 147a

A 100-mL single-neck round-bottomed flask equipped with a magnetic stirrer and a reflux condenser was charged with acetonitrile (50 mL), 5-fluoro-2-nitropyridine (1.2 g, 7.9 mmol), K$_2$CO$_3$ (2.1 g, 15.8 mmol), and azetidin-3-ol hydrochloride (1.3 g, 11.9 mmol). The mixture was heated at 60° C. for 1 h. After this time the reaction was cooled to room temperature. It was then filtered and the filtrate was evaporated under reduced pressure. The residue was purified by silica-gel column chromatography eluting with dichloromethane/methanol (50:1 to 20:1) to afford 147a (1.1 g, 73%) as a yellow solid. MS-ESI: [M+H]$^+$ 196.0.

Example 147b 1-(6-Aminopyridin-3-yl)azetidin-3-ol 147b

A 100-mL single-neck round-bottomed flask was purged with nitrogen and charged with 147a (1.0 g, 5.1 mmol), 10% palladium on carbon (10% wet, 100 mg), and ethanol (40 mL). The mixture was evacuated, charged with hydrogen gas, and stirred at room temperature for 5 h. The hydrogen was then evacuated and nitrogen was charged into the flask. The catalyst was removed by filtration through a pad of CELITE® and the filtrate was concentrated under reduced pressure to afford 147b as a yellow solid (792 mg, 85%). MS-ESI: [M+H]+ 166.1.

Example 147c

5-Bromo-3-(5-(3-hydroxyazetidin-1-yl)pyridin-2-ylamino)-1-methylpyridin-2(1H)-one 147c A 100-mL single-neck round-bottomed flask equipped with a magnetic stirrer and a reflux condenser was charged with 147b (792 mg, 4.8 mmol), 3,5-dibromo-1-methylpyridin-2(1H)-one (1.9 g, 7.2 mmol), tris-(dibenzylideneacetone)dipalladium(0) (440 mg, 0.48 mmol), XantPhos (555 mg, 0.96 mmol), $Cs_2CO_3$ (3.1 g, 9.6 mmol), and 1,4-dioxane (40 mL). After three cycles of vacuum/argon flush, the mixture was heated at 90° C. for 3.0 hrs. It was then cooled to room temperature and filtered. The filtrate was concentrated under reduced pressure and the resulting residue was purified by silica-gel column chromatography eluting with dichloromethane/methanol (50:1 to 20:1) to afford 147c as a yellow solid (1.5 g, 89%). MS-ESI: [M+H]+ 351.1

Example 147d (2-(6-tert-Butyl-8-fluoro-1-oxophthalazin-2(1H)-yl)-4-(5-(5-(3-hydroxyazetidin-1-yl)pyridin-2-ylamino)-1-methyl-6-oxo-1,6-dihydropyridin-3-yl)pyridin-3-yl)methyl Acetate 147d A 100-mL flask equipped with a reflux condenser was charged with 147c (285 mg, 0.81 mmol), 3-(acetoxymethyl)-2-(6-tert-butyl-8-fluoro-1-oxophthalazin-2(1H)-yl)pyridin-4-ylboronic acid 116c (669 mg, 1.62 mmol), $Pd(dppf)Cl_2$ (66.2 mg, 0.081 mmol), $K_3PO_4$ (343.4 mg, 1.62 mmol), sodium acetate (132.8 mg, 1.62 mmol), water (0.5 mL), and acetonitrile (15 mL). After three cycles of vacuum/argon flush, the mixture was heated at 100° C. for 3 hrs. It was then cooled to room temperature and filtered. The filtrate was concentrated under reduced pressure and the resulting residue was purified by silica-gel column chromatography eluting with dichloromethane/methanol (50:1 to 30:1) to afford 147d as a brown solid (140.0 mg, 27%). MS-ESI: [M+H]+ 640.3.

Example 147

6-tert-butyl-8-fluoro-2-[4-[5-[[5-(3-hydroxyazetidin-1-yl)-2-pyridyl]amino]-1-methyl-6-oxo-3-pyridyl]-3-(hydroxymethyl)-2-pyridyl]phthalazin-1-one 147

A mixture of 147d (140 mg, 0.22 mmol) and lithium hydroxide (132 mg, 5.5 mmol) in i-propanol/THF/water (2:2:1, 10 mL) was stirred at room temperature for 1 hour. The mixture was concentrated under reduced pressure and diluted with water (10 mL). The resulting mixture was extracted with dichloromethane three times. The combined organic layer was concentrated under reduced pressure and the resulting residue was purified by reverse-phase prep-HPLC to afford 147 (40 mg, 31%) as a yellow solid. MS-ESI: [M+H]+ 598.2. $^1$H NMR (500 MHz, DMSO-$d_6$) δ 8.57-8.53 (m, 3H), 8.32 (s, 1H), 7.90 (s, 1H), 7.77 (d, J=13.0 Hz, 1H), 7.51-7.49 (m, 2H), 7.43 (s, 1H), 7.19 (d, J=8.5 Hz, 1H), 6.88 (dd, J=3.0, 8.5 Hz, 1H), 5.57-5.56 (m, 1H), 4.89-4.87 (m, 1H), 4.55-4.52 (m, 1H), 4.43-4.41 (m, 2H), 4.05-4.02 (m, 2H), 3.60 (s, 3H), 3.45-3.42 (m, 2H), 1.39 (s, 9H).

Example 148a

2-Methyl-1-(2-nitro-6,7-dihydropyrazolo[1,5-a]pyrazin-5(4H)-yl)propan-1-one 148a

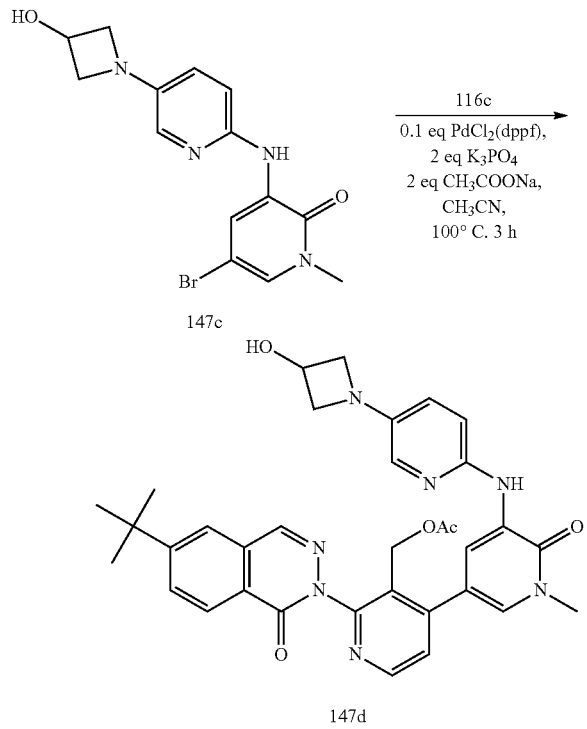

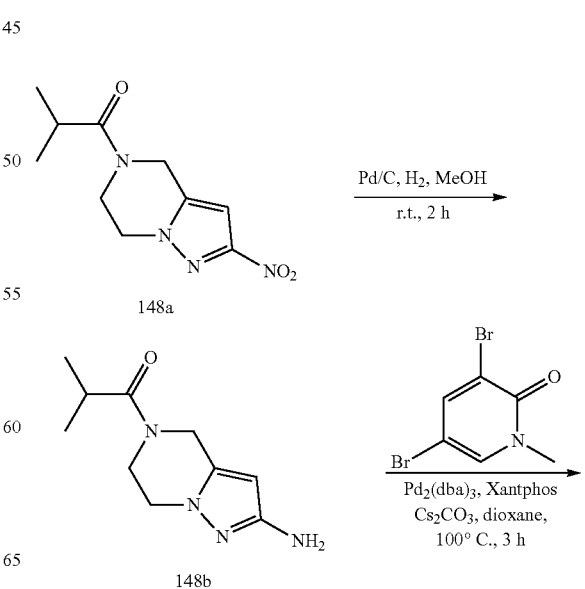

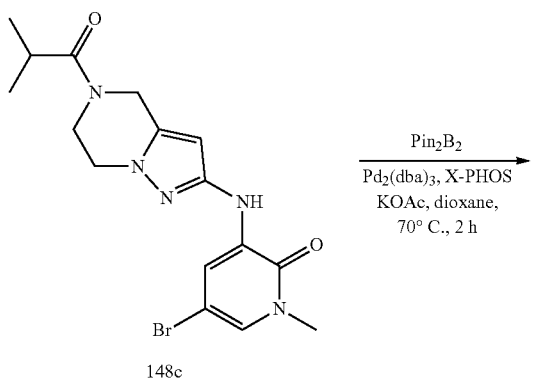

148c

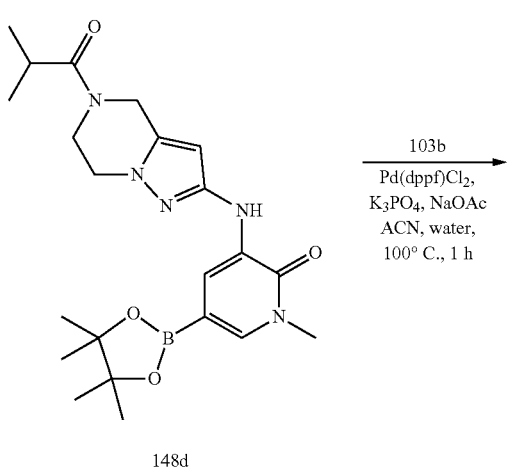

148d

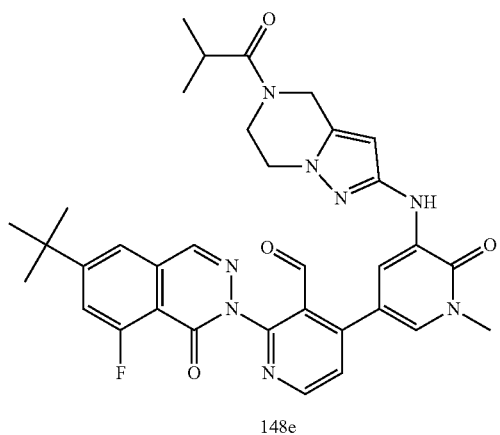

148e

To a solution of 2-nitro-4,5,6,7-tetrahydropyrazolo[1,5-a]pyrazine 124d (160 mg, 0.952 mmol) in dichloromethane (10 mL) was added triethylamine (197 mg, 1.90 mmol). After stirring at room temperature for 5 minutes, a solution of isobutyryl chloride (111.0 mg, 1.047 mmol) in dichloromethane (2 mL) was added and the mixture was stirred for 1 h. Analysis of the reaction mixture by LCMS showed complete conversion to the desired product. It was then concentrated under reduced pressure to afford 148a as a white solid (220 mg, 97%), which was used in the next step without further purification. MS-ESI: [M+H]$^+$ 239.0

Example 148b 1-(2-Amino-6,7-dihydropyrazolo[1,5-a]pyrazin-5(4H)-yl)-2-methylpropan-1-one 148b To a solution of 148a (220 mg, 0.924 mmol) in methanol (20 mL) was added Pd/C (22 mg). The system was evacuated and refilled with H$_2$. After stirring at room temperature for 2 h, the mixture was filtered. The filtrate was concentrated under reduced pressure to afford 148b as a yellow solid (190 mg, 98%), which was used in the next step without further purification. MS-ESI: [M+H]$^+$ 209.1

Example 148c

5-Bromo-3-(5-isobutyryl-4,5,6,7-tetrahydropyrazolo[1,5-a]pyrazin-2-ylamino-1-methylpyridin-2(1H)-one 148c A 100-mL round-bottomed flask equipped with a reflux condenser was charged with 148b (190 mg, 0.913 mmol), 3,5-dibromo-1-methylpyridin-2(1H)-one (365.6 mg, 1.37 mmol), Pd$_2$(dba)$_3$ (41.7 mg, 0.0456 mmol), Xantphos (52.8 mg, 0.0913 mmol), Cs$_2$CO$_3$ (595.3 mg, 1.826 mmol), and dioxane (20 mL). The system was subjected to three cycles of vacuum/nitrogen flush and heated at 100° C. under N$_2$ protection for 3 h. Analysis of the reaction mixture by LCMS showed complete conversion to the desired product. It was cooled to room temperature and filtered. The filtrate was concentrated under reduced pressure. The residue was washed with acetonitrile (2 mL) to afford 148c as a dark solid (240 mg, 67%), which was used in the next step without further purification. MS-ESI: [M+H]$^+$ 394.2

Example 148d 3-(5-Isobutyryl-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 148d A 100-mL round-bottomed flask equipped with a reflux condenser was charged with 148c (220 mg, 0.558 mmol), Pin$_2$B$_2$ (212.6 mg, 0.837 mmol), Pd$_2$(dba)$_3$ (25.5 mg, 0.0279 mmol), X-Phos (26.6 mg, 0.0558 mmol), potassium acetate (109.4 mg, 1.12 mmol), and dioxane (20 mL). The system was subjected to three cycles of vacuum/nitrogen flush and heated at 70° C. under N$_2$ protection for 2 h. Analysis of the reaction mixture by LCMS showed complete conversion to the desired product. It was then cooled to room temperature and filtered. The filtrate was concentrated under reduced pressure. The residue was washed with petroleum ether to afford 148d as a dark oil (200 mg, 81%), which was used in the next step without further purification. MS-ESI: [M+H]$^+$ 442.4

Example 148e 2-(6-tert-Butyl-8-fluoro-1-oxophthalazin-2(1H)-yl)-4-(5-(5-isobutyryl-4,5,6,7-tetrahydropyrazolo[1,5-a]pyrazin-2-ylamino)-1-methyl-6-oxo-1,6-dihydropyridin-3-yl)nicotinaldehyde 148e A 100-mL round-bottomed flask equipped with a reflux condenser was charged with 2-(6-tert-butyl-8-fluoro-1-oxophthalazin-2(1H)-yl)-4-chloronicotinaldehyde 103b (150 mg, 0.42 mmol), 148d (278 mg, 0.63 mmol), Pd(dppf)Cl$_2$ (17.1 mg, 0.021 mmol), K$_3$PO$_4$ (178.1 mg, 0.84 mmol), sodium acetate (68.9 mg, 0.84 mmol), acetonitrile (15 mL), and water (5 drops). The system was subjected to three cycles of vacuum/nitrogen flush and heated at 100° C. under N₂ protection for 1 h. Analysis of the reaction mixture by LCMS showed complete conversion to the desired product. It was cooled to room temperature and filtered. The filtrate was concentrated under reduced pressure. The residue was washed with acetonitrile (0.5 mL) to afford 148e as a white solid (100 mg, 37%), which was used in the next step without further purification. MS-ESI: [M+H]⁺ 638.8

Example 148

6-tert-butyl-8-fluoro-2-[3-(hydroxymethyl)-4-[1-methyl-5-[[5-(2-methylpropanoyl)-6,7-dihydro-4H-pyrazolo[1,5-a]pyrazin-2-yl]amino]-6-oxo-3-pyridyl]-2-pyridyl]phthalazin-1-one 148

To a solution of 148e (90 mg, 0.141 mmol) in dichloromethane (5 mL) and methanol (5 mL) was added NaBH₄ (10.7 mg, 0.282 mmol). After stirring at room temperature for 1 h, the reaction mixture was quenched with aqueous NH₄Cl and concentrated under reduced pressure. The residue was extracted with dichloromethane (3×15 mL). The combined organic layer was washed with brine, dried over Na₂SO₄, and concentrated under reduced pressure. The residue was purified by reverse-phase prep-HPLC to afford 148 (40 mg, 44%) as a white solid. MS-ESI: [M+H]⁺ 640.8. $^1$H NMR (500 MHz, DMSO-d₆) δ 8.57 (d, J=5.0 Hz, 1H), 8.54 (d, J=2.5 Hz, 1H), 8.35-8.28 (m, 1H), 8.06 (s, 1H), 7.90 (d, J=1.5 Hz, 1H), 7.78 (dd, J=1.0, 13.0 Hz, 1H), 7.51 (d, J=5.0 Hz, 1H), 7.40 (d, J=2.5 Hz, 1H), 6.01 (s, 1H), 4.90-4.88 (m, 1H), 4.78-4.76 (m, 1H), 4.64-4.62 (m, 1H), 4.42-4.41 (m, 2H), 4.03-3.92 (m, 4H), 3.59 (s, 3H), 3.00-2.96 (m, 1H), 1.40 (s, 9H), 1.04-1.01 (m, 6H).

Example 149a

1-Methyl-4-nitro-1H-1,2,3-triazole 149a

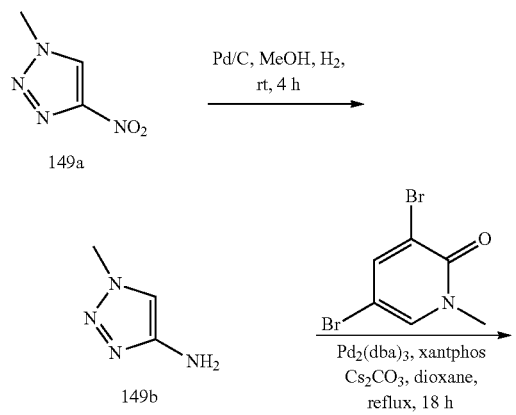

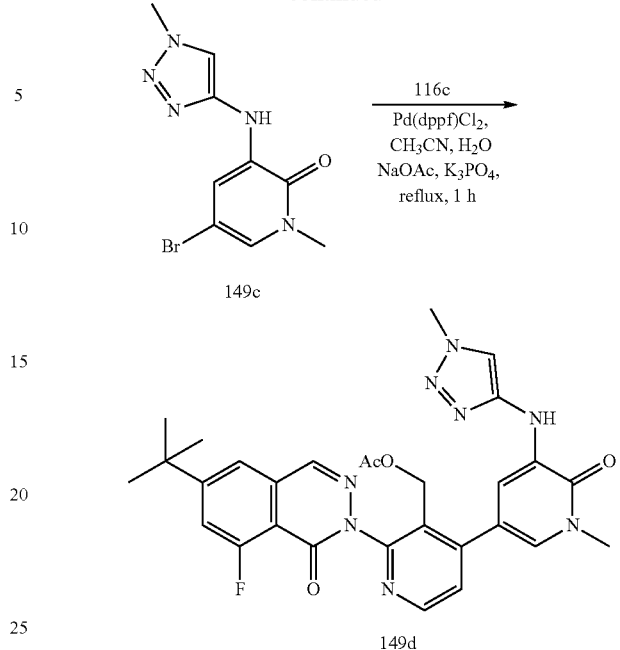

To a 100-mL single-neck round-bottomed containing 4-nitro-2H-1,2,3-triazole (2.0 g, 17.5 mmol) and THF (10 mL) at 0° C. was added NaH (1.7 g, 35.0 mmol, 2.0 eq.). The mixture was stirred at 0° C. for 15 min. A solution of CH₃I (3.68 g, 26.3 mmol, 1.5 eq.) in acetone (40 mL) was added and the resulting reaction mixture was stirred at room temperature for 2 h. After this time, the reaction was quenched by water (20 mL) at 0° C. and concentrated under reduced pressure. The residue was diluted with dichloromethane (100 mL). It was then washed with brine, dried over anhydrous Na₂SO₄, and concentrated under reduced pressure. The residue was purified by silica-gel column chromatography eluting with 6:1 petroleum ether/ethyl acetate to afford 1-methyl-5-nitro-1H-1,2,3-triazole (1.34 g, 60%) as a white solid and 149a (800 mg, 35%) as a slightly yellow solid. $^1$H NMR (500 MHz, CDCl₃) δ 8.34 (s, 1H), 4.26 (s, 3H). 1-Methyl-5-nitro-1H-1,2,3-triazole: $^1$H NMR (500 MHz, CDCl₃) δ 8.16 (s, 1H), 4.31 (s, 3H).

Example 149b

1-Methyl-1H-1,2,3-triazol-4-amine 149b

Following the procedure in Example 148b, and starting with 149a (800 mg, 6.25 mmol) and 10% palladium on carbon (50% wet, 160 mg), afforded 149b as a yellow solid (600 mg, 98%). $^1$H NMR (500 MHz, CDCl₃) δ 6.91 (s, 1H), 3.97 (s, 3H), 3.65 (brs, 2H).

Example 149c

5-Bromo-1-methyl-3-(1-methyl-1H-1,2,3-triazol-4-ylamino)pyridin-2(1H)-one 149c

Following the procedure in Example 148c, and starting with 149b (500 mg, 5.10 mmol, 1.0 eq.) and 3,5-dibromo-1-methylpyridin-2(1H)-one (2.04 g, 7.65 mmol, 1.5 eq.), 149c was obtained as a yellow solid (760 mg, 52%). MS-ESI: [M+H]⁺ 283.9.

Example 149d (2-(6-tert-Butyl-8-fluoro-1-oxophthalazin-2(1H)-yl)-4-(1-methyl-5-(1-methyl-1H-1,2,3-triazol-4-ylamino)-6-oxo-1,6-dihydropyridin-3-yl)pyridin-3-yl)methyl Acetate 149d Following the procedure in Example 147d, and starting with 149c (120 mg, 0.42 mmol, 1 eq.) and 3-(acetoxymethyl)-2-(6-tert-butyl-8-fluoro-1-oxophthalazin-2(1H)-yl)pyridin-4-ylboronic acid (116c) (485 mg, 1.18 mmol, 2.8 eq.), afforded 149d as a yellow solid (120 mg, 50%). MS-ESI: [M+H]+ 573.3.

Example 149

6-tert-butyl-8-fluoro-2-[3-(hydroxymethyl)-4-[1-methyl-5-[(1-methyltriazol-4-yl)amino]-6-oxo-3-pyridyl]-2-pyridyl]phthalazin-1-one 149

Following the procedure in Example 147, and starting with 149c (90 mg, 0.16 mmol), afforded 149 as a white solid (32 mg, 38%). MS-ESI: [M+H]+ 530.8. $^1$H NMR (500 MHz, CDCl$_3$) δ 8.65 (d, J=5.0 Hz, 1H), 8.37 (d, J=1.5 Hz, 1H), 7.69-7.67 (m, 3H), 7.60-7.57 (m, 2H), 7.50 (d, J=5.0 Hz, 1H), 7.34 (d, J=1.5 Hz, 1H), 4.53 (s, 2H), 4.27 (s, 1H), 4.10 (s, 3H), 3.74 (s, 3H), 1.46 (s, 9H).

Example 150a

N-Methoxy-N-methyl-3-nitro-1H-pyrazole-5-carboxamide 150a

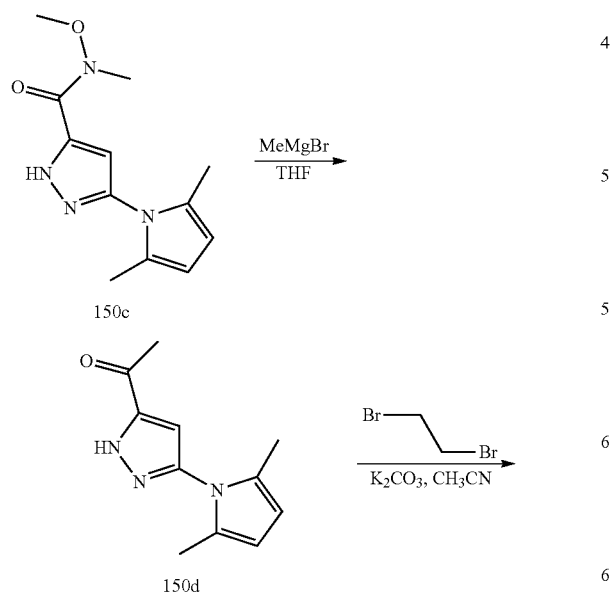

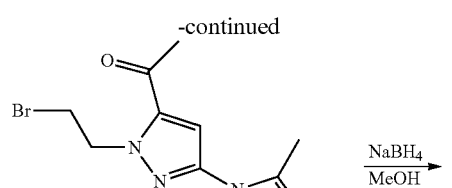

A 500-mL single-neck round-bottomed flask equipped with a magnetic stirrer was charged with 3-nitro-1H-pyrazole-5-carboxylic acid (15.7 g, 1.0 eq., 100 mmol), N,O-dimethylhydroxylamine hydrochloride (19.5 g, 2.0 eq., 200 mmol), HATU (76.0 g, 2.0 eq., 200 mmol), triethylamine (40.4 g, 4.0 eq., 400 mmol), and dichloromethane (300 mL). The reaction mixture was stirred at room temperature overnight. The solvent was removed under reduced pressure. The resulting residue was purified by silica-gel column chromatography eluting with 100:1 dichloromethane/methanol to afford 150a (16.0 g, 80%) as a white solid. MS-ESI: [M+H]+ 201.1

Example 150b

3-Amino-N-methoxy-N-methyl-1H-pyrazole-5-carboxamide 150b

A 250-mL single-neck round-bottomed flask was purged with nitrogen and charged with 150a (16.0 g, 1.0 eq., 80.0 mmol), 10% palladium on carbon (50% wet, 800 mg), and methanol (100 mL). The mixture was evacuated, charged with hydrogen gas, and stirred under hydrogen atmosphere at room temperature overnight. The hydrogen was then evacuated and nitrogen was charged into the flask. The catalyst was removed by filtration through a pad of CELITE®. The filtrate was concentrated under reduced pressure to afford 150b (11.0 g, 81%) as a white solid. MS-ESI: [M+H]+ 171.1

Example 150c 3-(2,5-Dimethyl-1H-pyrrol-1-yl)-N-methoxy-N-methyl-1H-pyrazole-5-carboxamide 150c A 250-mL round-bottomed flask equipped with a magnetic stirrer and a Dean-Stark trap was charged with 150b (11.0 g, 1.0 eq., 64.7 mmol), hexane-2,5-dione (11.1 g, 1.5 eq., 97.2 mmol), p-toluenesulfonic acid monohydrate (558 mg, 0.05 eq., 3.24 mmol), and toluene (100 mL). The reaction mixture was refluxed overnight. The resulting mixture was cooled to room temperature and concentrated under reduced pressure. The resulting residue was purified by silica-gel column chromatography eluting with 1:2 petroleum ether/ethyl acetate to afford 150c (10.4 g, 65%) as a white solid. MS-ESI: [M+H]+ 249.0

Example 150d 1-(3-(2,5-Dimethyl-1H-pyrrol-1-yl)-1H-pyrazol-5-yl)ethanone 150d A 250-mL round-bottomed flask equipped with a magnetic stirrer was charged with 150c (7.44 g, 1.0 eq., 30.0 mmol) and THF (100 mL). Under $N_2$ protection, a solution of MeMgBr (3.0 M in ether) (25 mL, 2.5 eq., 75.0 mmol) was added at 0° C. The mixture was stirred at room temperature for 5 h and quenched with saturated $NH_4Cl$ solution (30 mL). The mixture was concentrated under reduced pressure and the residue was extracted with ethyl acetate (3×50 mL). The combined organic layer was evaporated under reduced pressure and the residue was purified by silica-gel column chromatography eluting with 4:1 petroleum ether/ethyl acetate to afford 150d as a white solid (5.40 g, 89%). MS-ESI: [M+H]+ 204.0. $^1$H NMR (500 MHz, CDCl$_3$) δ 6.74 (s, 1H), 5.92 (s, 2H), 2.61 (s, 3H), 2.15 (s, 6H).

Example 150e 1-(1-(2-Bromoethyl)-3-(2,5-dimethyl-1H-pyrrol-1-yl)-1H-pyrazol-5-yl)ethanone 150e A 250-mL round-bottomed flask equipped with a magnetic stirrer and a reflux condenser was charged with 150d (5.4 g, 1.0 eq., 26.6 mmol), 1,2-dibromoethane (20.0 g, 4.0 eq., 106.4 mmol), $K_2CO_3$ (7.34 g, 2.0 eq., 53.2 mmol), and acetonitrile (100 mL). The reaction mixture was reflux for 5 hrs. It was cooled to room temperature and filtered. The filtrate was concentrated under reduced pressure. The residue was purified by silica-gel column chromatography eluting with 6:1 petroleum ether/ethyl acetate to afford 150e (7.5 g, 91%) as a colorless oil. MS-ESI: [M+H]+ 309.9

Example 150f 1-(1-(2-Bromoethyl)-3-(2,5-dimethyl-1H-pyrrol-1-yl)-1H-pyrazol-5-yl)ethanol 150f A 100-mL round-bottomed flask equipped with a magnetic stirrer was charged with 150e (2.1 g, 1.0 eq., 6.8 mmol), NaBH4 (1.29 g, 5.0 eq., 34.0 mmol), and methanol (50 mL). The mixture was stirred at room temperature for 2 h and quenched with water (30 mL). It was then concentrated under reduced pressure and the residue was extracted with dichloromethane (3×50 mL). The combined organic layer was concentrated under reduced pressure to afford crude 150f, which was used in the next step without further purification. MS-ESI: [M+H]+ 311.9

Example 150g 2-(2,5-Dimethyl-1H-pyrrol-1-yl)-4-methyl-6,7-dihydro-4H-pyrazolo[5,1-c][1,4]oxazine 150g A 100-mL round-bottomed flask equipped with a reflux condenser was charged with 150f (2.0 g, 1.0 eq., 6.4 mmol), $K_2CO_3$ (1.77 g, 2.0 eq., 12.8 mmol), acetonitrile (50 mL). The reaction mixture was reflux overnight. It was then cooled to room temperature and filtered. The filtrate was concentrated under reduced pressure. The residue was purified by silica-gel column chromatography eluting with 4:1 petroleum ether/ethyl acetate to afford 150g (550 mg, 37%, over two steps) as a colorless oil. MS-ESI: [M+H]+ 232.3

Example 150h

4-Methyl-6,7-dihydro-4H-pyrazolo[5,1-c][1,4]oxazin-2-amine 150h

A 100-mL round-bottomed flask equipped with a magnetic stirrer and a reflux condenser was charged with 150g (550 mg, 1.0 eq., 2.38 mmol), hydroxylamine hydrochloride (827 mg, 5.0 eq., 11.9 mmol), and ethanol (30 mL). The mixture was refluxed for 2 days. It was then cooled to room temperature and filtered. The filtrate was concentrated under reduced pressure. The residue was purified by reverse-phase prep-HPLC to afford 150h (30 mg, 8%) as a yellow oil. MS-ESI: [M+H]+ 154.1. $^1$H NMR (500 MHz, CDCl$_3$) δ 5.37 (s, 1H), 4.73 (q, J=7.0 Hz, 1H), 4.26-4.23 (m, 1H), 4.08-4.03 (m, 1H), 3.91-3.90 (m, 1H), 3.90-3.87 (m, 1H), 1.65 (d, J=7.0 Hz, 3H).

Example 150i (2-(6-tert-Butyl-8-fluoro-1-oxophthalazin-2(1H)-yl)-4-(1-methyl-5-(4-methyl-6,7-dihydro-4H-pyrazolo[5,1-c][1,4]oxazin-2-ylamino)-6-oxo-1,6-dihydropyridin-3-yl)pyridin-3-yl)methyl acetate 150i A 25-mL single-neck round-bottomed flask equipped with a magnetic stirrer and a reflux condenser was charged with 150h (25 mg, 1.0 eq., 0.16 mmol), (4-(5-bromo-1-methyl-6- oxo-1,6-dihydropyridin-3-yl)-2-(6-tert-butyl-8-fluoro-1-oxophthalazin-2(1H)-yl)pyridin-3-yl)methyl acetate 142c (181 mg, 2.0 eq., 0.32 mmol), Pd$_2$(dba)$_3$ (15 mg, 0.1 eq., 0.016 mmol), Xantphos (19 mg, 0.2 eq., 0.032 mmol), Cs$_2$CO$_3$ (105 mg, 2.0 eq., 0.32 mmol), and dioxane (10 mL). The mixture was subjected to three cycles of vacuum/argon flush and stirred at 100° C. for 2 hr. It was then cooled to room temperature and filtered. The filtrate was concentrated under reduced pressure. The resulting residue was purified by silica-gel column chromatography eluting with 20:1 dichloromethane/methanol to afford 150i as a brown solid (48 mg, 48%).

Example 150

6-tert-butyl-8-fluoro-2-[3-(hydroxymethyl)-4-[1-methyl-5-[(4-methyl-6,7-dihydro-4H-pyrazolo[5,1-c][1,4]oxazin-2-yl)amino]-6-oxo-3-pyridyl]-2-pyridyl]phthalazin-1-one 150

A 25-mL round-bottomed flask equipped with a magnetic stirrer was charged with 150i (48 mg, 1.0 eq., 0.077 mmol), lithium hydroxide (9.2 mg, 5.0 eq., 0.38 mmol), i-propanol/THF (4/4 mL), and water (1 mL). The mixture was stirred at room temperature for 1 h and concentrated under reduced pressure. The residue was purified by reverse-phase prep-HPLC to afford 150 as a yellow solid (6.8 mg, 15%). MS-ESI: [M+H]$^+$ 585.8. $^1$H NMR (500 MHz, CDCl$_3$) δ 8.66 (d, J=4.5 Hz, 1H), 8.35 (d, J=2.0 Hz, 1H), 8.03 (d, J=1.5 Hz, 1H), 7.59-7.53 (m, 4H), 7.47 (s, 1H), 5.72 (s, 1H), 4.82-4.78 (m, 1H), 4.52-4.49 (m, 2H), 4.33-4.30 (m, 1H), 4.30-4.27 (m, 1H), 4.02-3.98 (m, 3H), 3.73 (s, 3H), 1.54 (d, J=7.0 Hz, 3H), 1.48 (s, 9H).

Example 151a

Ethyl 2-(5-(Hydroxymethyl)-3-nitro-1H-pyrazol-1-yl)acetate 151a

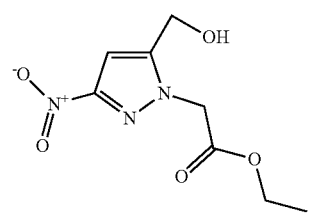

A 100-mL single-neck round-bottomed flask equipped with a magnetic stirrer was charged with acetonitrile (30 mL), (3-nitro-1H-pyrazol-5-yl)methanol (1.43 g, 10.0 mmol), Cs$_2$CO$_3$ (490 mg, 1.5 mmol), and ethyl 2-bromoacetate (2.00 g, 12 mmol). The mixture was stirred at 40° C. for 5 h. It was then cooled to room temperature and filtered. The filtrate was concentrated under reduced pressure and the residue was purified by silica-gel column chromatography eluting with 30:1 dichloromethane/methanol to afford 151a (1.65 g, 72%) as a yellow solid. MS-ESI: [M+H]$^+$ 229.9

Example 151b

Ethyl 2-(5-(Chloromethyl)-3-nitro-1H-pyrazol-1-yl)acetate 151b

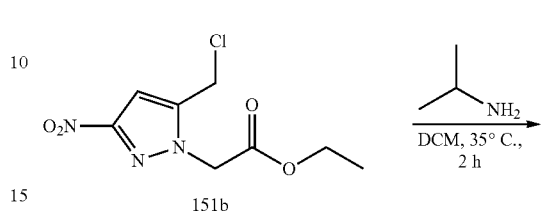

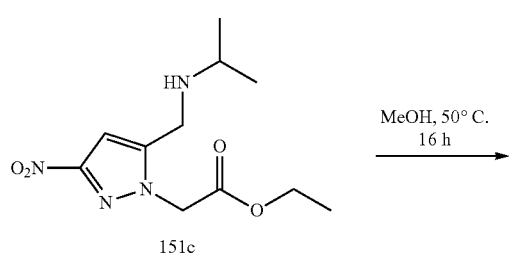

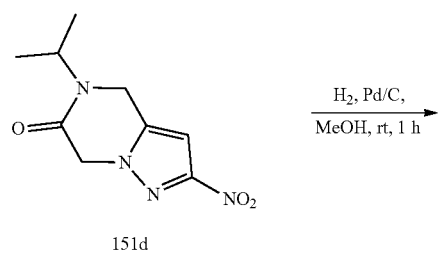

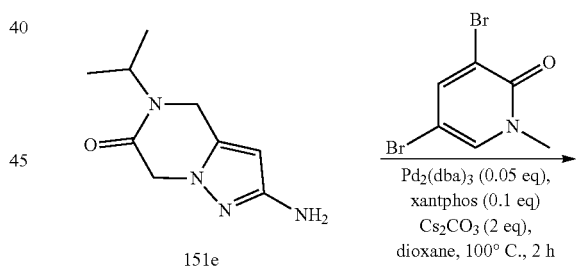

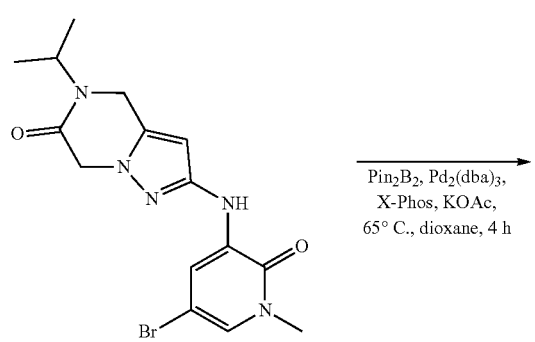

-continued

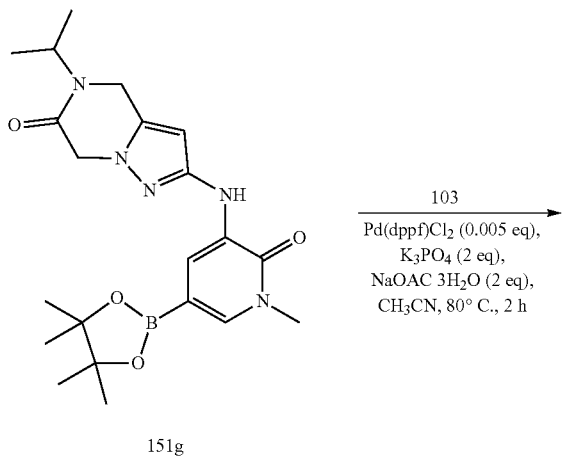

151g

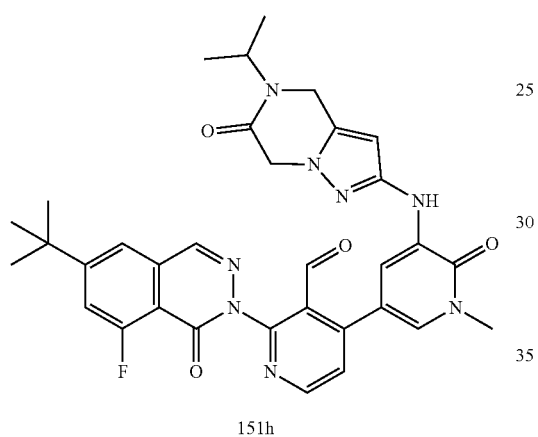

151h

To a mixture of 151a (1.50 g, 6.55 mmol) in CHCl₃ (60 mL) cooled at 0° C. was slowly added SOCl₂ (2.34 g, 19.6 mmol) while maintaining the internal temperature below 5° C. This reaction mixture was warmed to 50° C. and stirred at this temperature for 3 h. It was then cooled to 0° C. and quenched with water. The organic layer was separated and evaporated under reduced pressure. The residue was purified by silica-gel column chromatography eluting with 30:1 dichloromethane/methanol to afford 151b (1.1 g, 68%) as a yellow solid. MS-ESI: [M+H]⁺ 247.9

Example 151c

Ethyl 2-(5-((Isopropylamino)methyl)-3-nitro-1H-pyrazol-1-yl)acetate 151c

A mixture of 151b (500 mg, 2.04 mmol), propan-2-amine (180 mg, 3.06 mmol), and dichloromethane (20 mL) was stirred at room temperature for 2 h. The mixture was concentrated under reduced pressure to afford 151c (400 mg, 74%) as a yellow solid, which was used in the next step without further purification. MS-ESI: [M+H]⁺ 271.1

Example 151d

5-Isopropyl-2-nitro-4,5-dihydropyrazolo[1,5-a]pyrazin-6(7H)-one 151d

A mixture of 151c (400 mg, 1.48 mmol) and methanol (30 mL) was stirred at 50° C. for 16h. The mixture was the concentrated under reduced pressure. The residue was diluted with water (80 mL) and extracted with ethyl acetate (3×50 mL). The combined organic layer was dried over Na₂SO₄ and concentrated under reduced pressure to afford 151d (300 mg, 90%) as a yellow solid. MS-ESI: [M+H]⁺ 225.3

Example 151e

2-Amino-5-isopropyl-4,5-dihydropyrazolo[1,5-a]pyrazin-6(7H)-one 151e

To a solution of 151d (220 mg, 1.0 mmol) in ethanol (20 mL) was added Pd/C (10%, 22 mg). The reaction mixture was charged with hydrogen gas (via balloon) and stirred at room temperature for 1 h. The reaction mixture was filtered through a plug of CELITE® and the filtrate was concentrated under reduced pressure to afford 151e as a yellow solid (180 mg, 92%), which was used without further purification. MS-ESI: [M+H]⁺ 195.3

Example 151f 2-(5-Bromo-1-methyl-2-oxo-1,2-dihydropyridin-3-ylamino)-5-isopropyl-4,5-dihydropyrazolo[1,5-a]pyrazin-6(7H)-one 151f A 100-mL round-bottomed flask equipped with a reflux condenser was charged with 151e (200 mg, 1.0 mmol), 3,5-dibromo-1-methylpyridin-2(1H)-one (268 mg, 1.0 mmol), Pd₂(dba)₃ (50 mg, 0.050 mmol), xantphos (58 mg, 0.10 mmol), Cs₂CO₃ (652 mg, 2.0 mmol) and 1,4-dioxane (20 mL). The system was subjected to three cycles of vacuum/argon flush and heated at 100° C. for 2 h. It was then cooled to room temperature and filtered. The solid was washed with dichloromethane (2×10 mL). The combined filtrate was concentrated under reduced pressure. The residue was purified by silica-gel column chromatography eluting with dichloromethane/methanol (80:1 to 30:1) to afford 151f (300 mg, 79%) as a yellow solid. MS-ESI: [M+H]⁺ 380.2

Example 151g

5-Isopropyl-2-(1-methyl-2-oxo-5-(4,4,5,5-tetramethyl-1,3,2-dioxaborolan-2-yl)-1,2-dihydropyridin-3-ylamino)-4,5-dihydropyrazolo[1,5-a]pyrazin-6(7H)-one 151g A 50-mL single-neck round-bottomed flask equipped with a magnetic stirrer and a reflux condenser was charged with 151f (200 mg, 0.52 mmol), Pin₂B₂ (330 mg, 1.3 mmol), Pd₂(dba)₃ (25 mg, 0.026 mmol), X-phos (25 mg, 0.052 mmol), potassium acetate (150 mg, 1.5 mmol), and 1,4-dioxane (10 mL). The mixture was subjected to three cycles of vacuum/argon flush and heated at 65° C. for 4 h. It was then filtered and the filtrate was evaporated under reduced pressure. The residue was washed by petroleum ether to afford crude 151g (300 mg, purity: 50%) as a brown solid. MS-ESI: [M+H]⁺ 428.2.

Example 151h 2-(6-tert-Butyl-8-fluoro-1-oxophthalazin-2(1H)-yl)-4-(5-(5-isopropyl-6-oxo-4,5,6,7-tetrahydropyrazolo[1,5-a]pyrazin-2-ylamino)-1-methyl-6-oxo-1,6-dihydropyridin-3-yl)nicotinaldehyde 151h A 25-mL round-bottomed flask equipped with a reflux condenser was charged with 2-(6-tert-butyl-8-fluoro-1-oxoisoquinolin-2(1H)-yl)-4-chloronicotinaldehyde 103b (108 mg, 0.30 mmol), 151g (256 mg, 0.60 mmol), K$_3$PO$_4$ (127 mg, 0.60 mmol), sodium acetate.water (82 mg, 0.60 mmol), Pd(dppf)Cl$_2$ (12 mg, 0.015 mmol), water (0.5 mL), and acetonitrile (8 mL). The reaction mixture was subjected to three cycles of vacuum/nitrogen flush and heated at 80° C. under N$_2$ protection for 2 h. It was then cooled to room temperature and concentrated under reduced pressure. The residue was diluted with dichloromethane (20 mL) and water (10 mL). The organic layer was separated and the water layer was extracted with dichloromethane (2×10 mL). The combined organic extract was dried over Na$_2$SO$_4$, filtered, and concentrated under reduced pressure. The dark residue was purified by silica-gel column chromatography eluting with dichloromethane/methanol (80:1 to 30:1) to afford 151h (90 mg, 48%) as yellow solid. MS-ESI: [M+H]$^+$ 625.2.

Example 151

6-tert-Butyl-8-fluoro-2-(3-(hydroxymethyl)-4-(5-(5-isopropyl-6-oxo-4,5,6,7-tetrahydropyrazolo[1,5-a]pyrazin-2-ylamino)-1-methyl-6-oxo-1,6-dihydropyridin-3-yl)pyridin-2-yl)phthalazin-1(2H)-one 151

A 25-mL single-neck round-bottomed flask was charged with 151h (90 mg, 0.14 mmol), NaBH$_4$ (18 mg, 0.42 mmol), and methanol (5 mL). The mixture was stirred at room temperature for 1 h and concentrated under reduced pressure. To the resulting residue was added water (10 mL) and the mixture was extracted with dichloromethane (3×15 mL). The combined organic layer was concentrated under reduced pressure. The residue was purified by reverse-phase prep-HPLC to afford 151 (50 mg, 55%). MS-ESI: [M+H]$^+$ 626.8. $^1$H NMR (500 MHz, CDCl$_3$) δ 8.67 (d, J=5.0 Hz, 1H), 8.36 (d, J=2.5 Hz, 1H), 8.02 (d, J=2.0 Hz, 1H), 7.59-7.58 (m, 3H), 7.55-7.52 (m, 2H), 5.90 (s, 1H), 5.07-5.05 (m, 1H), 4.74 (s, 2H), 4.50-4.47 (m, 4H), 4.09-4.06 (m, 1H), 3.73 (s, 3H), 1.45 (s, 9H), 1.26 (d, J=7.0 Hz, 6H).

Example 152a tert-Butyl 3-Amino-1H-pyrazole-1-carboxylate 152a

To a mixture of 3-aminopyrazole (3.0 g, 36 mmol) and triethylamine (7.6 g, 75 mmol) in 1,4-dioxane (35 mL) was added (Boc)$_2$O (7.8 g, 36 mmol). The reaction mixture was stirred at 25° C. for 2 h. It was then concentrated under reduced pressure. The residue was purified by silica-gel column eluting with 3:1 petroleum ether/ethyl acetate to afford 152a as a white solid (3.4 g, 52%). MS-ESI: [M+H]$^+$ 184.1.

Example 152b 3-(1H-Pyrazol-3-ylamino)-5-bromo-1-methylpyridin-2(1H)-one 152a

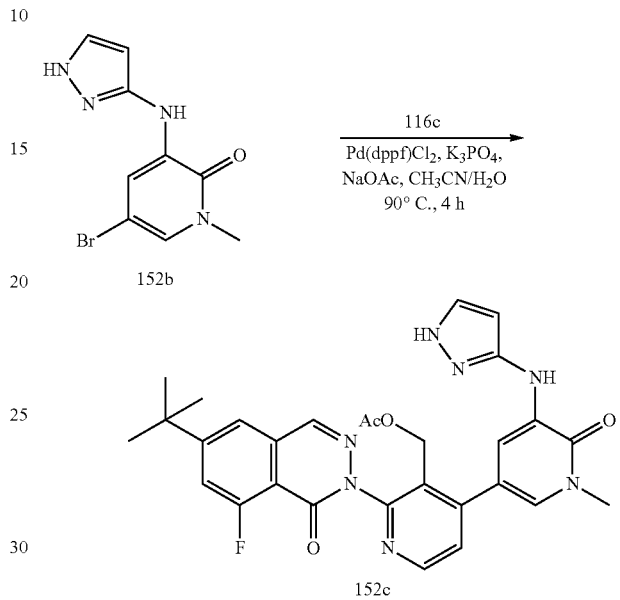

A 250-mL single-neck round-bottomed flask equipped with a magnetic stirrer and a reflux condenser was charged with 152a (2.2 g, 12 mmol), XantPhos (0.69 g, 1.2 mmol), Pd$_2$(dba)$_3$ (1.1 g, 1.2 mmol), 3,5-dibromo-1-methylpyridin-2(1H)-one (6.4 g, 24 mmol), Cs$_2$CO$_3$ (15.6 g, 48 mmol), and 1,4-dioxane (50 mL). After bubbling nitrogen through the resulting mixture for 10 minutes, it was heated at 105° C. for 15 h. The mixture was cooled to room temperature and filtered. The filtered was concentrated under reduced pressure and the residue the mixture was washed with methanol (8 mL) to afford 152b as a pale yellow solid (1.2 g, 37%). MS-ESI: [M+H]$^+$ 269.1.

Example 152c (4-(5-(1H-Pyrazol-3-ylamino)-1-methyl-6-oxo-1,6-dihydropyridin-3-yl)-2-(6-tert-butyl-8-fluoro-1-oxophthalazin-2(1H)-yl)pyridin-3-yl)methyl Acetate 152c A sealed tube equipped with a magnetic stirrer was charged with 152b (200 mg, 0.74 mmol), (2-(6-tert-butyl-8-fluoro-1-oxophthalazin-2(1H)-yl)-4-(4,4,5,5-tetramethyl-1,3,2-dioxaborolan-2-yl)pyridin-3-yl)methyl acetate 116c (370 mg, 0.74 mmol), Pd(dppf)Cl$_2$ (30 mg, 0.035 mmol), sodium acetate (74 mg, 0.90 mmol), K$_3$PO$_4$ (191 mg, 0.90 mmol), and acetonitrile/water (5 mL/0.5 mL). After three cycles of vacuum/argon flush, the mixture was heated at 100° C. for 2 h. It was then filtered and the filtrate was evaporated under reduced pressure. The residue was purified by silica-gel column chromatography eluting with 10:1 dichloromethane/methanol to afford 152c (100 mg, 25%) as a brown solid. MS-ESI: [M+H]$^+$ 558.3.

Example 152

6-tert-butyl-8-fluoro-2-[3-(hydroxymethyl)-4-[1-methyl-6-oxo-5-(1H-pyrazol-3-ylamino)-3-pyridyl]-2-pyridyl]phthalazin-1-one 152

A mixture of 152c (100 mg, 0.18 mmol) and lithium hydroxide hydrate (84 mg, 2.0 mmol) in THF (8 mL), i-propanol (8 mL) and water (2 mL) was stirred at 40° C. for 0.5 h. The mixture was evaporated under reduced pressure and the residue was diluted with water (5 mL). It was then extracted with ethyl acetate (2×10 mL). The combined extract was concentrated under reduced pressure and the residue was purified by reverse-phase prep-HPLC to afford 152 (6.5 mg, 7%) as a pale yellow solid. MS-ESI: [M+H]$^+$ 515.8. $^1$H NMR (500 MHz, CDCl$_3$) δ 8.62-8.61 (m, 1H), 8.32 (s, 1H), 8.04 (m, 1H), 7.55-7.53 (m, 4H), 7.50-7.49 (m, 1H), 7.44 (s, 1H), 6.01 (s, 1H), 4.49-4.48 (m, 2H), 3.71 (s, 3H), 1.45 (s, 9H).

Example 153a

6-Chloro-2-methyl-4-(5-methyl-4,5,6,7-tetrahydropyrazolo[1,5-a]pyrazin-2-ylamino)pyridazin-3(2H)-one 153a

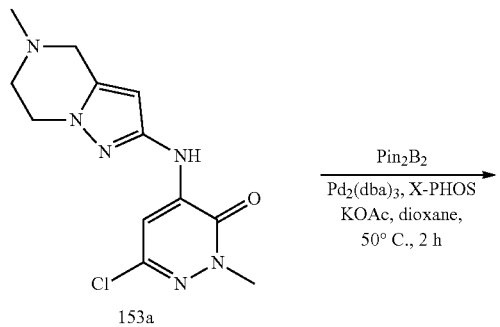

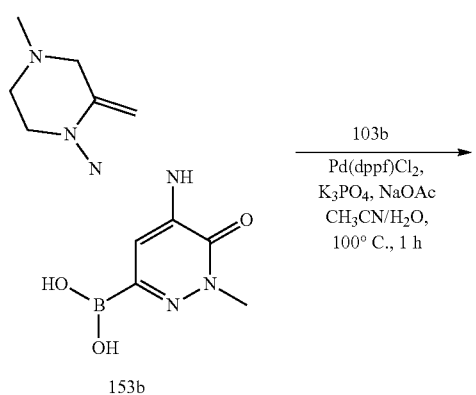

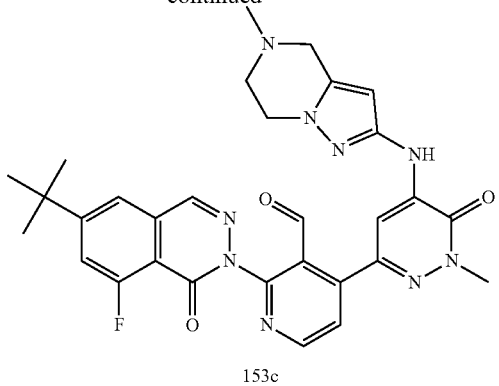

A 100-mL single-neck round-bottomed flask equipped with a magnetic stirrer and a reflux condenser was charged with 1,4-dioxane (30 mL), 5-methyl-4,5,6,7-tetrahydropyrazolo[1,5-a]pyrazin-2-amine 128b (1.70 g, 11.2 mmol), 4-bromo-6-chloro-2-methylpyridazin-3(2H)-one (2.68 g, 12.0 mmol), and cesium carbonate (7.30 g, 22.4 mmol). After bubbling nitrogen through the suspension for 30 minutes, Xantphos (0.59 g, 1.02 mmol) and tris(dibenzylideneacetone)dipalladium(0) (467 mg, 0.51 mmol) were added. The system was subjected to three cycles of vacuum/argon flush and heated at 90° C. for 2 h. It was then cooled to room temperature and filtered. The filtrate was evaporated in vacuo. The residue was purified by silica-gel column chromatography eluting with 30:1 dichloromethane/methanol to afford 153a (1.9 g, 60%) as a brown solid. LCMS: [M+H]$^+$ 295.1

Example 153b

1-Methyl-5-(5-methyl-4,5,6,7-tetrahydropyrazolo[1,5-a]pyrazin-2-ylamino)-6-oxo-1,6-dihydropyridazin-3-ylboronic Acid 153b A 50-mL round-bottomed flask equipped with a magnetic stirrer and a reflux condenser was charged with 153a (200 mg, 0.68 mmol), bis(pinacolato)diboron (Pin$_2$B$_2$, 863 mg, 3.40 mmol), Pd$_2$(dba)$_3$ (55 mg, 0.060 mmol), X-Phos (60 mg, 0.12 mmol), potassium acetate (60 mg, 1.36 mmol), and 1,4-dioxane (10 mL). The system was evacuated and then refilled with N$_2$. It was then heated at 50° C. for 2 h. After completion of the reaction, the mixture was filtered and the solid was washed with ethyl acetate (10 mL). The combined filtrate was evaporated under reduced pressure to afford 153b as a pale yellow solid, which was used in the next step. MS-ESI: [M+H]$^+$ 305.1.

Example 153c 2-(6-tert-Butyl-8-fluoro-1-oxophthalazin-2(1H)-yl)-4-(1-methyl-5-(5-methyl-4,5,6,7-tetrahydropyrazolo[1,5-a]pyrazin-2-ylamino)-6-oxo-1,6-dihydropyridazin-3-yl)nicotinaldehyde 153c A 25-mL round-bottomed flask equipped with a reflux condenser was charged with 153b (200 mg, 0.66 mmol), 2-(6-tert-butyl-8-fluoro-1-oxophthalazin-2(1H)-yl)-4-chloronicotinaldehyde 103b (240 mg, 0.66 mmol), PdCl$_2$(dppf) (54 mg, 0.066 mmol), K$_3$PO$_4$ (250 mg, 1.2 mmol), sodium acetate (100 mg, 1.20 mmol), acetonitrile (10 mL), and water (0.5 mL). The system was evacuated and then refilled with N$_2$. It was then heated at 100° C. for 1 h. The mixture was cooled

181 to room temperature and filtered. The filtrate was concentrated under reduced pressure and the residue was purified on silica-gel column eluting with 20:1 dichloromethane/methanol to afford 153c as a pale yellow solid (170 mg, 42%). MS-ESI: [M+H]⁺ 584.3.

Example 153

6-tert-butyl-8-fluoro-2-[3-(hydroxymethyl)-4-[1-methyl-5-[(5-methyl-6,7-dihydro-4H-pyrazolo[1,5-a]pyrazin-2-yl)amino]-6-oxo-pyridazin-3-yl]-2-pyridyl]phthalazin-1-one 153

A mixture of 153c (170 mg, 0.29 mmol) and NaBH₄(20 mg, 0.50 mmol) in methanol (5 mL) was stirred at room temperature for 0.5 h. The reaction mixture was then quenched with water (7 mL) and concentrated under reduced pressure. The residue was extracted with dichloromethane (2×10 mL). The combined dichloromethane extract was concentrated under reduced pressure and the residue was purified with reverse-phase prep-HPLC to afford the 153 as a pale yellow solid (35 mg, 21%). MS-ESI: [M+H]⁺ 586.3. ¹H NMR (500 MHz, DMSO-d₆) δ 9.39 (s, 1H), 8.63 (d, J=5.0 Hz, 1H), 8.54 (d, J=2.0 Hz 1H), 7.93 (s, 1H), 7.90 (d, J=2.0 Hz, 1H), 7.77 (dd, J=1.5, 12.5 Hz, 1H), 7.60-7.59 (m, 1H), 6.03 (s, 1H), 4.82-4.81 (m, 1H), 4.51-4.45 (m, 2H), 4.01-3.98 (m, 2H), 3.77 (s, 3H), 3.62-3.60 (m, 2H), 2.90-2.86 (m, 2H), 2.42-2.40 (m, 3H), 1.34 (s, 9H).

Example 154a

1-Methyl-1H-1,2,3-triazol-5-amine 154a

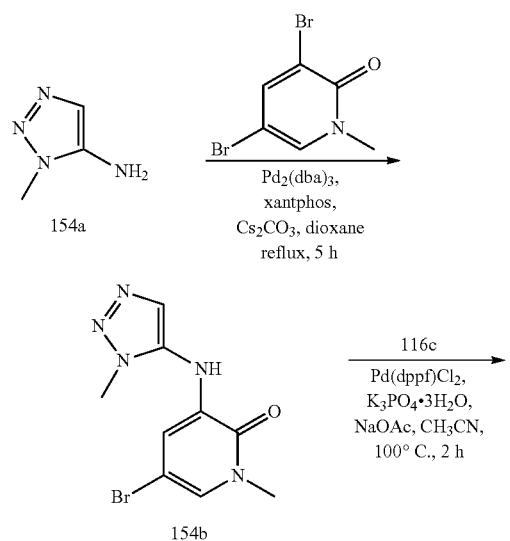

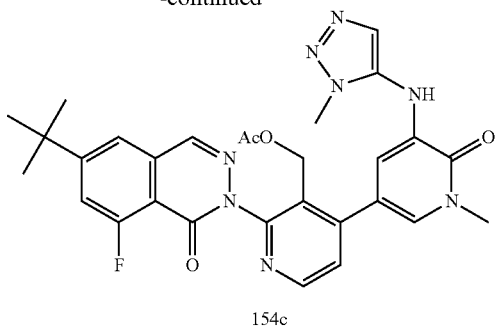

A 50-mL round-bottomed flask was purged with nitrogen and charged with 1-methyl-5-nitro-1H-1,2,3-triazole, from Example 149a (0.78 g, 6.09 mmol), 10% palladium on carbon (50% wet, 160 mg), and methanol (20 mL). The flask was evacuated, charged with hydrogen gas, and stirred for 4 h at room temperature. The hydrogen was then evacuated and nitrogen was charged into the flask. The catalyst was removed by filtration through a pad of CELITE® and the filtrate was concentrated under reduced pressure to afford 154a (418 mg, 70%) as a yellow solid. MS: [M+H]⁺ 99.3

Example 154b

5-Bromo-1-methyl-3-(1-methyl-1H-1,2,3-triazol-5-ylamino)pyridin-2(1H)-one 154b

A 100-mL single-neck round-bottomed flask equipped with a magnetic stirrer and a reflux condenser was charged with 1,4-dioxane (20 mL), 154a (500 mg, 5.10 mmol), 3,5-dibromo-1-methylpyridin-2(1H)-one (1362 mg, 5.10 mmol), and cesium carbonate (3.325 g, 10.2 mmol). After bubbling nitrogen through the suspension for 20 minutes, Xantphos (0.59 g, 1.02 mmol) and tris(dibenzylideneacetone)dipalladium(0) (467 mg, 0.51 mmol) were added. The system was subjected to three cycles of vacuum/nitrogen flush and heated at reflux for 5 h. It was then cooled to room temperature and filtered. The filtrate was evaporated under reduced pressure. The residue was purified by silica-gel column chromatography eluting with 50:1 dichloromethane/methanol to afford 154b (220 mg, 15%) as a brown solid. LCMS: [M+H]⁺ 284.1

Example 154c (2-(6-tert-Butyl-8-fluoro-1-oxophthalazin-2(1H)-yl)-4-(1-methyl-5-(1-methyl-1H-1,2,3-triazol-5-ylamino)-6-oxo-1,6-dihydropyridin-3-yl)pyridin-3-yl)methyl Acetate 154c A 25-mL round-bottomed flask equipped with a reflux condenser was charged with 1 Mb (100 mg, 0.35 mmol), 3-(acetoxymethyl)-2-(6-tert-butyl-8-fluoro-1-oxophthalazin-2(1H)-yl)pyridin-4-ylboronic acid 116c (174 mg, 0.42 mmol), Pd(dppf)Cl₂ (29 mg, 0.035 mmol), sodium acetate (57 mg, 0.70 mmol,), K₃PO₄ trihydrate (186 mg, 0.70 mmol), water (6 drops), and acetonitrile (6 mL). After three cycles of vacuum/argon flush, the mixture was heated at 100° C. for 2 h. It was then filtered and the filtrate was evaporated under reduced pressure. The residue was purified by silica-gel column chromatography eluting with 25:1 dichloromethane/methanol to afford 154c (85 mg, 42%) as a brown solid. MS-ESI: [M+H]⁺ 573.4

Example 154

6-tert-butyl-8-fluoro-2-[3-(hydroxymethyl)-4-[1-methyl-5-[(3-methyltriazol-4-yl)amino]-6-oxo-3-pyridyl]-2-pyridyl]phthalazin-1-one 154

A mixture of 154c (85 mg, 0.15 mmol) and lithium hydroxide (36 mg, 1.5 mmol) in i-propanol/THF (1:1, 4 mL) and water (1 mL) was stirred at 30° C. for 1 h. The mixture was evaporated under reduced pressure and the residue was extracted diluted with water (5 mL). It was then with ethyl acetate (2×10 mL). The combined ethyl acetate extract was concentrated under reduced pressure and the residue was purified by reverse-phase prep-HPLC to afford the title compound (11 mg, 16%) as a white solid. MS-ESI: [M+H]$^+$ 531.4. $^1$H NMR (500 MHz, DMSO-d$_6$) δ 8.54-8.53 (m, 2H), 8.03 (s, 1H), 7.91 (d, J=1.5 Hz, 1H), 7.80-7.76 (m, 1H), 7.75 (s, 1H), 7.55 (d, J=2.5 Hz, 1H), 7.52 (d, J=5.0 Hz, 1H), 6.89 (d, J=2.5 Hz, 1H), 5.04 (t, J=5.0 Hz, 1H), 4.34 (d, J=5.0 Hz, 2H), 3.88 (s, 3H), 3.63 (s, 3H), 1.40 (s, 9H).

Example 155a

2-Nitro-5-(oxetan-3-yl)-4,5,6,7-tetrahydropyrazolo[1,5-a]pyrazine 155a

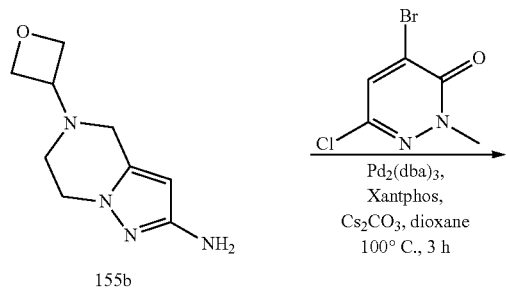

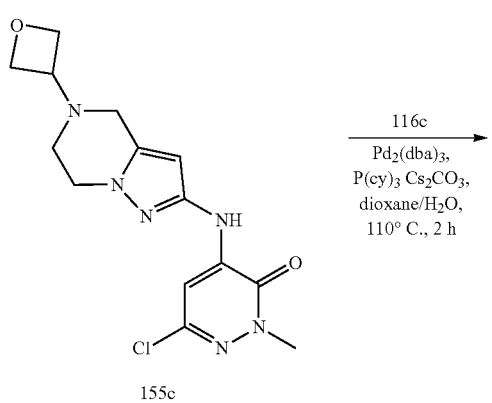

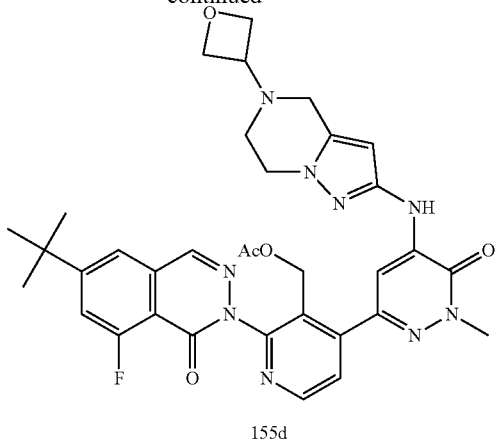

155d

A mixture of 2-nitro-4,5,6,7-tetrahydropyrazolo[1,5-a]pyrazine 124d (238 mg, 1.40 mmol), oxetan-3-one (252 mg, 3.5 mmol), NaBH$_3$CN (260 mg, 4.2 mmol), and zinc chloride (567 mg, 4.2 mmol) in methanol (10 mL) was stirred at 50° C. for 6 hours. The mixture was added to water and extracted with dichloromethane three times. The combined organic layer was concentrated under reduced pressure and the residue was purified by silica-gel column chromatography eluting with 50:1 dichloromethane/methanol to afford 155a (200 mg, 64%). MS: [M+H]$^+$ 225.3

Example 155b 5-(Oxetan-3-yl)-4,5,6,7-tetrahydropyrazolo[1,5-a]pyrazin-2-amine 155b A 50-mL single-neck round-bottomed flask was purged with nitrogen and charged with 155a (0.20 g, 0.89 mmol), 10% palladium on carbon (50% wet, 89 mg), and methanol (10 mL). The mixture was evacuated, charged with hydrogen gas, and stirred for 2 h at room temperature. The hydrogen was then evacuated and nitrogen was charged into the bottle. The catalyst was removed by filtration through a pad of CELITE® and the filtrate was concentrated under reduced pressure to afford 155b (140 mg, 81%). MS: [M+H]$^+$ 195.1

Example 155c

6-Chloro-2-methyl-4-(5-(oxetan-3-yl)-4,5,6,7-tetrahydropyrazolo[1,5-a]pyrazin-2-yl amino)pyridazin-3(2H)-one 155c A 100-mL single-neck round-bottomed flask equipped with a magnetic stirrer and a reflux condenser was charged with 1,4-dioxane (25 mL), 155b (640 mg, 3.3 mmol), 4-bromo-6-chloro-2-methylpyridazin-3(2H)-one (1.1 g, 4.95 mmol), Pd$_2$(dba)$_3$ (302 mg, 0.33 mmol), XantPhos (381 mg, 0.66 mmol), and cesium carbonate (2.15 g, 6.6 mmol). After three cycles of vacuum/argon flush, the mixture was heated at 100° C. for 3 h. After this time the reaction was cooled to room temperature. It was then filtered and the filtrate was evaporated under reduced pressure. The residue was washed with ethyl acetate to afford 155c (754 mg, 68%) as a yellow solid. MS-ESI: [M+H]$^+$ 337.3

Example 155d (2-(6-tert-Butyl-8-fluoro-1-oxophthalazin-2(1H)-yl)-4-(1-methyl-5-(5-(oxetan-3-yl)-4,5,6,7-tetrahydropyrazolo[1,5-a]pyrazin-2-ylamino)-6-oxo-1,6-dihydropyridazin-3-yl)pyridin-3-yl)methyl Acetate 155d A 100-mL single-neck round-bottomed flask equipped with a magnetic stirrer and a reflux condenser was charged with 155c (367 mg, 1.1 mmol), 3-(acetoxymethyl)-2-(6-tert-butyl-8-fluoro-1-oxophthalazin-2(1H)-yl)pyridine-4-ylboronic acid 116c (908.6 mg, 2.2 mmol), $Pd_2(dba)_3$ (100.6 mg, 0.11 mmol), $P(cy)_3$ (122.8 mg, 0.44 mmol), $Cs_2CO_3$ (717 mg, 2.2 mmol), dioxane (20 mL), and water (0.5 mL). After three cycles of vacuum/argon flush, the mixture was heated at 110° C. for 2 h. It was then filtered and the filtrate was evaporated under reduced pressure. The residue was purified by silica-gel column chromatography eluting with 35:1 dichloromethane/methanol to afford 155d (120 mg, 16%) as a yellow solid. MS-ESI: $[M+H]^+$ 669.8

Example 155

6-tert-butyl-8-fluoro-2-[3-(hydroxymethyl)-4-[1-methyl-5-[[5-(oxetan-3-yl)-6,7-dihydro-4H-pyrazolo[1,5-a]pyrazin-2-yl]amino]-6-oxo-pyridazin-3-yl]-2-pyridyl]phthalazin-1-one 155

A mixture of 155d (117 mg, 0.175 mmol) and lithium hydroxide.water (73.5 mg, 1.75 mmol) in i-propanol/THF (1:1, 8 mL) and water (1 mL) was stirred at 35° C. for 0.5 h. The mixture was evaporated under reduced pressure and the residue was diluted with water (6 mL). It was then extracted with dichloromethane (3×50 mL). The combined dichloromethane extract was concentrated under reduced pressure and the residue was purified by reverse-phase prep-HPLC to afford 155 (30 mg, 27%) as a yellow solid. MS-ESI: $[M+H]^+$ 628.3. $^1$H NMR (500 MHz, DMSO-$d_6$) δ 9.40 (s, 1H), 8.64 (d, J=5.5 Hz, 1H), 8.55 (d, J=2.0 Hz, 1H), 7.94 (s, 1H), 7.90 (d, J=1.5 Hz, 1H), 7.79-7.77 (m, 1H), 7.61 (d, J=4.5 Hz, 1H), 6.04 (s, 1H), 7.61-7.60 (m, 1H), 4.61-4.59 (m, 2H), 4.50-4.45 (m, 4H), 4.01-3.99 (m, 2H), 3.78 (s, 3H), 3.69-3.65 (m, 1H), 3.54 (s, 2H), 2.79-2.76 (m, 2H), 1.39 (s, 9H).

Example 156a

5-Fluoro-N,N-bis(4-methoxybenzyl)pyridin-2-amine 156

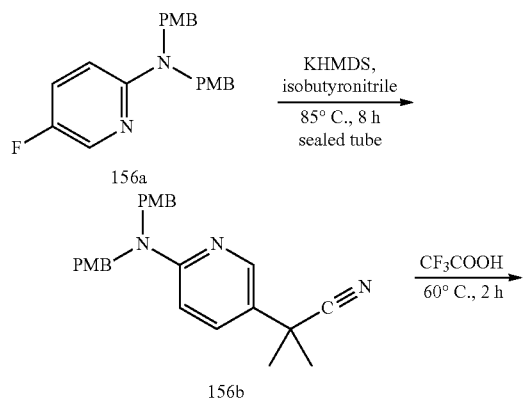

Example 156b 2-(6-(bis(4-Methoxybenzyl)amino)pyridin-3-yl)-2-methylpropanenitrile 156b A 25-mL sealed tube equipped with a magnetic stirrer was charged with 156a (528 mg, 1.5 mmol), KHMDS (15 mmol, 15 mL, 1 mol/L of THF), and isobutyronitrile (1.03 g, 15 mmol). After three cycles of vacuum/argon flush, the mixture was heated at 85° C. for 8 h. It was then cooled to room temperature and quenched with water was added. The mixture was concentrated under reduced pressure and the residue was extracted with ethyl acetate (3×20 mL). The combined extract was dried over $Na_2SO_4$, filtered, and evaporated under

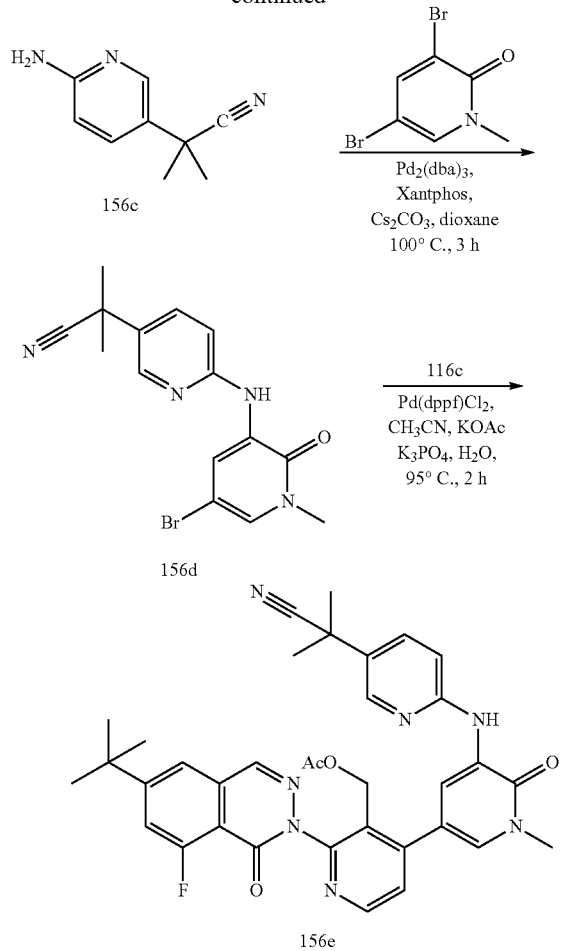

A 100-mL round-bottomed flask was charged with 5-fluoropyridin-2-amine (1.12 g, 10.0 mmol), NaH (288 mg, 12.0 mmol), and THF (20 mL) at 25° C. 4-Methoxybenzyl chloride (1.87 g, 12.0 mmol) was added and stirred at 25° C. for 2 h. It was then concentrated under reduced pressure. Water (30 mL) was added to the residue and the resulting mixture was extracted with dichloromethane (3×80 mL). The combined extract was dried over $Na_2SO_4$, filtered, and evaporated under reduced pressure. The residue was purified by silica-gel column chromatography eluting with 1:9 ethyl acetate/petroleum ether to afford 156a (620 mg, 18%) as a yellow liquid. MS-ESI: $[M+H]^+$ 353.0 reduced pressure to afford 156b (514 mg, 85%) as a yellow liquid. MS-ESI: [M+H]+ 402.0

Example 156c 2-(6-Aminopyridin-3-yl)-2-methylpropanenitrile 156c

A solution of 156b (514 mg, 1.28 mmol) in CF$_3$COOH (15 mL) was stirred at 60° C. for 2 h. After this time the reaction was cooled to room temperature. It was then evaporated under reduced pressure and residue was washed with petroleum ether and ethyl acetate to afford 156c (600 mg, crude) as a yellow solid. MS-ESI: [M+H]+ 162.3

Example 156d 2-(6-(5-Bromo-1-methyl-2-oxo-1,2-dihydropyridin-3-ylamino)pyridin-3-yl)-2-methylpropanenitrile 156d A 100-mL single-neck round-bottomed flask equipped with a magnetic stirrer and a reflux condenser was charged with 1,4-dioxane (35 mL), 156c (483 mg, 3.0 mmol), 3,5-dibromo-1-methylpyridin-2(1H)-one (1.6 g, 6.0 mmol), Pd$_2$(dba)$_3$ (274.5 mg, 0.30 mmol), XantPhos (346.8 mg, 0.60 mmol), and cesium carbonate (4.59 g, 15 mmol). After three cycles of vacuum/argon flush, the mixture was heated at 100° C. for 3 h. After this time the reaction was cooled to room temperature and filtered. The filtrate was evaporated under reduced pressure. The residue was purified by silica-gel column chromatography eluting with 1:1 ethyl acetate/petroleum ether to afford 156d (400 mg, 38%) as a yellow solid. MS-ESI: [M+H]+ 347.0

Example 156e (2-(6-tert-Butyl-8-fluoro-1-oxophthalazin-2(1H)-yl)-4-(5-(5-(2-cyanopropan-2-yl)pyridin-2-ylamino)-1-methyl-6-oxo-1,6-dihydropyridin-3-yl)pyridin-3-yl) methyl Acetate 156e A 100-mL single-neck round-bottomed flask equipped with a magnetic stirrer and a reflux condenser was charged with 156d (346 mg, 1.0 mmol), 3-(acetoxymethyl)-2-(6-tert-butyl-8-fluoro-1-oxophthalazin-2(1H)-yl)pyridin-4-ylboronic acid 116c (1.65 g, 4.0 mmol), Pd(dppf)Cl$_2$ (82.5 mg, 0.10 mmol), potassium acetate (196 mg, 2.0 mmol), K$_3$PO$_4$ (424 mg, 2.0 mmol), acetonitrile (15 mL), and water (0.5 mL). After three cycles of vacuum/argon flush, the mixture was heated at 95° C. for 2 h. It was then filtered and the filtrate was evaporated under reduced pressure. The residue was purified by silica-gel column chromatography eluting with 10:1 ethyl acetate/petroleum ether to afford 156e (210 mg, 33%) as a yellow solid. MS-ESI: [M+H]+ 635.8

Example 156

2-[6-[[5-[2-(6-tert-butyl-8-fluoro-1-oxo-phthalazin-2-yl)-3-(hydroxymethyl)-4-pyridyl]-1-methyl-2-oxo-3-pyridyl]amino]-3-pyridyl]-2-methyl-propanenitrile 156

A mixture of 156e (191 mg, 0.30 mmol) and lithium hydroxide.1water (126 mg, 3.0 mmol) in i-propanol/THF (1:1, 8 mL) and water (2 mL) was stirred at 35° C. for 0.5 h. The mixture was evaporated under reduced pressure and diluted with water (10 mL). It was then extracted with dichloromethane (3×20 mL). The combined dichloromethane extract was concentrated under reduced pressure and the residue was purified by reverse-phase prep-HPLC to afford 156 (30 mg, 17%) as a pale yellow solid. MS-ESI: [M+H]+ 594.3. $^1$H NMR (500 MHz, DMSO-d$_6$) δ 8.83 (s, 1H), 8.77 (d, J=2.0 Hz, 1H), 8.59 (d, J=5.0 Hz, 1H), 8.54 (d, J=2.5 Hz, 1H), 8.34 (d, J=2.5 Hz, 1H), 7.91 (s, 1H), 7.79-7.74 (m, 2H), 7.57-7.53 (m, 2H), 7.40 (d, J=9.0 Hz, 1H), 4.92 (bs, 1H), 4.43 (s, 2H), 3.62 (s, 3H), 1.67 (s, 6H), 1.39 (s, 9H).

Example 157a (2-(6-tert-Butyl-8-fluoro-1-oxophthalazin-2(1H)-yl)-4-(1-methyl-5-(5-methylisothiazol-3-ylamino)-6-oxo-1,6-dihydropyridin-3-yl)pyridin-3-yl)methyl Acetate 157a

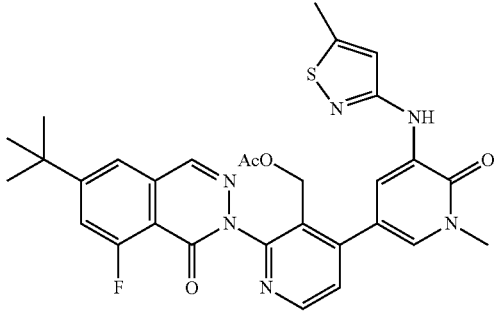

A 25-mL sealed tube was charged with (4-(5-bromo-1-methyl-6-oxo-1,6-dihydropyridin-3-yl)-2-(6-tert-butyl-8-fluoro-1-oxophthalazin-2(1H)-yl)pyridin-3-yl)methyl acetate 142c (155 mg, 0.28 mmol), 4-fluoro-2-(1-oxo-5-methylisothiazol-3-amine hydrochloride (55 mg, 0.33 mmol), Cs$_2$CO$_3$ (183 mg, 0.56 mmol), Pd$_2$(dba)$_3$ (27 mg, 0.030 mmol), XantPhos (35 mg, 0.060 mmol), and DMF (10 mL). After three cycles of vacuum/argon flush, the mixture was heated at 110° C. under microwave irradiation for 1 hour. It was then cooled to room temperature and evaporated under reduced pressure. The residue was purified by silica-gel column eluting with 20:1 methylene chloride/methanol to afford 157a as a yellow solid (64 mg, 39%). MS-ESI: [M+H]+ 589.2

Example 157

6-tert-butyl-8-fluoro-2-[3-(hydroxymethyl)-4-[1-methyl-5-[(5-methylisothiazol-3-yl)amino]-6-oxo-3-pyridyl]-2-pyridyl]phthalazin-1-one 157

To a solution of 157a (60 mg, 0.10 mmol) in THF/i-propanol/water (4 mL/4 mL/1 mL) was added lithium hydroxide (24 mg, 1.0 mmol). The reaction mixture was stirred at room temperature for 0.5 h and concentrated under reduced pressure. The residue was diluted with water (10 mL) and extracted with ethyl acetate (3×15 mL). The combined organic layer was dried with Na$_2$SO$_4$ and concentrated to afford a yellow solid, which was purified by reverse-phase prep-HPLC to afford 157 as a yellow solid (27 mg, 50%). MS-ESI: [M+H]+ 546.7. $^1$H NMR (500 MHz, DMSO-d$_6$) δ 9.28 (s, 1H), 8.60-8.54 (m, 3H), 7.90 (s, 1H), 7.78 (d, J=16.0

Hz, 1H), 7.55-7.50 (m, 2H), 7.04 (s, 1H), 4.89 (t, J=6.5 Hz, 1H), 4.43-4.41 (m, 2H), 3.61 (s, 3H), 2.48 (s, 3H), 1.40 (s, 9H).

Example 158a

5-Bromo-3-(5-ethylisoxazol-3-ylamino)-1-methylpyridin-2(1H)-one 158a

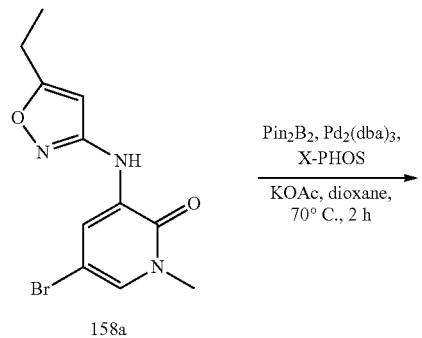

A 50-mL single-neck round-bottomed flask equipped with a magnetic stirred and a reflux condenser was charged with 5-ethylisoxazol-3-amine (250 mg, 2.23 mmol), 3,5-dibromo-1-methylpyridin-2(1H)-one (893 mg, 3.35 mmol), Pd$_2$(dba)$_3$ (102 mg, 0.112 mmol), Xantphos (129 mg, 0.223 mmol), Cs$_2$CO$_3$ (1.45 g, 4.46 mmol), and dioxane (20 mL). The system was subjected to three cycles of vacuum/nitrogen flush and heated at 100° C. under N$_2$ protection for 3 h. Analysis of the reaction mixture by LCMS showed complete conversion to the desired product. It was then cooled to room temperature and filtered. The filtrate was concentrated under reduced pressure and the residue was purified by reverse-phase prep-HPLC to afford 158a (300 mg, 45%) as a white solid. MS-ESI: [M+H]$^+$ 297.8

Example 158b 3-(5-Ethylisoxazol-3-ylamino)-1-methyl-5-(4,4,5,5-tetramethyl-1,3,2-dioxaborolan-2-yl)pyridin-2(1H)-one 158b A 50-mL round-bottomed flask equipped with a magnetic stirred and a reflux condenser was charged with 158a (250 mg, 0.839 mmol), Pin$_2$B$_2$ (320 mg, 1.26 mmol), Pd$_2$(dba)$_3$ (38.4 mg, 0.042 mmol), X-Phos (48.5 mg, 0.0839 mmol), potassium acetate (164.4 mg, 1.678 mmol), and dioxane (20 mL). The system was subjected to three cycles of vacuum/nitrogen flush and heated at 70° C. under N$_2$ protection for 2 h. Analysis of the reaction mixture by LCMS showed complete conversion to the desired product. It was then cooled to room temperature and filtered. The filtrate was concentrated under reduced pressure. The residue was washed with petroleum ether to afford 158b (330 mg, crude) as a dark solid, which was used in next step without further purification. MS-ESI: [M+H]$^+$ 346.0

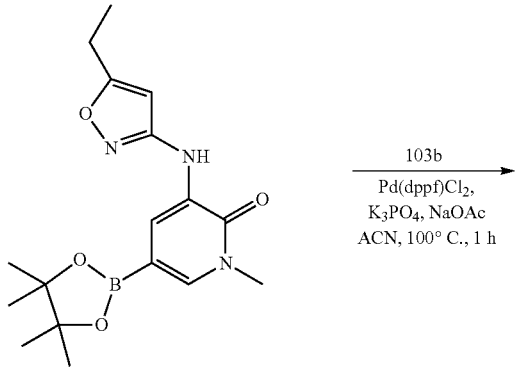

Example 158c 2-(6-tert-Butyl-8-fluoro-1-oxophthalazin-2(1H)-yl)-4-(5-(5-ethylisoxazol-3-ylamino)-1-methyl-6-oxo-1,6-dihydropyridin-3-yl)nicotinaldehyde 158c A 50-mL round-bottomed flask equipped with a reflux condenser was charged with 2-(6-tert-butyl-8-fluoro-1-oxophthalazin-2(1H)-yl)-4-chloronicotinaldehyde 103b (160 mg, 0.44 mmol), 158b (228 mg, 0.66 mmol), Pd(dppf)Cl$_2$ (18 mg, 0.022 mol), K$_3$PO$_4$ (187 mg, 0.88 mmol), sodium acetate (72.2 mg, 0.88 mmol), acetonitrile (15 mL), and water (5 drops). The system was subjected to three cycles of vacuum/nitrogen flush and heated at 100° C. under N$_2$ protection for 1 h. Analysis of the reaction mixture by LCMS showed complete conversion to the desired product. It was then cooled to room temperature and filtered. The filtrate was concentrated under reduced pressure and the residue was purified by silica-gel column chromatography eluting with 40:1 dichloromethane/methanol to afford 158c (210 mg, 88%) as yellow oil. MS-ESI: [M+H]$^+$ 543.3

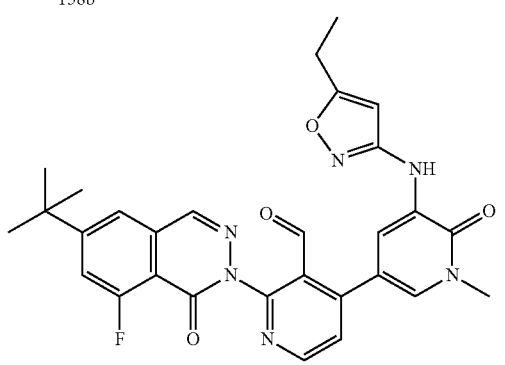

Example 158

6-tert-butyl-2-[4-[5-[(5-ethylisoxazol-3-yl)amino]-1-methyl-6-oxo-3-pyridyl]-3-(hydroxymethyl)-2-pyridyl]-8-fluoro-phthalazin-1-one 158

To a solution of 158c (190 mg, 0.35 mmol) in dichloromethane (5 mL) and methanol (5 mL) was added NaBH$_4$ (26.5 mg, 0.70 mmol). The reaction mixture was stirred at room temperature for 1 h and quenched with aqueous NH$_4$Cl. It was then concentrated under reduced pressure and the residue was extracted with dichloromethane. The combined extract was washed with brine, dried over Na$_2$SO$_4$, filtered, and concentrated under reduced pressure. The residue was purified by reverse-phase prep-HPLC to afford 158 (70 mg, 37%) as white solid. MS-ESI: [M+H]$^+$ 545.3. $^1$H NMR (500 MHz, DMSO-d$_6$) δ 9.01 (s, 1H), 8.58 (d, J=5.0 Hz, 1H), 8.54 (d, J=2.0 Hz, 1H), 8.01 (d, J=2.0 Hz, 1H), 7.90 (s, 1H), 7.79 (d, J=13 Hz, 1H), 7.57 (d, J=2.5 Hz, 1H), 7.51 (d, J=5.0 Hz, 1H), 6.26 (s, 1H), 4.90 (s, 1H), 4.44-4.43 (m, 2H), 3.61 (s, 3H), 2.69-2.65 (m, 2H), 1.40 (s, 9H), 1.19 (t, J=8.0 Hz, 3H)

Example 159a 2-(Difluoromethyl)-4-nitro-2H-1,2,3-triazole 159a

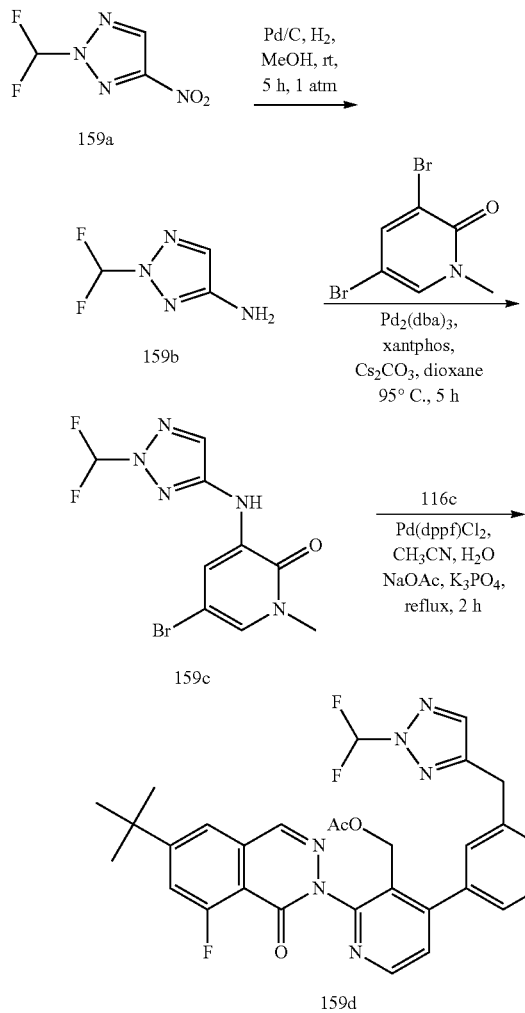

A 100-mL single-neck round-bottomed flask containing 4-nitro-2H-1,2,3-triazole (500 mg, 4.38 mmol, 1.0 eq.), sodium 2-chloro-2,2-difluoroacetate (1310 mg, 8.76 mmol, 2.0 eq.), K₂CO₃ (1140 mg, 8.76 mmol, 2.0 eq.), and acetonitrile (20 mL) was stirred at reflux for 5 h. After cooling to room temperature, the reaction mixture was filtered and the filtrate was evaporated under reduced pressure. The residue was purified by silica-gel column chromatography eluting with 4:1 petroleum ether/ethyl acetate to afford 159a (350 mg, 48%) as a brown liquid. ¹H NMR (500 MHz, CDCl₃) δ 8.38 (s, 1H), 7.39 (t, J=57.5 Hz, 1H).

Example 159b 2-(Difluoromethyl)-2H-1,2,3-triazol-4-amine 159b

Following the procedure of Example 151e, and starting with 159a (300 mg, 1.83 mmol) and 10% palladium on carbon (50% wet, 60 mg) afforded 159b as a yellow liquid (200 mg, 81%). ¹H NMR (500 MHz, CDCl₃) δ 7.24 (s, 1H), 7.14 (t, J=58.5 Hz, 1H), 4.08 (brs, 2H).

Example 159c

5-Bromo-3-(2-(difluoromethyl)-2H-1,2,3-triazol-4-ylamino)-1-methylpyridin-2(1H)-one 159c Following the procedure of Example 151f, and starting with 159b (170 mg, 1.25 mmol, 1.0 eq.) and 3,5-dibromo-1-methylpyridin-2(1H)-one (504 g, 1.89 mmol, 1.5 eq.) afforded 159c as a light yellow solid (280 mg, 70%). MS-ESI: [M+H]⁺ 320.1.

Example 159d (2-(6-tert-Butyl-8-fluoro-1-oxophthalazin-2(1H)-yl)-4-(5-(2-(difluoromethyl)-2H-1,2,3-triazol-4-ylamino)-1-methyl-6-oxo-1,6-dihydropyridin-3-yl) pyridin-3-yl)methyl Acetate 159d Following the procedure of Example 152c, and starting with 159c (150 mg, 0.46 mmol, 1.0 eq.) and 3-(acetoxymethyl)-2-(6-tert-butyl-8-fluoro-1-oxophthalazin-2(1H)-yl) pyridin-4-ylboronic acid (116c) (285 mg, 0.69 mmol, 1.5 eq.) afforded 159d as a yellow solid (90 mg, 32%). MS-ESI:[M+H]⁺ 609.3

Example 159

6-tert-butyl-2-[4-[5-[[2-(difluoromethyl)triazol-4-yl]amino]-1-methyl-6-oxo-3-pyridyl]-3-(hydroxymethyl)-2-pyridyl]-8-fluoro-phthalazin-1-one 159

Following the procedure of Example 152, and starting with 159d (80 mg, 0.13 mmol) afforded 159 as a white solid (29 mg, 40%). MS-ESI: [M+H]⁺ 567.3. ¹H NMR (500 MHz, CDCl₃) δ 8.70 (d, J=5.0 Hz, 1H), 8.36 (d, J=2.0 Hz, 1H), 8.15 (d, J=2.0 Hz, 1H), 7.84 (s, 1H), 7.74 (d, J=2.0 Hz, 1H), 7.62-7.53 (m, 4H), 7.25 (t, J=59.0 Hz, 1H), 4.50 (s, 2H), 4.09 (t, J=6.5 Hz, 1H), 3.75 (s, 3H), 1.45 (s, 9H).

Example 160a

5-Bromo-1-methyl-3-(pyrazin-2-ylamino)pyridin-2(1H)-one 160a

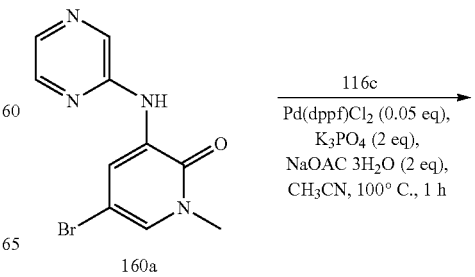

-continued

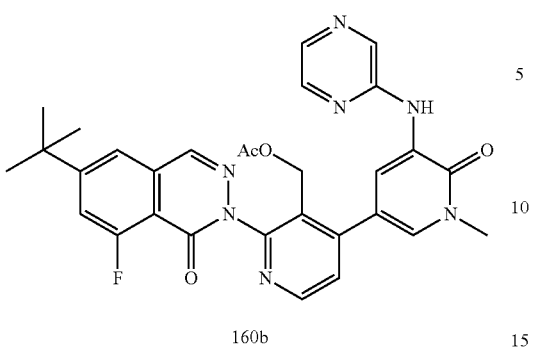

160b

A 250-mL single-neck round-bottomed flask equipped with a magnetic stirrer and a reflux condenser was charged with pyrazin-2-amine (1.0 g, 10 mmol), 3,5-dibromo-1-methylpyridin-2(1H)-one (2.7 g, 10 mmol), Pd$_2$(dba)$_3$ (460 mg, 0.50 mmol), XantPhos (600 mg, 1.0 mmol), cesium carbonate (6.52 g, 20 mmol), and 1,4-dioxane (150 mL). After three cycles of vacuum/argon flash, the mixture was heated at 100° C. for 2 h. It was then filtered and the filtrate was evaporated in vacuo. The residue was purified by recrystallization with methanol to afford 160a (1.3 g, 47%) as a light green solid. MS-ESI: [M+H]$^+$ 281.0.

Example 160b (2-(6-tert-Butyl-8-fluoro-1-oxophthalazin-2(1H)-yl)-4-(1-methyl-6-oxo-5-(pyrazin-2-ylamino)-1,6-dihydropyridin-3-yl)pyridin-3-yl)methyl Acetate 160b A 50-mL round-bottomed flask equipped with a reflux condenser was charged with 160a (140 mg, 0.50 mmol), 3-(acetoxymethyl)-2-(6-tert-butyl-8-fluoro-1-oxophthalazin-2(1H)-yl)pyridin-4-ylboronic acid 116c (410 mg, 1.0 mmol), Pd(dppf)Cl$_2$ (25 mg, 0.025 mmol), K$_3$PO$_4$ (220 mg, 1.0 mmol), sodium acetate trihydrate (136 mg, 1.0 mmol), acetonitrile (15 mL), and water (0.5 mL). The system was evacuated and refilled with N$_2$. The reaction mixture was heated at 100° C. for 1 h. It was then cooled to room temperature and filtered. The filtrate was concentrated under reduced pressure and the resulting residue was purified by silica-gel column chromatography eluting with dichloromethane/methanol (100:1 to 25:1) to afford 160b (150 mg, 52%) as a yellow solid. MS-ESI: [M+H]$^+$ 570.2.

Example 160

6-tert-butyl-8-fluoro-2-[3-(hydroxymethyl)-4-[1-methyl-6-oxo-5-(pyrazin-2-ylamino)-3-pyridyl]-2-pyridyl]phthalazin-1-one 160

A mixture of 160b (120 mg, 0.21 mmol) and lithium hydroxide monohydrate (88 mg, 2.1 mmol) in THF/i-propanol (4:2, 6 mL) and water (2 mL) was stirred at 30° C. for 1 h. The mixture was evaporated under reduced pressure and the residue was diluted with water (10 mL). It was then extracted with ethyl acetate (2×20 mL). The combined ethyl acetate extract was concentrated under reduced pressure and the residue was purified by reverse-phase prep-HPLC to afford 160 (50 mg, 45%) as a white solid. MS-ESI: [M+H]$^+$ 527.8. $^1$H NMR (500 MHz, CHCl$_3$) δ 8.78 (d, J=2.5 Hz, 1H), 8.71 (d, J=5.0 Hz, 1H), 8.36 (d, J=2.0 Hz, 1H), 8.31 (s, 1H), 8.19 (s, 1H), 8.14 (s, 1H), 8.05 (d, J=2.0 Hz, 1H), 7.81 (d, J=2.5 Hz, 1H), 7.59 (s, 1H), 7.56-7.55 (m, 2H)

Example 161a

1-Methyl-3-(5-methylisoxazol-3-ylamino)-5-(4,4,5,5-tetramethyl-1,3,2-dioxaborolan-2-yl)pyridin-2(1H)-one 161a

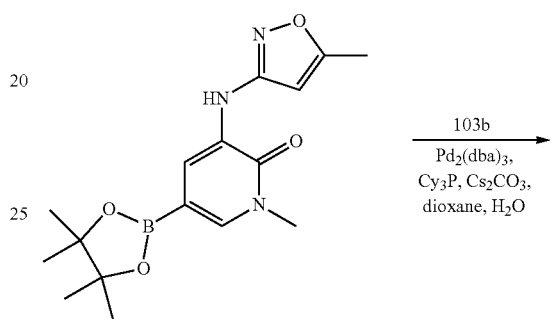

161a

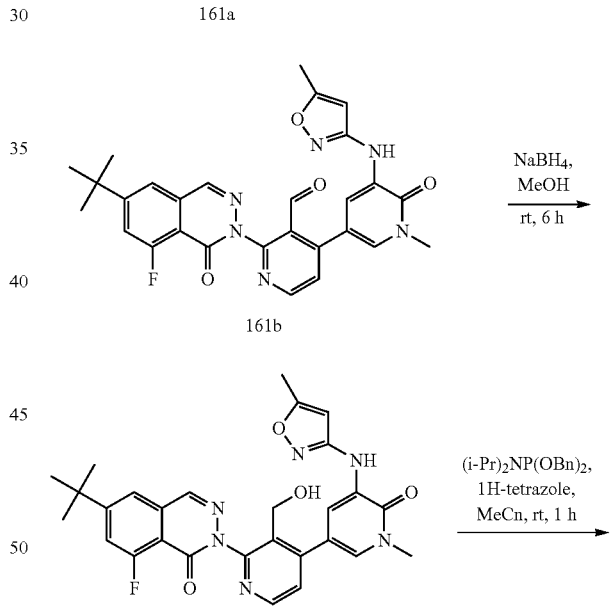

161b

161c

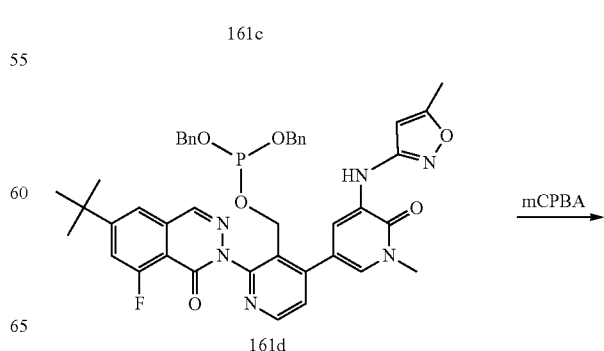

161d

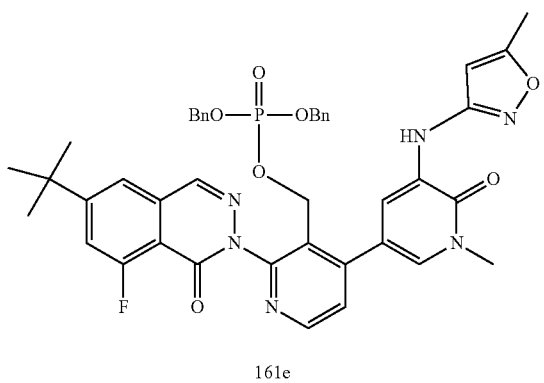

161e

A 50-mL round bottomed flask equipped with a magnetic stirrer and a reflux condenser was charged with 5-bromo-1-methyl-3-(5-methylisoxazol-3-ylamino)pyridin-2(1H)-one 129a (330 mg, 1.16 mmol), Pin$_2$B$_2$ (442 mg, 1.74 mmol), Pd$_2$(dba)$_3$ (53 mg, 0.058 mmol), X-Phos (55 mg, 0.116 mmol), potassium acetate (227 mg, 2.32 mmol), and dioxane (20 mL). After three cycles of vacuum/N$_2$ flush, the mixture was heated at 70° C. for 2 h. Analysis of the reaction mixture by LCMS showed complete conversion to the desired product. It was cooled to room temperature and filtered. The filtrate was concentrated under reduced pressure and the residue was washed with petroleum ether to afford 161a (300 mg, 78%) as a yellow solid. MS-ESI: [M+H]$^+$ 332.3

Example 161b 2-(6-tert-Butyl-8-fluoro-1-oxophthalazin-2(1H)-yl)-4-(1-methyl-5-(5-methylisoxazol-3-ylamino)-6-oxo-1,6-dihydropyridin-3-yl)nicotinaldehyde 161b A 100-mL round-bottomed flask equipped with a reflux condenser was charged with 2-(6-tert-butyl-8-fluoro-1-oxophthalazin-2(1H)-yl)-4-chloronicotinaldehyde 103b (390 mg, 1.08 mmol), 161a (537 mg, 1.62 mmol), cesium carbonate (704 mg, 2.16 mmol), 1,4-dioxane (30 mL), and water (3 mL). After bubbling nitrogen through the suspension for 10 minutes, Cy$_3$P (121 mg, 0.43 mmol) and Pd$_2$(dba)$_3$ (99 mg, 0.11 mmol) were added. The system was subjected to three cycles of vacuum/nitrogen flush and heated at reflux for 3 h. It was then cooled to room temperature and filtered. The solid was washed with dichloromethane (3×20 mL). The combined filtrate was concentrated under reduced pressure and the residue was purified by silica-gel column chromatography eluting with 20:1 ethyl acetate/petroleum ether to afford 161b (300 mg, 52%). MS-ESI: [M+H]$^+$ 528.8

Example 161c 6-tert-Butyl-8-fluoro-2-(3-(hydroxymethyl)-4-(1-methyl-5-(5-methylisoxazol-3-ylamino)-6-oxo-1,6-dihydropyridin-3-yl)pyridin-2-yl)phthalazin-1(2H)-one 161c To a solution of 161b (300 mg, 0.57 mmol) in methanol (10 mL) was added NaBH$_4$ (108 mg, 2.85 mmol) at room temperature. After the reaction was stirred for 6 h, LCMS indicated the reaction was complete. It was then quenched with water (10 mL) and concentrated under reduced pressure. The resulting residue was extracted with dichloromethane (3×20 mL). The combined organic layer was washed with brine (20 mL), dried over Na$_2$SO$_4$, filtered, and concentrated under reduced pressure. The residue solid was purified by silica-gel column chromatography eluting with petroleum ether/ethyl acetate (1:20 to 100% ethyl acetate) to afford 161c (164 mg, 54%) as a white solid. MS-ESI: [M+H]$^+$ 530.8

Example 161d

Dibenzyl (2-(6-tert-Butyl-8-fluoro-1-oxophthalazin-2(1H)-yl)-4-(1-methyl-5-(5-methylisoxazol-3-ylamino)-6-oxo-1,6-dihydropyridin-3-yl)pyridin-3-yl)methyl Phosphite 161d A mixture of 161c (100 mg, 0.19 mmol), dibenzyl diisopropylphosphoramidite (85 mg, 0.25 mmol), 1H-tetrazole (27 mg, 0.38 mmol) in acetonitrile was stirred at room temperature for 1 h. LCMS indicated no further reaction. The mixture containing 161d was used in the next step without further purification. MS-ESI: [M+H]$^+$ 775.3.

Example 161e

Dibenzyl (2-(6-tert-Butyl-8-fluoro-1-oxophthalazin-2(1H)-yl)-4-(1-methyl-5-(5-methylisoxazol-3-ylamino)-6-oxo-1,6-dihydropyridin-3-yl)pyridin-3-yl)methyl Phosphate 161e)

To a mixture of 161d in acetonitrile was added m-chloroperbenzoic acid (49 mg, 0.28 mmol). The reaction mixture was stirred at room temperature for 5 minutes and filtered. The filtrate was concentrated under reduced pressure and the residue was purified by reverse-phase prep-HPLC to afford 161e (15 mg, 10% two steps) as a white solid. MS-ESI: [M+H]$^+$ 791.3

Example 161

[2-(6-tert-butyl-8-fluoro-1-oxo-phthalazin-2-yl)-4-[1-methyl-5-[(5-methylisoxazol-3-yl)amino]-6-oxo-3-pyridyl]-3-pyridyl]methyl dihydrogen phosphate 161

A mixture of 161e (10 mg, 0.013 mmol) in trifluoroacetic acid (297 mg, 2.60 mmol) was stirred at room temperature for 1 h. The mixture was concentrated under reduced pressure and the residue was purified by reverse-phase prep-HPLC to afford 161 (6.7 mg, 84%) as a white solid. MS-ESI: [M+H]$^+$ 611.3. $^1$H NMR (500 MHz, DMSO-d$_6$) δ 9.00 (s, 1H), 8.61 (m, 1H), 8.50 (bs, 1H), 8.02 (s, 1H), 7.87-7.72 (m, 3H), 7.53 (m, 1H), 6.27 (s, 1H), 4.61-4.56 (m, 2H), 3.46 (s, 3H), 2.33 (s, 3H), 1.31 (s, 9H).

Example 162a 5,6-Dihydro-4H-pyrrolo[1,2-b]pyrazole-2-carboxylic Acid 162a

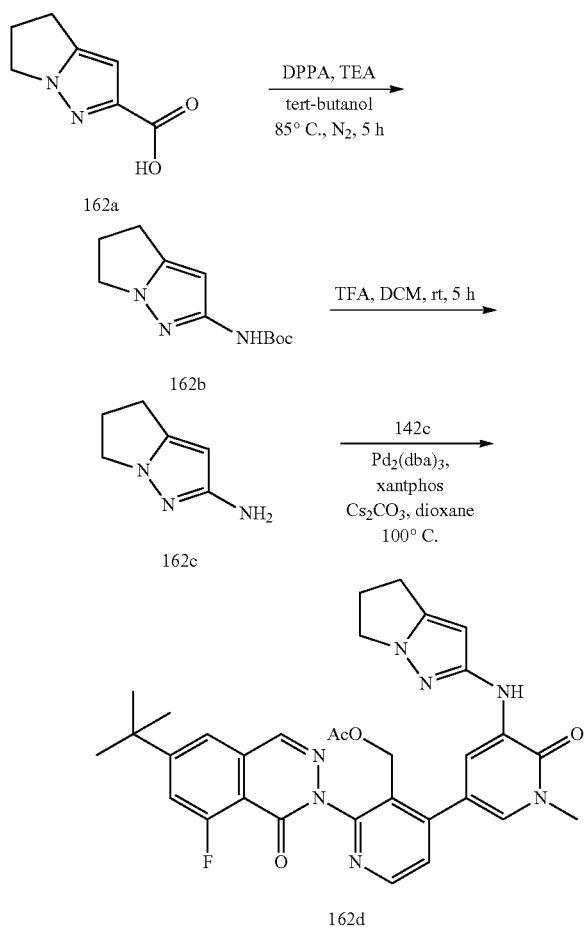

A 25-mL round-bottomed flask equipped with a reflux condenser was charged with ethyl 5,6-dihydro-4H-pyrrolo[1,2-b]pyrazole-2-carboxylate (540 mg, 3.0 mmol), 2N Aqueous sodium hydroxide solution (3.5 mL), and 1,4-dioxane (3.0 mL). The system was heated at 65° C. for 2.5 h. It was then cooled to room temperature and adjusted the pH to 2-3 with concentrated HCl. The solid was collected by filtration to afford 162a (260 mg, 57%) as a yellow solid. MS-ESI: [M+H]$^+$ 153.3

Example 162b tert-Butyl 5,6-Dihydro-4H-pyrrolo[1,2-b]pyrazol-2-ylcarbamate 162b A 25-mL single-neck round-bottomed flask equipped with a magnetic stirrer and a reflux condenser was charged with 162a (197.6 mg, 1.3 mmol), tert-butanol (5.0 mL), triethylamine (262.6 mg, 2.6 mmol), and DPPA (550 mg, 2.0 mmol). The system was subjected to three cycles of vacuum/nitrogen flush and heated at 85° C. for 5 h. It was then cooled to room temperature and purified with Combiflash (A: 1% NH$_4$HCO$_3$/water, B: acetonitrile) to afford 162b (45 mg, 15.5%) as a yellow solid. MS-ESI: [M+H-56]$^+$ 168.3

Example 162c 5,6-Dihydro-4H-pyrrolo[1,2-b]pyrazol-2-amine 162c

To a solution of 162b (45 mg, 0.20 mmol) in dichloromethane (1.5 mL) was added trifluoroacetic acid (1 mL) at room temperature. The solution was stirred for 5 h. It was then concentrated under reduced pressure to afford 162c which was used in the next step without further purification. MS-ESI: [M+H]$^+$ 124.3

Example 162d (2-(6-tert-Butyl-8-fluoro-1-oxophthalazin-2(1H)-yl)-4-(5-(5,6-dihydro-4H-pyrrolo[1,2-b]pyrazol-2-ylamino)-1-methyl-6-oxo-1,6-dihydropyridin-3-yl)pyridin-3-yl)methyl Acetate 162d A 25-mL single-neck round-bottomed flask equipped with a magnetic stirrer and a reflux condenser was charged with (4-(5-bromo-1-methyl-6-oxo-1,6-dihydropyridin-3-yl)-2-(6-tert-butyl-8-fluoro-1-oxophthalazin-2(1H)-yl)pyridin-3-yl)methyl acetate 142c (166.2 mg, 0.30 mmol), 162c (24.6 mg, 0.20 mmol), cesium carbonate (130 mg, 0.40 mmol), and 1,4-dioxane (4.0 mL). After bubbling nitrogen through the suspension for 10 minutes, Xantphos (23 mg, 0.040 mmol) and tris(dibenzylideneacetone)dipalladium(0) (14 mg, 0.020 mmol) were added. The system was subjected to three cycles of vacuum/nitrogen flush and heated at reflux for 2.5 h. It was then cooled to room temperature and filtered. The solid was washed with dichloromethane (3×10 mL). The combined organic layer was concentrated under reduced pressure. The residue was purified by silica-gel column chromatography eluting with dichloromethane/methanol (100:1 to 50:1 to afford 162d (50 mg, 42%) as a yellow solid. MS-ESI: [M+H]$^+$ 598.3

Example 162

6-tert-butyl-2-[4-[5-(5,6-dihydro-4H-pyrrolo[1,2-b]pyrazol-2-ylamino)-1-methyl-6-oxo-3-pyridyl]-3-(hydroxymethyl)-2-pyridyl]-8-fluoro-phthalazin-1-one 162

To a solution of 162d (50 mg, 0.080 mmol) in THF/i-propanol/water (1/1/0.5 ml) was added lithium hydroxide (19 mg, 0.80 mmol) at room temperature. After the reaction was stirred for 2.5 h, LCMS indicated the reaction was complete. Then the mixture was poured into water (15 mL) and extracted with dichloromethane (3×20 mL). The combined organic layer was washed with brine (30 mL), dried over Na$_2$SO$_4$, filtered, and concentrated under reduced pressure. The residue solid was purified by reverse-phase prep-HPLC (A: 1% NH$_4$HCO$_3$/water, B: acetonitrile) to afford 162 (15 mg, 33.3%) as white solid. MS-ESI: [M+H]$^+$ 556.3. $^1$H NMR (500 MHz, CDCl$_3$) δ 8.62 (d, J=5.0 Hz, 1H), 8.32 (s, 1H), 7.93 (d, J=2.0 Hz, 1H), 7.55-7.47 (m, 4H), 7.26 (s, 1H), 5.74 (s, 1H), 4.47 (d, J=4.0 Hz, 2H), 4.07 (t, J=2.0 Hz, 2H), 3.70 (s, 3H), 2.87 (t, J=6.5 Hz, 2H), 2.55-2.52 (m, 2H), 1.45 (s, 9H).

Example 901

Biochemical Btk Assay

A generalized procedure for a standard biochemical Btk Kinase Assay that can be used to test Formula I and II compounds is as follows. A master mix minus Btk enzyme is prepared containing 1× Cell Signaling kinase buffer (25 mM Tris-HCl, pH 7.5, 5 mM beta-glycerophosphate, 2 mM dithiothreitol, 0.1 mM $Na_3VO_4$, 10 mM $MgCl_2$), 0.5 µM Promega PTK Biotinylated peptide substrate 2, and 0.01% BSA. A master mix plus Btk enzyme is prepared containing 1× Cell Signaling kinase buffer, 0.5 µM PTK Biotinylated peptide substrate 2, 0.01% BSA, and 100 ng/well (0.06 mU/well) Btk enzyme. Btk enzyme is prepared as follows: full length human wildtype Btk (accession number NM-000061) with a C-terminal V5 and 6×His tag was subcloned into pFastBac vector for making baculovirus carrying this epitope-tagged Btk. Generation of baculovirus is done based on Invitrogen's instructions detailed in its published protocol "Bac-to-Bac Baculovirus Expression Systems" (Cat. Nos. 10359-016 and 10608-016). Passage 3 virus is used to infect Sf9 cells to overexpress the recombinant Btk protein. The Btk protein is then purified to homogeneity using Ni-NTA column. The purity of the final protein preparation is greater than 95% based on the sensitive Sypro-Ruby staining A solution of 200 µM ATP is prepared in water and adjusted to pH7.4 with 1N NaOH. A quantity of 1.25 µL of compounds in 5% DMSO is transferred to a 96-well ½ area Costar polystyrene plate. Compounds are tested singly and with an 11-point dose-responsive curve (starting concentration is 10 µM; 1:2 dilution). A quantity of 18.75 µL of master mix minus enzyme (as a negative control) and master mix plus enzyme is transferred to appropriate wells in 96-well ½ area costar polystyrene plate. 5 µL of 200 µM ATP is added to that mixture in the 96-well ½ area Costar polystyrene plate for final ATP concentration of 40 µM. The reaction is allowed to incubate for 1 hour at room temperature. The reaction is stopped with Perkin Elmer 1× detection buffer containing 30 mM EDTA, 20 nM SA-APC, and 1 nM PT66 Ab. The plate is read using time-resolved fluorescence with a Perkin Elmer Envision using excitation filter 330 nm, emission filter 665 nm, and $2^{nd}$ emission filter 615 nm. $IC_{50}$ values are subsequently calculated. Alternatively, the Lanthascreen assay can be used to evaluate Btk activity through quantification of its phosphorylated peptide product. The FRET (Fluorescence Resonance Energy Transfer) that occurs between the fluorescein on the peptide product and the terbium on the detection antibody decreases with the addition of inhibitors of Btk that reduce the phosphorylation of the peptide. In a final reaction volume of 25 uL, Btk (h) (0.1 ng/25 ul reaction) is incubated with 50 mM Hepes pH 7.5, 10 mM $MgCl_2$, 2 mM $MnCl_2$, 2 mM DTT, 0.2 mM NaVO4, 0.01% BSA, and 0.4 uM fluorescein poly-GAT. The reaction is initiated by the addition of ATP to 25 uM (Km of ATP). After incubation for 60 minutes at room temperature, the reaction is stopped by the addition of a final concentration of 2 nM Tb-PY20 detection antibody in 60 mM EDTA for 30 minutes at room temperature. Detection is determined on a Perkin Elmer Envision with 340 nM excitation and emission at 495 nm and 520 nm. Exemplary Btk inhibition IC50 values are in Tables 1, 2, and 3.

Example 902

Ramos Cell Btk Assay

Another generalized procedure for a standard cellular Btk Kinase Assay that can be used to test Formula I and II compounds is as follows. Ramos cells are incubated at a density of $0.5 \times 10^7$ cells/ml in the presence of test compound for 1 hr at 37° C. Cells are then stimulated by incubating with 10 µg/ml anti-human IgM $F(ab)_2$ for 5 minutes at 37° C. Cells are pelleted, lysed, and a protein assay is performed on the cleared lysate. Equal protein amounts of each sample are subject to SDS-PAGE and western blotting with either anti-phosphoBtk(Tyr223) antibody (Cell Signaling Technology #3531; Epitomics, cat. #2207-1) or phosphoBtk(Tyr551) antibody (BD Transduction Labs #558034) to assess Btk autophosphorylation or an anti-Btk antibody (BD Transduction Labs #611116) to control for total amounts of Btk in each lysate.

Example 903

B-Cell Proliferation Assay

A generalized procedure for a standard cellular B-cell proliferation assay that can be used to test Formula I and II compounds is as follows. B-cells are purified from spleens of 8-16 week old Balb/c mice using a B-cell isolation kit (Miltenyi Biotech, Cat #130-090-862). Testing compounds are diluted in 0.25% DMSO and incubated with $2.5 \times 10^5$ purified mouse splenic B-cells for 30 min prior to addition of 10 µg/ml of an anti-mouse IgM antibody (Southern Biotechnology Associates Cat #1022-01) in a final volume of 100 µl. Following 24 hr incubation, 1 µCi $^3$H-thymidine is added and plates are incubated an additional 36 hr prior to harvest using the manufacturer's protocol for SPA [$^3$H] thymidine uptake assay system (Amersham Biosciences # RPNQ 0130). SPA-bead based fluorescence is counted in a microbeta counter (Wallace Triplex 1450, Perkin Elmer).

Example 904

T Cell Proliferation Assay

A generalized procedure for a standard T cell proliferation assay that can be used to test Formula I and II compounds is as follows. T cells are purified from spleens of 8-16 week old Balb/c mice using a Pan T cell isolation kit (Miltenyi Biotech, Cat #130-090-861). Testing compounds are diluted in 0.25% DMSO and incubated with $2.5 \times 10^5$ purified mouse splenic T cells in a final volume of 100 µl in flat clear bottom plates precoated for 90 min at 37° C. with 10 µg/ml each of anti-CD3 (BD #553057) and anti-CD28 (BD #553294) antibodies. Following 24 hr incubation, 1 µCi $^3$H-thymidine is added and plates incubated an additional 36 hr prior to harvest using the manufacturer's protocol for SPA [$^3$H] thymidine uptake assay system (Amersham Biosciences # RPNQ 0130). SPA-bead based fluorescence was counted in a microbeta counter (Wallace Triplex 1450, Perkin Elmer).

Example 905

CD86 Inhibition Assay

A generalized procedure for a standard assay for the inhibition of B cell activity that can be used to test Formula I and II compounds is as follows. Total mouse splenocytes are purified from spleens of 8-16 week old Balb/c mice by red blood cell lysis (BD Pharmingen #555899). Testing compounds are diluted to 0.5% DMSO and incubated with $1.25 \times 10^6$ splenocytes in a final volume of 200 µl in flat clear bottom plates (Falcon 353072) for 60 min at 37° C. Cells are then stimulated with the addition of 15 µg/ml IgM (Jackson ImmunoResearch 115-006-020), and incubated for 24 hr at 37° C., 5% $CO_2$. Following the 24 hr incubation, cells are transferred to conical bottom clear 96-well plates and pelleted by centrifugation at 1200×g×5 min. Cells are preblocked by CD16/CD32 (BD Pharmingen #553142), followed by triple staining with CD19-FITC (BD Pharmingen #553785), CD86-PE (BD Pharmingen #553692), and 7AAD (BD Pharmingen #51-68981E). Cells are sorted on a BD FACSCalibur and gated on the $CD19^+/7AAD^-$ population. The levels of CD86 surface expression on the gated population is measured versus test compound concentration.

Example 906

B-ALL Cell Survival Assay

The following is a procedure for a standard B-ALL (acute lymphoblastic leukemia) cell survival study using an XTT readout to measure the number of viable cells. This assay can be used to test Formula I and II compounds for their ability to inhibit the survival of B-ALL cells in culture. One human B-cell acute lymphoblastic leukemia line that can be used is SUP-B15, a human Pre-B-cell ALL line that is available from the ATCC.

SUP-B15 pre-B-ALL cells are plated in multiple 96-well microtiter plates in 100 µl of Iscove's media+20% FBS at a concentration of $5 \times 10^5$ cells/ml. Test compounds are then added with a final conc. of 0.4% DMSO. Cells are incubated at 37° C. with 5% $CO_2$ for up to 3 days. After 3 days cells are split 1:3 into fresh 96-well plates containing the test compound and allowed to grow up to an additional 3 days. After each 24 h period, 50 ul of an XTT solution is added to one of the replicate 96-well plates and absorbance readings are taken at 2, 4 and 20 hours following manufacturer's directions. The reading taken with an OD for DMSO only treated cells within the linear range of the assay (0.5-1.5) is then taken and the percentage of viable cells in the compound treated wells are measured versus the DMSO only treated cells.

Example 907

CD69 Whole Blood Assay

Human blood is obtained from healthy volunteers, with the following restrictions: 1 week drug-free, non-smokers. Blood (approximately 20 mls to test 8 compounds) is collected by venipuncture into Vacutainer® (Becton, Dickinson and Co.) tubes with sodium heparin.

Solutions of Formula I and II compounds at 10 mM in DMSO are diluted 1:10 in 100% DMSO, then are diluted by three-fold serial dilutions in 100% DMSO for a ten point dose-response curve. The compounds are further diluted 1:10 in PBS and then an aliquot of 5.5 µl of each compound is added in duplicate to a 2 ml 96-well plate; 5.5 µl of 10% DMSO in PBS is added as control and no-stimulus wells. Human whole blood—HWB (100 µl) is added to each well. After mixing the plates are incubated at 37° C., 5% $CO_2$, 100% humidity for 30 minutes. Goat F(ab')2 anti-human IgM (10 µl of a 500 µg/ml solution, 50 µg/ml final) is added to each well (except the no-stimulus wells) with mixing and the plates are incubated for an additional 20 hours. At the end of the 20 hour incubation, samples are incubated with fluorescent labeled antibodies for 30 minutes, at 37° C., 5% $CO_2$, 100% humidity. Include induced control, unstained and single stains for compensation adjustments and initial voltage settings. Samples are then lysed with PharM Lyse™ (BD Biosciences Pharmingen) according to the manufacturer's instructions. Samples are then transferred to a 96 well plate suitable to be run on the BD Biosciences HTS 96 well system on the LSRII machine. Data acquired and Mean Fluorescence Intensity values were obtained using BD Biosciences DIVA Software. Results are initially analyzed by FACS analysis software (Flow Jo). The IC50 for test compounds is defined as the concentration which decreases by 50% the percent positive of CD69 cells that are also CD20 positive stimulated by anti-IgM (average of 8 control wells, after subtraction of the average of 8 wells for the no-stimulus background). The inhibitory concentration (IC50, IC70, IC90) values are calculated by Prism version 5, using a nonlinear regression curve fit.

Example 908

In Vitro Cell Proliferation Assay

Efficacy of Formula I and II compounds are measured by a cell proliferation assay employing the following protocol (Mendoza et al (2002) Cancer Res. 62:5485-5488). The Cell-Titer-Glo® Luminescent Cell Viability Assay, including reagents and protocol are commercially available (Promega Corp., Madison, Wis., Technical Bulletin TB288). The assay assesses the ability of compounds to enter cells and inhibit cell proliferation. The assay principle is based on the determination of the number of viable cells present by quantitating the ATP present in a homogenous assay where addition of the Cell-Titer Glo reagent results in cell lysis and generation of a luminescent signal through the luciferase reaction. The luminescent signal is proportional to the amount of ATP present.

A panel of B-cell lymphoma cell lines (BJAB, SUDHL-4, TMD8, OCI-Ly10, OCI-Ly3, WSU-DLCL2) are plated into 384-well plate in normal growth medium, and serially diluted BTK inhibitors or DMSO alone were added to each well. Cell viability is assessed after 96 hour incubation by CellTiter-Glo® (Promega). Data may be presented as Relative cell viability in BTK inhibitor-treated cells relative to DMSO-treated control cells. Data points are the mean of 4 replicates at each dose level. Error bars represent SD from the mean.

Procedure: Day 1—Seed Cell Plates (384-well black, clear bottom, microclear, TC plates with lid from Falcon #353962), Harvest cells, Seed cells at 1000 cells per 54 µl per well into 384 well Cell Plates for 3 days assay. Cell Culture Medium: RPMI or DMEM high glucose, 10% Fetal Bovine Serum, 2 mM L-Glutamine, P/S. Incubate 0/N at 37° C., 5% CO2.

Day 2—Add Drug to Cells, Compound Dilution, DMSO Plates (serial 1:2 for 9 points), Add 20 µl compounds at 10 mM in the 2nd column of 96 well plate. Perform serial 1:2 across the plate (10 µl+20 µl 100% DMSO) for a total of 9 points using Precision. Media Plates 96-well conical bottom polypropylene plates from Nunc (cat.#249946) (1:50 dilution) Add 147 µl of Media into all wells. Transfer 3 µl of DMSO+compound from each well in the DMSO Plate to each corresponding well on Media Plate using Rapidplate.

Drug Addition to Cells, Cell Plate (1:10 dilution), Add 6 µl of media+compound directly to cells (54 µl of media on the cells already). Incubate 3 days at 37 C, 5% CO2 in an incubator that will not be opened often.

Day 5—Develop Plates, Thaw Cell Titer Glo Buffer at room temperature. Remove Cell Plates from 37° C. and equilibrate to room temperature. for about 30 minutes. Add Cell Titer Glo Buffer to Cell Titer Glo Substrate (bottle to bottle). Add 30 µA Cell Titer Glo Reagent (Promega cat.# G7572) to each well of cells. Place on plate shaker for about 30 minutes. Read luminescence on Analyst HT Plate Reader (half second per well).

Cell viability assays and combination assays: Cells were seeded at 1000-2000 cells/well in 384-well plates for 16 h. On day two, nine serial 1:2 compound dilutions are made in DMSO in a 96 well plate. The compounds are further diluted into growth media using a Rapidplate robot (Zymark Corp., Hopkinton, Mass.). The diluted compounds are then added to quadruplicate wells in 384-well cell plates and incubated at 37° C. and 5% CO2. After 4 days, relative numbers of viable cells are measured by luminescence using Cell-Titer Glo (Promega) according to the manufacturer's instructions and read on a Wallac Multilabel Reader (PerkinElmer, Foster City). EC50 values are calculated using Prism® 4.0 software (GraphPad, San Diego). Formula I or II compounds, and chemotherapeutic agents are added simultaneously or separated by 4 hours (one before the other) in all assays.

An additional exemplary in vitro cell proliferation assay includes the following steps:

1. An aliquot of 100 μl of cell culture containing about $10^4$ cells in medium is deposited in each well of a 384-well, opaque-walled plate.

2. Control wells are prepared containing medium and without cells.

3. The compound is added to the experimental wells and incubated for 3-5 days.

4. The plates are equilibrated to room temperature for approximately 30 minutes.

5. A volume of CellTiter-Glo Reagent equal to the volume of cell culture medium present in each well is added.

6. The contents are mixed for 2 minutes on an orbital shaker to induce cell lysis.

7. The plate is incubated at room temperature for 10 minutes to stabilize the luminescence signal.

8. Luminescence is recorded and reported in graphs as RLU=relative luminescence units.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

We claim:

1. A method of treating an hematological malignancy in a patient comprising administering a therapeutically effective amount of a pharmaceutical composition to the patient wherein the pharmaceutical composition comprises a Formula I compound and a pharmaceutically acceptable carrier, glidant, diluent, or excipient, wherein the Formula I compound has the structure:

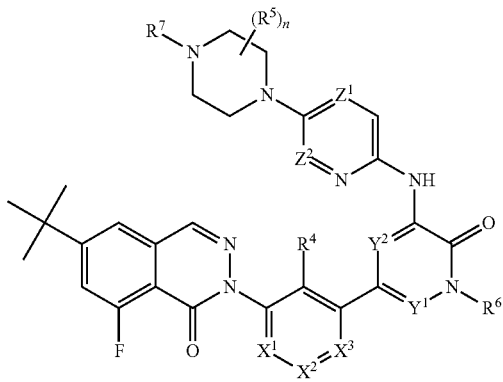

or stereoisomers, tautomers, or pharmaceutically acceptable salts thereof, wherein:

$X^1$ is $CR^1$ or N;

$X^2$ is $CR^2$ or N;

$X^3$ is $CR^3$ or N;

where one or two of $X^1$, $X^2$, and $X^3$ are N;

$R^1$, $R^2$ and $R^3$ are independently selected from H, F, Cl, CN, —$CH_3$, —$CH_2CH_3$, —$CH_2OH$, —$CH_2F$, —$CHF_2$, —$CF_3$, —$CH_2CH_2OH$, —$NH_2$, —$NHCH_3$, —$N(CH_3)_2$, —OH, —$OCH_3$, —$OCH_2CH_3$, and —$OCH_2CH_2OH$;

$R^4$ is selected from H, F, Cl, CN, —$CH_2OH$, —$CH(CH_3)$OH, —$C(CH_3)_2OH$, —$CH(CF_3)OH$, —$CH_2F$, —$CHF_2$, —$CH_2CHF_2$, —$CF_3$, —$C(O)NH_2$, —$C(O)NHCH_3$, —$C(O)N(CH_3)_2$, —$NH_2$, —$NHCH_3$, —$N(CH_3)_2$, —$NHC(O)CH_3$, —OH, —$OCH_3$, —$OCH_2CH_3$, —$OCH_2CH_2OH$, —$OP(O)(OH)_2$, cyclopropyl, cyclopropylmethyl, 1-hydroxycyclopropyl, imidazolyl, pyrazolyl, 3-hydroxy-oxetan-3-yl, oxetan-3-yl, and azetidin-1-yl;

$R^5$ is selected from —$CH_3$, —$CH_2CH_3$, —$CH_2OH$, —$CH_2F$, —$CHF_2$, —$CF_3$, —CN, and —$CH_2CH_2OH$;

or two $R^5$ groups form a 3-, 4-, 5-, or 6-membered carbocyclic or heterocyclic ring;

or an $R^5$ group and an $R^7$ group form a 3-, 4-, 5-, or 6-membered carbocyclic or heterocyclic ring;

n is 0, 1, 2, 3, or 4;

$R^6$ is selected from H, —$CH_3$, —$CH_2CH_3$, —$CH_2CH_2OH$, —$CH_2F$, —$CHF_2$, —$CF_3$, —$NH_2$, —$NHCH_3$, —$N(CH_3)_2$, —OH, —$OCH_3$, —$OCH_2CH_3$, and —$OCH_2CH_2OH$;

$R^7$ is selected from H, —$CH_3$, —$S(O)_2CH_3$, cyclopropyl, azetidin-3-yl, oxetan-3-yl, and morpholin-4-yl;

$Z^1$ is $CR^8$ or N, where $R^8$ is selected from H, F, Cl, —$CH_3$, —$CH_2CH_3$, —$CH_2CH_2OH$, —$NH_2$, —$NHCH_3$, —$N(CH_3)_2$, —OH, —$OCH_3$, —$OCH_2CH_3$, and —$OCH_2CH_2OH$;

$Z^2$ is $CR^9$ or N, where $R^9$ is selected from H, —$CH_3$, —$CH_2CH_3$, and —$CH_2CH_2OH$; and $Y^1$ and $Y^2$ are independently selected from CH and N, where $Y^1$ and $Y^2$ are not each N.

2. The method of claim 1 wherein the Formula I compound is selected from Formulas Ia-If having the structures:

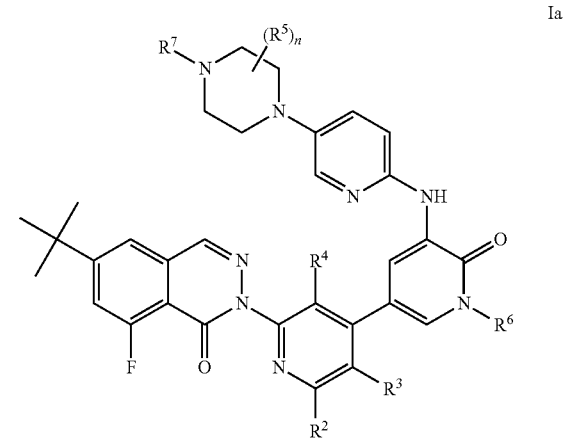

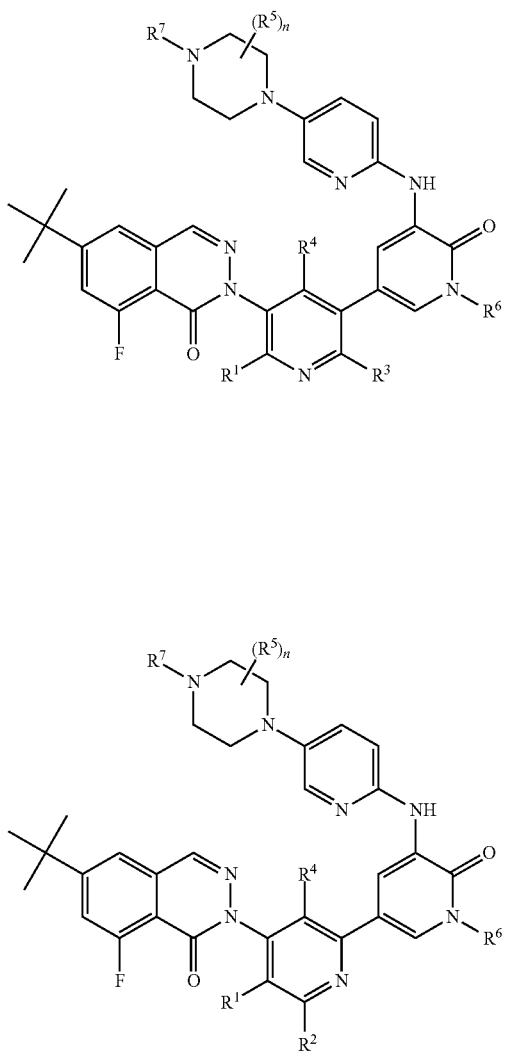

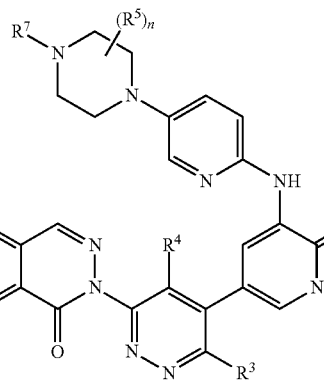

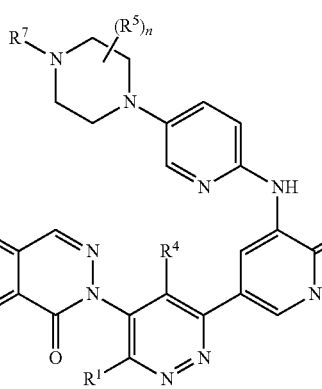

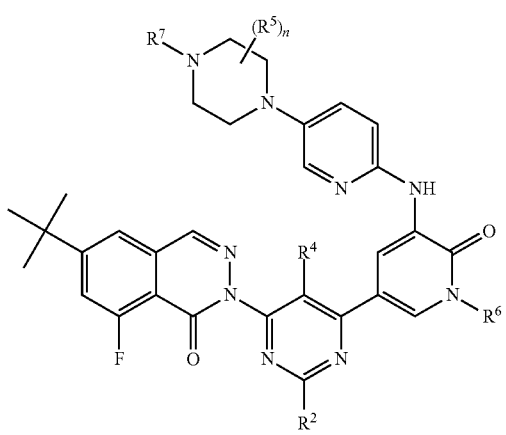

3. The method of claim 1 wherein $X^1$ is N, $X^2$ is $CR^2$, and $X^3$ is $CR^3$.

4. The method of claim 1 wherein $X^1$ is $CR^1$, $X^2$ is N, and $X^3$ is $CR^3$.

5. The method of claim 1 wherein $X^1$ is $CR^1$, $X^2$ is $CR^2$, and $X^3$ is N.

6. The method of claim 5 wherein $X^1$ and $X^3$ are CH.

7. The method of claim 1 selected from: $X^1$ and $X^3$ are N, $X^1$ and $X^2$ are N, or $X^2$ and $X^3$ are N.

8. The method of claim 1 wherein $X^2$ is $CR^2$, and $R^2$ is F.

9. The method of claim 1 wherein $R^4$ is —$CH_2OH$.

10. The method of claim 1 wherein $R^5$ is —$CH_3$, and n is 1 or 2.

11. The method of claim 1 wherein $R^7$ is oxetan-3-yl.

12. The method of claim 1 wherein $Y^1$ is CH.

13. The method of claim 1 wherein $Y^2$ is CH.

14. The method of claim 1 wherein $Z^1$ is CH.

15. The method of claim 1 wherein $Z^2$ is CH.

16. The method of claim 1 wherein the Formula I compound is selected from:
   6-tert-butyl-8-fluoro-2-(3-(hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)phthalazin-1(2H)-one;
   (S)-6-tert-butyl-8-fluoro-2-(3-(hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)phthalazin-1(2H)-one;
   (R)-6-tert-butyl-8-fluoro-2-(3-(hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)phthalazin-1(2H)-one;

(S)-6-tert-butyl-8-fluoro-2-(4-(hydroxymethyl)-5-(1-methyl-5-(5-(2-methyl-4-(oxetan-3-yl)piperazin-1-yl)pyridin-2-ylamino)-6-oxo-1,6-dihydropyridin-3-yl)pyridin-3-yl)phthalazin-1(2H)-one;

6-tert-butyl-2-(4-(5-(5-((2S,5R)-2,5-dimethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-8-fluorophthalazin-1(2H)-one; and (S)-6-tert-butyl-2-(4-(5-(5-(2-ethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-8-fluorophthalazin-1(2H)-one.

17. The method of claim 1 wherein the Formula I compound is selected from 6-tert-butyl-8-fluoro-2-[3-(hydroxymethyl)-4-[1-methyl-5-[[5-[(2S)-2-methyl-4-(oxetan-3-yl)piperazin-1-yl]-2-pyridyl]amino]-6-oxo-pyridazin-3-yl]-2-pyridyl]phthalazin-1-one; and 6-tert-butyl-8-fluoro-2-[3-(hydroxymethyl)-4-[5-[[5-[(2S)-2-methyl-4-(oxetan-3-yl)piperazin-1-yl]-2-pyridyl]amino]-6-oxo-1H-pyridin-3-yl]-2-pyridyl]phthalazin-1-one.

18. The method of claim 1 wherein the hematological malignancy is selected from lymphomas, lymphocytic leukemias, and myeloma.

19. The method of claim 18 wherein the lymphocytic leukemia is Acute lymphoblastic leukemia (ALL), Acute myelogenous leukemia (AML), Chronic lymphocytic leukemia (CLL), Chronic myelogenous leukemia (CML), or Acute monocytic leukemia (AMOL).

20. The method of claim 18 wherein the lymphoma is non-Hodgkin lymphoma.

21. The method of claim 18 further comprising administering an additional therapeutic agent selected from an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders.

* * * * *